(12) United States Patent
Smith et al.

(10) Patent No.: US 8,071,581 B2
(45) Date of Patent: Dec. 6, 2011

(54) TRIAZOLOPYRIDAZINE PROTEIN KINASE MODULATORS

(75) Inventors: Christopher Ronald Smith, San Diego, CA (US); Pierre-Yves Bounaud, San Diego, CA (US); Elizabeth Anne Jefferson, La Jolla, CA (US); Patrick S. Lee, San Diego, CA (US); Eduardo Torres, San Diego, CA (US)

(73) Assignee: SGX Pharmaceuticals, Inc., San Diego, CA (US)

( * ) Notice: Subject to any disclaimer, the term of this patent is extended or adjusted under 35 U.S.C. 154(b) by 94 days.

(21) Appl. No.: 12/442,987

(22) PCT Filed: Oct. 18, 2007

(86) PCT No.: PCT/US2007/081832
§ 371 (c)(1),
(2), (4) Date: Mar. 26, 2009

(87) PCT Pub. No.: WO2008/051805
PCT Pub. Date: May 2, 2008

(65) Prior Publication Data
US 2010/0120739 A1   May 13, 2010

Related U.S. Application Data

(60) Provisional application No. 60/862,552, filed on Oct. 23, 2006, provisional application No. 60/871,384, filed on Dec. 21, 2006, provisional application No. 60/913,752, filed on Apr. 24, 2007, provisional application No. 60/952,833, filed on Jul. 30, 2007.

(51) Int. Cl.
*A01N 43/00* (2006.01)

(52) U.S. Cl. ............. 514/210.18; 435/184; 514/248; 514/184; 514/243; 544/118; 544/236

(58) Field of Classification Search ............. 514/243, 514/231.5, 210.21, 233.2, 248; 544/112, 544/184, 118, 236; 435/184
See application file for complete search history.

(56) References Cited

FOREIGN PATENT DOCUMENTS
WO    WO 02/083139    10/2002
(Continued)

OTHER PUBLICATIONS
Vippagunta, et al. Advanced Drug Delivery Reviews, 48, 2001, p. 18).*
(Continued)

*Primary Examiner* — Brandon Fetterolf
*Assistant Examiner* — Jean Cornet
(74) *Attorney, Agent, or Firm* — Francis O. Ginah; James J. Sales; Tina M. Tucker

(57) ABSTRACT

The present disclosure relates to triazolopyridazine protein kinase modulators of Formula (I), methods of using these compounds to treat diseases mediated by kinase activity.

(I)

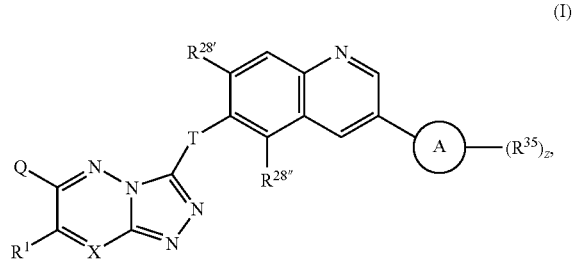

2 Claims, 7 Drawing Sheets

FOREIGN PATENT DOCUMENTS

WO    WO 02/083675    10/2002

OTHER PUBLICATIONS bian et al "Azabenzenes (Azines)—The nitrogen derivatives of benzene with one to six N atoms: stability, homodesmotic stabilization energy, electron distribution, and magnetic ring current; a computational study", Can. J. Chem. vol. 82, pp. 50-69, 2004.*

Target et al "Synthetic inhibitors of interleukin-6 II: 3,5-diaryl pyridines and meta-terphenyls", Biorganic & Medicinal Chemistry Letters, vol. 5, No. 18, pp. 2143-2146, 1995.*

Schafer et al. Drug Discovery Today 2008, 13 (21/22), 913-916.*

Horig et al. Journal of Translational Medicine 2004, 2(44).*

Sawyer et al "Synthesis and activity of New Aryl- and heteroaryl-substituted pyrazole inhibitors of the transforming growth factor-β type I receptor kinase domain". Journal of Medicinal Chemistry, vol. 46, No. 19, Sep. 11, 2003.*

Wolff Burgers Medicinal Chemistry and Drug Discovery, Fifth Edition, vol. I: Principles and Practice, Wiley-Interscience 1995, pp. 974-977.*

* cited by examiner

TRIAZOLOPYRIDAZINE PROTEIN KINASE MODULATORS

CROSS-REFERENCE TO RELATED APPLICATIONS

This application is a U.S. national counterpart application filed under 35 U.S.C. §371 of international application serial No. PCT/US2007/081832 filed Oct. 18, 2007, which claims priority to U.S. Provisional Application Ser. No. 60/862,552 filed Oct. 23, 2006, U.S. Provisional Application Ser. No. 60/871,384 filed Dec. 21, 2006, U.S. Provisional Application Ser. No. 60/913,752 filed Apr. 24, 2007, and U.S. Provisional Application Ser. No. 60/952,833 filed Jul. 30, 2007. The entireties of each of these applications are hereby incorporated herein by reference.

BACKGROUND OF THE DISCLOSURE

Mammalian protein kinases are important regulators of cellular functions. Because disfunctions in protein kinase activity have been associated with several diseases and disorders, protein kinases are targets for drug development. The Tyrosine kinase family, and particularly the subset of receptor tyrosine kinases, is enriched with proven and putative cancer targets. Receptor tyrosine kinases (RTKs) such as EGFR, HER2, KIT and KDR are well characterized proteins with a clearly established role in cancer. Drugs targeting these RTKs, such as Gleevec, Iressa, and Tarceva, have been approved for the treatment of certain cancers. Other RTKs are less well characterized but have also been implicated in cancer. For example, emerging data suggests that inhibitors of TRKC, ROS, CSF1R/FMS and ALK may be useful in the treatment of cancer. MET and RON are two particularly attractive RTK targets for the development of new agents to treat cancer.

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, c-Met, a receptor tyrosine kinase. c-Met, a widely expressed heterodimeric protein comprising of a 50 kilodalton (kDa) α-subunit and a 145 kDa β-subunit (Maggiora et al., J. Cell Physiol., 173:183-186, 1997), is overexpressed in a significant percentage of human cancers and is amplified during the transition between primary tumors and metastasis. The various cancers in which c-Met overexpression is implicated include, but are not limited to, gastric adenocarcinoma, renal cancer, small cell lung carcinoma, colorectal cancer, prostate cancer, brain cancer, liver cancer, pancreatic cancer, and breast cancer. c-Met is also implicated in atherosclerosis and lung fibrosis.

MET was first identified as a transforming DNA rearrangement (TPR-MET) in a human osteosarcoma cell line that had been treated with N-methyl-N'-nitro-nitrosoguanidine (Cooper et al. 1984). The MET receptor tyrosine kinase (also known as hepatocyte growth factor receptor, HGFR, MET or c-Met) and its ligand hepatocyte growth factor ("HGF") have numerous biological activities including the stimulation of proliferation, survival, differentiation and morphogenesis, branching tubulogenesis, cell motility and invasive growth. Pathologically, MET has been implicated in the growth, invasion and metastasis of many different forms of cancer including kidney cancer, gastric cancer, lung cancer, ovarian cancer, liver cancer and breast cancer. Somatic, activating mutations in MET have been found in human carcinoma metastases and in sporadic cancers such as papillary renal cell carcinoma. There is also evidence the MET signaling pathway can play an important role in resistance to cancer therapies. For example, the MET gene has been found to be amplified in lung cancer patients that have relapsed after initial response to EGFR inhibitors such as gefitinib and erlotininb. In addition to cancer there is evidence that MET inhibition may have value in the treatment of various indications including: *Listeria* invasion, osteolysis associated with multiple myeloma, malaria infection, diabetic retinopathies, psoriasis, and arthritis. Mutations in the MET coding sequence are relatively uncommon in human cancers. However, based on the precedent of the selection of BCR-ABL mutations in chronic myelogenous leukemia patients treated with imatinib and EGFR mutations in cancer patients treated with erlotinib and gefitinib, these and/or perhaps additional MET mutations that might confer drug resistance are predicted to become increasingly prevalent if MET inhibitors become widely use in cancer. Therefore drugs that effectively inhibit some of these MET mutations could become very important tools in future cancer therapies.

MET is closely related to a group of five receptor tyrosine kinases which have not been as thoroughly studied as MET itself. These include Tyro3/Sky, MER, AXL, RYK and RON. The tyrosine kinase RON is the receptor for the macrophage stimulating protein and is the closest relative of MET, belonging to the MET family of receptor tyrosine kinases. Like MET, RON is implicated in growth, invasion and metastasis of several different forms of cancer including colorectal cancer and bladder cancer. There is also evidence that deregulated AXL and MER can play important roles in cancer. MER has many properties consistent with activity as an oncogene. Transgenic mice expressing MER in the hematopoietic lineage develop symptoms similar to T-cell lymphoblastic leukemia/lymphoma and it is expressed in most T cell acute lymphoblastic leukemia (T-ALL) patients. Studies in mouse models suggested that AXL is important for the growth of breast cancer where AXL appeared to regulate both angiogenic and tumorigenic processes. Additional studies with human cancer cell lines suggest that AXL is involved in NSCLC metastasis and drug resistance. Although very little is known of the normal and pathological roles of Tyro3/Sky this receptor tyrosine kinase shares certain properties and functions with its better studied relatives and may also eventually prove to have an important role in cancer. RYK is also expressed in certain cancers but it is an atypical orphan receptor tyrosine kinase that lacks detectable kinase activity and thus its tractability as a target for small molecule cancer therapeutics is currently uncertain.

Because kinases have been implicated in numerous diseases and conditions, such as cancer, there is a need to develop new and potent protein kinase inhibitors that can be used for treatment. The present invention fulfills these and other needs in the art. Although certain protein kinases are specifically named herein, the present invention is not limited to inhibitors of these kinases, and, includes, within its scope, inhibitors of related protein kinases, and inhibitors of homologous proteins.

BRIEF SUMMARY OF THE DISCLOSURE

It has been discovered that the triazalopyridazine compounds of the present disclosure may be used to modulate kinase activity and to treat diseases mediated by kinase activity. In particular, the compounds of the present disclosure may be used to modulate and/or inhibit tyrosine kinases, including MET. Further, the compounds of the present disclosure may be used to reduce or inhibit kinase activity of MET in a cell or subject, and to modulate MET expression in a cell or subject. The disclosed compounds are also useful for preventing or treating in a subject a cell proliferative disorder and/or disorders related to MET. The disclosed triazalopyridazine kinase modulators are described in detail below. In addition, inhibitory activities of selected compounds are disclosed herein.

In one aspect, the disclosure provides compounds having formula I:

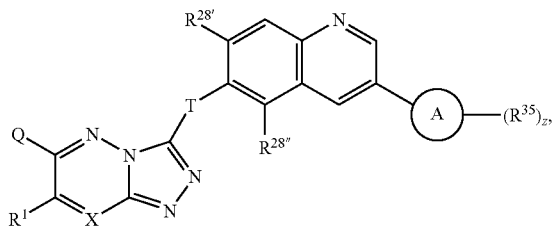

(I)

or an enantiomer, diastereomer, racemate or pharmaceutically acceptable salt or solvate thereof, wherein:

A is independently substituted or unsubstituted aryl or substituted or unsubstituted heteroaryl;

Q is independently substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, wherein Q is optionally independently substituted with 1 to 3 $R^{22}$;

T is independently $CH_2$, CH(halogen), C(halogen)$_2$, CH(($C_1$-$C_6$)alkyl), or C(($C_1$-$C_6$)alkyl)$_2$;

X is N or $CR^2$;

$R^1$ and $R^2$ are each optionally independently hydrogen, halogen, nitro, cyano, hydroxyl, substituted or unsubstituted alkyl, perfluoroalkyl, —(CH$_2$)$_j$CN, —(CH$_2$)$_j$OR$^3$, —(CH$_2$)$_j$C(O)R$^3$, —(CH$_2$)$_j$C(O)OR$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$NR$^6$C(O)OR$^3$, —(CH$_2$)$_j$NR$^6$C(O)NR$^4$R$^5$, —(CH$_2$)$_j$S(O)$_m$R$^7$, —(CH$_2$)$_j$NR$^6$S(O)$_2$R$^7$, —(CH$_2$)$_j$S(O)$_2$NR$^4$R$^5$, wherein each j is independently an integer from 0 to 6; and m is independently an integer from 0 to 2; or $R^1$ and $R^2$ form substituted or unsubstituted cycloalkyl, substituted or unsubstituted heterocycloalkyl, substituted or unsubstituted aryl, or substituted or unsubstituted heteroaryl;

$R^3$, $R^4$, $R^5$, $R^6$ and $R^7$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^3$, $R^6$ and $R^7$ are as described above, and $R^4$ and $R^5$, together with the N atom to which they are attached, form substituted or unsubstituted heterocycloalkyl, or substituted or unsubstituted heteroaryl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, substituted or unsubstituted heteroarylalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$, wherein each j is independently an integer from 0 to 6, and each m is independently an integer from 0 to 2;

$R^{23}$, $R^{24}$, $R^{25}$, $R^{26}$, and $R^{27}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{23}$, $R^{26}$, and $R^{27}$ are as described above, and $R^{24}$ and $R^{25}$, together with the N atom to which they are attached, form substituted or unsubstituted heterocycloalkyl, or substituted or unsubstituted heteroaryl;

$R^{28'}$ and $R^{28''}$ are each independently hydrogen, halogen, nitro, cyano, hydroxyl, substituted or unsubstituted alkyl, substituted or unsubstituted cycloalkyl, perfluoroalkyl, substituted or unsubstituted alkoxy, amino, aminomonoalkyl, or aminodialkyl;

$R^{35}$ is independently a bond, hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$N$^{33}$C(O)NR$^{31}$R$^{32}$, —(CH$_2$)$_j$S(O)$_m$R$^{34}$, (CH$_2$)$_j$S(O)$_2$NR$^{31}$R$^{32}$, or —(CH$_2$)$_j$NR$^{33}$S(O)$_2$R$^{34}$, wherein each j is independently an integer from 0 to 6, and m is independently an integer from 0 to 2;

z is independently an integer from 0 to 3;

$R^{30}$, $R^{31}$, $R^{32}$, $R^{33}$, and $R^{34}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{30}$, $R^{33}$, and $R^{34}$ are as described above, and $R^{31}$ and $R^{32}$, together with the N atom to which they are attached, form substituted or unsubstituted heterocycloalkyl, or substituted or unsubstituted heteroaryl; and wherein $R^1$, $R^2$, $R^3$, $R^4$, $R^5$, $R^6$, $R^7$, $R^{22}$, $R^{23}$, $R^{24}$, $R^{25}$, $R^{26}$, $R^{27}$, $R^{28'}$, $R^{28''}$, $R^{30}$, $R^{31}$, $R^{32}$, $R^{33}$, $R^{34}$, and $R^{35}$ are each optionally independently substituted with 1 to 3 groups, each group independently selected from hydrogen, halogen, hydroxyl, amino, aminomonoalkyl, aminodialkyl, cyano, nitro, difluoromethyl, trifluoromethyl, oxo, alkyl, —O-alkyl, and —S-alkyl.

In other embodiments, the present disclosure relates to methods for modulating the activity of protein kinases; methods for treating cancer and pharmaceutical compositions using a compound of formula I.

DETAILED DESCRIPTION OF THE DISCLOSURE

Definitions

Figure 1:
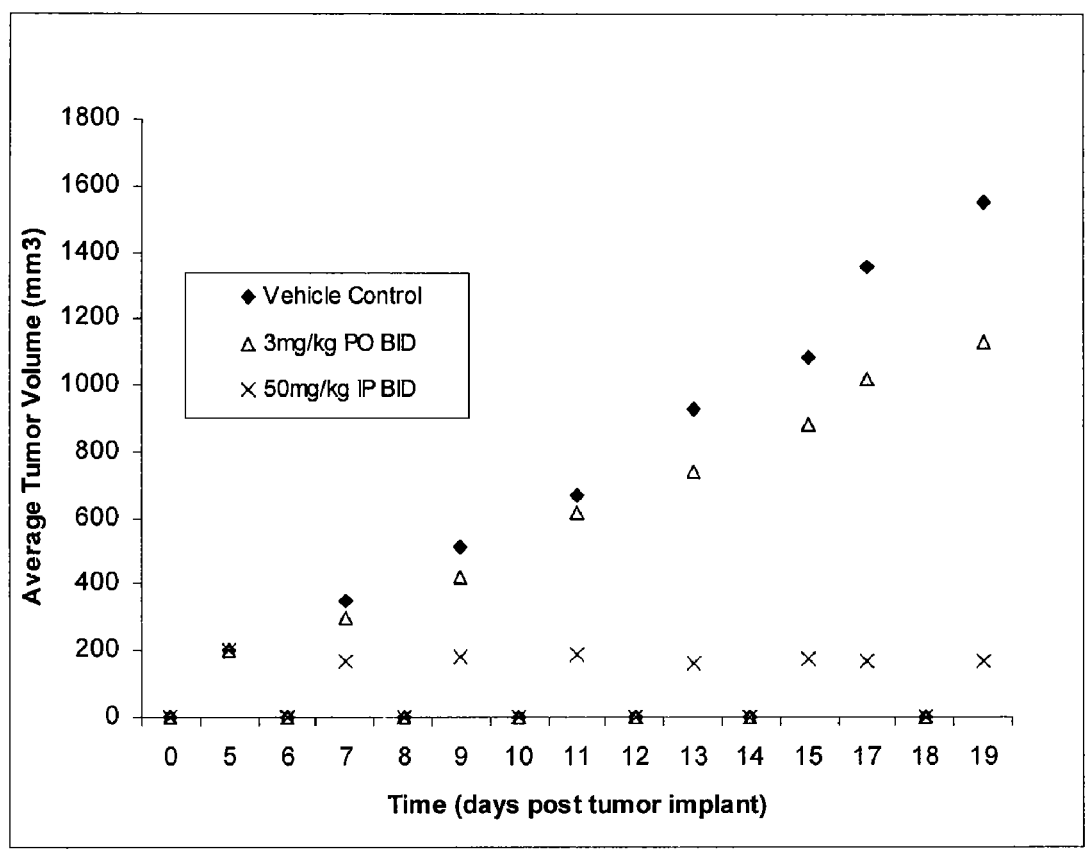
FIG. 1 illustrates the effects on GTL16 tumor growth inhibition by administering compound 30 orally (PO) twice a day and via intraperitoneal injection (IP) for 14 consecutive days.

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

An "alkylesteryl," as used herein, refers to a moiety having the formula R'—C(O)O—R", wherein R' is an alkylene moiety and R" is an alkyl moiety.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkyl" or "cycloalkylalkyl" also refers to a 3 to 7 membered cycloalkyl group attached to the remainder of the molecule via an unsubstituted alkylene group. Recitation of a specific number of carbon atoms (e.g. C$_1$-C$_{10}$ cycloalkylalkyl) refers to the number of carbon atoms in the alkylene group.

The term "heterocycloalkyl" or "heterocycloalkylalkyl" also refers to a 3 to 7 membered heterocycloalkyl group attached to the remainder of the molecule via an unsubstituted alkylene group. Recitation of a specific number of carbon atoms (e.g. $C_1$-$C_{10}$ hetero-cycloalkylalkyl) refers to the number of carbon atoms in the alkylene group.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. Substituents for each of above noted aryl and heteroaryl ring systems are selected from the group of acceptable substituents described below. The terms "arylene" and "heteroarylene" refer to the divalent derivatives of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

The term "oxo" as used herein means an oxygen that is double bonded to a carbon atom.

Each of above terms (e.g., "alkyl," "heteroalkyl," "cycloalkyl", and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —$CO_2$R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"', —S(O)R', —$S(O)_2$R', —$S(O)_2$NR'R", —$NRSO_2$R', —CN and —$NO_2$ in a number ranging from zero to (2 m'+1), where m' is the total number of carbon atoms in such radical. R', R", R"' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From above discussion of substituents, one of skill in art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', —$CO_2$R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"', —S(O)R', —$S(O)_2$R', —$S(O)_2$NR'R", —$NRSO_2$R', —CN and —$NO_2$, -R', —$N_3$, —CH(Ph)$_2$, fluoro($C_1$-$C_4$)alkoxo, and fluoro($C_1$-$C_4$)alkyl, in a number ranging from zero to the total number of open valences on aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —$S(O)_2$—, —$S(O)_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —$S(O)_2$—, or —$S(O)_2$NR'—. The substituents R, R', R" and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogen-phosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C— or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

In addition to salt forms, the present disclosure relates to compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, physiological conditions.

The terms "treating" or "treatment" in reference to a particular disease includes prevention of the disease.

The symbol  denotes the point of attachment of a moiety to the remainder of the molecule.

Triazalopyridazine Protein Kinase Modulators

In one aspect, the disclosure relates to compounds having formula I:

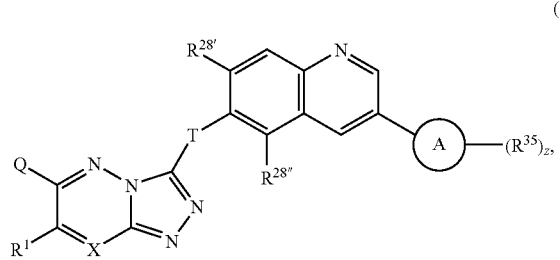

or an enantiomer, diastereomer, racemate or pharmaceutically acceptable salt or solvate thereof, wherein:

A is independently substituted or unsubstituted aryl or substituted or unsubstituted heteroaryl;

Q is independently substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, wherein Q is optionally independently substituted with 1 to 3 $R^{22}$;

T is independently $CH_2$, CH(halogen), C(halogen)$_2$, CH(($C_1$-$C_6$)alkyl), or C(($C_1$-$C_6$)alkyl)$_2$;

X is N or $CR^2$;

$R^1$ and $R^2$ are each optionally independently hydrogen, halogen, nitro, cyano, hydroxyl, substituted or unsubstituted alkyl, perfluoroalkyl, —(CH$_2$)$_j$CN, —(CH$_2$)$_j$OR$^3$, —(CH$_2$)$_j$C(O)R$^3$, —(CH$_2$)$_j$C(O)OR$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$NR$^6$C(O)OR$^3$, —(CH$_2$)$_j$NR$^6$C(O)NR$^4$R$^5$, —(CH$_2$)$_j$S(O)$_m$R$^7$, —(CH$_2$)$_j$NR$^6$S(O)$_2$R$^7$, —(CH$_2$)$_j$S(O)$_2$NR$^4$R$^5$, wherein each j is independently an integer from 0 to 6; and m is independently an integer from 0 to 2; or $R^1$ and $R^2$ form substituted or unsubstituted cycloalkyl, substituted or unsubstituted heterocycloalkyl, substituted or unsubstituted aryl, or substituted or unsubstituted heteroaryl;

$R^3$, $R^4$, $R^5$, $R^6$ and $R^7$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^3$, $R^6$ and $R^7$ are as described above, and $R^4$ and $R^5$, together with the N atom to which they are attached, form substituted or unsubstituted heterocycloalkyl, or substituted or unsubstituted heteroaryl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, substituted or unsubstituted heteroarylalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$, wherein each j is independently an integer from 0 to 6, and each m is independently an integer from 0 to 2;

$R^{23}$, $R^{24}$, $R^{25}$, $R^{26}$, and $R^{27}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{23}$, $R^{26}$, and $R^{27}$ are as described above, and $R^{24}$ and $R^{25}$, together with the N atom to which they are attached, form substituted or unsubstituted heterocycloalkyl, or substituted or unsubstituted heteroaryl;

$R^{28'}$ and $R^{28''}$ are each independently hydrogen, halogen, nitro, cyano, hydroxyl, substituted or unsubstituted alkyl, substituted or unsubstituted cycloalkyl, perfluoroalkyl, substituted or unsubstituted alkoxy, amino, aminomonoalkyl, or aminodialkyl;

$R^{35}$ is independently a bond, hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$N$^{33}$C(O)NR$^{31}$R$^{32}$, —(CH$_2$)$_j$S(O)$_m$R$^{34}$, (CH$_2$)$_j$S(O)$_2$NR$^{31}$R$^{32}$, or —(CH$_2$)$_j$NR$^{33}$S(O)$_2$R$^{34}$, wherein each j is independently an integer from 0 to 6, and m is independently an integer from 0 to 2;

z is independently an integer from 0 to 3;

$R^{30}$, $R^{31}$, $R^{32}$, $R^{33}$, and $R^{34}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{30}$, $R^{33}$, and $R^{34}$ are as described above, and $R^{31}$ and $R^{32}$, together with the N atom to which they are attached, form substituted or unsubstituted heterocycloalkyl, or substituted or unsubstituted heteroaryl; and wherein $R^1$, $R^2$, $R^3$, $R^4$, $R^5$, $R^6$, $R^7$, $R^{22}$, $R^{23}$, $R^{24}$, $R^{25}$, $R^{26}$, $R^{27}$, $R^{28'}$, $R^{28''}$, $R^{30}$, $R^{31}$, $R^{32}$, $R^{33}$, $R^{34}$, and $R^{35}$ are each optionally independently substituted with 1 to 3 groups, each group independently selected from hydrogen, halogen, hydroxyl, amino, aminomonoalkyl, aminodialkyl, cyano, nitro, difluoromethyl, trifluoromethyl, oxo, alkyl, —O-alkyl, and —S-alkyl.

In another aspect, the disclosure provides compounds having formula I, wherein:

A is independently substituted or unsubstituted phenyl, substituted or unsubstituted naphthyl, substituted or unsubstituted biphenyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted isoxazolyl, substituted or unsubstituted isothiazolyl, substituted or unsubstituted triazolyl, substituted or unsubstituted pyrazinyl, substituted or unsubstituted pyridinyl, substituted or unsubstituted pyrimidyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl;

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted —O-pyridinyl, substituted or unsubstituted isoxazolyl, substituted or unsubstituted isothiazolyl, or substituted or unsubstituted triazolyl;

$R^1$ and $R^2$ are each optionally independently hydrogen, halogen, nitro, cyano, hydroxyl, substituted or unsubstituted alkyl, perfluoroalkyl, —$(CH_2)_j$CN, —$(CH_2)_j$OR$^3$, —$(CH_2)_j$C(O)R$^3$, —$(CH_2)_j$C(O)OR$^3$, —$(CH_2)_j$NR$^4$R$^5$, —$(CH_2)_j$C(O)NR$^4$R$^5$, —$(CH_2)_j$C(O)NR$^4$R$^5$, —$(CH_2)_j$NR$^6$C(O)R$^3$, —$(CH_2)_j$NR$^6$C(O)OR$^3$, —$(CH_2)_j$NR$^6$C(O)NR$^4$R$^5$, —$(CH_2)_j$S(O)$_m$R$^7$, —$(CH_2)_j$NR$^6$S(O)$_2$R$^7$, —$(CH_2)_j$S(O)$_2$NR$^4$R$^5$;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —$(CH_2)_j$CN, —$(CH_2)_j$OR$^{23}$, —$(CH_2)_j$C(O)R$^{23}$, —$(CH_2)_j$C(O)OR$^{23}$, —$(CH_2)_j$NR$^{24}$R$^{25}$, —$(CH_2)_j$C(O)NR$^{24}$R$^{25}$, —$(CH_2)_j$OC(O)NR$^{24}$R$^{25}$, —$(CH_2)_j$NR$^{26}$C(O)R$^{23}$, —$(CH_2)_j$NR$^{26}$C(O)OR$^{23}$, —$(CH_2)_j$NR$^{26}$C(O)NR$^{24}$R$^{25}$, —$(CH_2)_j$S(O)$_m$R$^{27}$, —$(CH_2)_j$S(O)$_2$NR$^{24}$R$^{25}$, or —$(CH_2)_j$NR$^{26}$S(O)$_2$R$^{27}$;

$R^{28'}$ and $R^{28''}$ are each independently hydrogen, halogen, cyano, hydroxyl, substituted or unsubstituted alkyl, or perfluoroalkyl; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —$(CH_2)_jCN$, —$(CH_2)_jOR^{30}$, —$(CH_2)_jC(O)R^{30}$, —$(CH_2)_jC(O)OR^{30}$, —$(CH_2)_jNR^{31}R^{32}$, —$(CH_2)_jC(O)NR^{31}R^{32}$, —$(CH_2)_jOC(O)NR^{31}R^{32}$, —$(CH_2)_jNR^{33}C(O)R^{30}$, —$(CH_2)_jNR^{33}C(O)OR^{30}$, —$(CH_2)_jNR^{33}C(O)NR^{31}R^{32}$, —$(CH_2)_jS(O)_mR^{34}$, —$(CH_2)_jS(O)_2NR^{31}R^{32}$, or —$(CH_2)_jNR^{33}S(O)_2R^{34}$.

In another aspect, the disclosure provides compounds having formula I, wherein:

A is independently substituted or unsubstituted phenyl, substituted or unsubstituted naphthyl, substituted or unsubstituted biphenyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted isoxazolyl, substituted or unsubstituted isothiazolyl, substituted or unsubstituted triazolyl, substituted or unsubstituted pyrazinyl, substituted or unsubstituted pyridinyl, substituted or unsubstituted pyrimidyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, or substituted or unsubstituted quinolinyl;

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, or substituted or unsubstituted —O-pyridinyl;

$R^1$ and $R^2$ are each independently hydrogen, halogen, nitro, cyano, hydroxyl, substituted or unsubstituted alkyl, or perfluoroalkyl;

X is $CR^2$;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —$(CH_2)_jCN$, —$(CH_2)_jOR^{23}$, —$(CH_2)_jC(O)R^{23}$, —$(CH_2)_jC(O)OR^{23}$, —$(CH_2)_jNR^{24}R^{25}$, —$(CH_2)_jC(O)NR^{24}R^{25}$, —$(CH_2)_jNR^{26}C(O)R^{23}$, —$(CH_2)_jOC(O)NR^{24}R^{25}$, —$(CH_2)_jNR^{26}C(O)OR^{23}$, —$(CH_2)_jNR^{26}C(O)NR^{24}R^{25}$, —$(CH_2)_jS(O)_mR^{27}$, —$(CH_2)_jS(O)_2NR^{24}R^{25}$, or —$(CH_2)_jNR^{26}S(O)_2R^{27}$;

$R^{28'}$ and $R^{28''}$ are each independently hydrogen, halogen, hydroxyl, alkyl, or perfluoroalkyl; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —$(CH_2)_jCN$, —$(CH_2)_jOR^{30}$, —$(CH_2)_jC(O)R^{30}$, —$(CH_2)_jC(O)OR^{30}$, —$(CH_2)_jNR^{31}R^{32}$, —$(CH_2)_jC(O)NR^{31}R^{32}$, —$(CH_2)_jOC(O)NR^{31}R^{32}$, —$(CH_2)_jNR^{33}C(O)R^{30}$, —$(CH_2)_jNR^{33}C(O)OR^{30}$, —$(CH_2)_jN^{33}C(O)NR^{31}R^{32}$, —$(CH_2)_jS(O)_mR^{34}$, —$(CH_2)_jS(O)_2NR^{31}R^{32}$, —$(CH_2)_jNR^{33}S(O)_2R^{34}$,

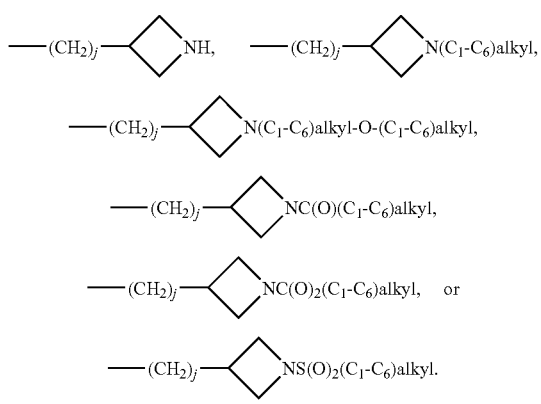

In another aspect, the disclosure provides compounds having formula I, wherein:

A is independently:

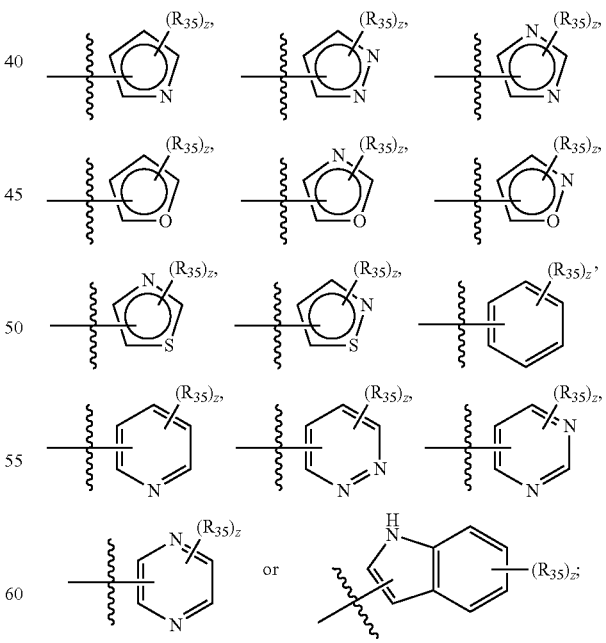

Q is independently hydrogen, chloro, substituted or unsubstituted alkyl, perfluoroalkyl, —$NH_2$, —$NH(C_1-C_6)alkyl$, or —$N[(C_1-C_6)alkyl]_2$,

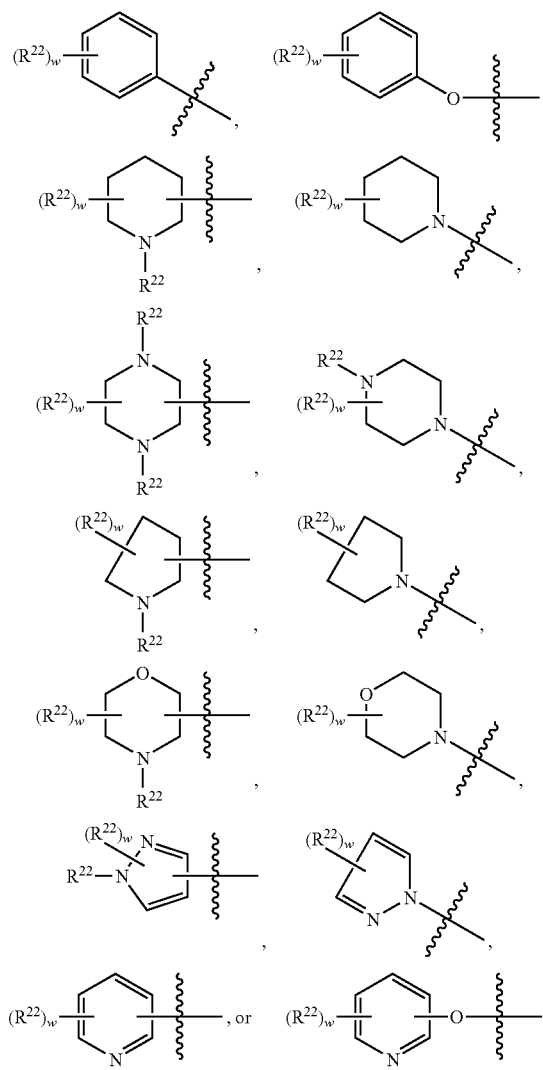

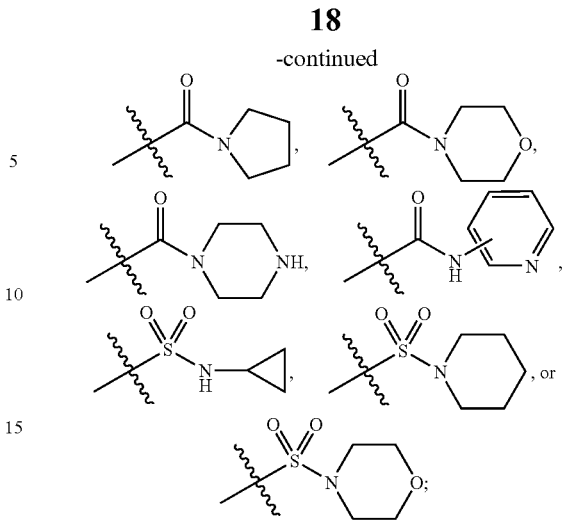

$R^{28'}$ and $R^{28''}$ are each independently hydrogen, halogen, hydroxyl, $(C_1-C_6)$alkyl, or trifluoromethyl; and $R^{35}$ is independently hydrogen, halogen, nitro, cyano, hydroxyl, $(C_1-C_6)$alkyl, cyclo$(C_3-C_{10})$alkyl, perfluoro$(C_1-C_6)$alkyl, $-(CH_2)_jCN$, $-(CH_2)_jO(C_1-C_6)$alkyl, $-(CH_2)_jC(O)(C_1-C_6)$alkyl, $-(CH_2)_jC(O)O(C_1-C_6)$alkyl, $-(CH_2)_jNH_2$, $-(CH_2)_jNH(C_1-C_6)$alkyl), $-(CH_2)_jN((C_1-C_6)$alkyl)$_2$, $-(CH_2)_jC(O)NH_2$, $-(CH_2)_jC(O)NH(C_1-C_6)$alkyl), $-(CH_2)_jC(O)N((C_1-C_6)$alkyl), $-(CH_2)_jOC(O)NH_2$, $-(CH_2)_jOC(O)NH(C_1-C_6)$alkyl), $-(CH_2)_jOC(O)N((C_1-C_6)$alkyl)$_2$, $-(CH_2)_jNHC(O)(C_1-C_6)$alkyl, $-(CH_2)_jN((C_1-C_6)$alkyl)C(O)(C_1-C_6)$alkyl, $-(CH_2)_jNHC(O)O(C_1-C_6)$alkyl, $-(CH_2)_jN((C_1-C_6)$alkyl)C(O)O(C_1-C_6)$alkyl, $-(CH_2)_jNHC(O)NH_2$, $-(CH_2)_jNHC(O)NH(C_1-C_6)$alkyl), $-(CH_2)_jNHC(O)N((C_1-C_6)$alkyl)$_2$, $-(CH_2)_jN((C_1-C_6)$alkyl)C(O)NH(C_1-C_6)$alkyl), $-(CH_2)_jN((C_1-C_6)$alkyl)C(O)N((C_1-C_6)$alkyl, $-(CH_2)_jS(O)_m(C_1-C_6)$alkyl, $-(CH_2)_jS(O)_2NH_2$, $-(CH_2)_jS(O)_2NH(C_1-C_6)$alkyl), $-(CH_2)_jS(O)_2N((C_1-C_6)$alkyl)$_2$, $-(CH_2)_jNHS(O)_2(C_1-C_6)$alkyl, $-(CH_2)_jN((C_1-C_6)$alkyl)S(O)_2(C_1-C_6)$alkyl,

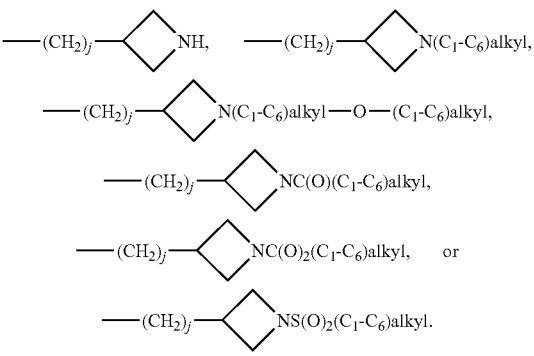

In another aspect, the disclosure provides compounds having formula I, wherein:

wherein each alkyl is optionally independently substituted with 1 to 3 $R^{22}$ groups, and wherein w is independently an integer from 0 to 3; and wherein two $R^{22}$ groups optionally form a cyclic structure with $-O(CH_2CH_2)O-$;

$R^1$ and $R^2$ are each independently hydrogen;

$R^{22}$ is independently $-H$, $-F$, Cl, Br, I, $-(C_1-C_6)$alkyl, $-(CH_2)_jCN$, $-(CH_2)_jO(C_1-C_6)$alkyl, $-(CH_2)_jOH$, $-(CH_2)_jC(O)(C_1-C_6)$alkyl, $-(CH_2)_jNH_2$, $-(CH_2)_jNH(C_1-C_6)$alkyl, $-(CH_2)_jN((C_1-C_6)$alkyl)$_2$, $-(CH_2)_jC(O)NH_2$, $-(CH_2)_jC(O)NH(C_1-C_6)$alkyl, $-C(O)N((C_1-C_6)$alkyl)$_2$, $-(CH_2)_jNHC(O)(C_1-C_6)$alkyl, $-(CH_2)_jNHSO_2(C_1-C_6)$alkyl, $-(CH_2)_jNHSO_2(C_1-C_6)$alkyl, $-(CH_2)_jSO_2CH_3$, $-(CH_2)_jSO_2NH_2$, $-(CH_2)_jSO_2NH(C_1-C_6)$-alkyl, $-(CH_2)_jSO_2N((C_1-C_6)$alkyl)$_2$, $-(CH_2)_jSO_2NH(C_1-C_6)$alkyl(OH), phenyl,

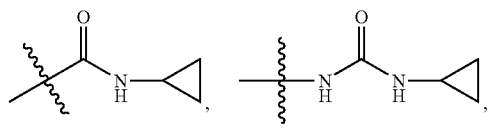

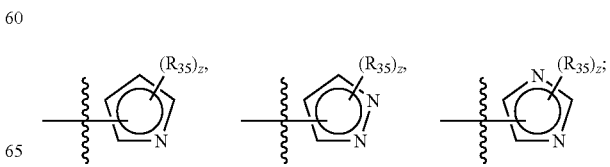

A is independently:

Q is independently $(C_1-C_6)$alkyl, perfluoroalkyl, —NH$_2$, —NH$(C_1-C_6)$alkyl, —N$[(C_1-C_6)$alkyl$]_2$,

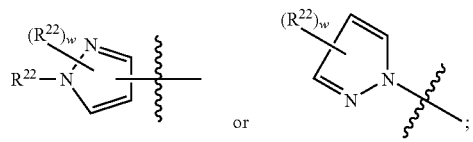

or

;

$R^{28'}$ and $R^{28''}$ are each independently hydrogen, halogen, $(C_1-C_6)$alkyl, or trifluoromethyl; and $R^{35}$ is independently hydrogen, halogen, cyano, hydroxyl, —$(C_1-C_6)$alkyl, —$(CH_2)_j$CN, —$(CH_2)_j$O$(C_1-C_6)$alkyl, —$(CH_2)_j$OH, —$(CH_2)_j$C(O)$(C_1-C_6)$alkyl, —$(CH_2)_j$C(O)OH, —$(CH_2)_j$NH$_2$, —$(CH_2)_j$NH$(C_1-C_6)$alkyl, —$(CH_2)_j$N$((C_1-C_6)$alkyl$)_2$, —$(CH_2)_j$C(O)NH$_2$, —$(CH_2)_j$C(O)NH$(C_1-C_6)$alkyl, —C(O)N$((C_1-C_6)$alkyl$)_2$, —$(CH_2)_j$NHC(O)$(C_1-C_6)$alkyl, —$(CH_2)_j$NHSO$_2(C_1-C_6)$alkyl, —$(CH_2)_j$NHSO$_2$$(C_1-C_6)$alkyl, —$(CH_2)_j$SO$_2$CH$_3$, —$(CH_2)_j$SO$_2$NH$_2$, —$(CH_2)_j$SO$_2$NH$(C_1-C_6)$-alkyl, —$(CH_2)_j$SO$_2$N$((C_1-C_6)$alkyl$)_2$, —$(CH_2)_j$SO$_2$NH$(C_1-C_6)$alkyl(OH), phenyl,

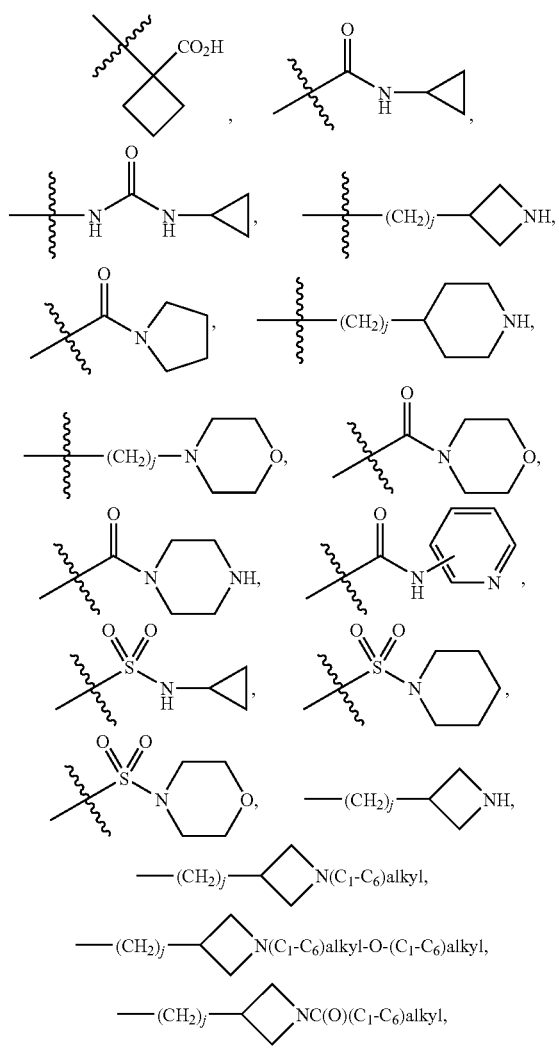

-continued

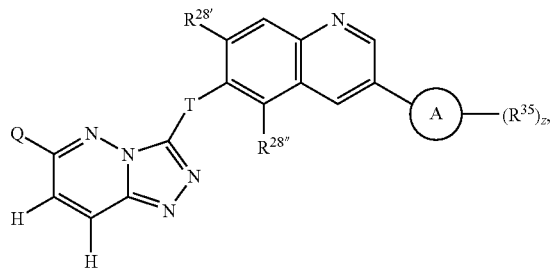

In another aspect, the disclosure provides compounds having formula II:

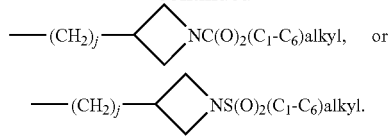

wherein:

A is independently substituted or unsubstituted phenyl, substituted or unsubstituted naphthyl, substituted or unsubstituted biphenyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted isoxazolyl, substituted or unsubstituted isothiazolyl, substituted or unsubstituted triazolyl, substituted or unsubstituted pyrazinyl, substituted or unsubstituted pyridinyl, substituted or unsubstituted pyrimidyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted[1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl;

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted —O-pyridinyl, substituted or unsubstituted isoxazolyl, substituted or unsubstituted isothiazolyl, or substituted or unsubstituted triazolyl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, (CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

$R^{28'}$ and $R^{28''}$ are each independently hydrogen, halogen, cyano, hydroxyl, substituted or unsubstituted alkyl, or perfluoroalkyl; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$NR$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, or —(CH$_2$)$_j$NR$^{33}$S(O)$_2$R$^{34}$.

In another aspect, the disclosure provides compounds having formula II, wherein:

A is independently substituted or unsubstituted phenyl, substituted or unsubstituted naphthyl, substituted or unsubstituted biphenyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted isoxazolyl, substituted or unsubstituted isothiazolyl, substituted or unsubstituted triazolyl, substituted or unsubstituted pyrazinyl, substituted or unsubstituted pyridinyl, substituted or unsubstituted pyrimidyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, or substituted or unsubstituted quinolinyl;

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, or substituted or unsubstituted —O-pyridinyl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

$R^{28'}$ and $R^{28''}$ are each independently hydrogen, halogen, hydroxyl, alkyl, or perfluoroalkyl; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$N$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, —(CH$_2$)$_j$NR$^{33}$S(O)$_2$R$^{34}$,

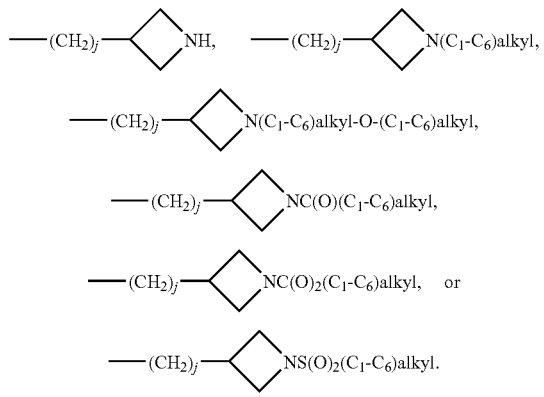

In another aspect, the disclosure provides compounds having formula II, wherein:

A is independently:

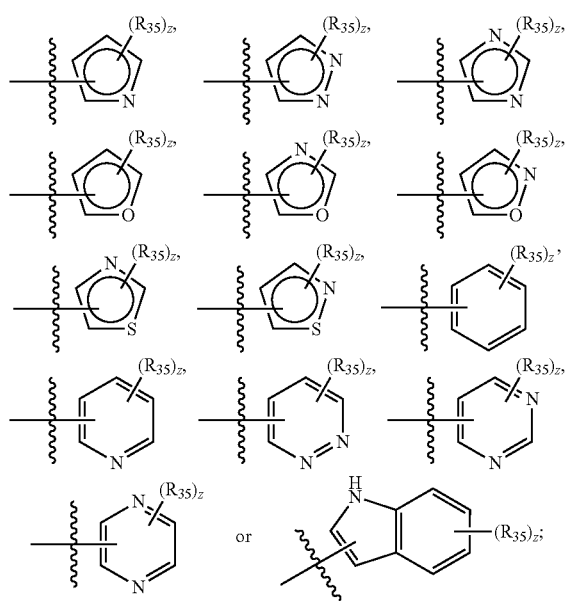

Q is independently hydrogen, chloro, substituted or unsubstituted alkyl, perfluoroalkyl, —NH$_2$, —NH(C$_1$-C$_6$)alkyl, or —N[(C$_1$-C$_6$)alkyl]$_2$,

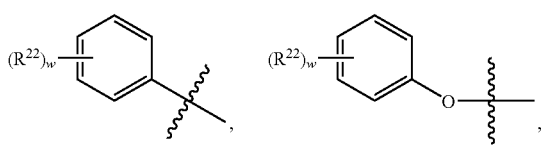

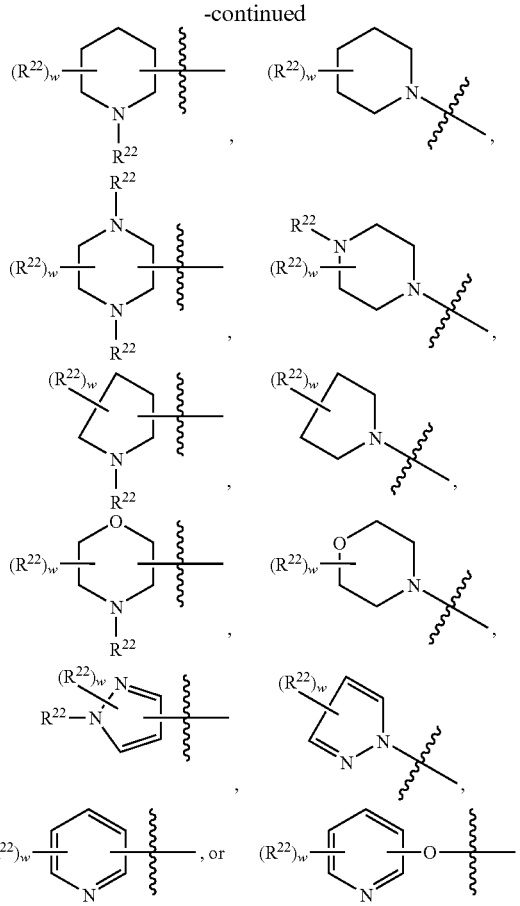

wherein each alkyl is optionally independently substituted with 1 to 3 R$^{22}$ groups, and wherein w is independently an integer from 0 to 3; and wherein two R$^{22}$ groups optionally form a cyclic structure with —O(CH$_2$CH$_2$)O—;

R$^{22}$ is independently —H, —F, Cl, Br, I, —(C$_1$-C$_6$)alkyl, —(CH$_2$)$_j$CN, —(CH$_2$)$_j$O(C$_1$-C$_6$)alkyl, —(CH$_2$)$_j$OH, —(CH$_2$)$_j$C(O)(C$_1$-C$_6$)alkyl, —(CH$_2$)$_j$NH$_2$, —(CH$_2$)$_j$NH(C$_1$-C$_6$)alkyl, —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl, —C(O)N((C$_1$-C$_6$)alkyl)$_2$, —(CH$_2$)$_j$NHC(O)(C$_1$-C$_6$)alkyl, —(CH$_2$)$_j$NHSO$_2$(C$_1$-C$_6$)alkyl, —(CH$_2$)$_j$NHSO$_2$(C$_1$-C$_6$)alkyl, —(CH$_2$)$_j$SO$_2$CH$_3$, —(CH$_2$)$_j$SO$_2$NH$_2$, —(CH$_2$)$_j$SO$_2$NH(C$_1$-C$_6$)-alkyl, —(CH$_2$)$_j$SO$_2$N((C$_1$-C$_6$)alkyl)$_2$, —(CH$_2$)$_j$SO$_2$NH(C$_1$-C$_6$)alkyl(OH), phenyl,

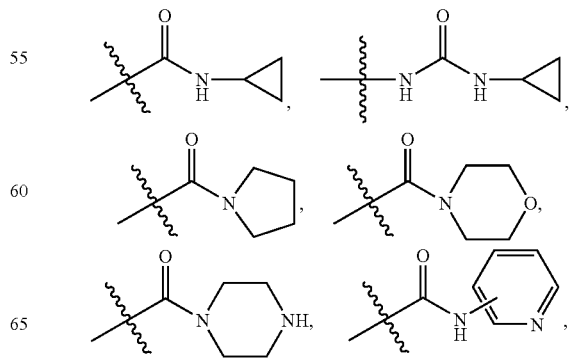

-continued

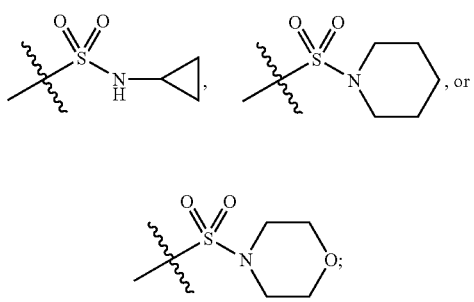

$R^{28'}$ and $R^{28''}$ are each independently hydrogen, halogen, hydroxyl, $(C_1-C_6)$alkyl, or trifluoromethyl; and $R^{35}$ is independently hydrogen, halogen, nitro, cyano, hydroxyl, $(C_1-C_6)$alkyl, cyclo$(C_3-C_{10})$alkyl, perfluoro$(C_1-C_6)$alkyl, $-(CH_2)_j$CN, $-(CH_2)_j$O$(C_1-C_6)$alkyl, $-(CH_2)_j$C(O)$(C_1-C_6)$alkyl, $-(CH_2)_j$C(O)O$(C_1-C_6)$alkyl, $-(CH_2)_j$NH$_2$, $-(CH_2)_j$NH$(C_1-C_6)$alkyl), $-(CH_2)_j$N$((C_1-C_6)$alkyl$)_2$, $-(CH_2)_j$C(O)NH$_2$, $-(CH_2)_j$C(O)NH$(C_1-C_6)$alkyl), $-(CH_2)_j$C(O)N$((C_1-C_6)$alkyl$)_2$, $-(CH_2)_j$OC(O)NH$_2$, $-(CH_2)_j$OC(O)NH$(C_1-C_6)$alkyl), $-(CH_2)_j$OC(O)N$((C_1-C_6)$alkyl$)_2$, $-(CH_2)_j$NHC(O)$(C_1-C_6)$alkyl, $-(CH_2)_j$N$((C_1-C_6)$alkyl)C(O)$(C_1-C_6)$alkyl, $-(CH_2)_j$NHC(O)O$(C_1-C_6)$alkyl, $-(CH_2)_j$N$((C_1-C_6)$alkyl)C(O)O$(C_1-C_6)$alkyl, $-(CH_2)_j$NHC(O)NH$_2$, $-(CH_2)_j$NHC(O)NH$(C_1-C_6)$alkyl), $-(CH_2)_j$NHC(O)N$((C_1-C_6)$alkyl$)_2$, $-(CH_2)_j$N$((C_1-C_6)$alkyl)C(O)NH$(C_1-C_6)$alkyl), $-(CH_2)_j$N$((C_1-C_6)$alkyl)C(O)N$((C_1-C_6)$alkyl$)_2$, $-(CH_2)_j$S(O)$_m$$(C_1-C_6)$alkyl, $-(CH_2)_j$S(O)$_2$NH$_2$, $-(CH_2)_j$S(O)$_2$NH$(C_1-C_6)$alkyl), $-(CH_2)_j$S(O)$_2$N$((C_1-C_6)$alkyl$)_2$, $-(CH_2)_j$NHS(O)$_2$$(C_1-C_6)$alkyl, $-(CH_2)_j$N$((C_1-C_6)$alkyl)S(O)$_2$$(C_1-C_6)$alkyl,

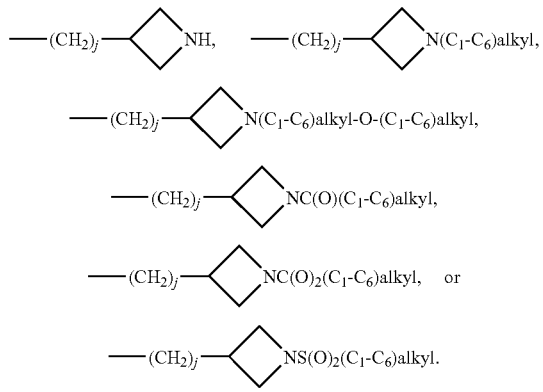

In another aspect, the disclosure provides compounds having formula II, wherein:

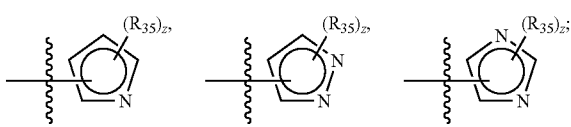

A is independently:

Q is independently $(C_1-C_6)$alkyl, perfluoroalkyl, $-NH_2$, $-NH(C_1-C_6)$alkyl, $-N[(C_1-C_6)$alkyl]$_2$,

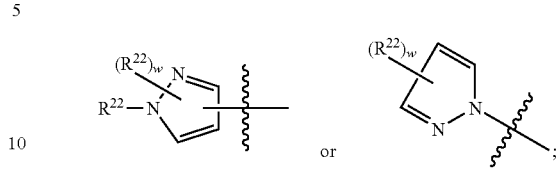

$R^{28'}$ and $R^{28''}$ are each independently hydrogen, halogen, $(C_1-C_6)$alkyl, or trifluoromethyl; and $R^{35}$ is independently hydrogen, halogen, cyano, hydroxyl, $-(C_1-C_6)$alkyl, $-(CH_2)_j$CN, $-(CH_2)_j$O$(C_1-C_6)$alkyl, $-(CH_2)_j$OH, $-(CH_2)_j$C(O)$(C_1-C_6)$alkyl, $-(CH_2)_j$C(O)OH, $-(CH_2)_j$NH$_2$, $-(CH_2)_j$NH$(C_1-C_6)$alkyl, $-(CH_2)_j$N$((C_1-C_6)$alkyl$)_2$, $-(CH_2)_j$C(O)NH$_2$, $-(CH_2)_j$C(O)NH$(C_1-C_6)$alkyl, $-C(O)N((C_1-C_6)$alkyl$)_2$, $-(CH_2)_j$NHC(O)$(C_1-C_6)$alkyl, $-(CH_2)_j$NHSO$_2$$(C_1-C_6)$alkyl, $-(CH_2)_j$NHSO$_2$$(C_1-C_6)$alkyl, $-(CH_2)_j$SO$_2$CH$_3$, $-(CH_2)_j$SO$_2$NH$_2$, $-(CH_2)_j$SO$_2$NH$(C_1-C_6)$-alkyl, $-(CH_2)_j$SO$_2$N$((C_1-C_6)$alkyl$)_2$, $-(CH_2)_j$SO$_2$NH$(C_1-C_6)$alkyl(OH), phenyl,

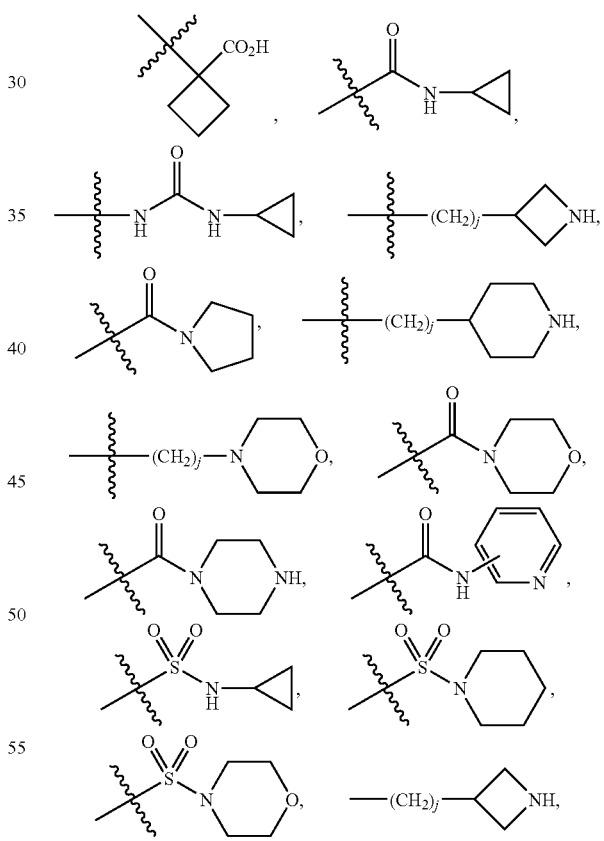

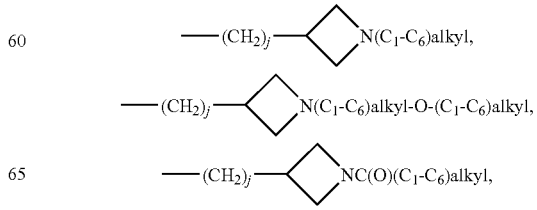

-continued

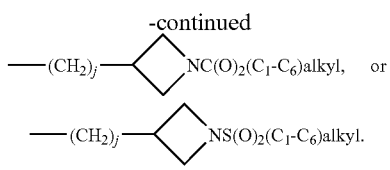

In another aspect, the disclosure provides compounds having formula III:

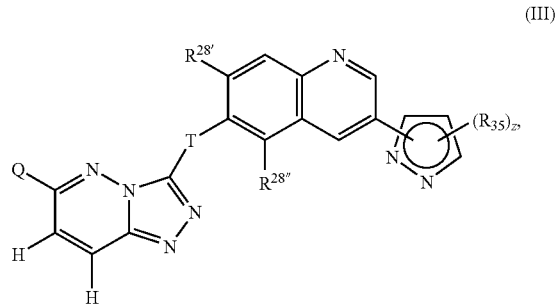

(III)

wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted —O-pyridinyl, substituted or unsubstituted isoxazolyl, substituted or unsubstituted isothiazolyl, or substituted or unsubstituted triazolyl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —$(CH_2)_jCN$, —$(CH_2)_jOR^{23}$, —$(CH_2)_jC(O)R^{23}$, —$(CH_2)_jC(O)OR^{23}$, —$(CH_2)_jNR^{24}R^{25}$, —$(CH_2)_jC(O)NR^{24}R^{25}$, —$(CH_2)_jOC(O)NR^{24}R^{25}$, —$(CH_2)_jNR^{26}C(O)R^{23}$, —$(CH_2)_jNR^{26}C(O)OR^{23}$, —$(CH_2)_jNR^{26}C(O)NR^{24}R^{25}$, —$(CH_2)_jS(O)_mR^{27}$, —$(CH_2)_jS(O)_2NR^{24}R^{25}$, or —$(CH_2)_jNR^{26}S(O)_2R^{27}$;

$R^{28'}$ and $R^{28''}$ are each independently hydrogen, halogen, hydroxyl, alkyl, or perfluoroalkyl; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —$(CH_2)_jCN$, —$(CH_2)_jOR^{30}$, —$(CH_2)_jC(O)R^{30}$, —$(CH_2)_jC(O)OR^{30}$, —$(CH_2)_jNR^{31}R^{32}$, —$(CH_2)_jC(O)NR^{31}R^{32}$, —$(CH_2)_jOC(O)NR^{31}R^{32}$, —$(CH_2)_jNR^{33}C(O)R^{30}$, —$(CH_2)_jNR^{33}C(O)OR^{30}$, —$(CH_2)_jNR^{33}C(O)NR^{31}R^{32}$, —$(CH_2)_jS(O)_mR^{34}$, —$(CH_2)_jS(O)_2NR^{31}R^{32}$, or —$(CH_2)_jNR^{33}S(O)_2R^{34}$.

In another aspect, the disclosure provides compounds having formula III, wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, or substituted or unsubstituted —O-pyridinyl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

$R^{28'}$ and $R^{28''}$ are each independently hydrogen, halogen, hydroxyl, alkyl, or perfluoroalkyl; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$N$^{33}$C(O)NR$^{31}$R$^{32}$, —(CH$_2$)$_j$S(O)R$^{34}$, —(CH$_2$)$_j$S(O)$_2$NR$^{31}$R$^{32}$, —(CH$_2$)$_j$NR$^{33}$S(O)$_2$R$^{34}$,

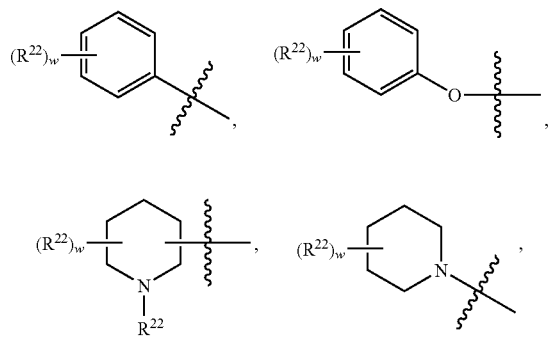

In another aspect, the disclosure provides compounds having formula III, wherein:

Q is independently hydrogen, chloro, substituted or unsubstituted alkyl, perfluoroalkyl, —NH$_2$, —NH(C$_1$-C$_6$)alkyl, or —N[(C$_1$-C$_6$)alkyl]$_2$,

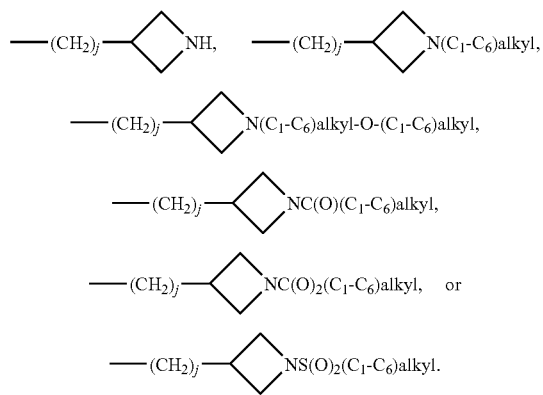

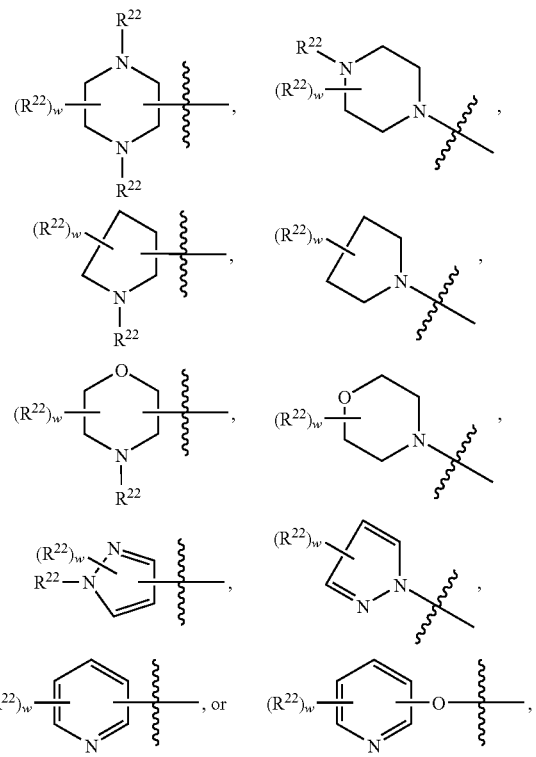

wherein each alkyl is optionally independently substituted with 1 to 3 R$^{22}$ groups, and wherein w is independently an integer from 0 to 3; and wherein two R$^{22}$ groups optionally form a cyclic structure with —O(CH$_2$CH$_2$)O—;

R$^{22}$ is independently —H, —F, Cl, Br, I, —(C$_1$-C$_6$)alkyl, —(CH$_2$)$_j$CN, —(CH$_2$)$_j$O(C$_1$-C$_6$)alkyl, —(CH$_2$)$_j$OH, —(CH$_2$)$_j$C(O)(C$_1$-C$_6$)alkyl, —(CH$_2$)$_j$NH$_2$, —(CH$_2$)$_j$NH(C$_1$-C$_6$)alkyl, —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl, —C(O)N((C$_1$-C$_6$)alkyl)$_2$, —(CH$_2$)$_j$NHC(O)(C$_1$-C$_6$)alkyl, —(CH$_2$)$_j$NHSO$_2$(C$_1$-C$_6$)alkyl, —(CH$_2$)$_j$NHSO$_2$(C$_1$-C$_6$)alkyl, —(CH$_2$)$_j$SO$_2$CH$_3$, —(CH$_2$)$_j$SO$_2$NH$_2$, —(CH$_2$)$_j$SO$_2$NH(C$_1$-C$_6$)-alkyl, —(CH$_2$)$_j$SO$_2$N((C$_1$-C$_6$)alkyl)$_2$, —(CH$_2$)$_j$SO$_2$NH(C$_1$-C$_6$)alkyl(OH), phenyl,

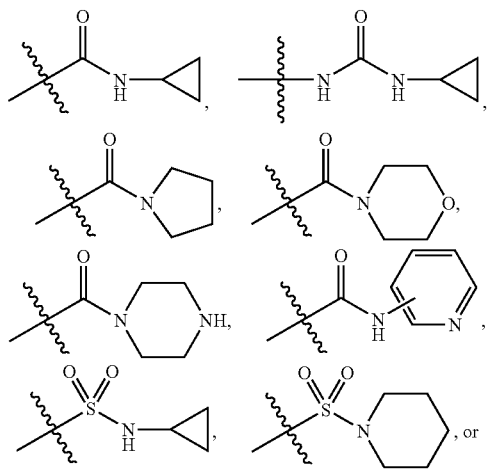

-continued

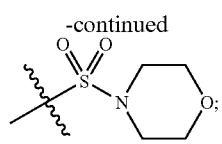

R$^{28'}$ and R$^{28''}$ are each independently hydrogen, halogen, hydroxyl, (C$_1$-C$_6$)alkyl, or trifluoromethyl; and R$^{35}$ is independently hydrogen, halogen, nitro, cyano, hydroxyl, (C$_1$-C$_6$)alkyl, cyclo(C$_3$-C$_{10}$)alkyl, perfluoro(C$_1$-C$_6$)alkyl, —(CH$_2$)$_j$CN, —(CH$_2$)$_j$O(C$_1$-C$_6$)alkyl, —(CH$_2$)$_j$C(O)(C$_1$-C$_6$)alkyl, —(CH$_2$)$_j$C(O)O(C$_1$-C$_6$)alkyl, —(CH$_2$)$_j$NH$_2$, —(CH$_2$)$_j$NH(C$_1$-C$_6$)alkyl), —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl), —(CH$_2$)$_j$C(O)N((C$_1$-C$_6$)alkyl)$_2$, —(CH$_2$)$_j$OC(O)NH$_2$, —(CH$_2$)$_j$OC(O)NH(C$_1$-C$_6$)alkyl), —(CH$_2$)$_j$OC(O)N((C$_1$-C$_6$)alkyl)$_2$, —(CH$_2$)$_j$NHC(O)(C$_1$-C$_6$)alkyl, —(CH$_2$)$_j$N((C$_1$-C$_6$)alkyl)C(O)(C$_1$-C$_6$)alkyl, —(CH$_2$)$_j$NHC(O)O(C$_1$-C$_6$)alkyl, —(CH$_2$)$_j$N((C$_1$-C$_6$)alkyl)C(O)O(C$_1$-C$_6$)alkyl, —(CH$_2$)$_j$NHC(O)NH$_2$, —(CH$_2$)$_j$NHC(O)NH(C$_1$-C$_6$)alkyl), —(CH$_2$)$_j$NHC(O)N((C$_1$-C$_6$)alkyl)$_2$, —(CH$_2$)$_j$N((C$_1$-C$_6$)alkyl)C(O)NH(C$_1$-C$_6$)alkyl), —(CH$_2$)$_j$N((C$_1$-C$_6$)alkyl)C(O)N((C$_1$-C$_6$)alkyl)$_2$, —(CH$_2$)$_j$S(O)$_m$(C$_1$-C$_6$)alkyl, —(CH$_2$)$_j$S(O)$_2$NH$_2$, —(CH$_2$)$_j$S(O)$_2$NH(C$_1$-C$_6$)alkyl), —(CH$_2$)$_j$S(O)$_2$N((C$_1$-C$_6$)alkyl)$_2$, —(CH$_2$)$_j$NHS(O)$_2$(C$_1$-C$_6$)alkyl, —(CH$_2$)$_j$N((C$_1$-C$_6$)alkyl)S(O)$_2$(C$_1$-C$_6$)alkyl,

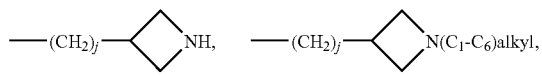

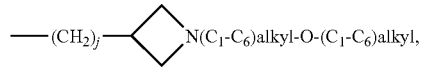

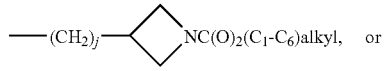

In another aspect, the disclosure provides compounds having formula III, wherein:

Q is independently (C$_1$-C$_6$)alkyl, perfluoroalkyl, —NH$_2$, —NH(C$_1$-C$_6$)alkyl, —N[(C$_1$-C$_6$)alkyl]$_2$,

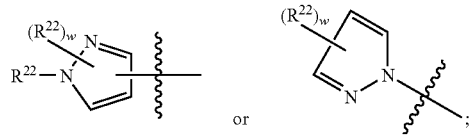

R$^{28'}$ and R$^{28''}$ are each independently hydrogen, halogen, (C$_1$-C$_6$)alkyl, or trifluoromethyl; and R$^{35}$ is independently hydrogen, halogen, cyano, hydroxyl, —(C$_1$-C$_6$)alkyl, —(CH$_2$)$_j$CN, —(CH$_2$)$_j$O(C$_1$-C$_6$)alkyl, —(CH$_2$)$_j$OH, —(CH$_2$)$_j$C(O)(C$_1$-C$_6$)alkyl, —(CH$_2$)$_j$C(O) OH, —(CH$_2$)$_j$NH$_2$, —(CH$_2$)$_j$NH(C$_1$-C$_6$)alkyl, —(CH$_2$)$_j$N ((C$_1$-C$_6$)alkyl)$_2$, —(CH$_2$)$_j$C(O)NH$_2$, —(CH$_2$)$_j$C(O)NH(C$_1$-C$_6$)alkyl, —C(O)N((C$_1$-C$_6$)alkyl)$_2$, —(CH$_2$)$_j$NHC(O)(C$_1$-C$_6$)alkyl, —(CH$_2$)$_j$NHSO$_2$(C$_1$-C$_6$)alkyl, —(CH$_2$)$_j$NHSO$_2$ (C$_1$-C$_6$)alkyl, —(CH$_2$)$_j$SO$_2$CH$_3$, —(CH$_2$)$_j$SO$_2$NH$_2$, —(CH$_2$)$_j$SO$_2$NH(C$_1$-C$_6$)-alkyl, —(CH$_2$)$_j$SO$_2$N((C$_1$-C$_6$) alkyl)$_2$, —(CH$_2$)$_j$SO$_2$NH(C$_1$-C$_6$)alkyl(OH), phenyl,

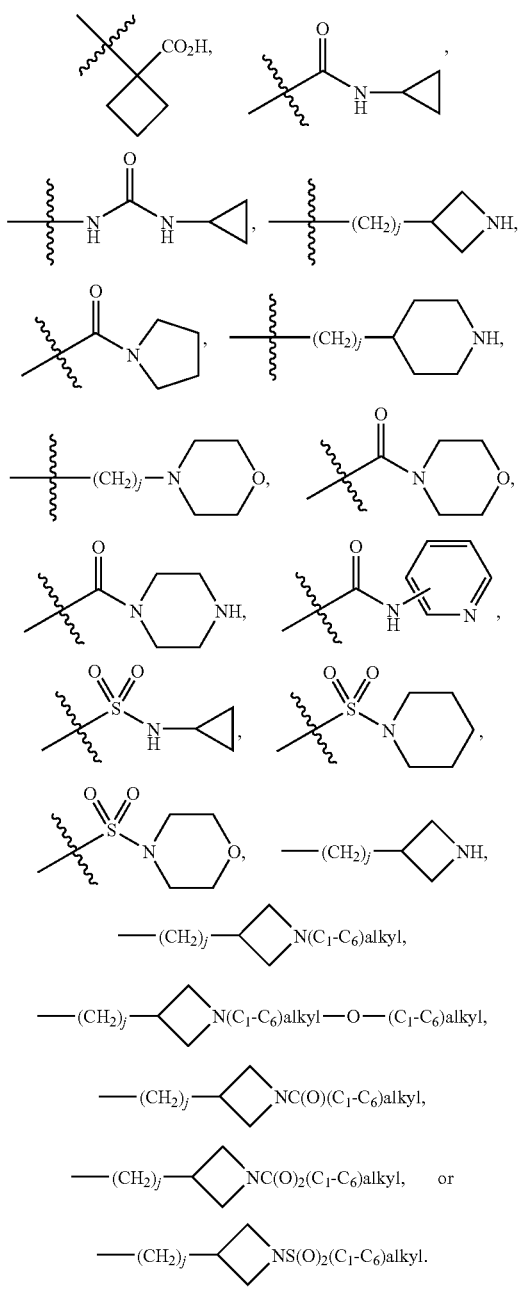

In another aspect, the disclosure provides compounds having formula III, wherein:

Q is independently (C$_1$-C$_6$)alkyl;

T is CH$_2$;

R$^{28}$ and R$^{28'}$ are each independently hydrogen; and

R$^{35}$ is —(C$_1$-C$_6$)alkyl.

In another aspect, the disclosure provides compounds having formula:
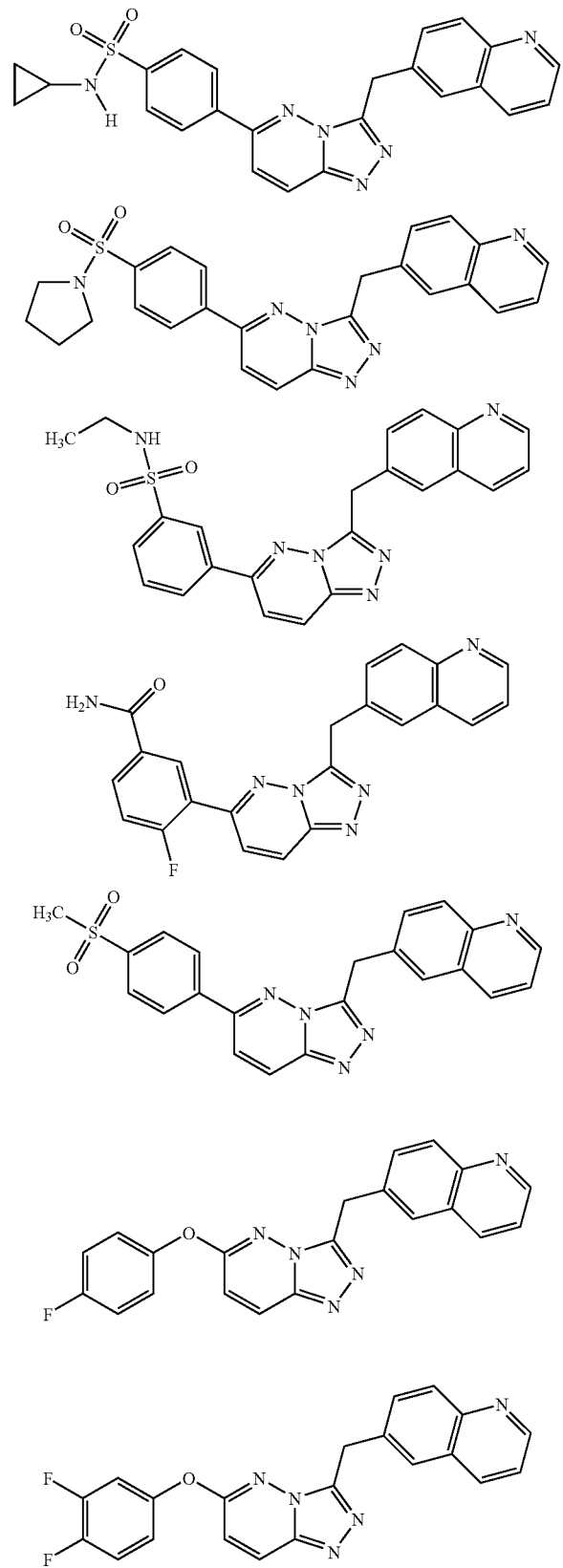
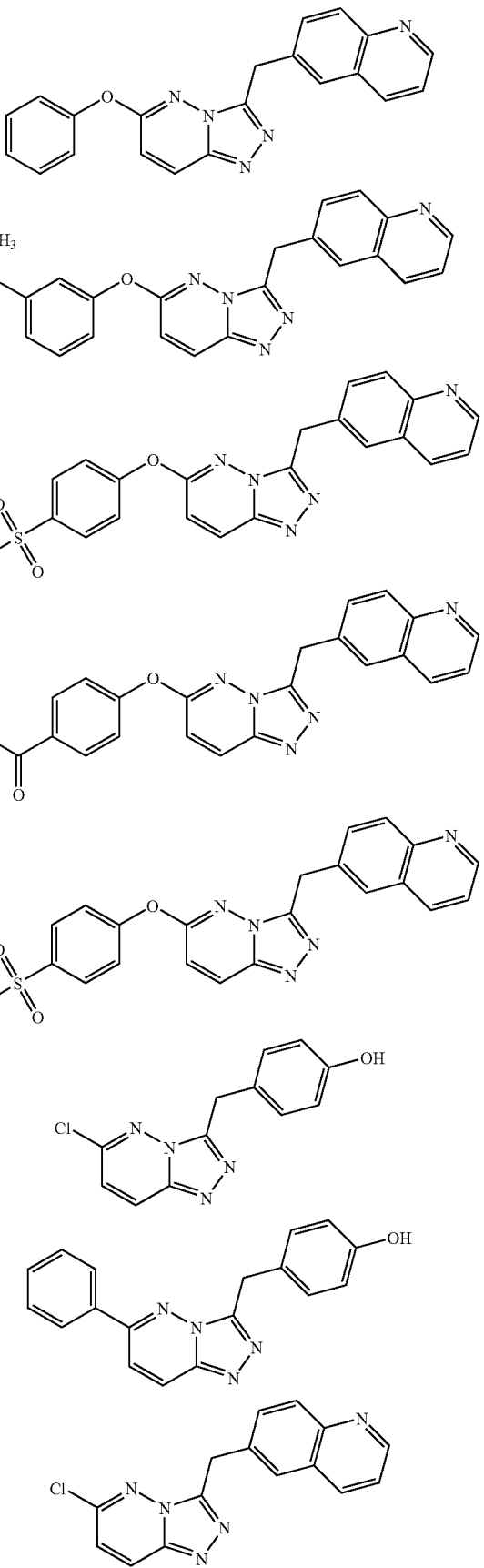

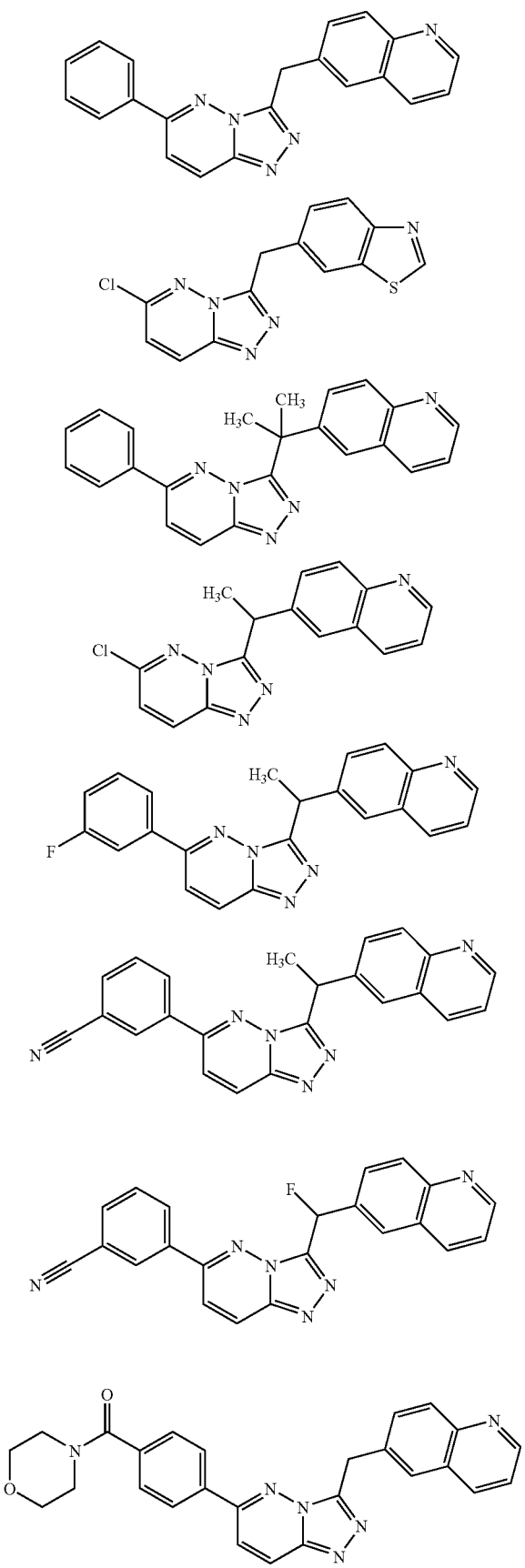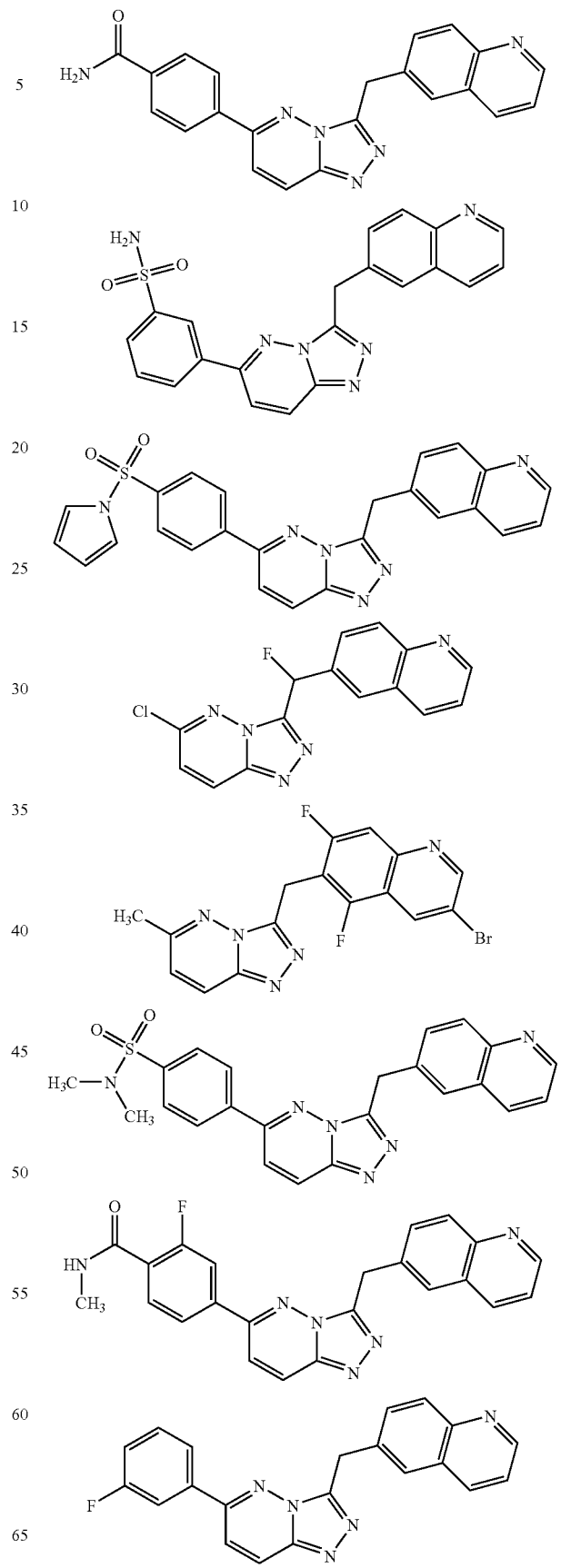

37
-continued
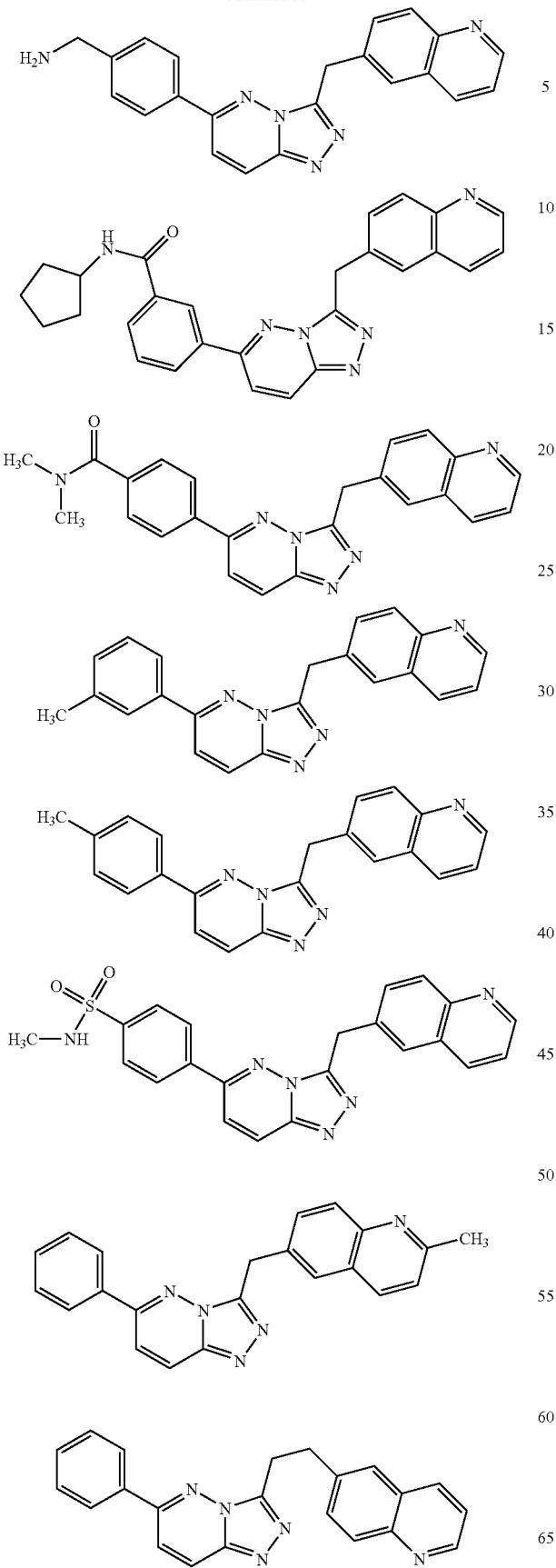
38
-continued
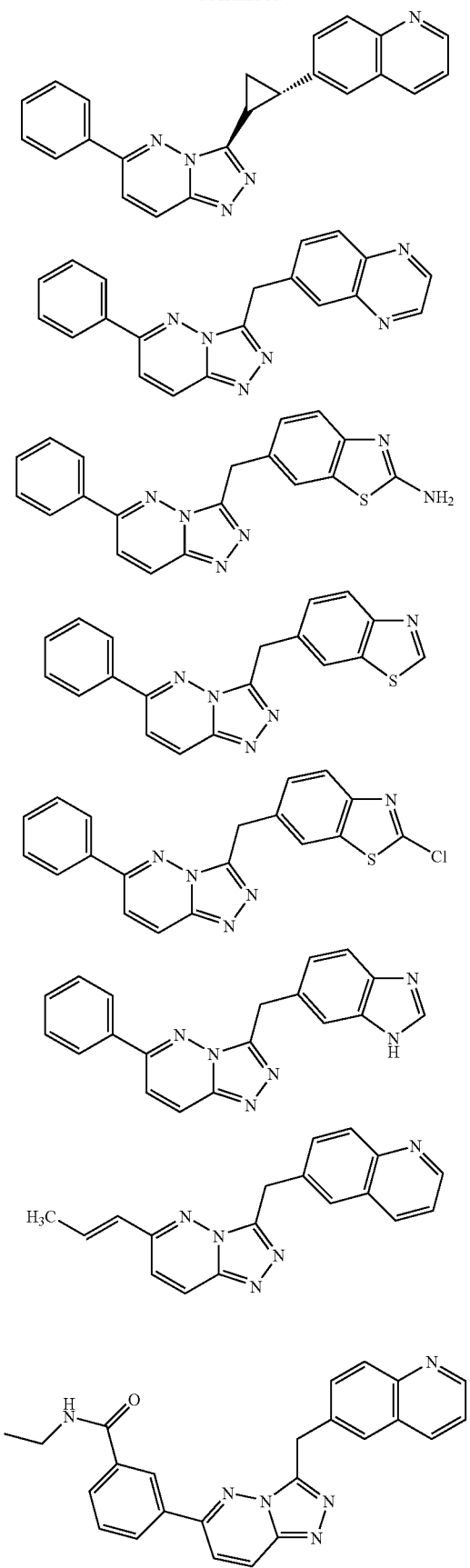

-continued
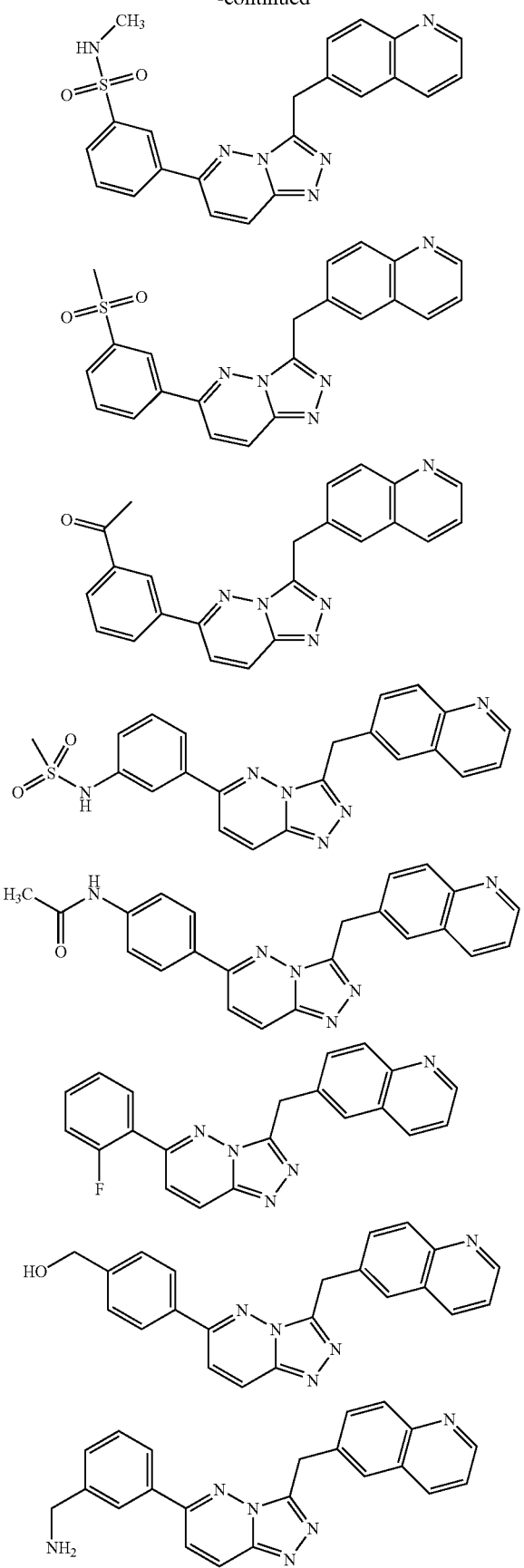
-continued
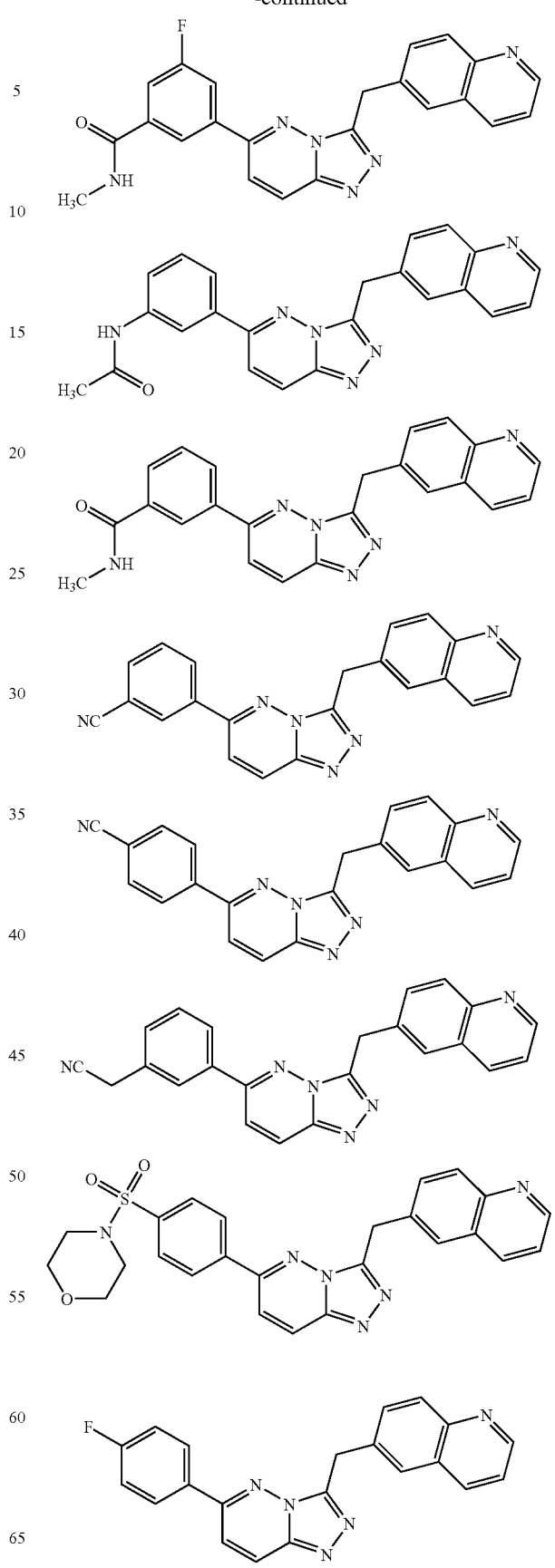

41
-continued
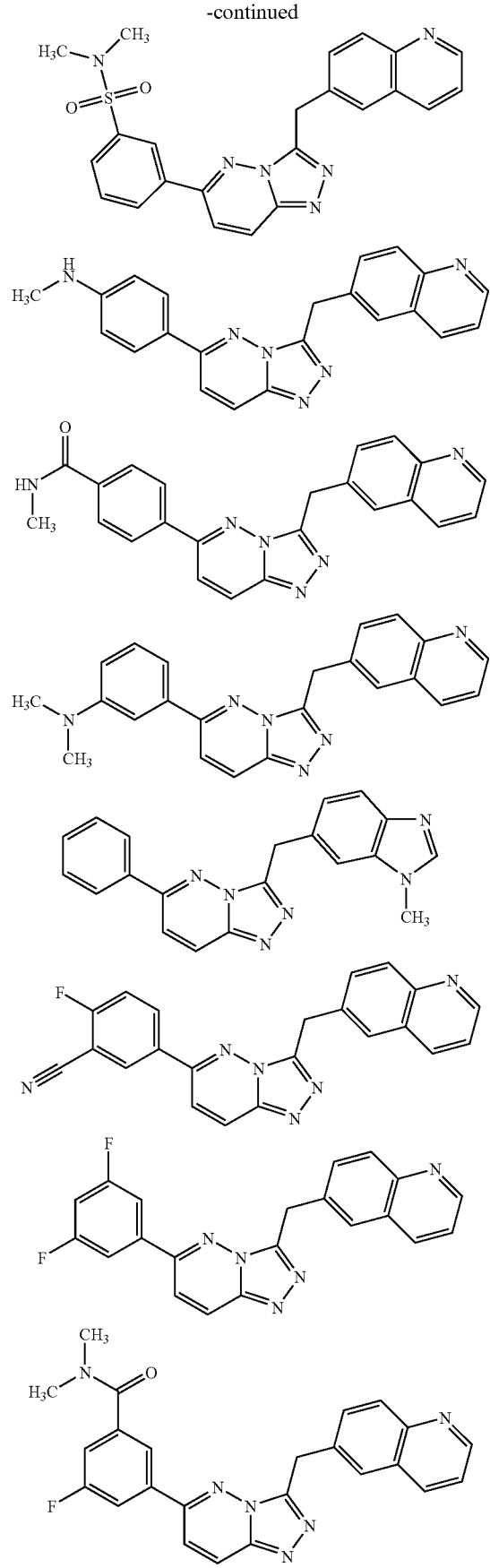
42
-continued
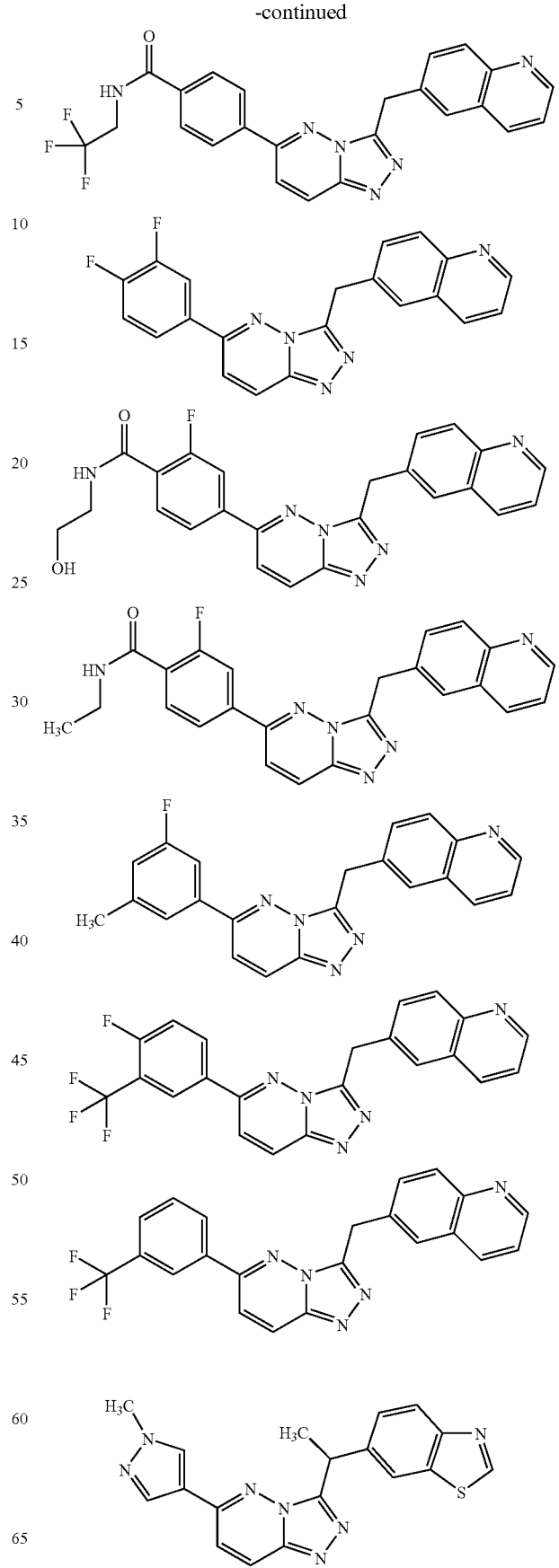

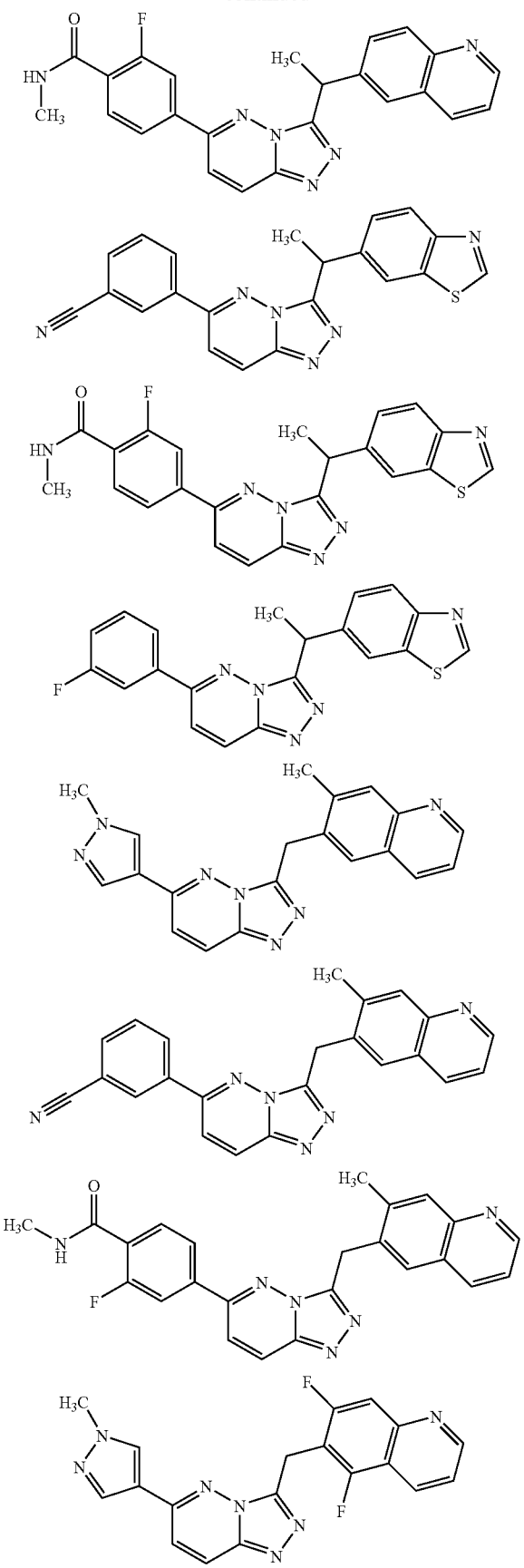
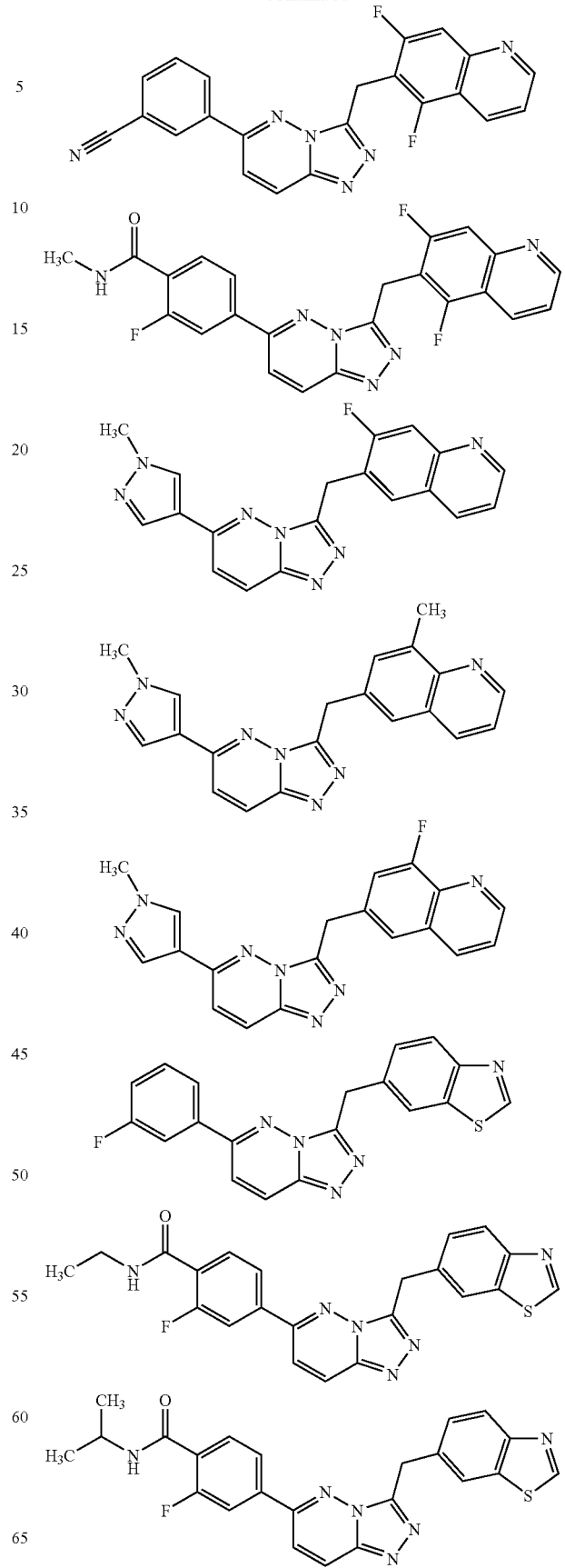

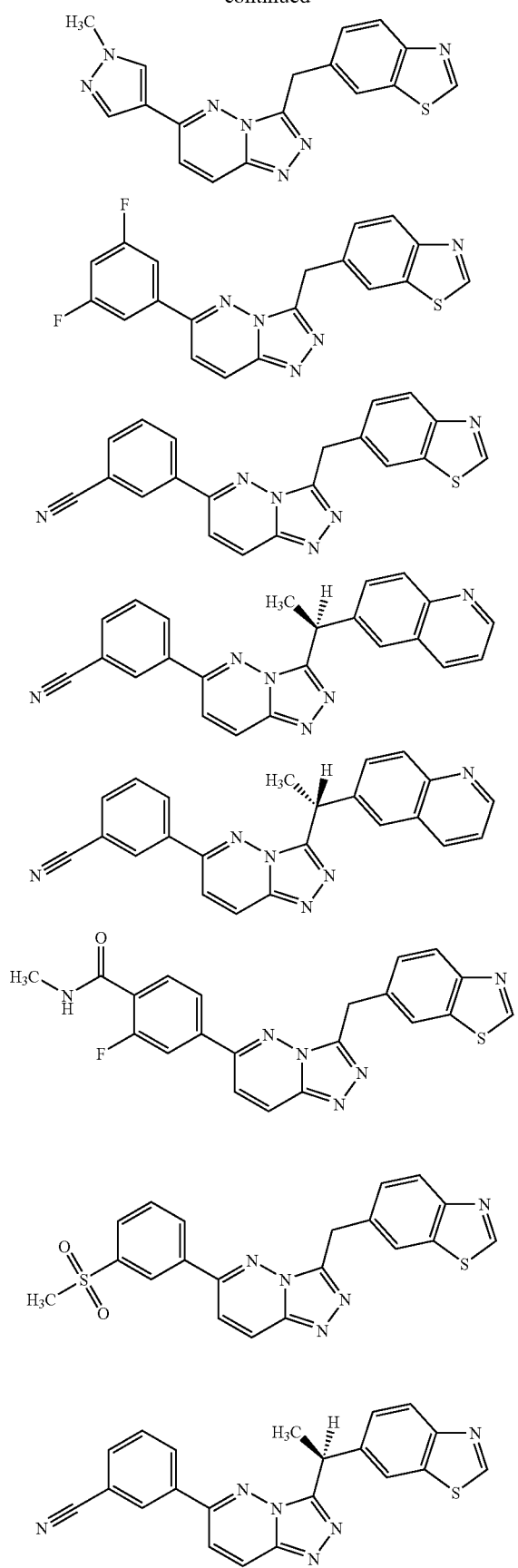
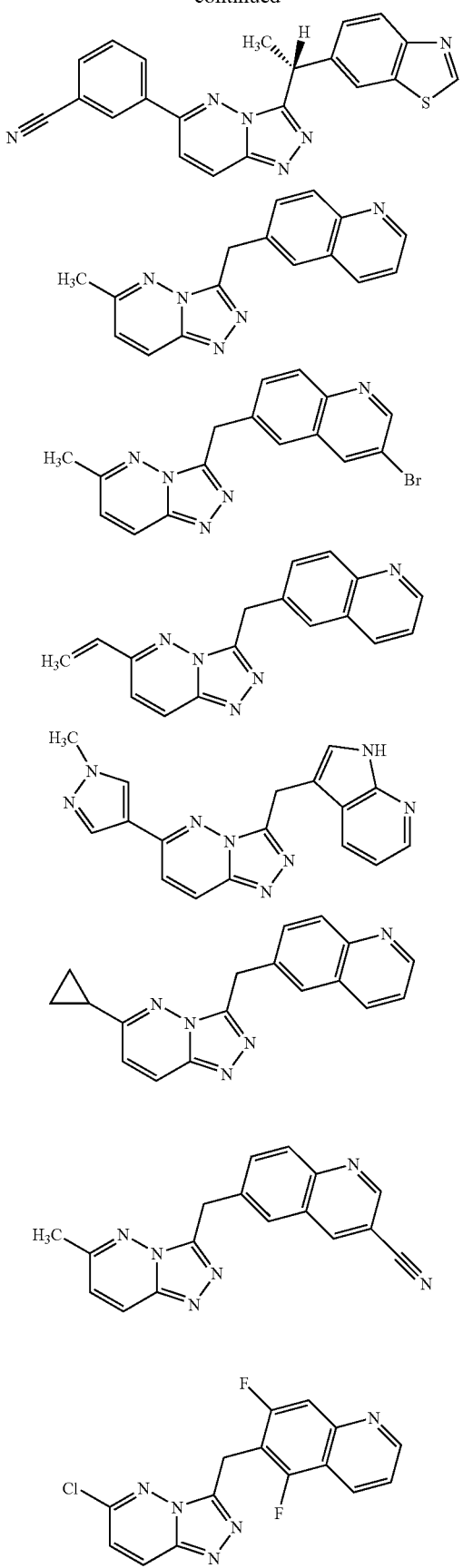

-continued
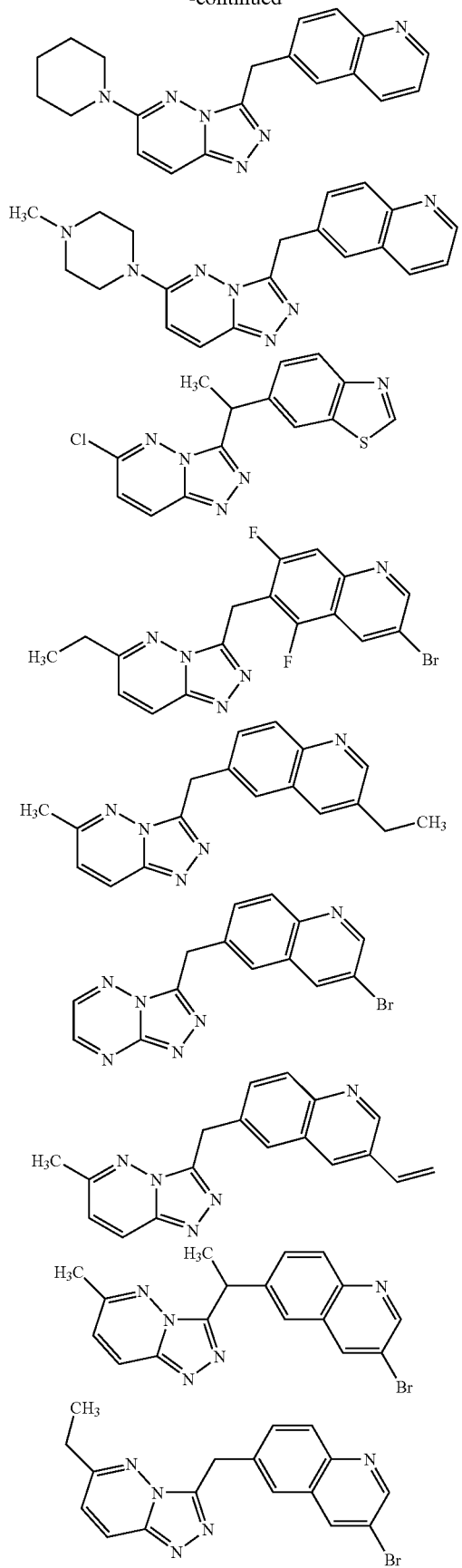
-continued
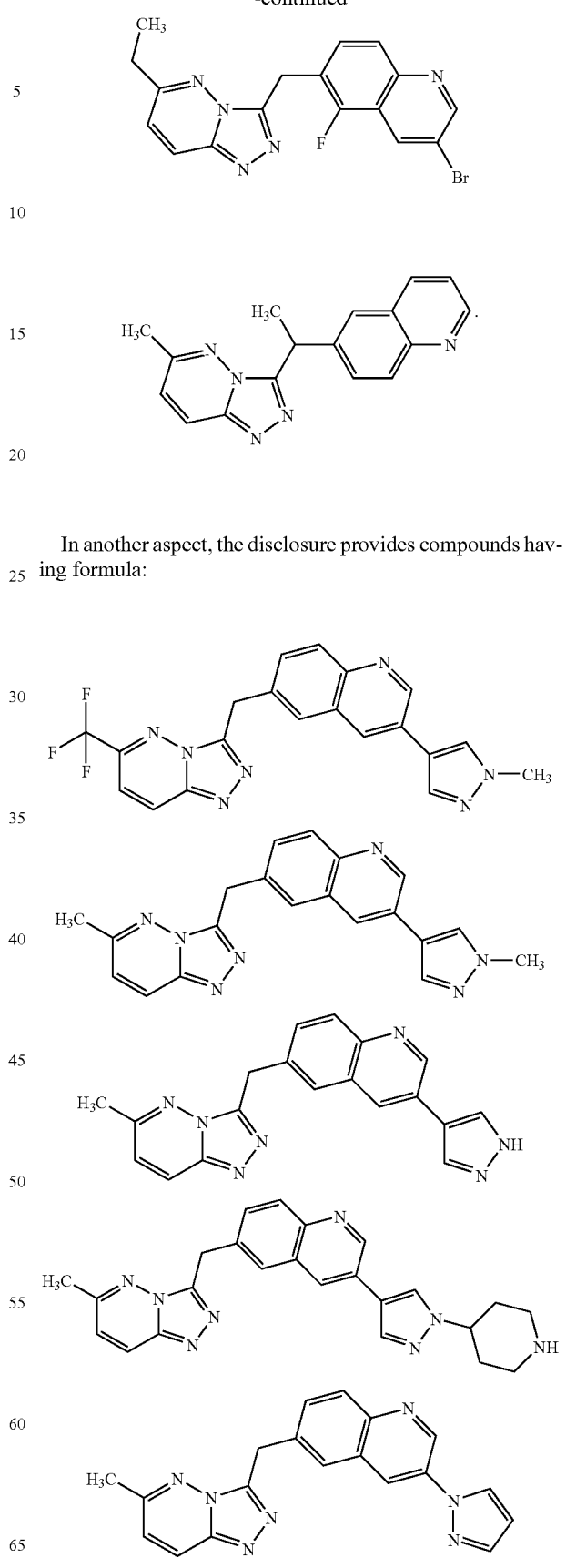
In another aspect, the disclosure provides compounds having formula:

49
-continued
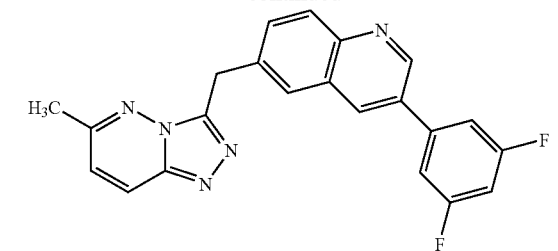
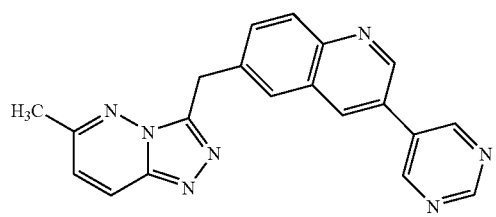
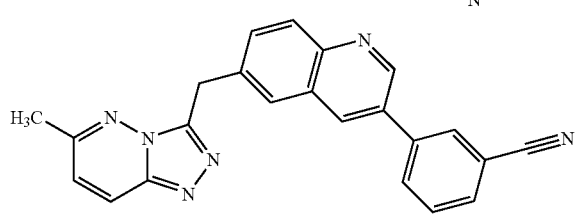
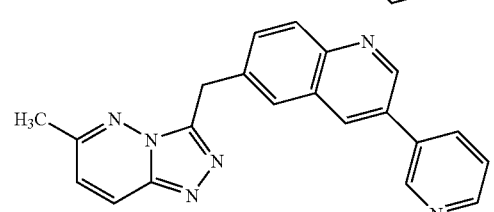
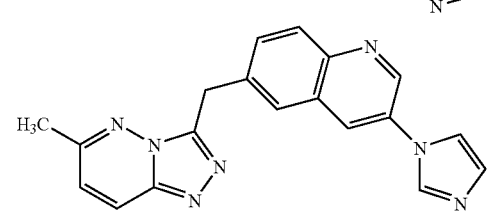
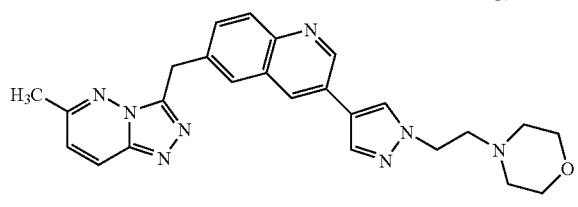
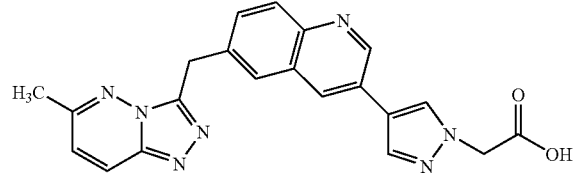
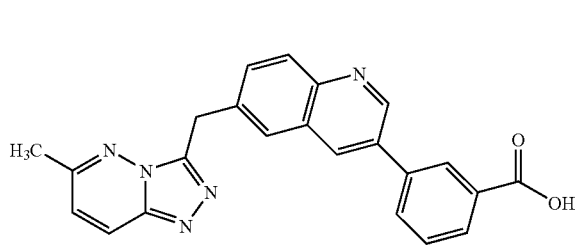
50
-continued
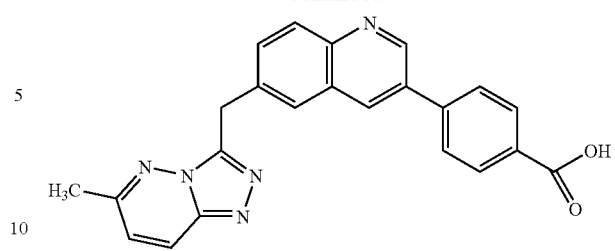
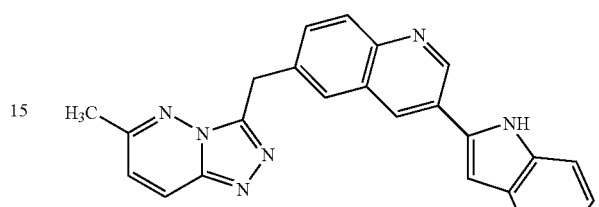
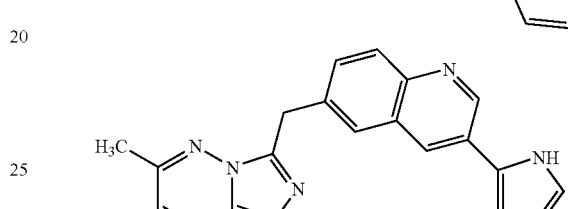
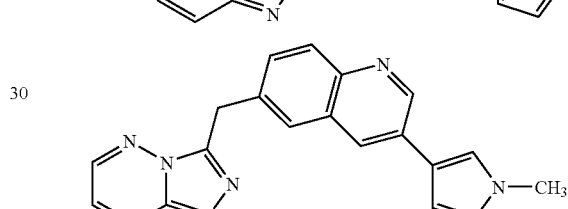
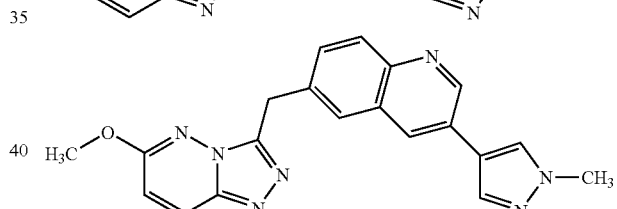
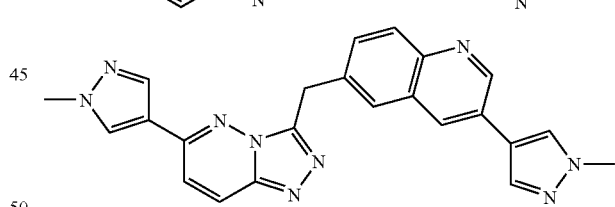
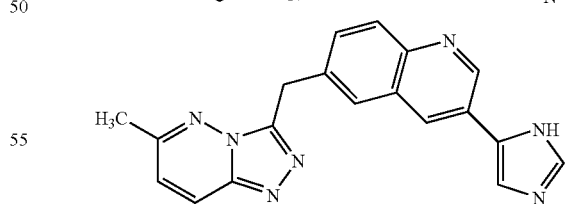
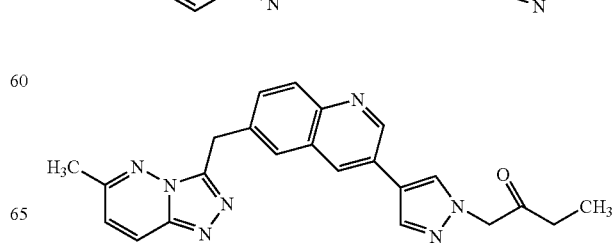

51 -continued
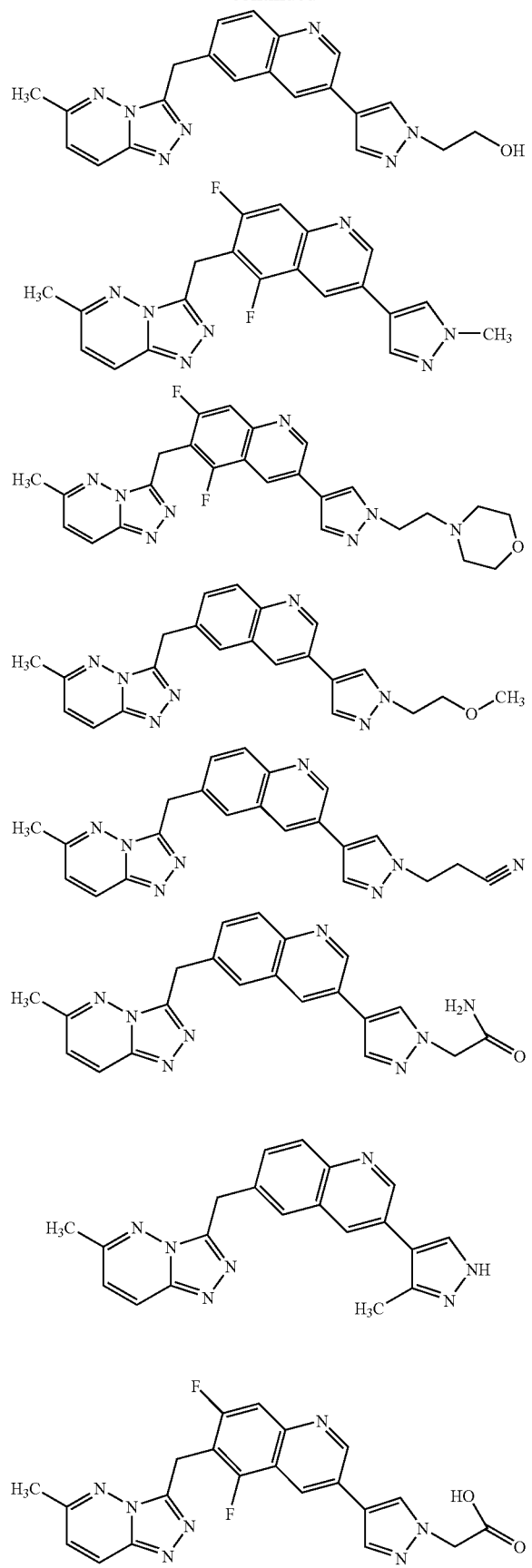
52 -continued
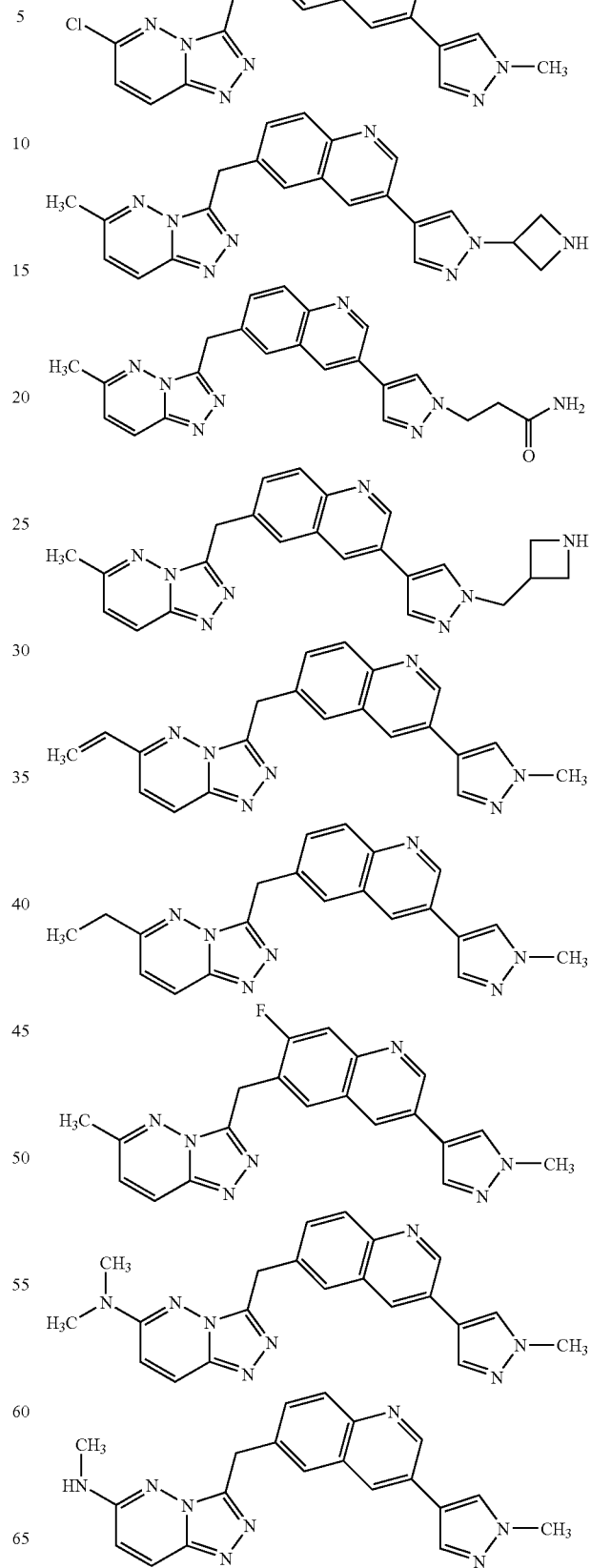

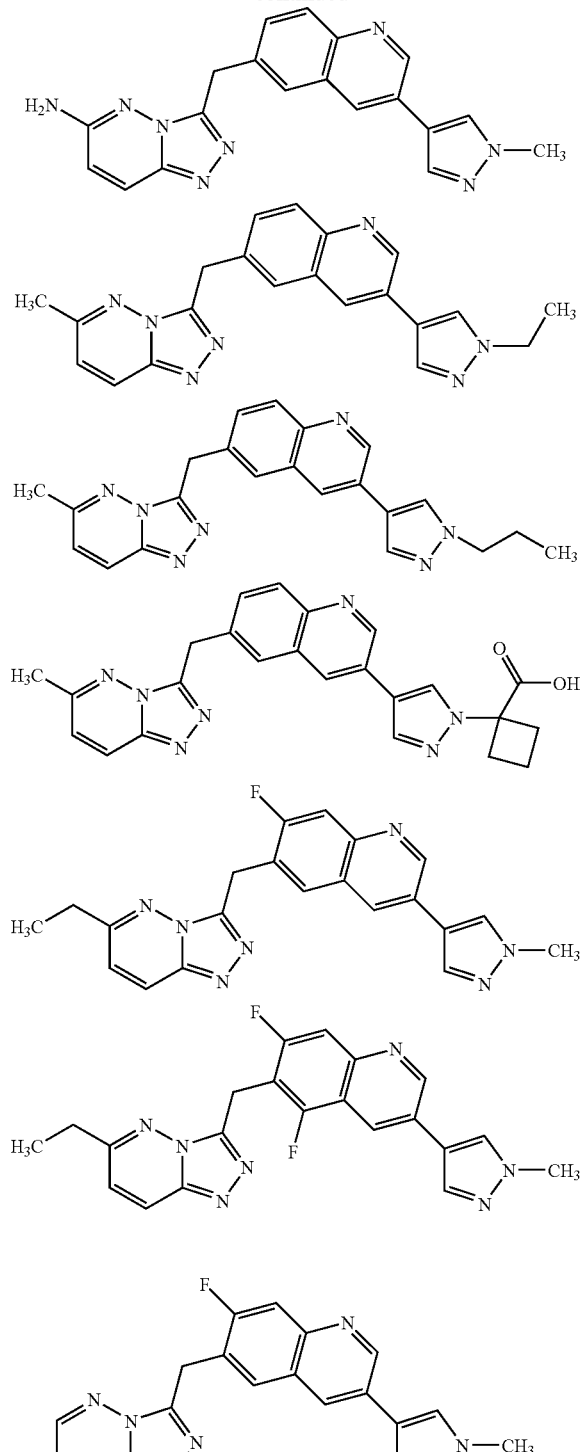
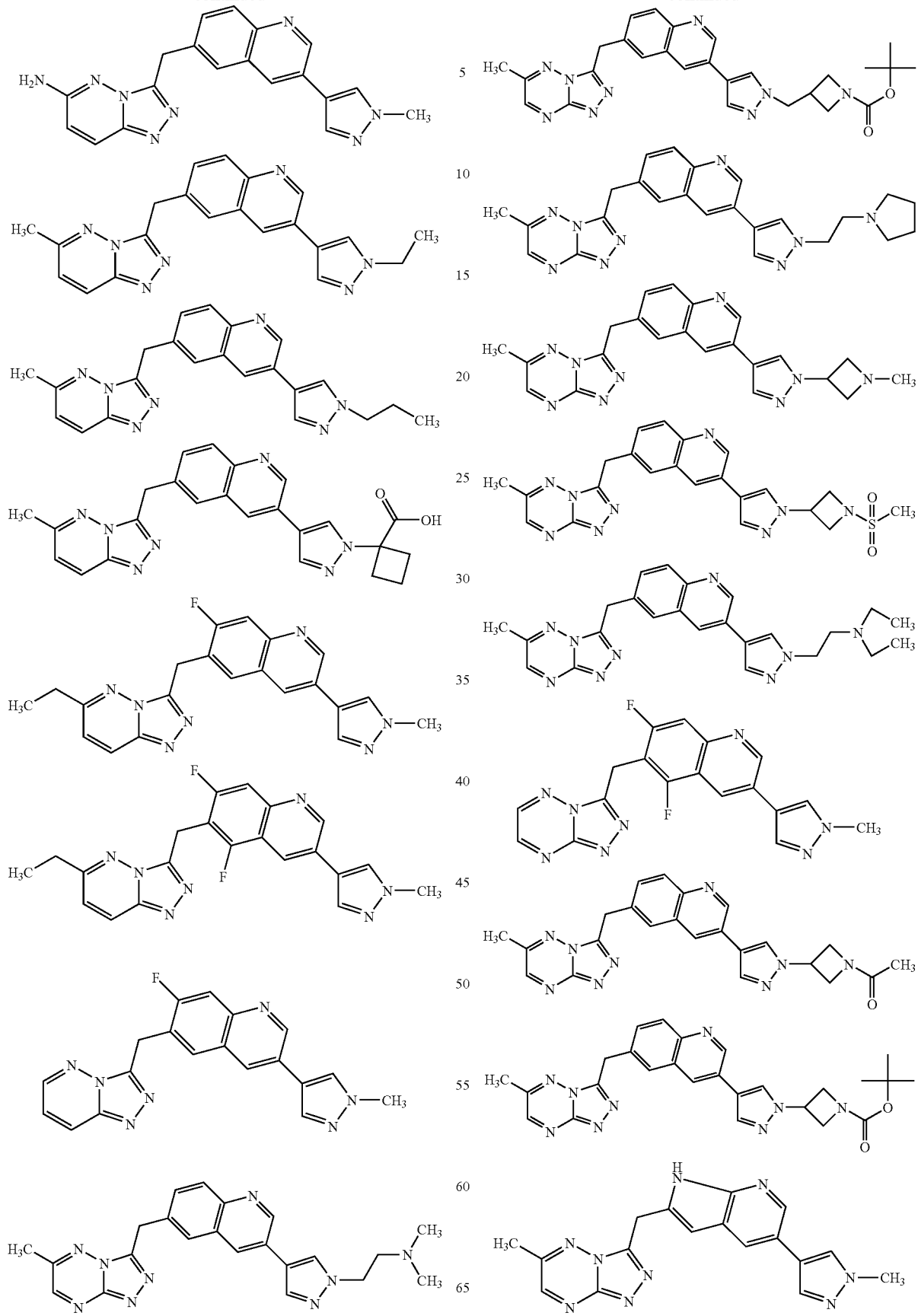

55
-continued
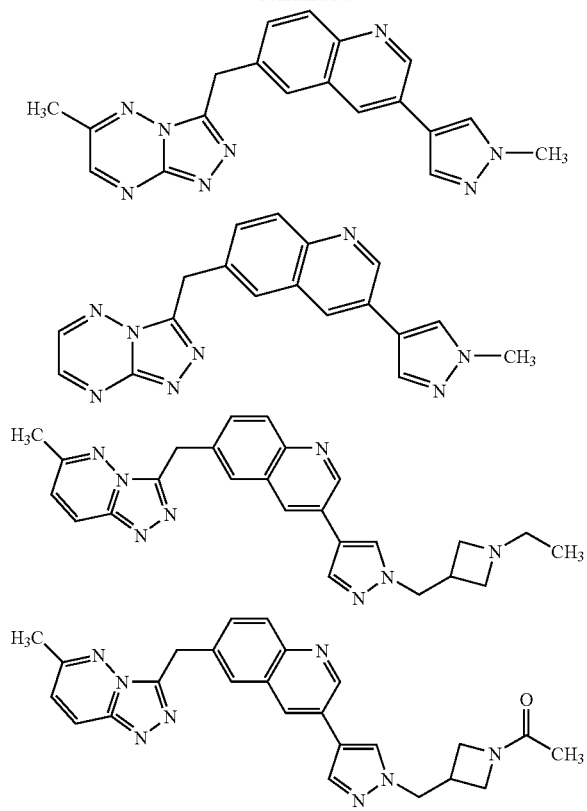
56
-continued
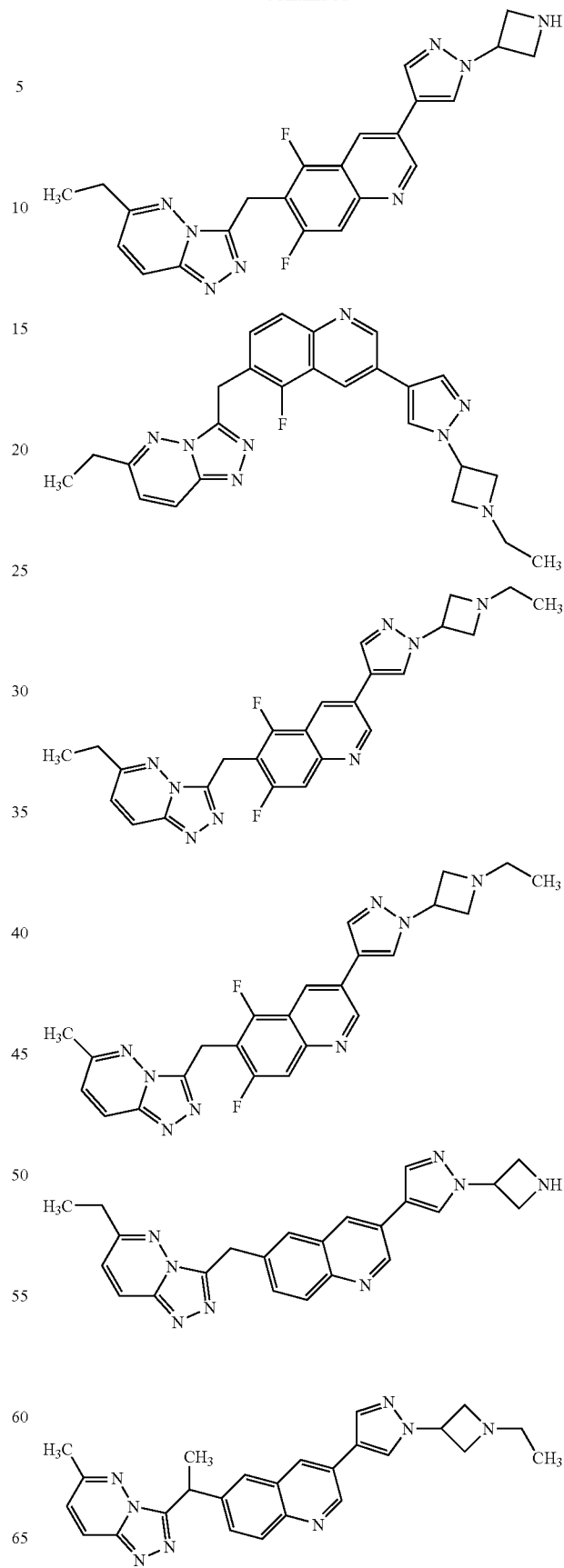

-continued

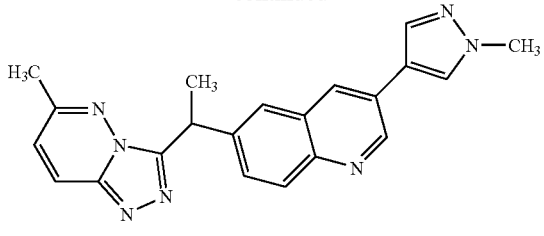

In another aspect, the disclosure provides methods for modulating the activity of a protein kinase comprising contacting the protein kinase with a compound of formula I.

In another aspect, the disclosure provides methods for modulating the activity of a protein kinase comprising contacting the protein kinase with a compound of formula I, wherein the protein kinase is Ron receptor tyrosine kinase, Met receptor tyrosine kinase, ALK receptor tyrosine kinase, MER receptor tyrosine kinase, Tyro3/Sky receptor tyrosine kinase, AXL receptor tyrosine kinase, TRKC receptor tyrosine kinase, ROS receptor tyrosine kinase, CSF1R/FMS receptor tyrosine kinase, BRAF kinase, or Raf1 kinase.

In another aspect, the disclosure provides methods for modulating the activity of a protein kinase comprising contacting the protein kinase with a compound of formula I, wherein the protein kinase is Met receptor tyrosine kinase.

In another aspect, the disclosure provides methods for treating cancer in a human patient in need of such treatment, the method comprising administering to the patient a therapeutically effective amount of a compound of formula I.

In another aspect, the disclosure provides methods for treating cancer in a human patient in need of such treatment, the method comprising administering to the patient a therapeutically effective amount of a compound of formula I, wherein the cancer is breast cancer, lung cancer, melanoma, colorectal cancer, bladder cancer, ovarian cancer, prostate cancer, renal cancer, squamous cell cancer, glioblastoma, pancreatic cancer, leiomyosarcoma, multiple myeloma, papillary renal cell carcinoma, gastric cancer, liver cancer, head and neck cancer, melanoma, or leukemia (e.g. myeloid, chronic myeloid, acute lymphoblastic, chronic lymphoblastic, Hodgkins, and other leukemias and hematological cancers).

In another aspect, the disclosure provides pharmaceutical compositions having a compound of formula I in a pharmaceutically acceptable excipient.

In another aspect, the disclosure provides methods for preventing and/or inhibiting metastasis of proliferative cells in a patient in need of such treatment, by administering to the patient a therapeutically effective amount of a compound of formula I.

In another aspect, the disclosure provides methods for preventing and/or inhibiting metastasis of proliferative cells in a patient in need of such treatment, by administering to the patient a therapeutically effective amount of a pharmaceutical composition containing a compound of formula I in a pharmaceutically acceptable excipient.

In another aspect, the disclosure provides methods for preparing the compound of formula I by:

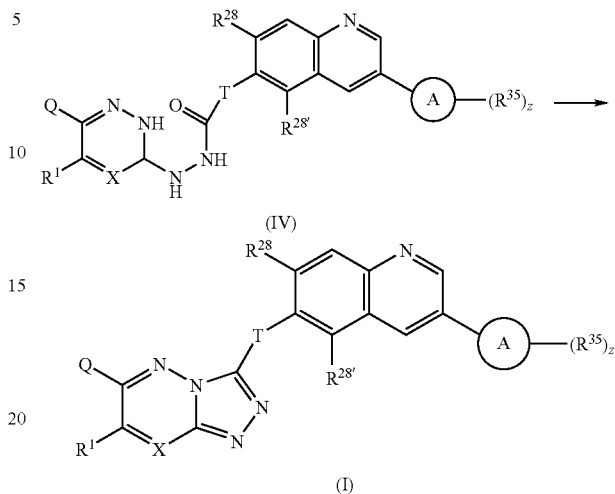

a) cyclodehydrating the compound of formula IV under acidic or dehydration conditions.

In another aspect, the disclosure provides methods for preparing the compound of formula I by cyclodehydrating the compound of formula IV under acidic or dehydration conditions, wherein the acidic condition is acetic acid, POCl$_3$ or trifluoromethanesulfonic acid.

In another aspect, the disclosure provides methods for preparing the compound of formula I by:

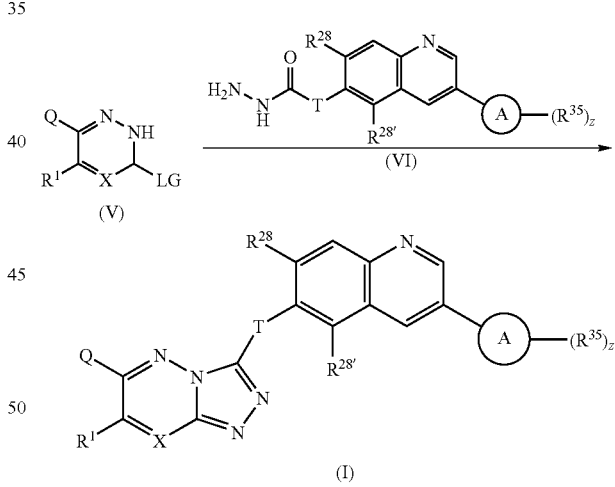

a) coupling the compound of formula V with the compound of formula VI in a solvent, wherein LG is halogen or triflate.

In another aspect, the disclosure provides methods for preparing the compound of formula I by coupling the compound of formula V with the compound of formula VI in a solvent, wherein LG is halogen or triflate.

In another aspect, the disclosure provides methods for preparing the compound of formula I by coupling the compound of formula V with the compound of formula VI in a solvent, wherein the solvent is an alcohol.

In another aspect, the disclosure provides methods for preparing the compound of formula I, the method comprising the steps of:

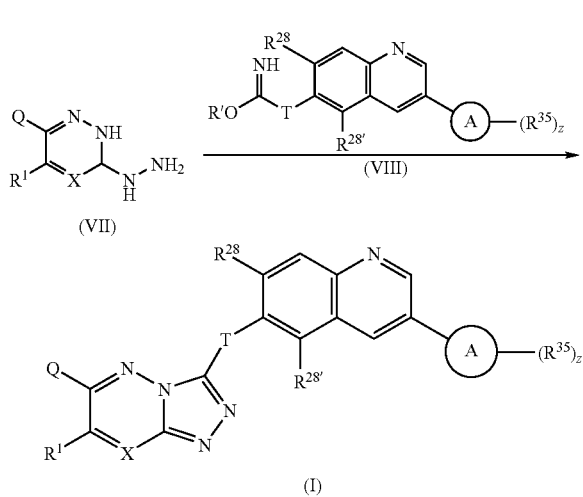

a) condensing the compound of formula VII with the compound of formula VIII, wherein R' is $C_1$-$C_6$ alkyl.

In another aspect, the disclosure provides compounds having formula IX:

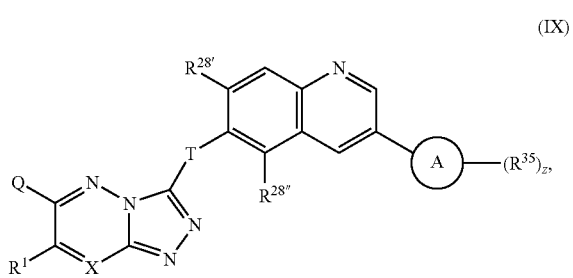

or an enantiomer, diastereomer, racemate or pharmaceutically acceptable salt or solvate thereof, wherein:

A is independently substituted or unsubstituted aryl or substituted or unsubstituted heteroaryl;

Q is independently hydrogen, amino, halogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted —O-heteroaryl, or substituted or unsubstituted heteroarylalkyl, wherein Q is optionally independently substituted with 1 to 3 $R^{22}$;

T is independently CH(halogen), C(halogen)$_2$;

X is N or $CR^2$;

$R^1$ and $R^2$ are each optionally independently hydrogen, halogen, nitro, cyano, hydroxyl, substituted or unsubstituted alkyl, perfluoroalkyl, —(CH$_2$)$_j$CN, —(CH$_2$)$_j$OR$^3$, —(CH$_2$)$_j$C(O)R$^3$, —(CH$_2$)$_j$C(O)OR$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$NR$^6$C(O)OR$^3$, —(CH$_2$)$_j$NR$^6$C(O)NR$^4$R$^5$, —(CH$_2$)$_j$S(O)$_m$R$^7$, —(CH$_2$)$_j$NR$^6$S(O)$_2$R$^7$, —(CH$_2$)$_j$S(O)$_2$NR$^4$R$^5$, wherein each j is independently an integer from 0 to 6; and m is independently an integer from 0 to 2; or $R^1$ and $R^2$ form substituted or unsubstituted cycloalkyl, substituted or unsubstituted heterocycloalkyl, substituted or unsubstituted aryl, or substituted or unsubstituted heteroaryl;

$R^3$, $R^4$, $R^5$, $R^6$ and $R^7$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^3$, $R^6$ and $R^7$ are as described above, and $R^4$ and $R^5$, together with the N atom to which they are attached, form substituted or unsubstituted heterocycloalkyl, or substituted or unsubstituted heteroaryl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, substituted or unsubstituted heteroarylalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$NR$^{27}$, —(CH$_2$)$_j$S(O)$_2$NR$^{24}$R$^{25}$, or —(CH$_2$)$_j$NR$^{26}$S(O)$_2$R$^{27}$, wherein each j is independently an integer from 0 to 6, and each m is independently an integer from 0 to 2;

$R^{23}$, $R^{24}$, $R^{25}$, $R^{26}$, and $R^{27}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{23}$, $R^{26}$, and $R^{27}$ are as described above, and $R^{24}$ and $R^{25}$, together with the N atom to which they are attached, form substituted or unsubstituted heterocycloalkyl, or substituted or unsubstituted heteroaryl;

$R^{28'}$ and $R^{28''}$ are each independently hydrogen, halogen, nitro, cyano, hydroxyl, substituted or unsubstituted alkyl, substituted or unsubstituted cycloalkyl, perfluoroalkyl, substituted or unsubstituted alkoxy, amino, aminomonoalkyl, or aminodialkyl;

$R^{35}$ is independently a covalent bond, hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, substituted or unsubstituted heteroarylalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$N$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, or —(CH$_2$)$_j$NR$^{33}$S(O)$_2$R$^{34}$, wherein each j is independently an integer from 0 to 6, and m is independently an integer from 0 to 2;

z is independently an integer from 0 to 3;

$R^{30}$, $R^{31}$, $R^{32}$, $R^{33}$, and $R^{34}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{30}$, $R^{33}$, and $R^{34}$ are as described above, and $R^{31}$ and $R^{32}$, together with the N atom to which they are attached, form substituted or unsubstituted heterocycloalkyl, or substituted or unsubstituted heteroaryl; and wherein $R^1$, $R^2$, $R^3$, $R^4$, $R^5$, $R^6$, $R^7$, $R^{22}$, $R^{23}$, $R^{24}$, $R^{25}$, $R^{26}$, $R^{27}$, $R^{28'}$, $R^{28''}$, $R^{30}$, $R^{31}$, $R^{32}$, $R^{33}$, $R^{34}$, and $R^{35}$ are each optionally independently substituted with 1 to 3 groups, each group independently selected from hydrogen, halogen, hydroxyl, amino, aminomonoalkyl, aminodialkyl, cyano, nitro, difluoromethyl, trifluoromethyl, oxo, alkyl, —O-alkyl, and —S-alkyl.

In another aspect, the disclosure provides compounds having formula IX, wherein:

A is independently substituted or unsubstituted phenyl, substituted or unsubstituted naphthyl, substituted or unsubstituted biphenyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted isoxazolyl, substituted or unsubstituted isothiazolyl, substituted or unsubstituted triazolyl, substituted or unsubstituted pyrazinyl, substituted or unsubstituted pyrimidyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl;

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted —O-pyridinyl;

$R^1$ and $R^2$ are each optionally independently hydrogen, halogen, nitro, cyano, hydroxyl, substituted or unsubstituted alkyl, perfluoroalkyl, —(CH$_2$)$_j$CN, —(CH$_2$)$_j$OR$^3$, —(CH$_2$)$_j$C(O)R$^3$, —(CH$_2$)$_j$C(O)OR$^3$, —(CH$_2$)$_j$NR$^4$R$^5$, —(CH$_2$)$_j$C(O)NR$^4$R$^5$, —(CH$_2$)$_j$OC(O)NR$^4$R$^5$, —(CH$_2$)$_j$NR$^6$C(O)R$^3$, —(CH$_2$)$_j$NR$^6$C(O)OR$^3$, —(CH$_2$)$_j$NR$^6$C(O)NR$^4$R$^5$, —(CH$_2$)$_j$S(O)$_m$R$^7$, —(CH$_2$)$_j$NR$^6$S(O)$_2$R$^7$, —(CH$_2$)$_j$S(O)$_2$NR$^4$R$^5$;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

$R^{28'}$ and $R^{28''}$ are each independently hydrogen, halogen, cyano, hydroxyl, substituted or unsubstituted alkyl, or perfluoroalkyl; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$NR$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, or —(CH$_2$)$_j$NR$^{33}$S(O)$_2$R$^{34}$.

In another aspect, the disclosure provides compounds having formula IX, wherein:

A is independently substituted or unsubstituted phenyl, substituted or unsubstituted naphthyl, substituted or unsubstituted biphenyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted isoxazolyl, substituted or unsubstituted isothiazolyl, substituted or unsubstituted triazolyl, substituted or unsubstituted pyrazinyl, substituted or unsubstituted pyrimidyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, or substituted or unsubstituted quinolinyl;

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, or substituted or unsubstituted —O-pyridinyl;

R$^1$ and R$^2$ are each independently hydrogen, halogen, nitro, cyano, hydroxyl, substituted or unsubstituted alkyl, or perfluoroalkyl;

X is CR$^2$;

R$^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

R$^{28'}$ and R$^{28'''}$ are each independently hydrogen, halogen, hydroxyl, alkyl, or perfluoroalkyl; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$N$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, —(CH$_2$)$_j$NR$^{33}$S(O)$_2$R$^{34}$,

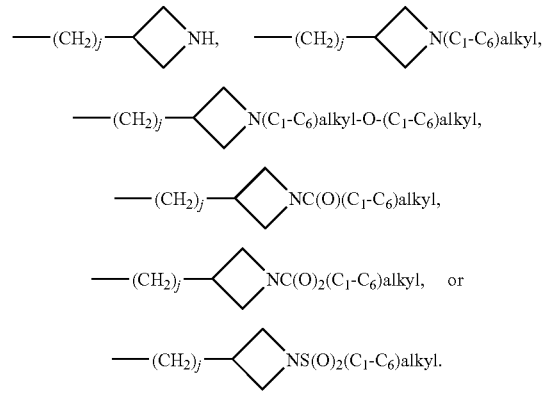

In another aspect, the disclosure provides compounds having formula IX, wherein:

A is independently:

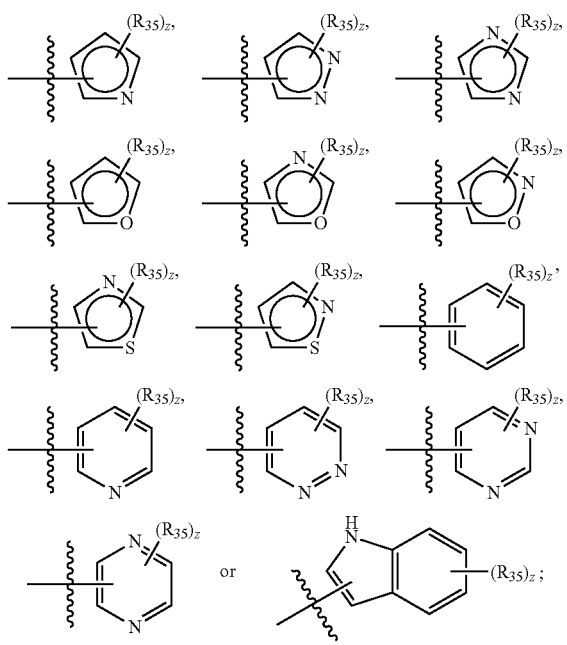

Q is independently hydrogen, chloro, substituted or unsubstituted alkyl, perfluoroalkyl, —NH$_2$, —NH(C$_1$-C$_6$)alkyl, or —N[(C$_1$-C$_6$)alkyl]$_2$,

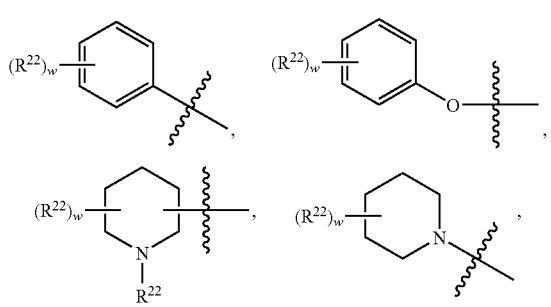

-continued

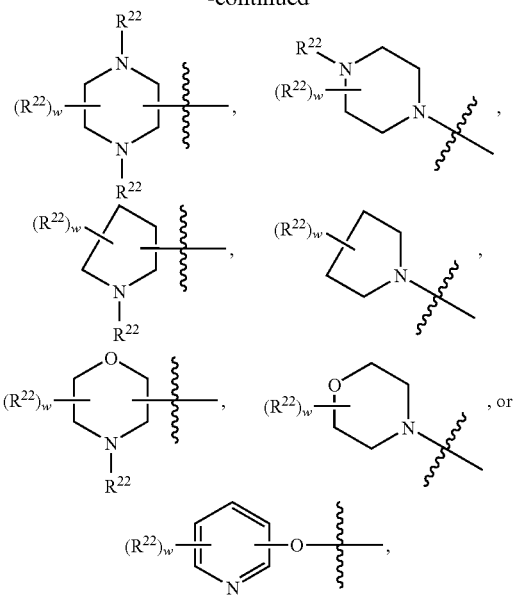

wherein each alkyl is optionally independently substituted with 1 to 3 $R^{22}$ groups, and wherein w is independently an integer from 0 to 3; and wherein two $R^{22}$ groups optionally form a cyclic structure with —O(CH$_2$CH$_2$)O—;

$R^1$ and $R^2$ are each independently hydrogen;

$R^{22}$ is independently —H, —F, Cl, Br, I, —(C$_1$-C$_6$)alkyl, —(CH$_2$)$_j$CN, —(CH$_2$)$_j$O(C$_1$-C$_6$)alkyl, —(CH$_2$)$_j$OH, —(CH$_2$)$_j$C(O)(C$_1$-C$_6$)alkyl, —(CH$_2$)$_j$NH$_2$, —(CH$_2$)$_j$NH(C$_1$-C$_6$)alkyl, —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl, —C(O)N((C$_1$-C$_6$)alkyl)$_2$, —(CH$_2$)$_j$NHC(O)(C$_1$-C$_6$)alkyl, —(CH$_2$)$_j$NHSO$_2$(C$_1$-C$_6$)alkyl, —(CH$_2$)$_j$NHSO$_2$(C$_1$-C$_6$)alkyl, —(CH$_2$)$_j$SO$_2$CH$_3$, —(CH$_2$)$_j$SO$_2$NH$_2$, —(CH$_2$)$_j$SO$_2$NH(C$_1$-C$_6$)-alkyl, —(CH$_2$)$_j$SO$_2$N((C$_1$-C$_6$)alkyl)$_2$, —(CH$_2$)$_j$SO$_2$NH(C$_1$-C$_6$)alkyl(OH), phenyl,

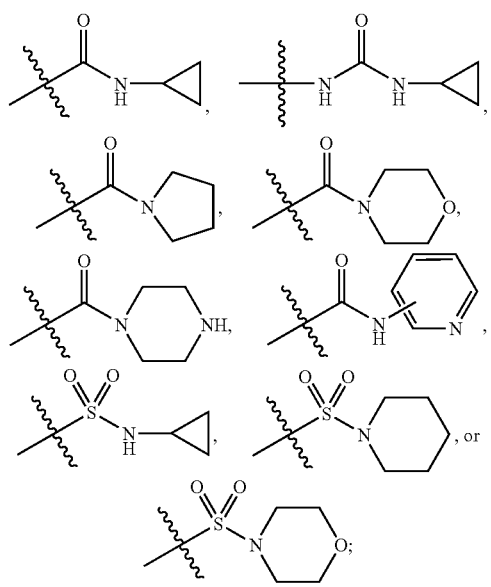

$R^{28'}$ and $R^{28''}$ are each independently hydrogen, halogen, hydroxyl, (C$_1$-C$_6$)alkyl, or trifluoromethyl; and $R^{35}$ is independently hydrogen, halogen, nitro, cyano, hydroxyl, (C$_1$-C$_6$)alkyl, cyclo(C$_3$-C$_{10}$)alkyl, perfluoro(C$_1$-C$_6$)alkyl, —(CH$_2$)$_j$CN, —(CH$_2$)$_j$O(C$_1$-C$_6$)alkyl, —(CH$_2$)$_j$C(O)(C$_1$-C$_6$)alkyl, —(CH$_2$)$_j$C(O)O(C$_1$-C$_6$)alkyl, —(CH$_2$)$_j$NH$_2$, —(CH$_2$)$_j$NH(C$_1$-C$_6$)alkyl, —(CH$_2$)$_j$N(C$_1$-C$_6$)alkyl)$_2$, —(CH$_2$)$_j$C(O)NH$_2$, —(CH$_2$)$_j$C(O)NH(C$_1$-C$_6$)alkyl, —(CH$_2$)$_j$C(O)N((C$_1$-C$_6$)alkyl)$_2$, —(CH$_2$)$_j$OC(O)NH$_2$, —(CH$_2$)$_j$OC(O)NH(C$_1$-C$_6$)alkyl, —(CH$_2$)$_j$OC(O)N((C$_1$-C$_6$)alkyl)$_2$, —(CH$_2$)$_j$NHC(O)(C$_1$-C$_6$)alkyl, —(CH$_2$)$_j$N((C$_1$-C$_6$)alkyl)C(O)(C$_1$-C$_6$)alkyl, —(CH$_2$)$_j$NHC(O)O(C$_1$-C$_6$)alkyl, —(CH$_2$)$_j$N((C$_1$-C$_6$)alkyl)C(O)O(C$_1$-C$_6$)alkyl, —(CH$_2$)$_j$NHC(O)NH$_2$, (CH$_2$)$_j$NHC(O)NH(C$_1$-C$_6$)alkyl, —(CH$_2$)$_j$NHC(O)N((C$_1$-C$_6$)alkyl)$_2$, —(CH$_2$)$_j$N((C$_1$-C$_6$)alkyl)C(O)NH(C$_1$-C$_6$)alkyl), —(CH$_2$)$_j$N((C$_1$-C$_6$)alkyl)C(O)N((C$_1$-C$_6$)alkyl)$_2$, —(CH$_2$)$_j$S(O)$_m$(C$_1$-C$_6$)alkyl, —(CH$_2$)$_j$S(O)$_2$NH$_2$, —(CH$_2$)$_j$S(O)$_2$NH(C$_1$-C$_6$)alkyl, —(CH$_2$)$_j$S(O)$_2$N((C$_1$-C$_6$)alkyl)$_2$, —(CH$_2$)$_j$NHS(O)$_2$(C$_1$-C$_6$)alkyl, —(CH$_2$)$_j$N((C$_1$-C$_6$)alkyl)S(O)$_2$(C$_1$-C$_6$)alkyl,

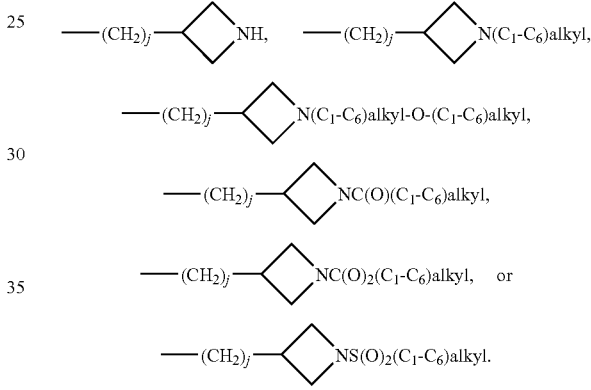

In another aspect, the disclosure provides compounds having formula IX, wherein:

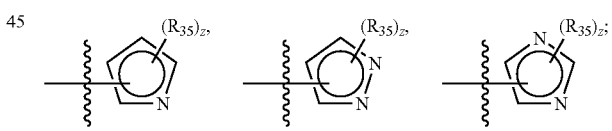

A is independently:

Q is independently (C$_1$-C$_6$)alkyl, perfluoroalkyl, —NH$_2$, —NH(C$_1$-C$_6$)alkyl, —N[(C$_1$-C$_6$)alkyl]$_2$;

$R^{28'}$ and $R^{28'}$ are each independently hydrogen, halogen, (C$_1$-C$_6$)alkyl, or trifluoromethyl; and $R^{35}$ is independently hydrogen, halogen, cyano, hydroxyl, —(C$_1$-C$_6$)alkyl, —(CH$_2$)$_j$CN, —(CH$_2$)$_j$O(C$_1$-C$_6$)alkyl, —(CH$_2$)$_j$OH, —(CH$_2$)$_j$C(O)(C$_1$-C$_6$)alkyl, —(CH$_2$)$_j$C(O)OH, —(CH$_2$)$_j$NH$_2$, —(CH$_2$)$_j$NH(C$_1$-C$_6$)alkyl, —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl, —C(O)N((C$_1$-C$_6$)alkyl)$_2$, —(CH$_2$)$_j$NHC(O)(C$_1$-C$_6$)alkyl, —(CH$_2$)$_j$NHSO$_2$(C$_1$-C$_6$)alkyl, —(CH$_2$)$_j$NHSO$_2$(C$_1$-C$_6$)alkyl, —(CH$_2$)$_j$SO$_2$CH$_3$, —(CH$_2$)$_j$SO$_2$NH$_2$, —(CH$_2$)$_j$SO$_2$NH(C$_1$-C$_6$)-alkyl, —(CH$_2$)$_j$SO$_2$N((C$_1$-C$_6$)alkyl)$_2$, —(CH$_2$)$_j$SO$_2$NH(C$_1$-C$_6$)alkyl(OH), phenyl,

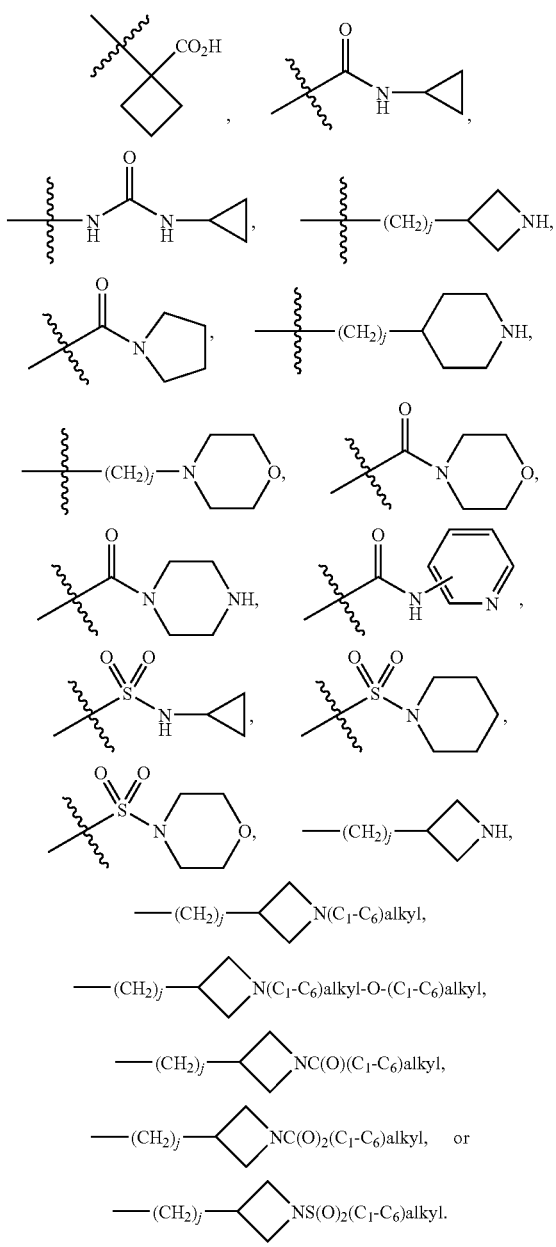

In another aspect, the disclosure provides compounds having formula X:

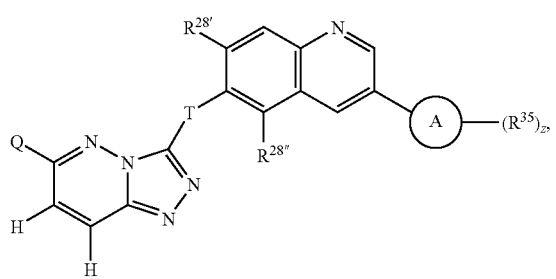

wherein:

T is independently CH(halogen), C(halogen)$_2$;

A is independently substituted or unsubstituted phenyl, substituted or unsubstituted naphthyl, substituted or unsubstituted biphenyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted isoxazolyl, substituted or unsubstituted isothiazolyl, substituted or unsubstituted triazolyl, substituted or unsubstituted pyrazinyl, substituted or unsubstituted pyrimidyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7] naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl;

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted —O-pyridinyl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

R$^{28'}$ and R$^{28''}$ are each independently hydrogen, halogen, cyano, hydroxyl, substituted or unsubstituted alkyl, or perfluoroalkyl; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$NR$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, or —(CH$_2$)$_j$NR$^{33}$S(O)$_2$R$^{34}$.

In another aspect, the disclosure provides compounds having formula X, wherein:

A is independently substituted or unsubstituted phenyl, substituted or unsubstituted naphthyl, substituted or unsubstituted biphenyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted isoxazolyl, substituted or unsubstituted isothiazolyl, substituted or unsubstituted triazolyl, substituted or unsubstituted pyrazinyl, substituted or unsubstituted pyrimidyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, or substituted or unsubstituted quinolinyl;

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, or substituted or unsubstituted —O-pyridinyl;

R$^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

R$^{28'}$ and R$^{28''}$ are each independently hydrogen, halogen, hydroxyl, alkyl, or perfluoroalkyl; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$N$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, —(CH$_2$)$_j$NR$^{33}$S(O)$_2$R$^{34}$,

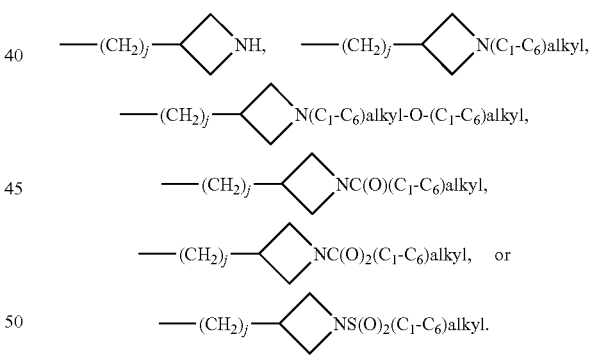

In another aspect, the disclosure provides compounds having formula X, wherein:

A is independently:

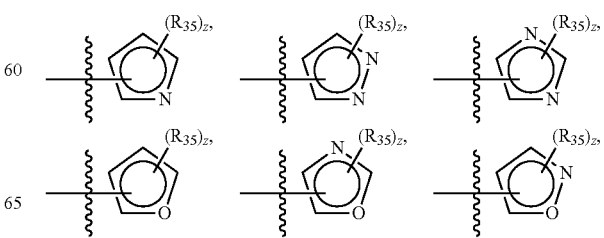

-continued

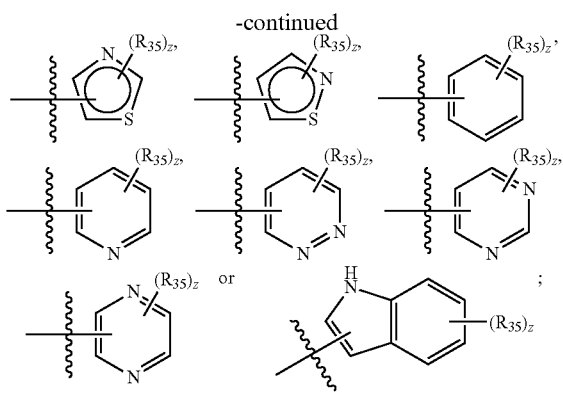

Q is independently hydrogen, chloro, substituted or unsubstituted alkyl, perfluoroalkyl, —NH$_2$, —NH(C$_1$-C$_6$)alkyl, or —N[C$_1$-C$_6$)alkyl]$_2$,

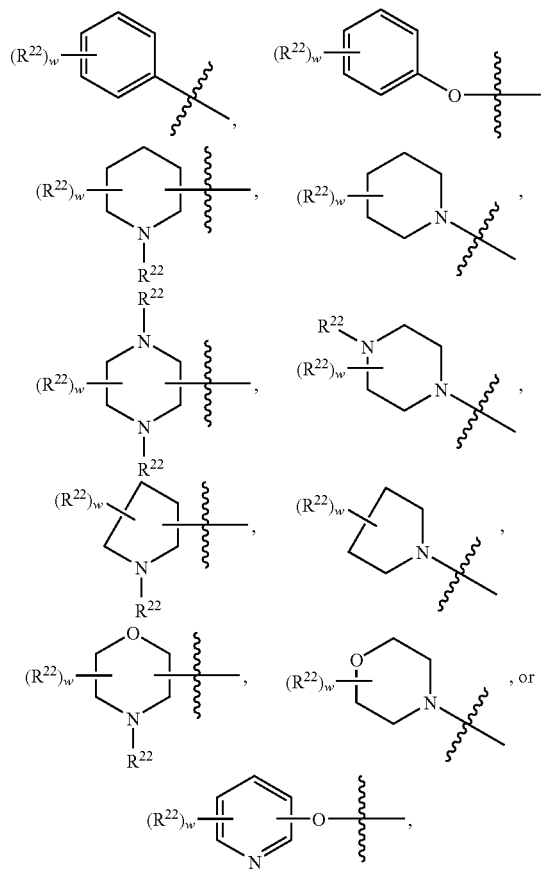

wherein each alkyl is optionally independently substituted with 1 to 3 R$^{22}$ groups, and wherein w is independently an integer from 0 to 3; and wherein two R$^{22}$ groups optionally form a cyclic structure with —O(CH$_2$CH$_2$)O—;

R$^{22}$ is independently —H, —F, Cl, Br, I, —(C$_1$-C$_6$)alkyl, —(CH$_2$)$_j$CN, —(CH$_2$)$_j$O(C$_1$-C$_6$)alkyl, —(CH$_2$)$_j$OH, —(CH$_2$)$_j$C(O)(C$_1$-C$_6$)alkyl, —(CH$_2$)$_j$NH$_2$, —(CH$_2$)$_j$NH(C$_1$-C$_6$)alkyl, —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl, —C(O)N((C$_1$-C$_6$)alkyl)$_2$, —(CH$_2$)$_j$NHC(O)(C$_1$-C$_6$)alkyl, —(CH$_2$)$_j$NHSO$_2$(C$_1$-C$_6$)alkyl, —(CH$_2$)$_j$NHSO$_2$(C$_1$-C$_6$)alkyl, —(CH$_2$)$_j$SO$_2$CH$_3$, —(CH$_2$)$_j$SO$_2$NH$_2$, —(CH$_2$)$_j$SO$_2$NH(C$_1$-C$_6$)-alkyl, —(CH$_2$)$_j$SO$_2$N((C$_1$-C$_6$)alkyl)$_2$, —(CH$_2$)$_j$SO$_2$NH(C$_1$-C$_6$)alkyl(OH), phenyl,

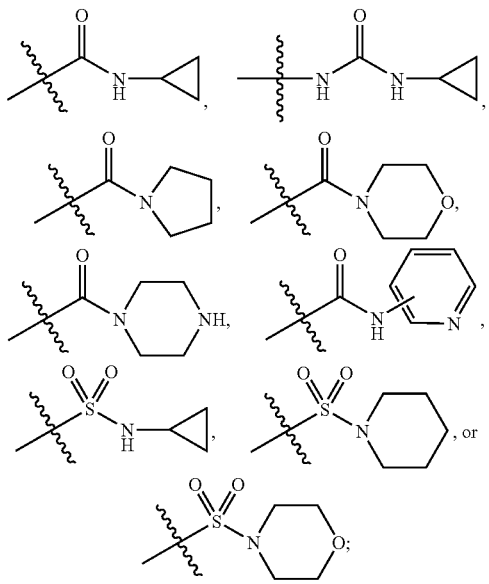

R$^{28'}$ and R$^{28''}$ are each independently hydrogen, halogen, hydroxyl, (C$_1$-C$_6$)alkyl, or trifluoromethyl; and R$^{35}$ is independently hydrogen, halogen, nitro, cyano, hydroxyl, (C$_1$-C$_6$)alkyl, cyclo(C$_3$-C$_{10}$)alkyl, perfluoro(C$_1$-C$_6$)alkyl, —(CH$_2$)$_j$CN, —(CH$_2$), O(C$_1$-C$_6$)alkyl, —(CH$_2$)$_j$C(O)(C$_1$-C$_6$)alkyl, —(CH$_2$)$_j$C(O)O(C$_1$-C$_6$)alkyl, —(CH$_2$)$_j$NH$_2$, —(CH$_2$)$_j$NH(C$_1$-C$_6$)alkyl), —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl), —(CH$_2$)$_j$C(O)N((C$_1$-C$_6$)alkyl)$_2$, —(CH$_2$)$_j$OC(O)NH$_2$, —(CH$_2$)$_j$OC(O)NH(C$_1$-C$_6$)alkyl), —(CH$_2$)$_j$OC(O)N((C$_1$-C$_6$)alkyl)$_2$, —(CH$_2$)$_j$NHC(O)(C$_1$-C$_6$)alkyl, —(CH$_2$)$_j$N((C$_1$-C$_6$)alkyl)C(O)(C$_1$-C$_6$)alkyl, —(CH$_2$)$_j$NHC(O)O(C$_1$-C$_6$)alkyl, —(CH$_2$)$_j$N((C$_1$-C$_6$)alkyl)C(O)O(C$_1$-C$_6$)alkyl, —(CH$_2$)$_j$NHC(O)NH$_2$, —(CH$_2$)$_j$NHC(O)NH(C$_1$-C$_6$)alkyl), —(CH$_2$)$_j$NHC(O)N((C$_1$-C$_6$)alkyl)$_2$, —(CH$_2$)$_j$N((C$_1$-C$_6$)alkyl)C(O)NH(C$_1$-C$_6$)alkyl), —(CH$_2$)$_j$N((C$_1$-C$_6$)alkyl)C(O)N((C$_1$-C$_6$)alkyl)$_2$, —(CH$_2$)$_j$S(O)$_m$(C$_1$-C$_6$)alkyl, —(CH$_2$)$_j$S(O)$_2$NH$_2$, —(CH$_2$)$_j$S(O)$_2$NH(C$_1$-C$_6$)alkyl), —(CH$_2$)$_j$S(O)$_2$N((C$_1$-C$_6$)alkyl)$_2$, —(CH$_2$)$_j$NHS(O)$_2$(C$_1$-C$_6$)alkyl, —(CH$_2$)$_j$N((C$_1$-C$_6$)alkyl)S(O)$_2$(C$_1$-C$_6$)alkyl,

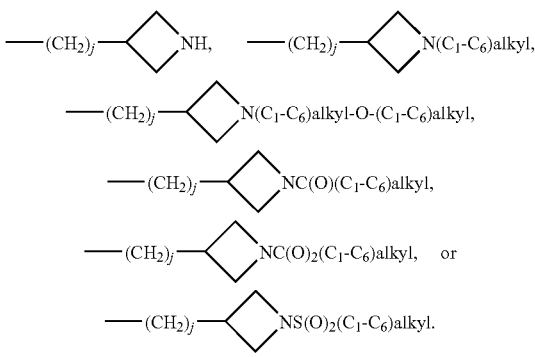

In another aspect, the disclosure provides compounds having formula X, wherein:

A is independently:

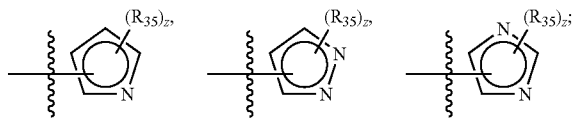

Q is independently $(C_1-C_6)$alkyl, perfluoroalkyl, —$NH_2$, —$NH(C_1-C_6)$alkyl, —$N[(C_1-C_6)$alkyl$]_2$;

$R^{28'}$ and $R^{28''}$ are each independently hydrogen, halogen, $(C_1-C_6)$alkyl, or trifluoromethyl; and $R^{35}$ is independently hydrogen, halogen, cyano, hydroxyl, —$(C_1-C_6)$alkyl, —$(CH_2)_j$CN, —$(CH_2)_j$O$(C_1-C_6)$alkyl, —$(CH_2)_j$OH, —$(CH_2)_j$C(O)$(C_1-C_6)$alkyl, —$(CH_2)_j$C(O)OH, —$(CH_2)_j$NH$_2$, —$(CH_2)_j$NH$(C_1-C_6)$alkyl, —$(CH_2)_j$N$((C_1-C_6)$alkyl$)_2$, —$(CH_2)_j$C(O)NH$_2$, —$(CH_2)_j$C(O)NH$(C_1-C_6)$alkyl, —C(O)N$((C_1-C_6)$alkyl$)_2$, —$(CH_2)_j$NHC(O)$(C_1-C_6)$alkyl, —$(CH_2)_j$NHSO$_2(C_1-C_6)$alkyl, —$(CH_2)_j$NHSO$_2(C_1-C_6)$alkyl, —$(CH_2)_j$SO$_2$CH$_3$, —$(CH_2)_j$SO$_2$NH$_2$, —$(CH_2)_j$SO$_2$NH$(C_1-C_6)$-alkyl, —$(CH_2)_j$SO$_2$N$((C_1-C_6)$alkyl$)_2$, —$(CH_2)_j$SO$_2$NH$(C_1-C_6)$alkyl(OH), phenyl,

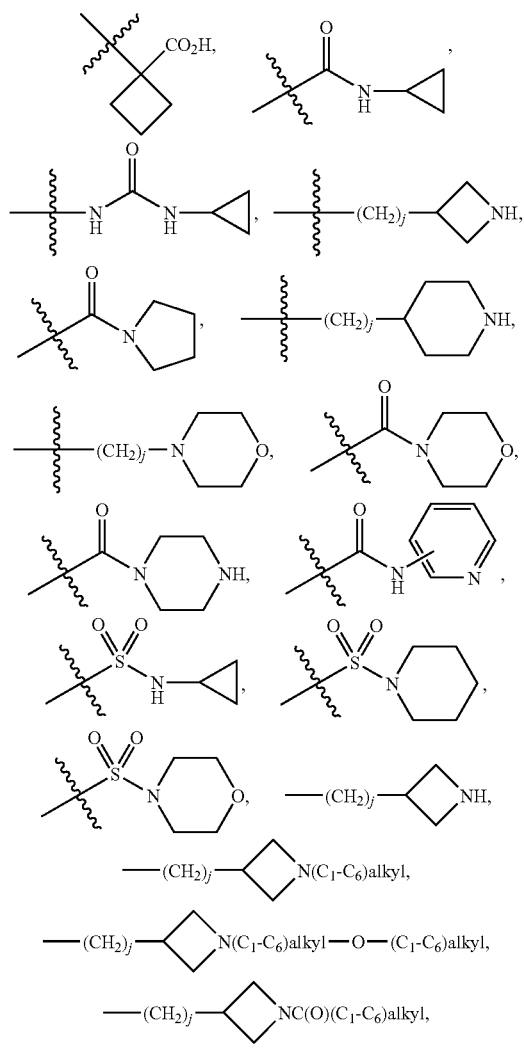

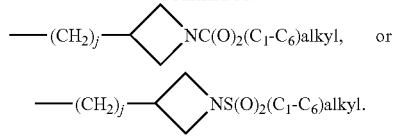

In another aspect, the disclosure provides compounds having formula XI:

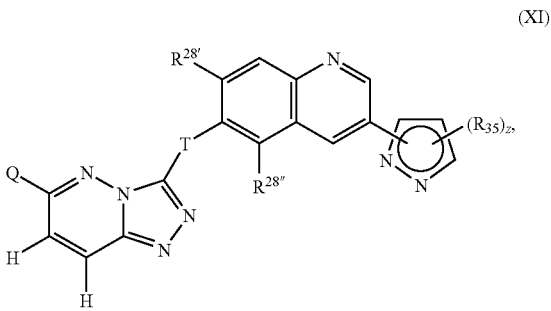

(XI)

wherein:

T is independently CH(halogen), C(halogen)$_2$;

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted —O-pyridinyl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(C$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

R$^{28'}$ and R$^{28''}$ are each independently hydrogen, halogen, hydroxyl, alkyl, or perfluoroalkyl; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$NR$^{33}$C(O)NR$^{31}$R$^{32}$, —(CH$_2$)$_j$S(O)R$^{34}$, —(CH$_2$)$_j$S(O)$_2$NR$^{31}$R$^{32}$, or —(CH$_2$)$_j$NR$^{33}$S(O)$_2$R$^{34}$.

In another aspect, the disclosure provides compounds having formula XI, wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, or substituted or unsubstituted —O-pyridinyl;

R$^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$C(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

R$^{28'}$ and R$^{28''}$ are each independently hydrogen, halogen, hydroxyl, alkyl, or perfluoroalkyl; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$N$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, —(CH$_2$)$_j$NR$^{33}$S(O)$_2$R$^{34}$,

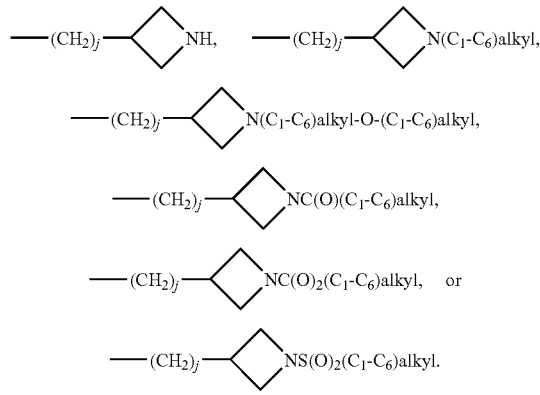

In another aspect, the disclosure provides compounds having formula XI, wherein:

Q is independently hydrogen, chloro, substituted or unsubstituted alkyl, perfluoroalkyl, —NH$_2$, —NH(C$_1$-C$_6$)alkyl, or —N[(C$_1$-C$_6$)alkyl]$_2$,

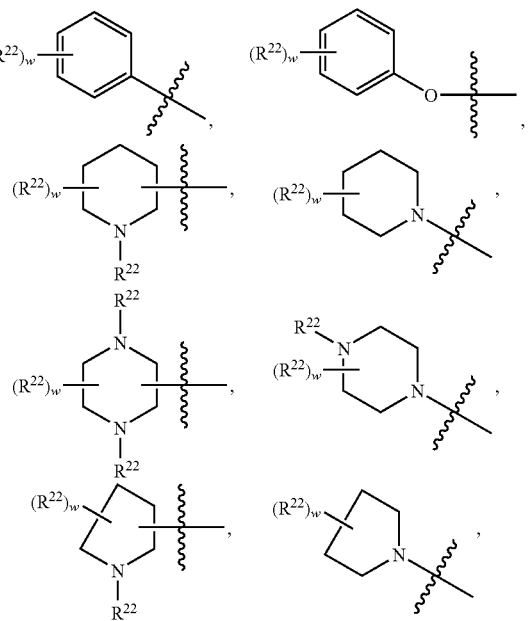

-continued

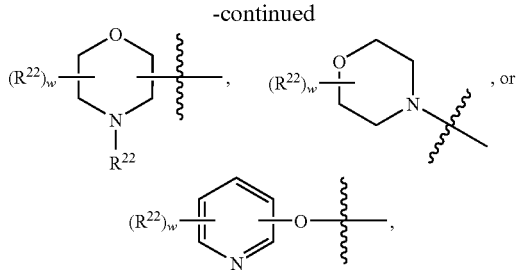

wherein each alkyl is optionally independently substituted with 1 to 3 $R^{22}$ groups, and wherein w is independently an integer from 0 to 3; and wherein two $R^{22}$ groups optionally form a cyclic structure with —O(CH$_2$CH$_2$)O—;

$R^{22}$ is independently —H, —F, Cl, Br, I, —(C$_1$-C$_6$)alkyl, —(CH$_2$)$_j$CN, —(CH$_2$)$_j$O(C$_1$-C$_6$)alkyl, —(CH$_2$)$_j$OH, —(CH$_2$)$_j$C(O)(C$_1$-C$_6$)alkyl, —(CH$_2$)$_j$NH$_2$, —(CH$_2$)$_j$NH(C$_1$-C$_6$)alkyl, —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl, —C(O)N((C$_1$-C$_6$)alkyl)$_2$, —(CH$_2$)$_j$NHC(O)(C$_1$-C$_6$)alkyl, —(CH$_2$)$_j$NHSO$_2$(C$_1$-C$_6$)alkyl, —(CH$_2$)$_j$NHSO$_2$(C$_1$-C$_6$)alkyl, —(CH$_2$)$_j$SO$_2$CH$_3$, —(CH$_2$)$_j$SO$_2$NH$_2$, —(CH$_2$)$_j$SO$_2$NH(C$_1$-C$_6$)alkyl, —(CH$_2$)$_j$SO$_2$N((C$_1$-C$_6$)alkyl)$_2$, —(CH$_2$)$_j$SO$_2$NH(C$_1$-C$_6$)alkyl(OH), phenyl,

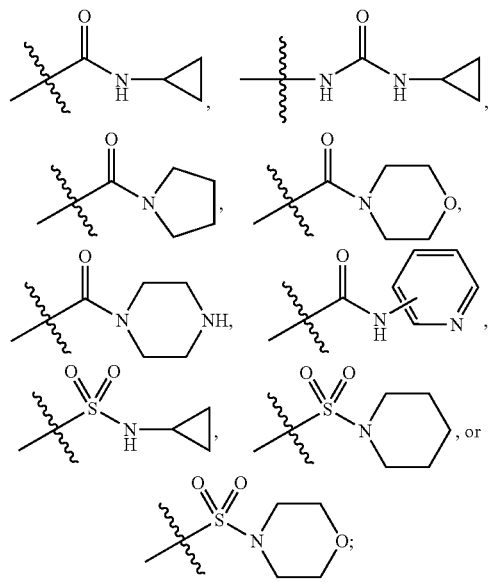

$R^{28'}$ and $R^{28''}$ are each independently hydrogen, halogen, hydroxyl, (C$_1$-C$_6$)alkyl, or trifluoromethyl; and $R^{35}$ is independently hydrogen, halogen, nitro, cyano, hydroxyl, (C$_1$-C$_6$)alkyl, cyclo(C$_3$-C$_{10}$)alkyl, perfluoro(C$_1$-C$_6$)alkyl, —(CH$_2$)$_j$CN, —(CH$_2$)$_j$O(C$_1$-C$_6$)alkyl, —(CH$_2$)$_j$C(O)(C$_1$-C$_6$)alkyl, —(CH$_2$)$_j$C(O)O(C$_1$-C$_6$)alkyl, —(CH$_2$)$_j$NH$_2$, —(CH$_2$)$_j$NH(C$_1$-C$_6$)alkyl, —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl), —(CH$_2$)$_j$C(O)N((C$_1$-C$_6$)alkyl)$_2$, —(CH$_2$)$_j$OC(O)NH$_2$, —(CH$_2$)$_j$OC(O)NH(C$_1$-C$_6$)alkyl), —(CH$_2$)$_j$OC(O)N((C$_1$-C$_6$)alkyl)$_2$, —(CH$_2$)$_j$NHC(O)(C$_1$-C$_6$)alkyl, —(CH$_2$)$_j$N(C$_1$-C$_6$)alkyl)C(O)(C$_1$-C$_6$)alkyl, —(CH$_2$)$_j$NHC(O)O(C$_1$-C$_6$)alkyl, —(CH$_2$)$_j$N((C$_1$-C$_6$)alkyl)C(O)O(C$_1$-C$_6$)alkyl, —(CH$_2$)$_j$NHC(O)NH$_2$, —(CH$_2$)$_j$NHC(O)NH(C$_1$-C$_6$)alkyl), —(CH$_2$)$_j$NHC(O)N((C$_1$-C$_6$)alkyl)$_2$, —(CH$_2$)$_j$N((C$_1$-C$_6$)alkyl)C(O)NH(C$_1$-C$_6$)alkyl), —(CH$_2$)$_j$N((C$_1$-C$_6$)alkyl)C(O)N((C$_1$-C$_6$)alkyl)$_2$, —(CH$_2$)$_j$S(O)$_m$(C$_1$-C$_6$)alkyl, —(CH$_2$)$_j$S(O)$_2$NH$_2$, —(CH$_2$)$_j$S(O)$_2$NH(C$_1$-C$_6$)alkyl), —(CH$_2$)$_j$S(O)$_2$N((C$_1$-C$_6$)alkyl)$_2$, —(CH$_2$)$_j$NHS(O)$_2$(C$_1$-C$_6$)alkyl, —(CH$_2$)$_j$N((C$_1$-C$_6$)alkyl)S(O)$_2$(C$_1$-C$_6$)alkyl,

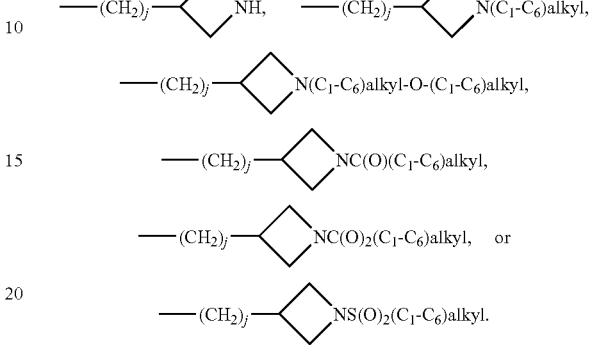

In another aspect, the disclosure provides compounds having formula XI, wherein:

Q is independently (C$_1$-C$_6$)alkyl, perfluoroalkyl, —NH$_2$, —NH(C$_1$-C$_6$)alkyl, —N[(C$_1$-C$_6$)alkyl]$_2$;

$R^{28'}$ and $R^{28''}$ are each independently hydrogen, halogen, (C$_1$-C$_6$)alkyl, or trifluoromethyl; and $R^{35}$ is independently hydrogen, halogen, cyano, hydroxyl, —(C$_1$-C$_6$)alkyl, —(CH$_2$)$_j$CN, —(CH$_2$)$_j$O(C$_1$-C$_6$)alkyl, —(CH$_2$)$_j$OH, —(CH$_2$)$_j$C(O)(C$_1$-C$_6$)alkyl, —(CH$_2$)$_j$C(O)OH, —(CH$_2$)$_j$NH$_2$, —(CH$_2$)$_j$NH(C$_1$-C$_6$)alkyl, —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl, —C(O)N((C$_1$-C$_6$)alkyl)$_2$, —(CH$_2$)$_j$NHC(O)(C$_1$-C$_6$)alkyl, —(CH$_2$)$_j$NHSO$_2$(C$_1$-C$_6$)alkyl, —(CH$_2$)$_j$NHSO$_2$(C$_1$-C$_6$)alkyl, —(CH$_2$)$_j$SO$_2$CH$_3$, —(CH$_2$)$_j$SO$_2$NH$_2$, —(CH$_2$)$_j$SO$_2$NH(C$_1$-C$_6$)-alkyl, —(CH$_2$)$_j$SO$_2$N((C$_1$-C$_6$)alkyl)$_2$, —(CH$_2$)$_j$SO$_2$NH(C$_1$-C$_6$)alkyl(OH), phenyl,

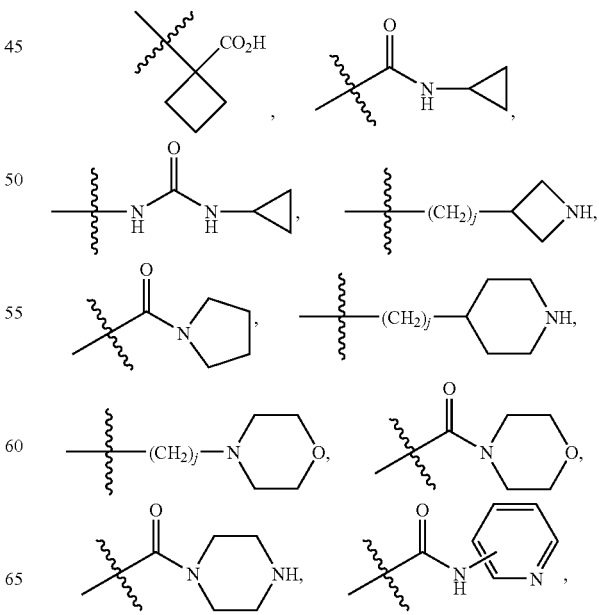

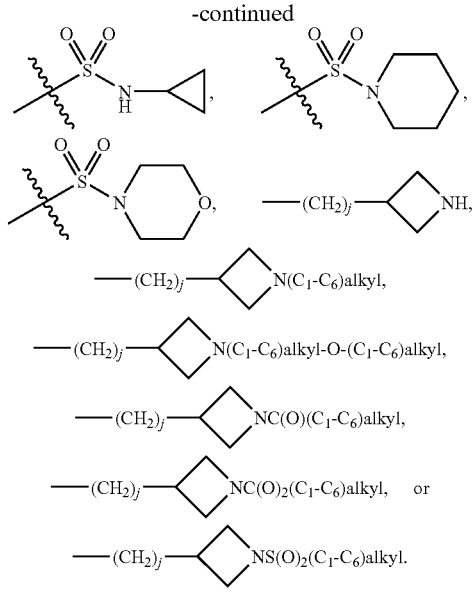
In another aspect, the disclosure provides compounds having formula XII:
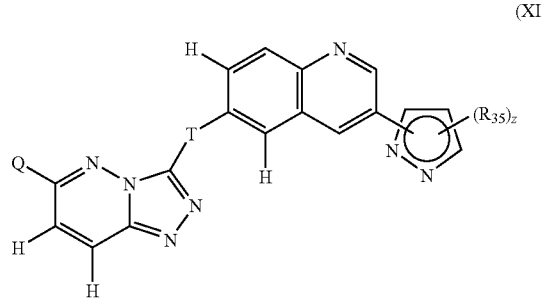
(XII)
wherein:
Q is independently (C₁-C₆)alkyl;
T is CHF or CF₂; and
R³⁵ is —(C₁-C₆)alkyl.
In another aspect, the disclosure provides compounds selected from:
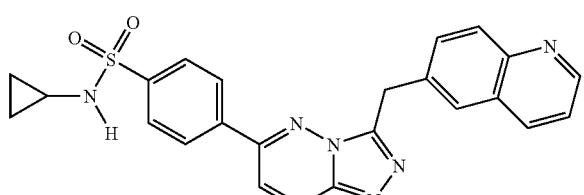
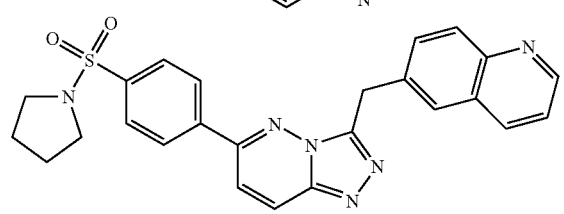
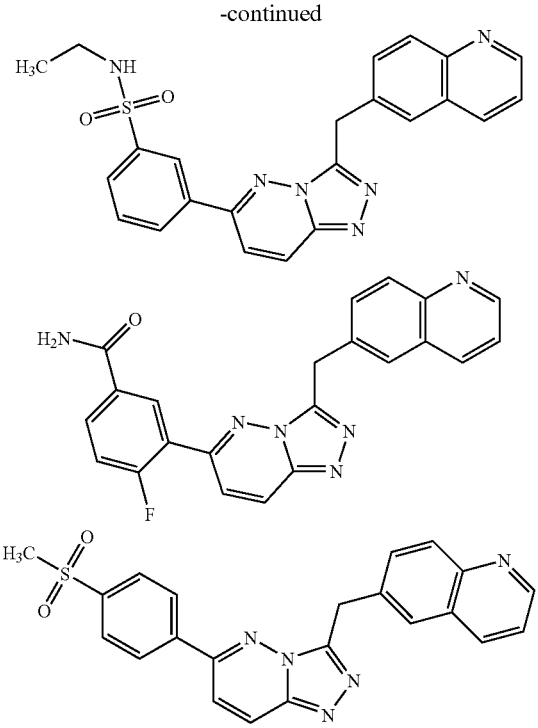
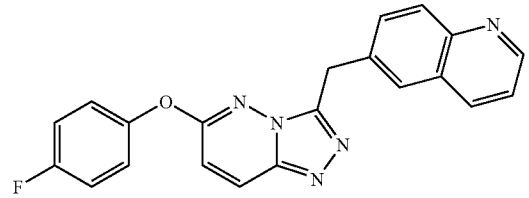
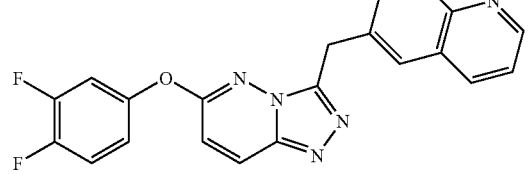
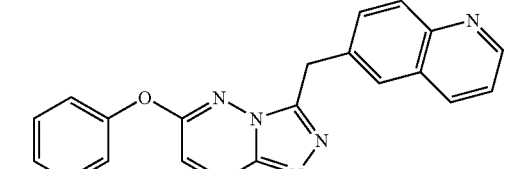
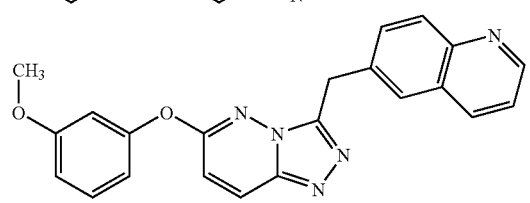
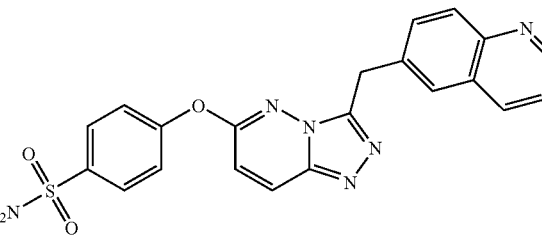

81
-continued
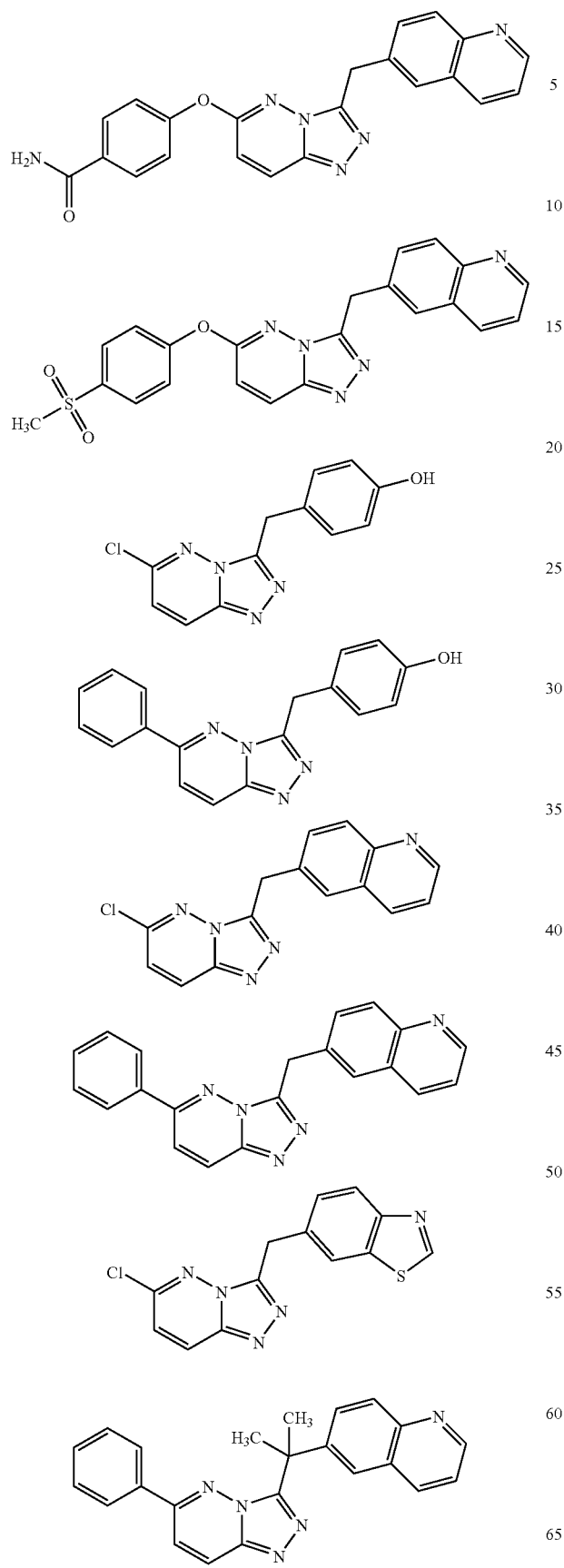
82
-continued
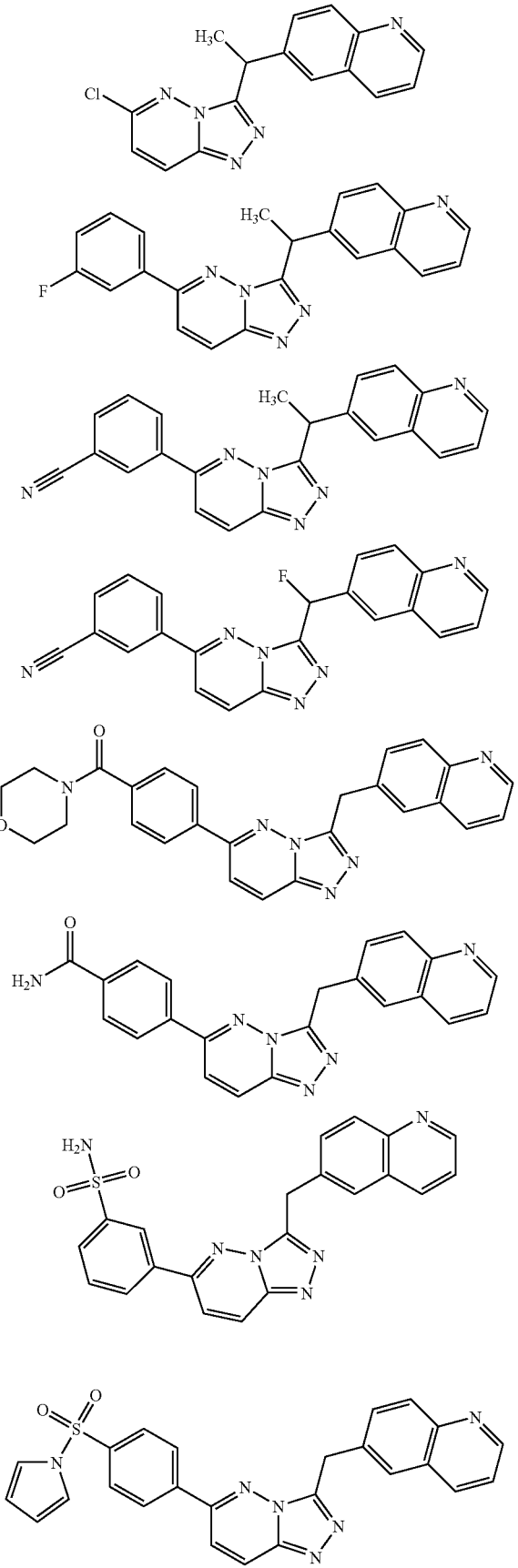

83
-continued
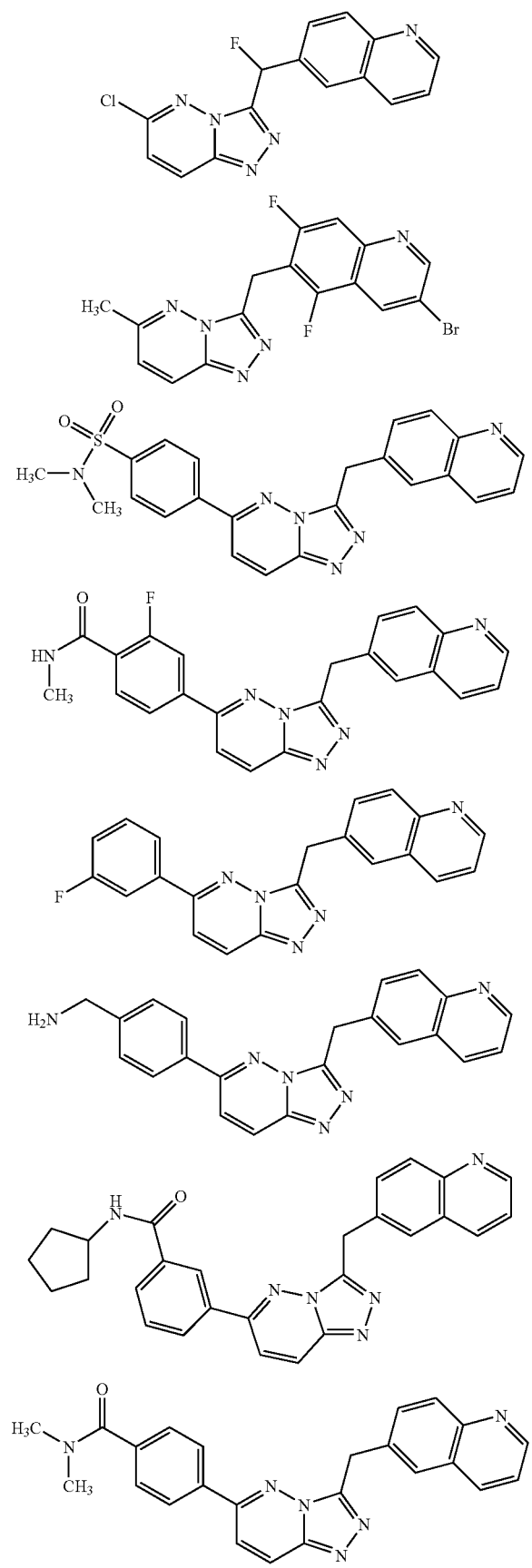
84
-continued
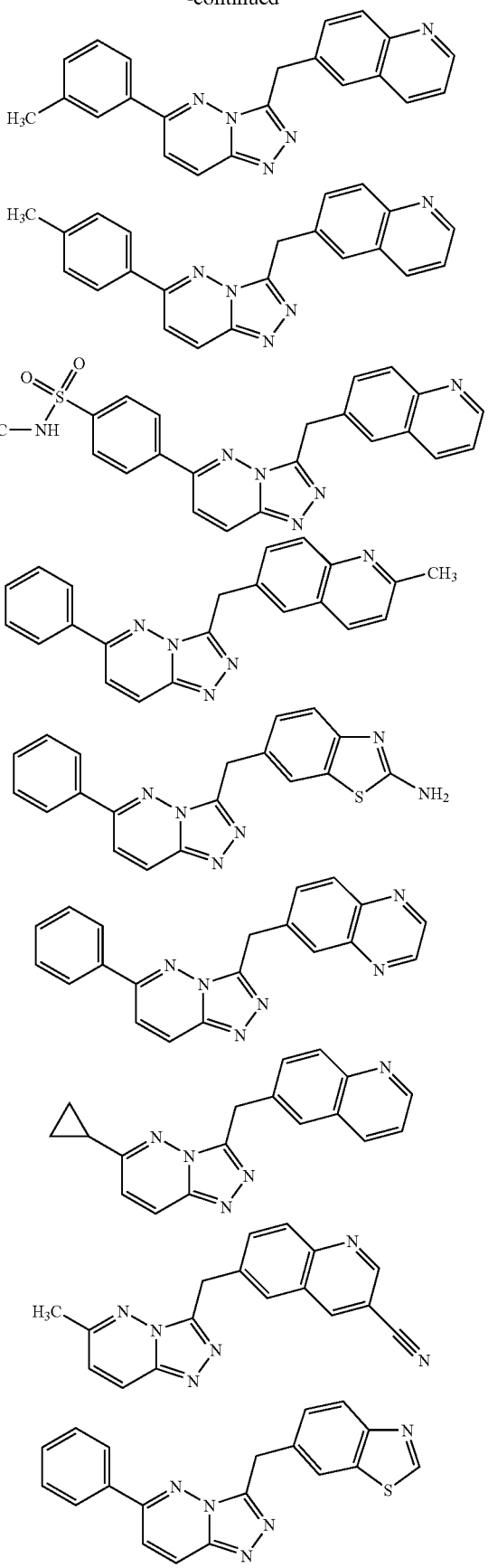

85
-continued
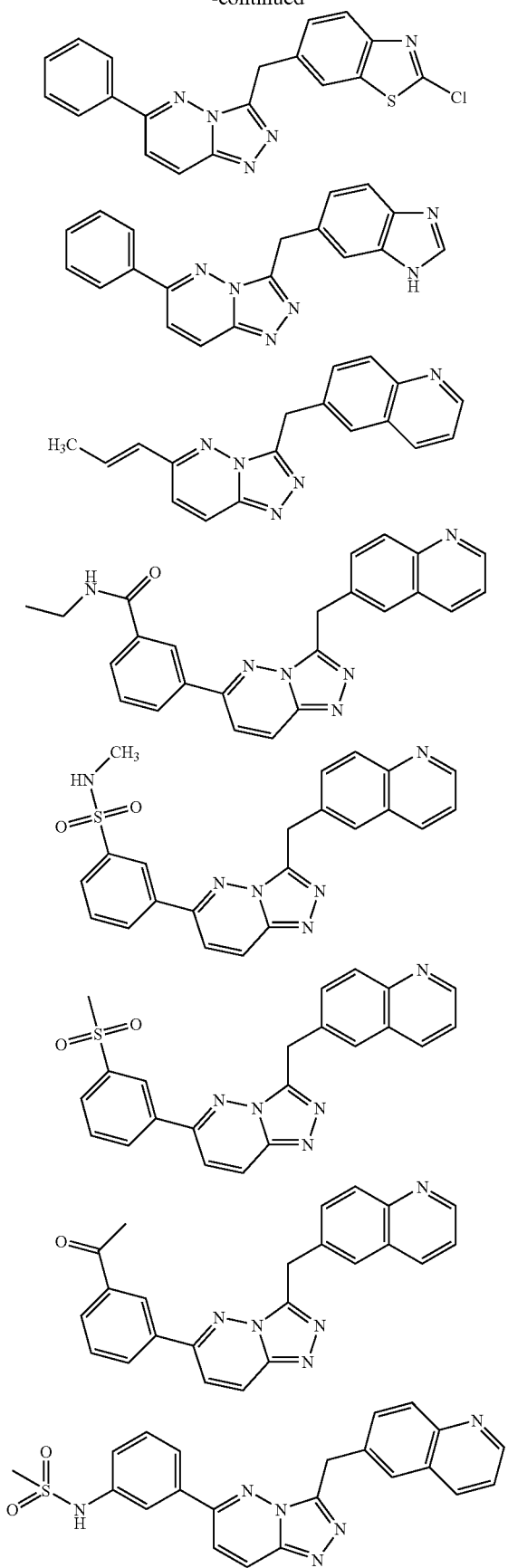
86
-continued
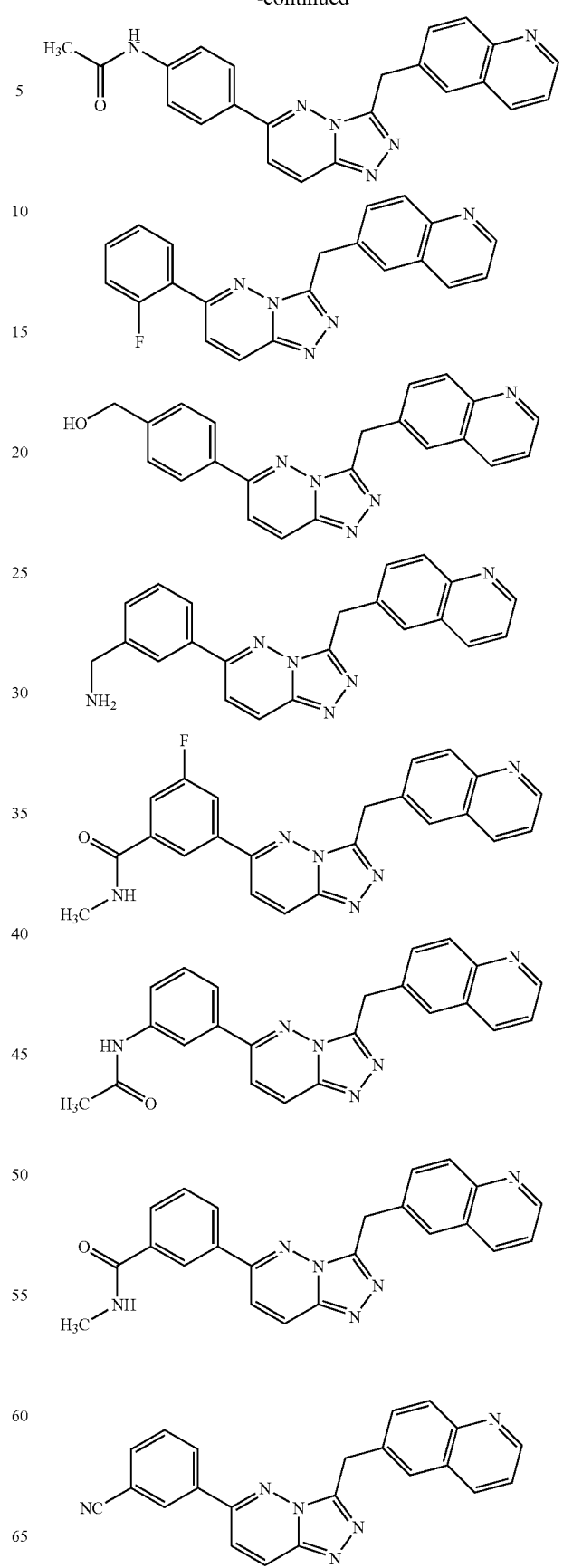

87
-continued
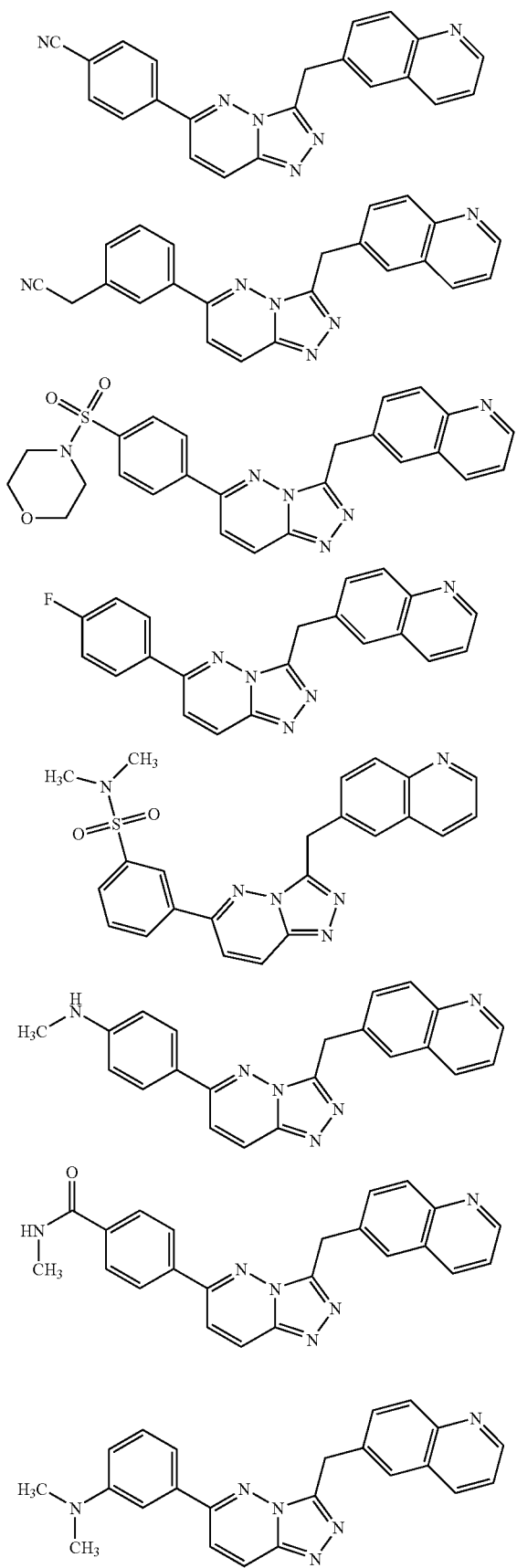
88
-continued
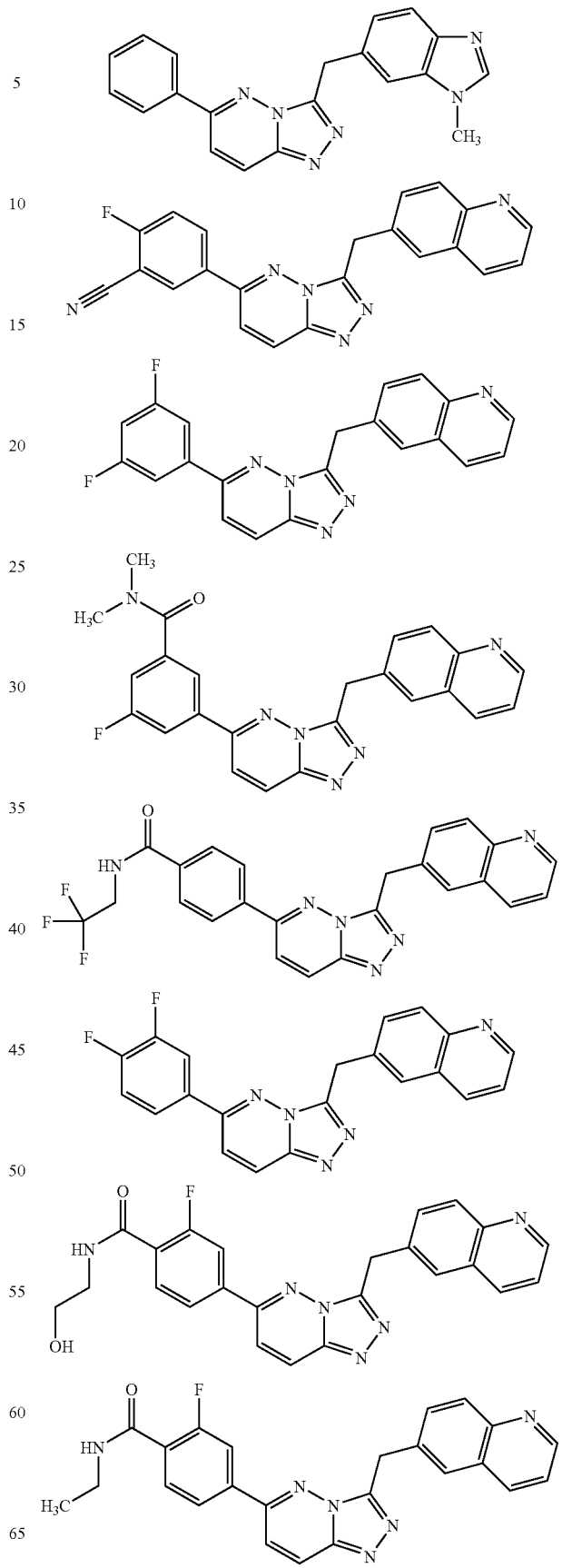

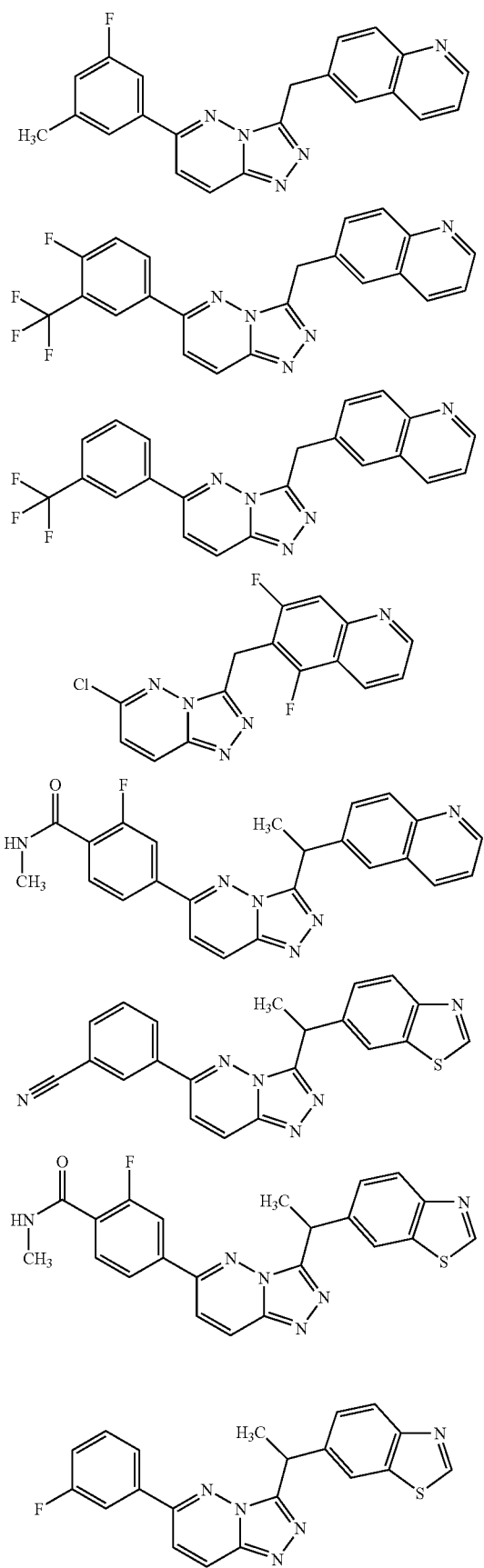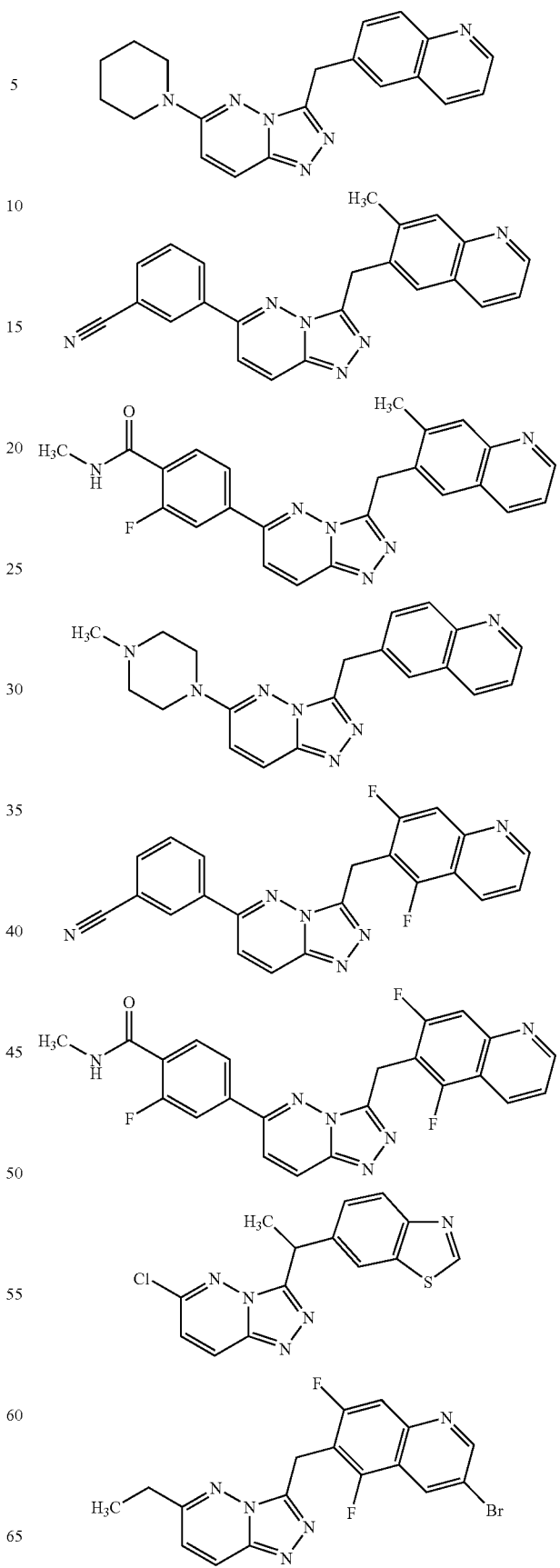

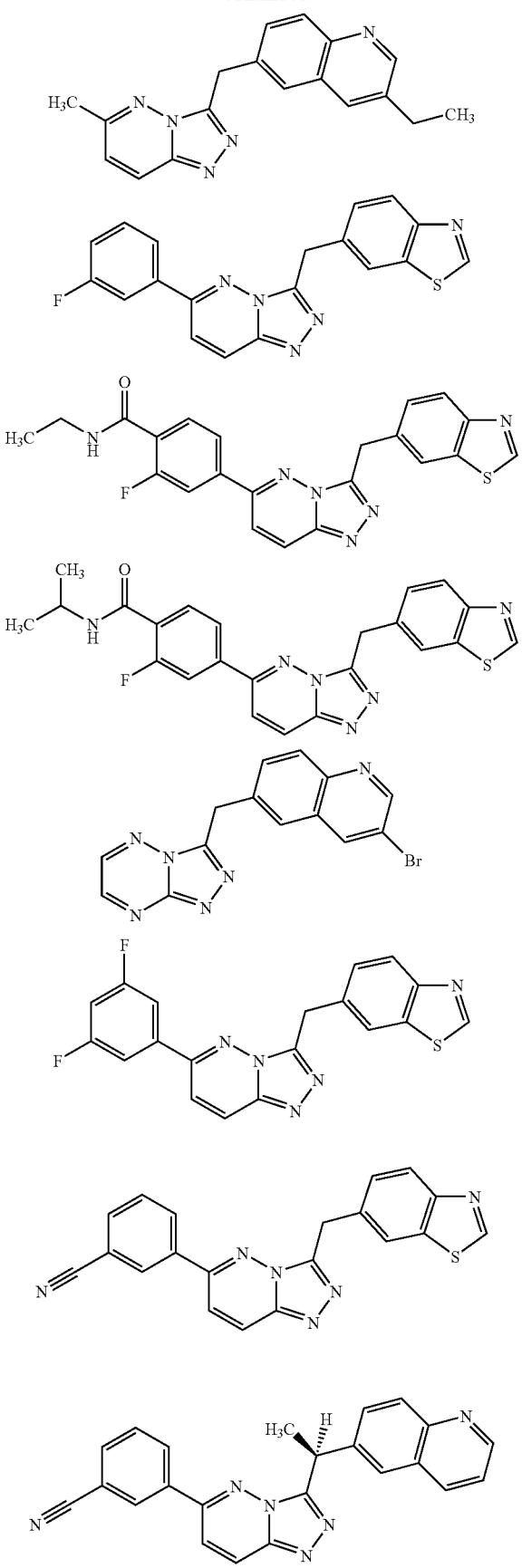
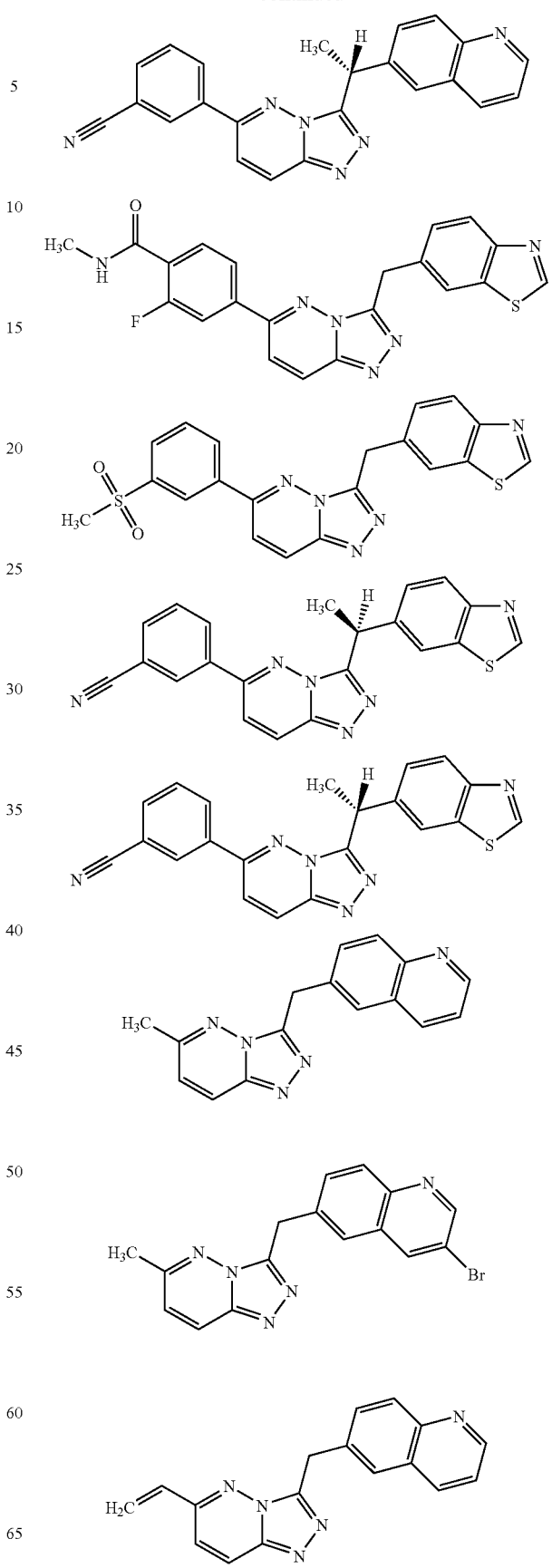

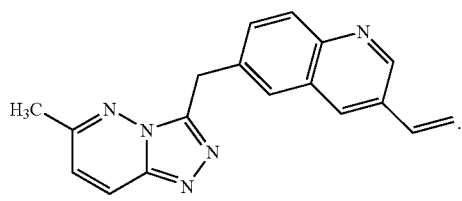
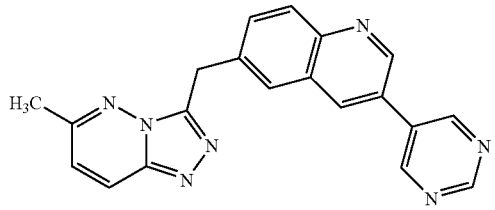
In another aspect, the disclosure provides compounds having formula:
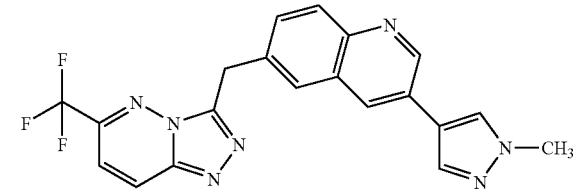
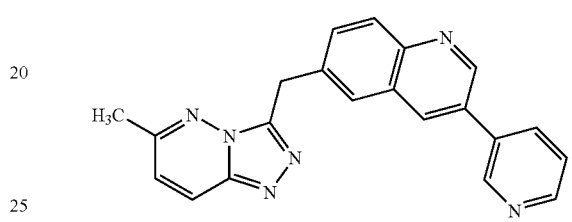
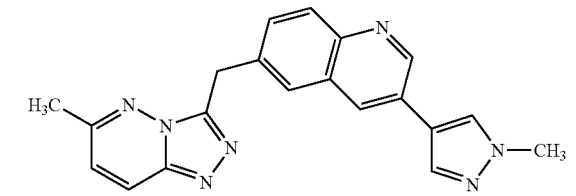
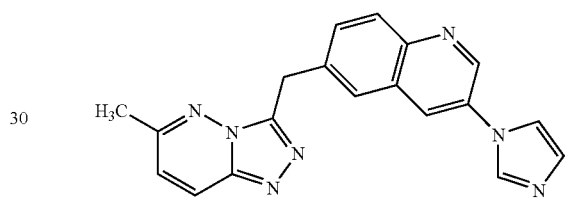
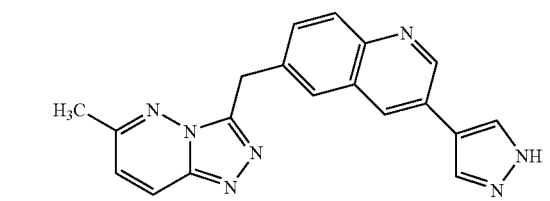
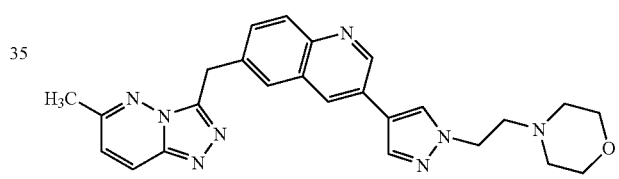
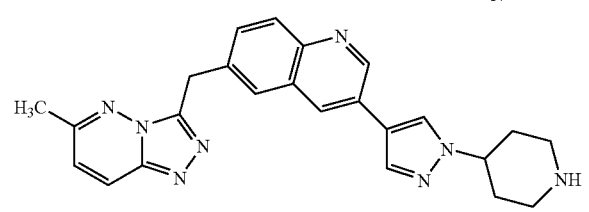
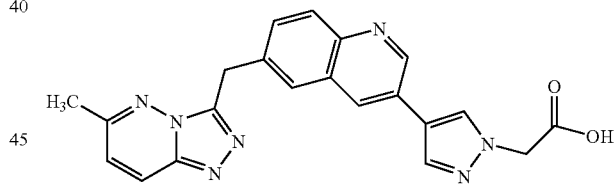
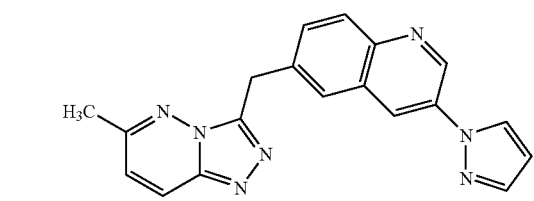
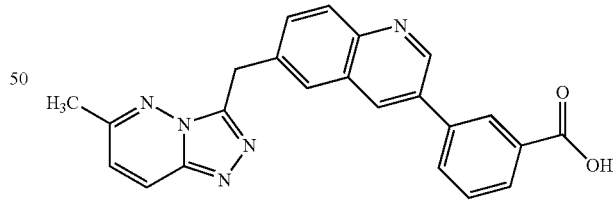
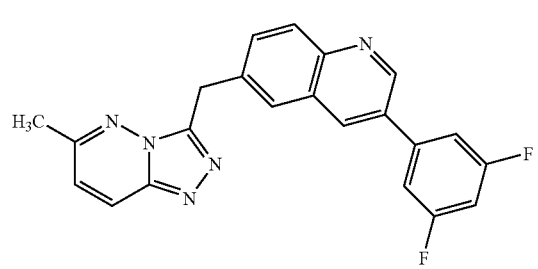
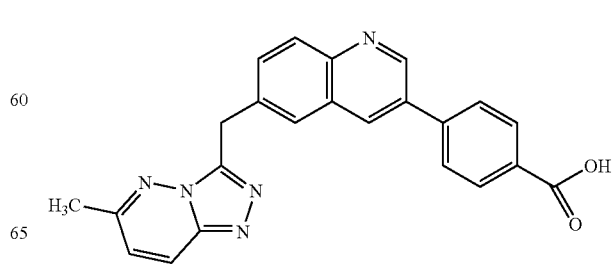

95
-continued
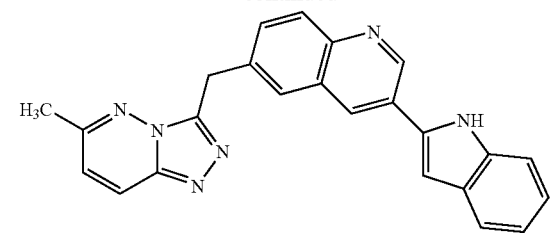
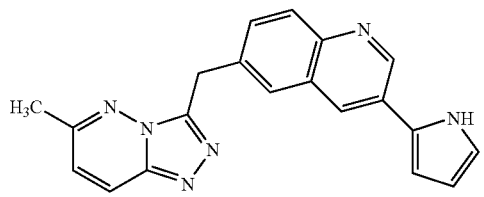
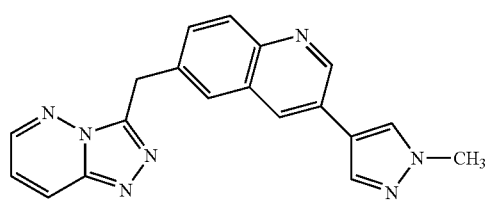
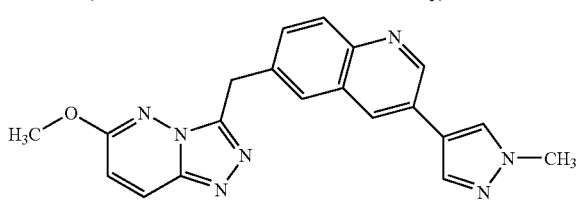
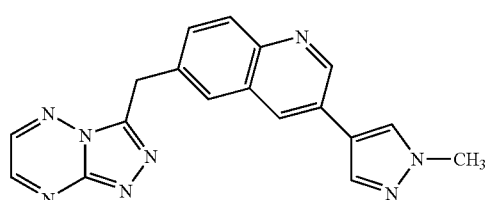
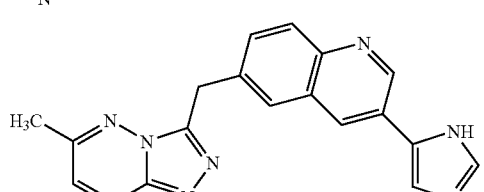
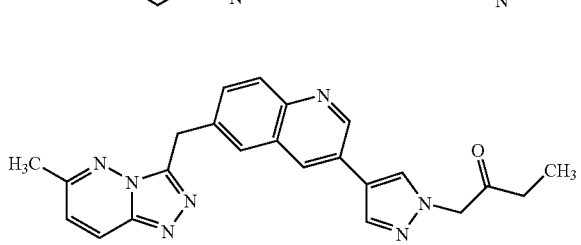
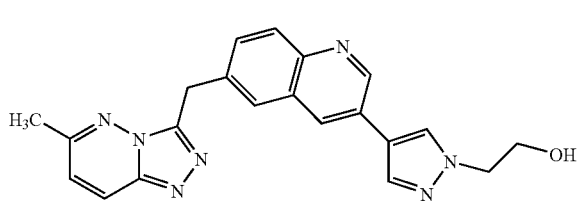
96
-continued
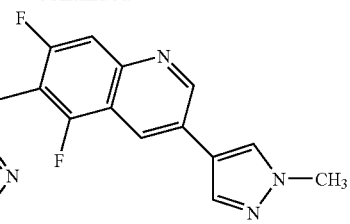
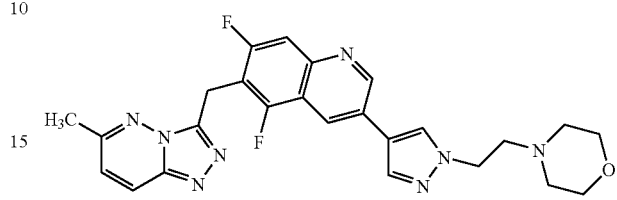
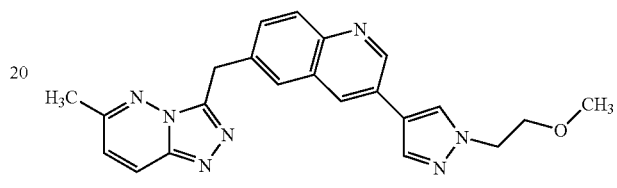
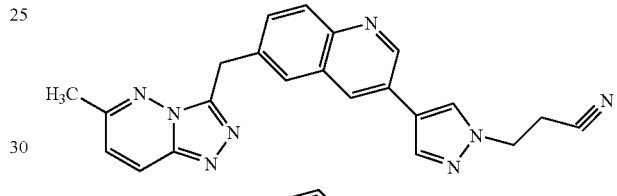
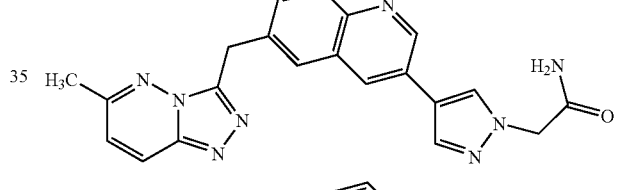
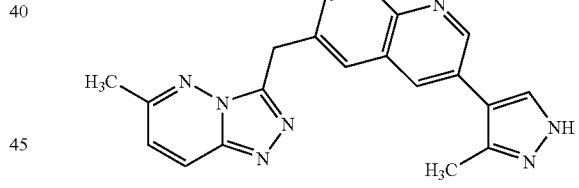
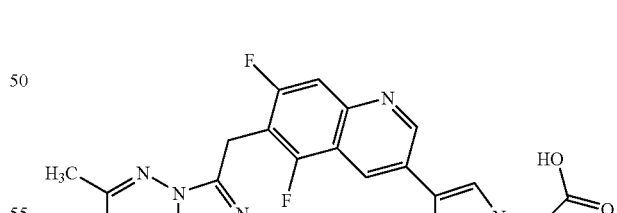
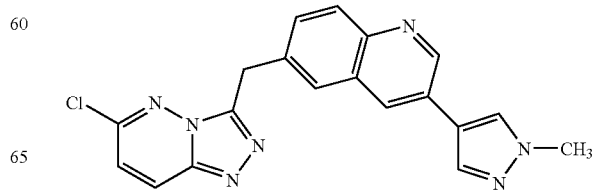

97
-continued
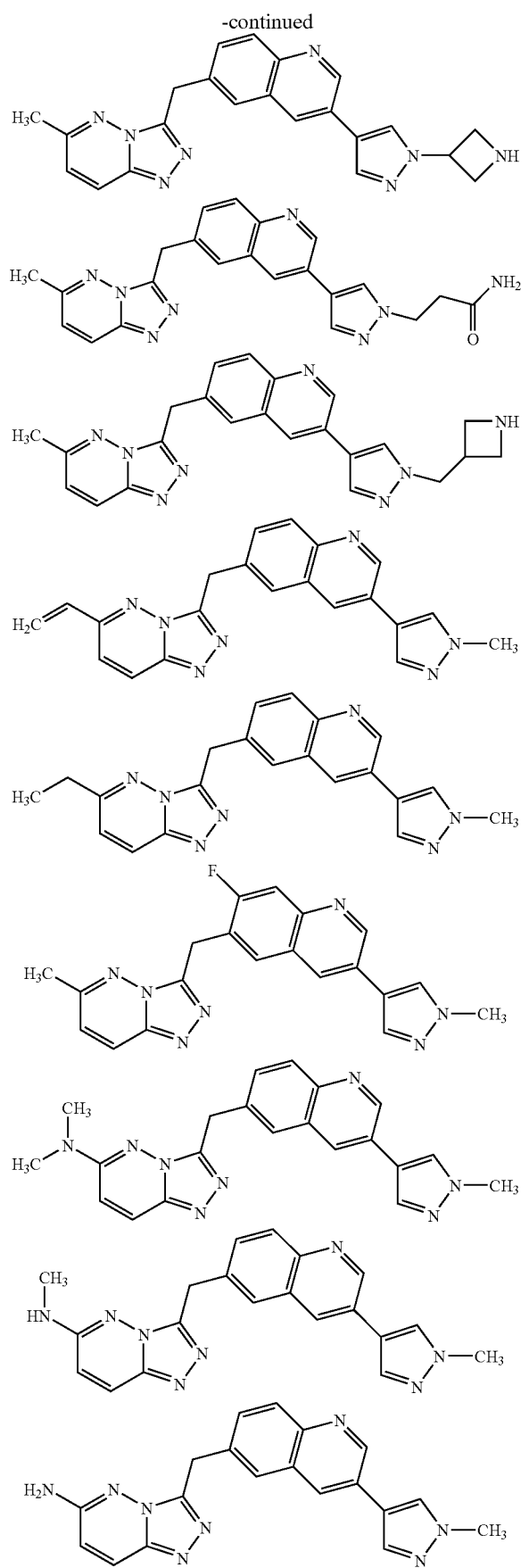
98
-continued
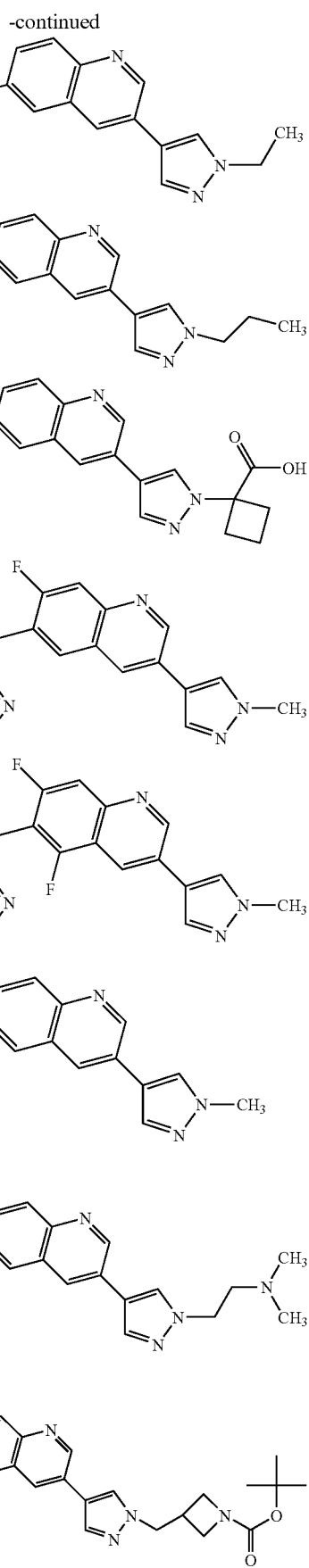

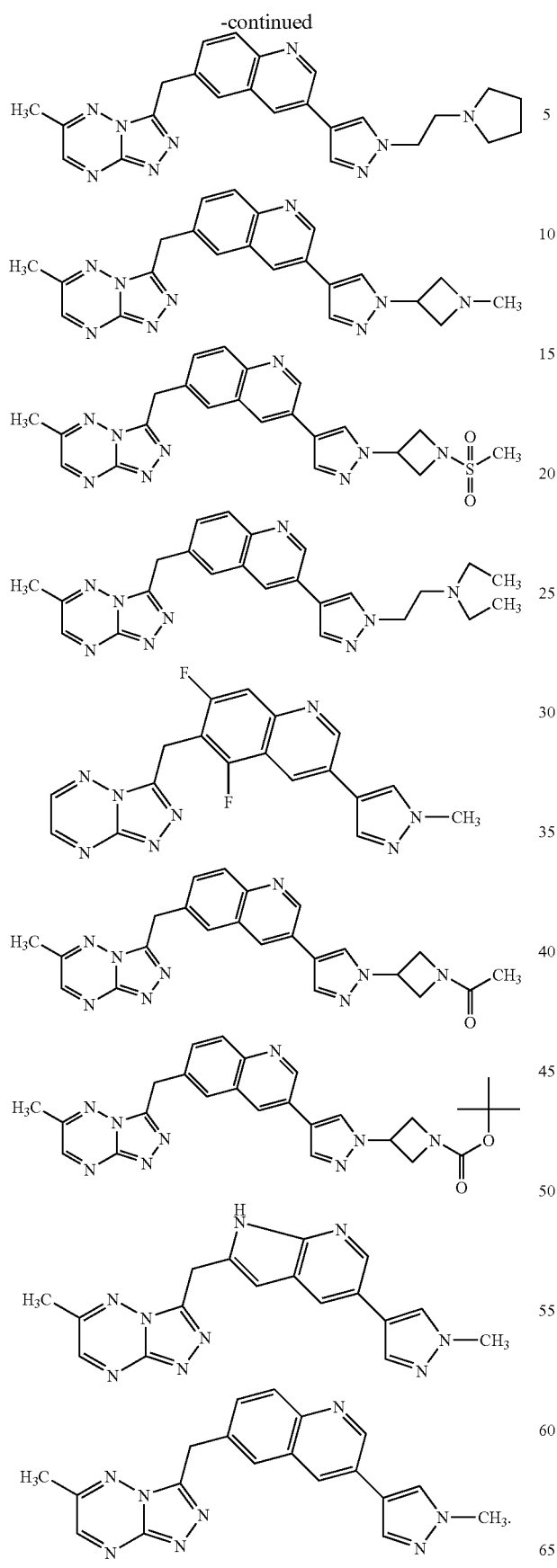
In another aspect, the disclosure provides compounds having formula:
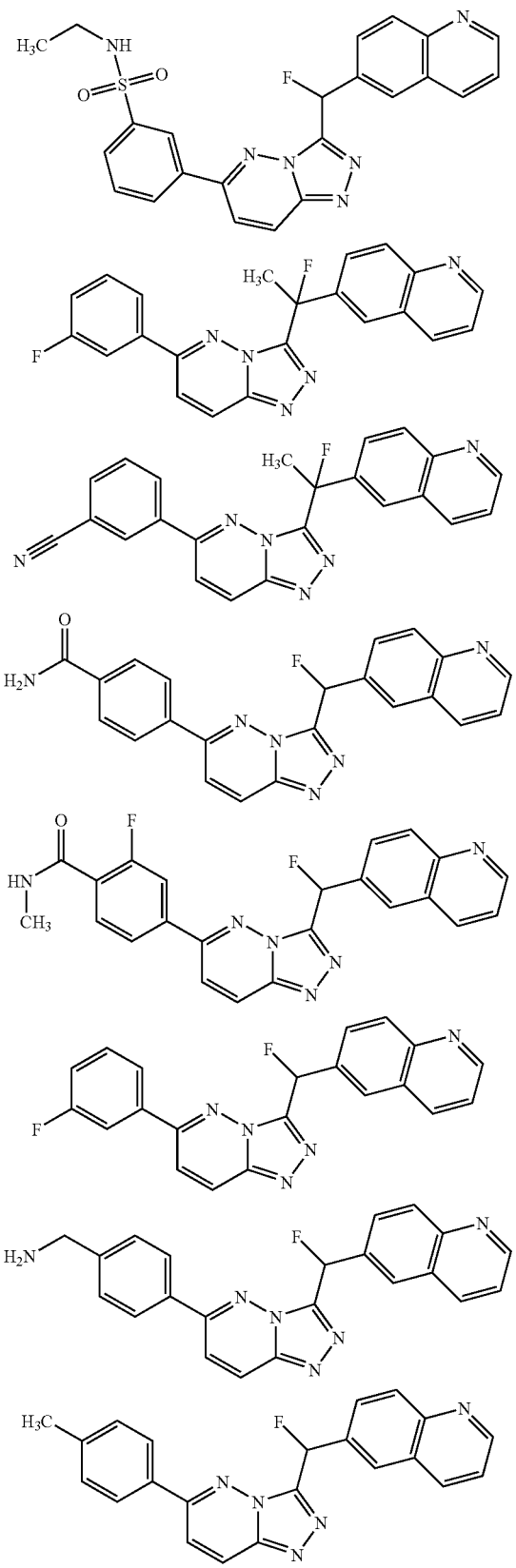

101
-continued
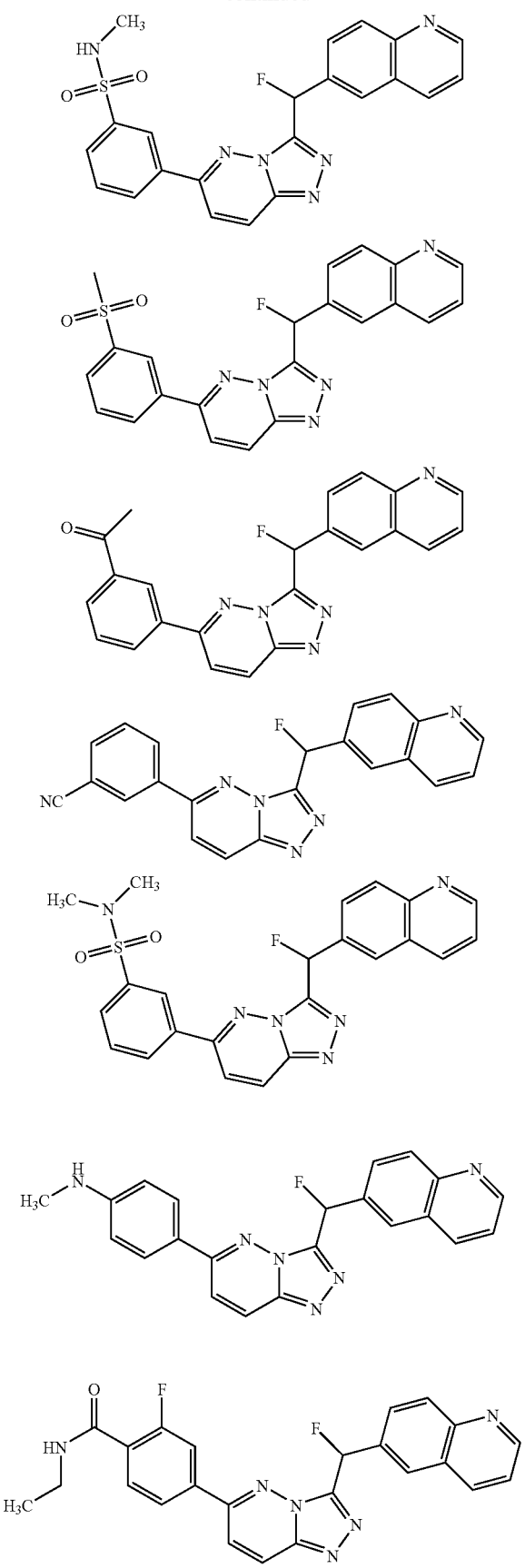
102
-continued
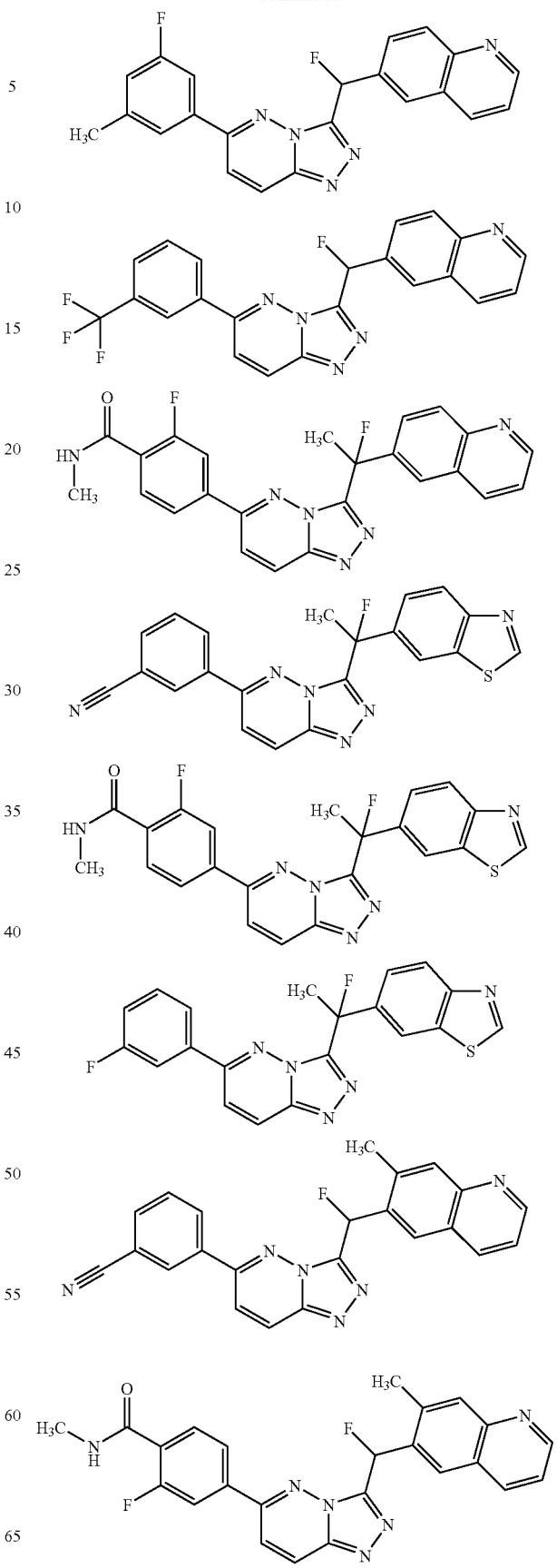

103
-continued
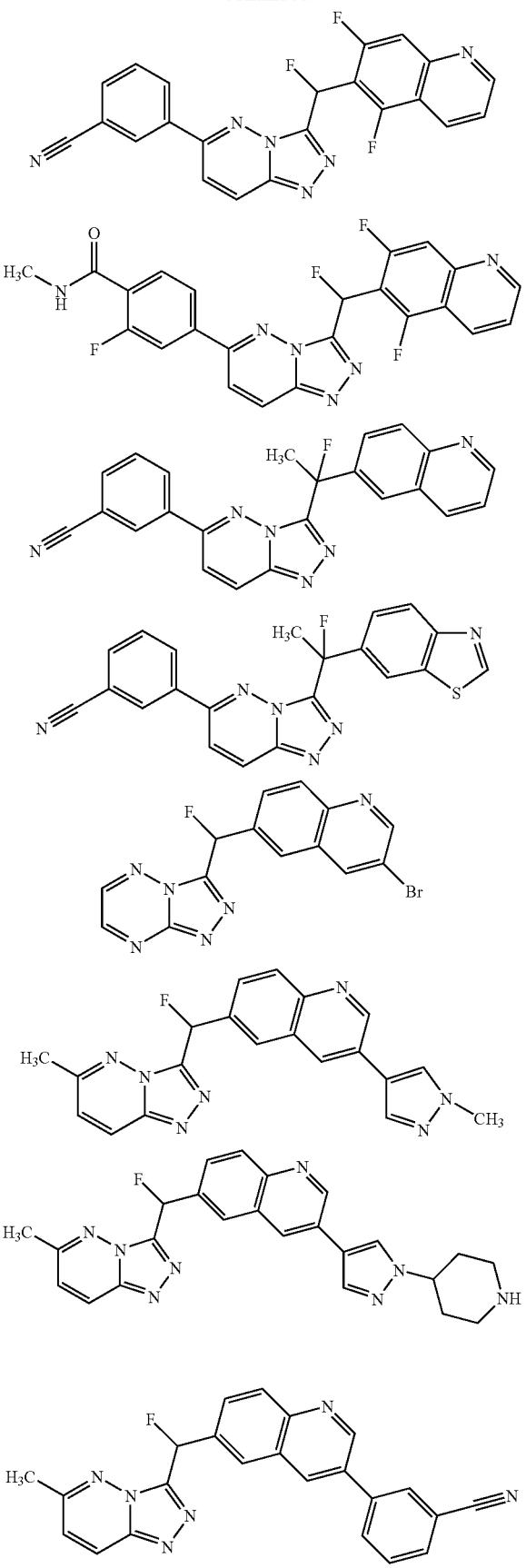
104
-continued
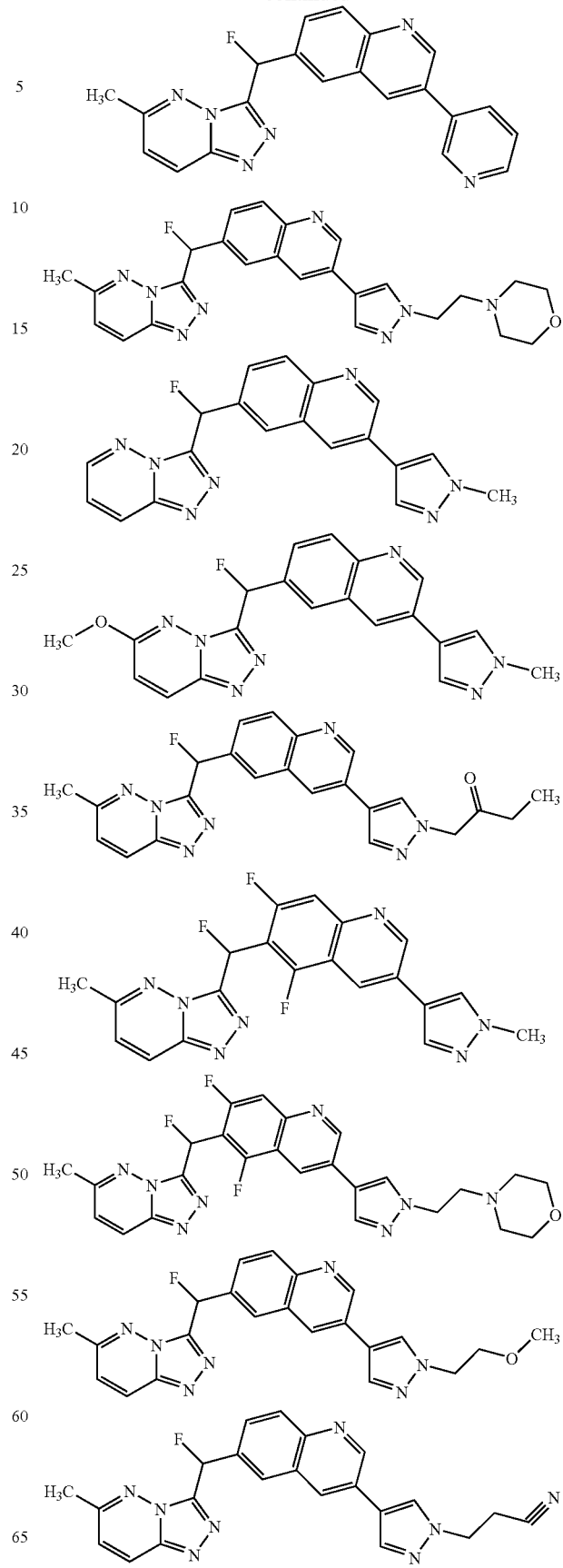

105
-continued

106
-continued

In another aspect, the disclosure provides compounds having formula:
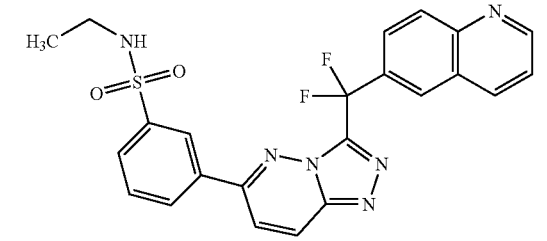
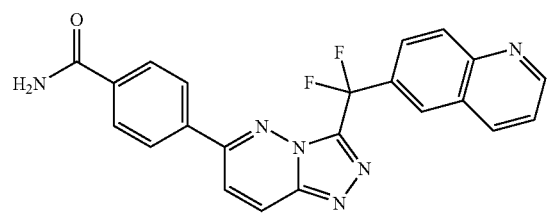
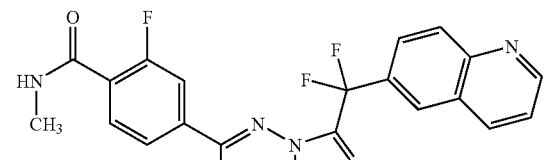
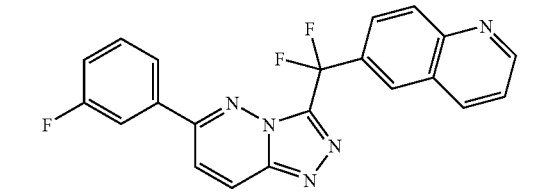
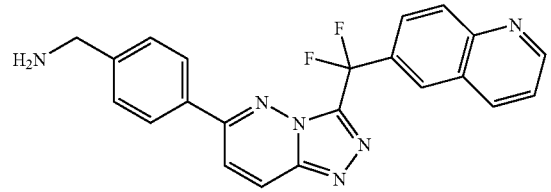
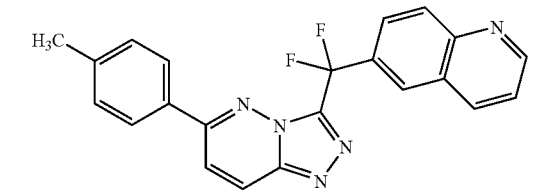
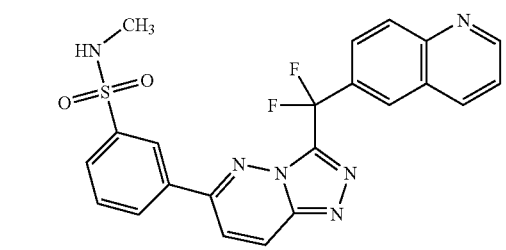
-continued
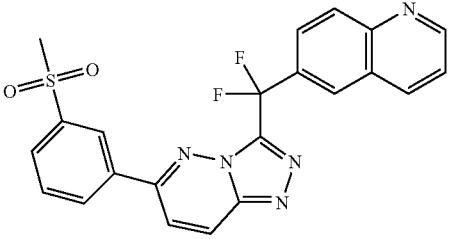
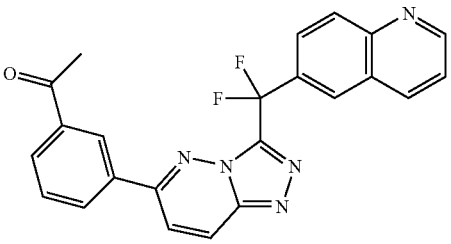
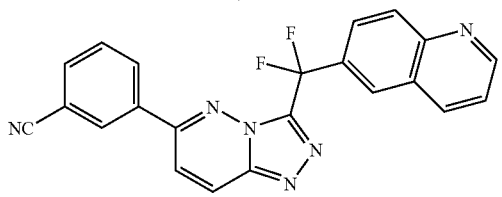
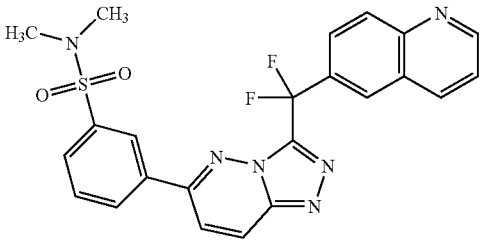
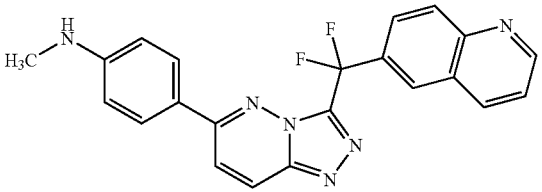
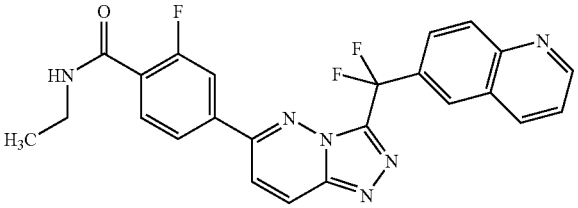
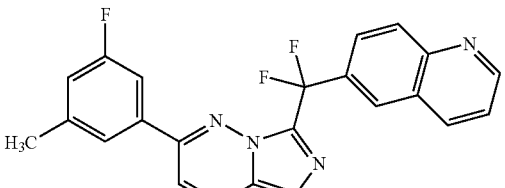
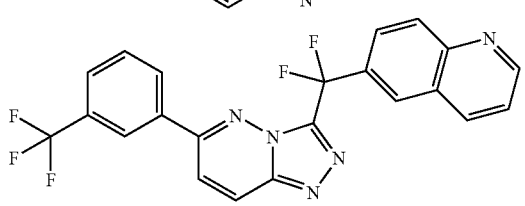

-continued

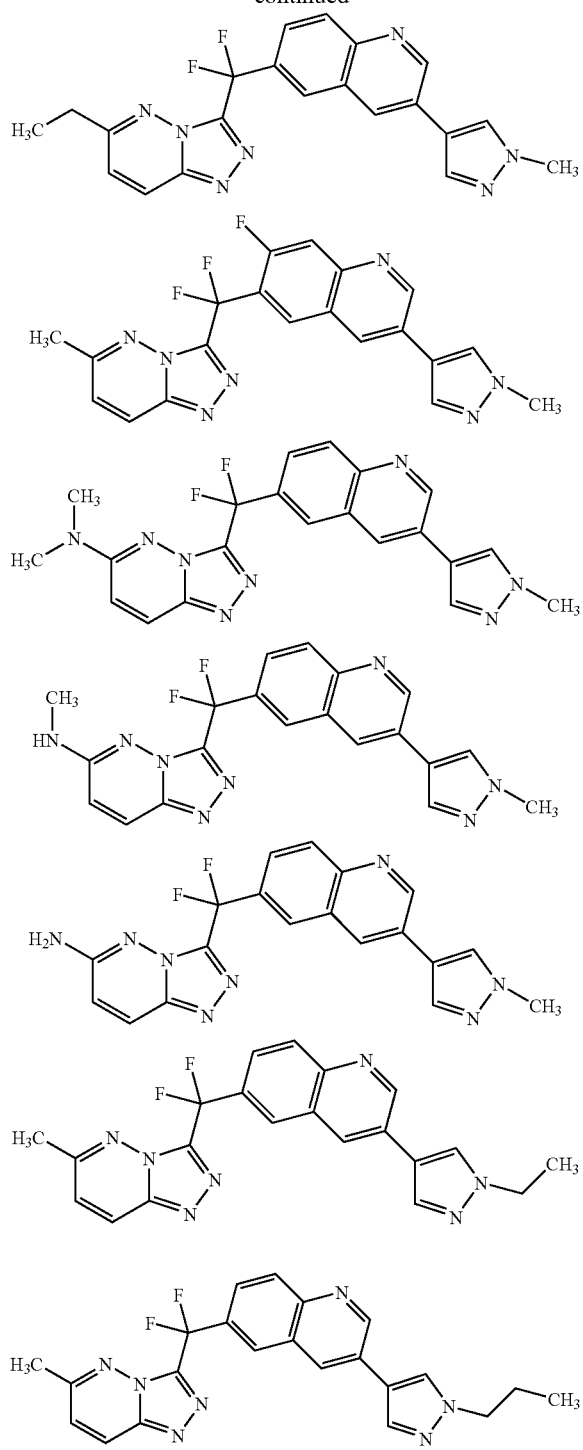

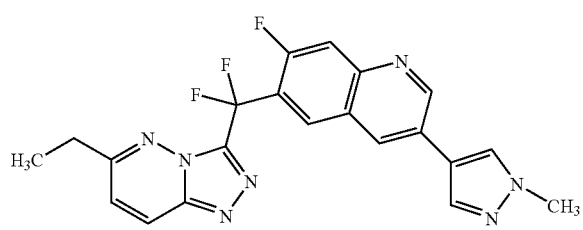

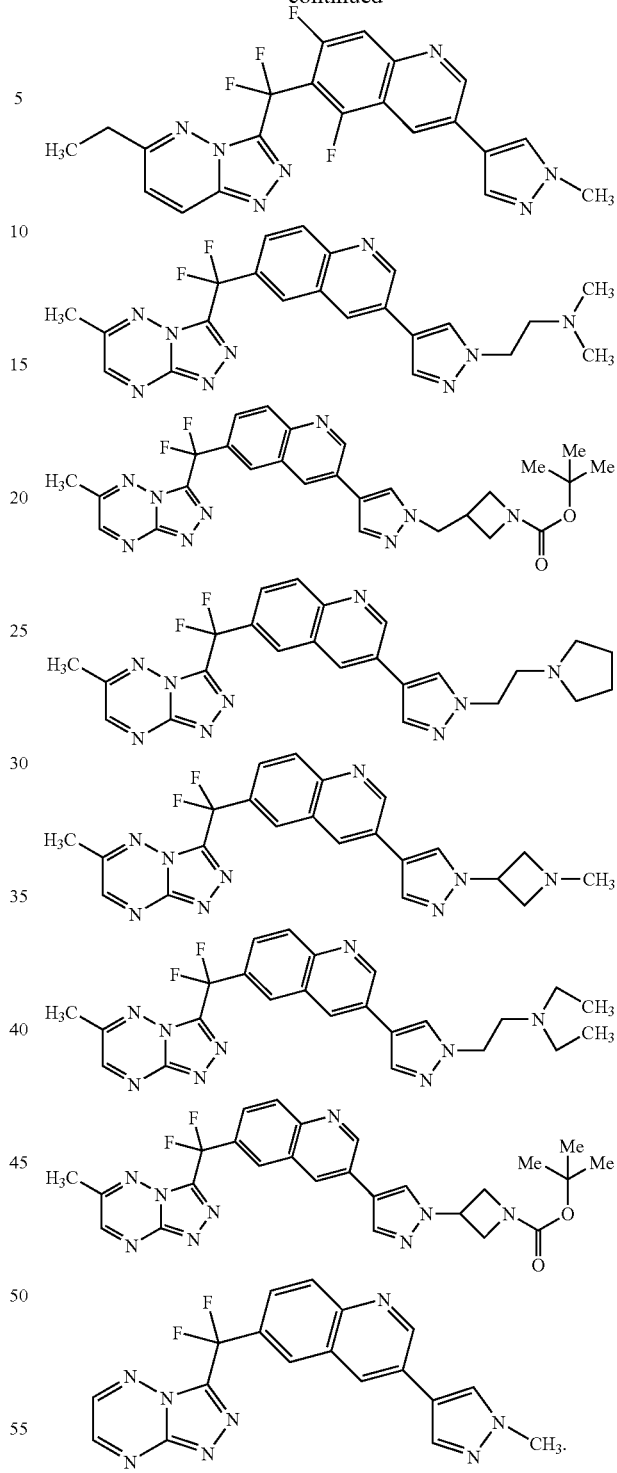

In another aspect, the disclosure provides methods for modulating the activity of a protein kinase comprising contacting the protein kinase with any of the disclosed compounds.

In another aspect, the disclosure provides methods for modulating the activity of a protein kinase comprising contacting the protein kinase with any of the disclosed compounds, wherein the protein kinase is Ron receptor tyrosine kinase, Met receptor tyrosine kinase, ALK receptor tyrosine kinase, MER receptor tyrosine kinase, Tyro3/Sky receptor tyrosine kinase, AXL receptor tyrosine kinase, TRKC receptor tyrosine kinase, ROS receptor tyrosine kinase, CSF1R/FMS receptor tyrosine kinase, BRAF kinase, or Raf1 kinase.

In another aspect, the disclosure provides methods for modulating the activity of a protein kinase comprising contacting the protein kinase with any of the disclosed compounds, wherein the protein kinase is Met receptor tyrosine kinase.

In another aspect, the disclosure provides methods for treating cancer in a human patient in need of such treatment, by administering to the patient a therapeutically effective amount of a compound of any of the disclosed compounds.

In another aspect, the disclosure provides pharmaceutical compositions having any of the disclosed compounds and a pharmaceutically acceptable excipient.

In another aspect, the disclosure provides methods for preparing any of the disclosed compounds, by:

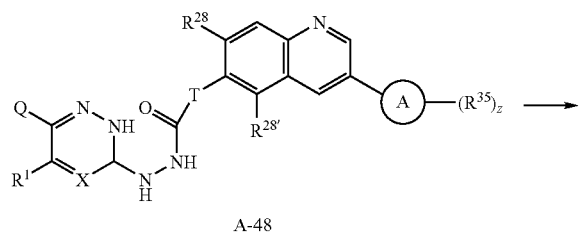

A-48

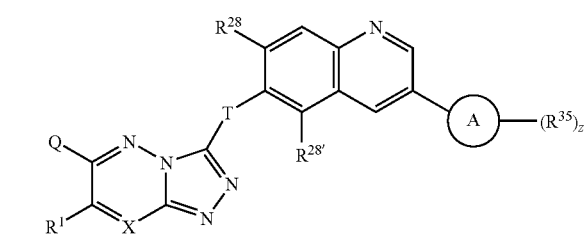

a) cyclodehydrating the compound A-48 under acidic or dehydration conditions.

In another aspect, the disclosure provides methods for preparing any of the disclosed compounds, by a) cyclodehydrating the compound A-48 under acidic or dehydration conditions, wherein the acidic condition is acetic acid, POCl₃ or trifluoromethanesulfonic acid.

In another aspect, the disclosure provides methods for preparing any of the disclosed compounds, by:

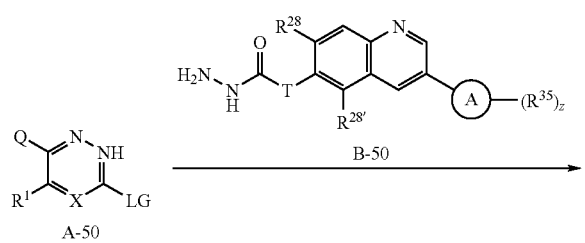

A-50

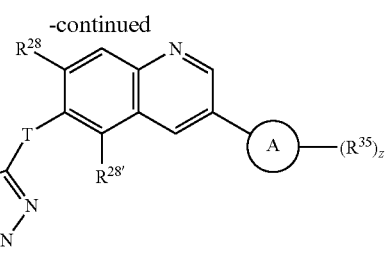

-continued a) coupling the compound of formula A-50 with the compound of formula B-50 in a solvent, wherein LG is halogen or triflate.

In another aspect, the disclosure provides methods for preparing any of the disclosed compounds, by a) coupling the compound of formula A-50 with the compound of formula B-50 in a solvent, wherein LG is halogen or triflate, and wherein the solvent is an alcohol.

In another aspect, the disclosure provides methods for preparing any of the disclosed compounds, by:

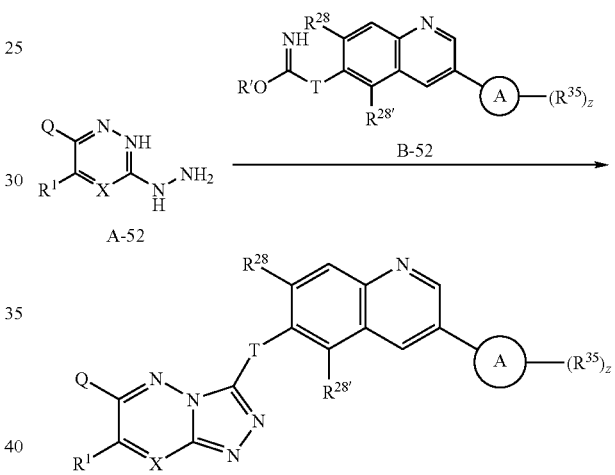

a) condensing the compound of formula A-52 with the compound of formula B-52, wherein R' is $C_1$-$C_6$ alkyl.

Exemplary Syntheses

The compounds of the disclosure are synthesized by an appropriate combination of generally well known synthetic methods. Techniques useful in synthesizing the compounds of the disclosure are both readily apparent and accessible to those of skill in the relevant art. The discussion below is offered to illustrate certain of the diverse methods available for use in assembling the compounds of the disclosure. However, the discussion is not intended to define the scope of reactions or reaction sequences that are useful in preparing the compounds of the present disclosure. The compounds of this disclosure may be made by the procedures and techniques disclosed in the Examples section below, as well as by known organic synthesis techniques.

Protecting Groups

The compounds of the present disclosure may be synthesized using one or more protecting groups generally known in the art of chemical synthesis. The term "protecting group" refers to chemical moieties that block some or all reactive moieties of a compound and prevent such moieties from participating in chemical reactions until the protective group is removed, for example, those moieties listed and described in Greene, et al., Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking or protecting groups include, for example:

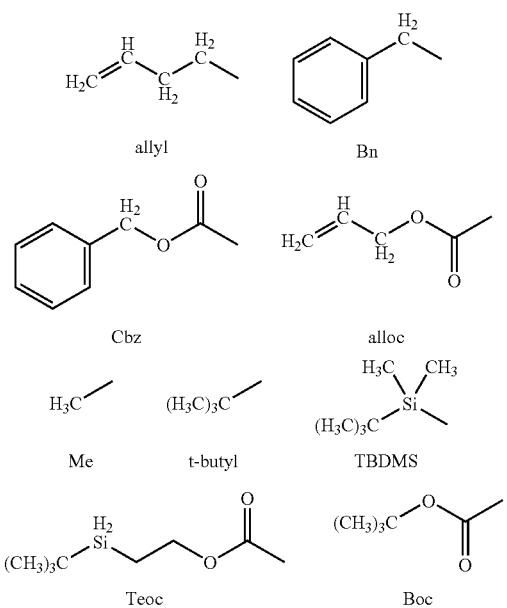

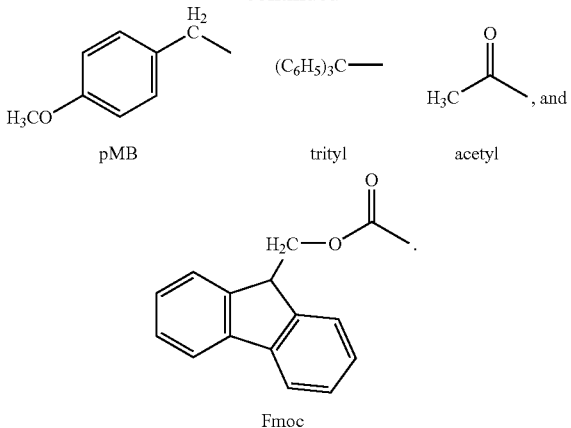

Methods of Inhibiting Kinases

In another aspect, the present disclosure relates to methods of modulating protein kinase activity using the triazalopyridazine kinase modulators of the present disclosure. The term "modulating kinase activity," as used herein, means that the activity of the protein kinase is increased or decreased when contacted with a triazalopyridazine kinase modulator of the present disclosure relative to the activity in the absence of the triazalopyridazine kinase modulator. Therefore, the present disclosure relates to a method of modulating protein kinase activity by contacting the protein kinase with a triazalopyridazine kinase modulator of the present disclosure.

In an exemplary embodiment, the triazalopyridazine kinase modulator inhibits kinase activity. The term "inhibit," as used herein inreference to kinase activity, means that the kinase activity is decreased when contacted with a triazalopyridazine kinase modulator relative to the activity in the absence of the triazalopyridazine kinase modulator. Therefore, the present disclosure further relates to a method of inhibiting protein kinase activity by contacting the protein kinase with a triazalopyridazine kinase modulator of the present disclosure.

In certain embodiments, the protein kinase is a protein tyrosine kinase. A protein tyrosine kinase, as used herein, refers to an enzyme that catalyzes the phosphorylation of tyrosine residues in proteins with a phosphate donors (e.g. a nucleotide phosphate donor such as ATP). Protein tyrosine kinases include, for example, Abelson tyrosine kinases ("Abl") (e.g. c-Abl and v-Abl), Ron receptor tyrosine kinases ("RON"), Met receptor tyrosine kinases ("MET"), Fms-like tyrosine kinases ("FLT") (e.g. FLT3), src-family tyrosine kinases (e.g. lyn, CSK), and p21-activated kinase-4 ("PAK"), FLT3, aurora-A kinases, B-lymphoid tyrosine kinases ("Blk"), cyclin-dependent kinases ("CDK") (e.g. CDK1 and CDK5), src-family related protein tyrosine kinases (e.g. Fyn kinase), glycogen synthase kinases ("GSK") (e.g. GSK3α and GSK3β), lymphocyte protein tyrosine kinases ("Lck"), ribosomal S6 kinases (e.g. Rsk1, Rsk2, and Rsk3), sperm tyrosine kinases (e.g. Yes), and subtypes and homologs thereof exhibiting tyrosine kinase activity.

In certain embodiments, the protein kinase is a Met receptor tyrosine kinase.

In another embodiment, the kinase is a mutant kinase, such as a mutant MET. Useful mutant MET kinases include, for example, MET kinases having mutations, including insertions and deletions, in the extracellular or transmembrane domains, or in the cytoplasmic domain, including one of more of the following mutations: Ser1058Pro, Val1110Ile, His1112Tyr, His1124Asp, Met1149Thr, Val1206Leu, or Met1268Thr.

MET kinases include, for example, MET kinases having mutations, including insertions and deletions, in the extracellular or transmembrane domains, or in the cytoplasmic domain, including one of more of the following mutations: Ser1058Pro, Val1110Ile, His1112Tyr, His1124Asp, Met1149Thr, Val1206Leu, or Met1268Thr.

In some embodiments, the kinase is homologous to a known kinase (also referred to herein as a "homologous kinase"). Compounds and compositions useful for inhibiting the biological activity of homologous kinases may be initially screened, for example, in binding assays. Homologous enzymes comprise an amino acid sequence of the same length that is at least 50%, at least 60%, at least 70%, at least 80%, or at least 90% identical to the amino acid sequence of full length known kinase, or 70%, 80%, or 90% homology to the known kinase active domains. Homology may be determined using, for example, a PSI BLAST search, such as, but not limited to that described in Altschul, et al., *Nuc. Acids Rec.* 25:3389-3402 (1997). In certain embodiments, at least 50%, or at least 70% of the sequence is aligned in this analysis. Other tools for performing the alignment include, for example, DbClustal and ESPript, which may be used to generate the PostScript version of the alignment. See Thompson et al., *Nucleic Acids Research*, 28:2919-26, 2000; Gouet, et al., *Bioinformatics*, 15:305-08 (1999). Homologs may, for example, have a BLAST E-value of $1 \times 10^{-6}$ over at least 100 amino acids (Altschul et al., *Nucleic Acids Res.*, 25:3389-402 (1997) with FLT3, Abl, or another known kinase, or any functional domain of FLT3, Abl, or another known kinase.

Homology may also be determined by comparing the active site binding pocket of the enzyme with the active site binding pockets of a known kinase. For example, in homologous enzymes, at least 50%, 60%, 70%, 80%, or 90% of the amino acids of the molecule or homolog have amino acid structural coordinates of a domain comparable in size to the kinase domain that have a root mean square deviation of the alpha carbon atoms of up to about 1.5 Å, about 1.25 Å, about 1 Å, about 0.75 Å, about 0.5 Å, and or about 0.25 Å.

The compounds and compositions of the present disclosure are useful for inhibiting kinase activity and also for inhibiting other enzymes that bind ATP. They are thus useful for the treatment of diseases and disorders that may be alleviated by inhibiting such ATP-binding enzyme activity. Methods of determining such ATP binding enzymes include those known to those of skill in the art, those discussed herein relating to selecting homologous enzymes, and by the use of the database PROSITE, where enzymes containing signatures, sequence patterns, motifs, or profiles of protein families or domains may be identified.

The compounds of the present disclosure, and their derivatives, may also be used as kinase-binding agents. As binding agents, such compounds and derivatives may be bound to a stable resin as a tethered substrate for affinity chromatography applications. The compounds of this disclosure, and their derivatives, may also be modified (e.g., radiolabelled or affinity labelled, etc.) in order to utilize them in the investigation of enzyme or polypeptide characterization, structure, and/or function.

In an exemplary embodiment, the triazalopyridazine kinase modulator of the present disclosure is a kinase inhibitor. In some embodiments, the kinase inhibitor has an $IC_{50}$ of inhibition constant ($K_i$) of less than 1 micromolar. In another embodiment, the kinase inhibitor has an $IC_{50}$ or inhibition constant ($K_i$) of less than 500 micromolar. In another embodiment, the kinase inhibitor has an $IC_{50}$ or $K_i$ of less than 10 micromolar. In another embodiment, the kinase inhibitor has an $IC_{50}$ or $K_i$ of less than 1 micromolar. In another embodiment, the kinase inhibitor has an $IC_{50}$ or $K_i$ of less than 500 nanomolar. In another embodiment, the kinase inhibitor has an $IC_{50}$ or $K_i$ of less than 10 nanomolar. In another embodiment, the kinase inhibitor has an $IC_{50}$ or $K_i$ of less than 1 nanomolar.

Methods of Treatment

In another aspect, the present disclosure relates to methods of treating a disease mediated by kinase activity (kinase-mediated disease or disorder) in an organism (e.g. mammals, such as humans). By "kinase-mediated" or "kinase-associated" diseases is meant diseases in which the disease or symptom can be alleviated by inhibiting kinase activity (e.g. where the kinase is involved in signaling, mediation, modulation, or regulation of the disease process). By "diseases" is meant diseases, or disease symptoms.

Examples of kinase associated diseases include cancer (e.g. leukemia, tumors, and metastases), allergy, asthma, inflammation (e.g. inflammatory airways disease), obstructive airways disease, autoimmune diseases, metabolic diseases, infection (e.g. bacterial, viral, yeast, fungal), CNS diseases, brain tumors, degenerative neural diseases, cardiovascular diseases, and diseases associated with angiogenesis, neovascularization, and vasculogenesis. In an exemplary embodiment, the compounds are useful for treating cancer, including leukemia, and other diseases or disorders involving abnormal cell proliferation, myeloproliferative disorders, hematological disorders, asthma, inflammatory diseases or obesity.

More specific examples of cancers treated with the compounds of the present disclosure include breast cancer, lung cancer, melanoma, colorectal cancer, bladder cancer, ovarian cancer, prostate cancer, renal cancer, squamous cell cancer, glioblastoma, pancreatic cancer, leiomyosarcoma, multiple myeloma, papillary renal cell carcinoma, gastric cancer, liver cancer, head and neck cancer, melanoma, and leukemia (e.g. myeloid, chronic myeloid, acute lymphoblastic, chronic lymphoblastic, Hodgkins, and other leukemias and hematological cancers).

Other specific examples of diseases or disorders for which treatment by the compounds or compositions of the disclosure are useful for treatment or prevention include, but are not limited to transplant rejection (for example, kidney, liver, heart, lung, islet cells, pancreas, bone marrow, cornea, small bowel, skin allografts or xenografts and other transplants), graft vs. host disease, osteoarthritis, rheumatoid arthritis, multiple sclerosis, diabetes, diabetic retinopathy, inflammatory bowel disease (for example, Crohn's disease, ulcerative colitis, and other bowel diseases), renal disease, cachexia, septic shock, lupus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, ocular disease, retinopathies (for example, macular degeneration, diabetic retinopathy, and other retinopathies), corneal disease, glaucoma, infections (for example bacterial, viral, or fungal), heart disease, including, but not limited to, restenosis.

Combination Therapy

In another aspect, the disclosure provides a combination therapy for treating or inhibiting the onset of a cell proliferative disorder or a disorder related to c-Met in a subject. The combination therapy comprises administering to the subject a therapeutically or prophylactically effective amount of a compound of Formula I, and one or more other anti-cell proliferation therapy including chemotherapy, radiation therapy, gene therapy and immunotherapy.

In another aspect, the compounds of the disclosure may be administered in combination with chemotherapy. As used herein, chemotherapy refers to a therapy involving a chemotherapeutic agent. A variety of chemotherapeutic agents may be used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine) alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracylines (e.g. idarubicin, actinomycin D, bleomycin, daunorubicin, doxorubicin, mitomycin C, dactinomycin, caminomycin, daunomycin); antimetabolites (e.g., clofarabine, aminopterin, cytosine arabinoside, methotrexate); tubulin-binding agents (e.g. combretastatin, colchicine, nocodazole); topoisomerase inhibitors (e.g., camptothecin); differentiating agents (e.g., retinoids, vitamin D and retinoic acid); retinoic acid metabolism blocking agents (RAMBA) (e.g., accutane); kinase inhibitors (e.g., flavoperidol, imatinib mesylate, gefitinib, erlotinib, sunitinib, lapatinib, sorafinib, temsirolimus, dasatinib); farnesyltransferase inhibitors (e.g., tipifarnib); histone deacetylase inhibitors; inhibitors of the ubiquitin-proteasome pathway (e.g., bortezomib, Yondelis).

Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. December 1985; 6(6): 449-67. Additionally, yet to emerge chemotherapeutic agents are contemplated as being useful in combination with the compound of the present disclosure.

In another aspect, the disclosure provides compounds which may be administered in combination with radiation therapy. As used herein, "radiation therapy" refers to a therapy comprising exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another aspect, the disclosure provides compounds which may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other aspect, the disclosure provides compounds which may be administered in combination with an immunotherapy.

As used herein, "immunotherapy" refers to a therapy targeting particular protein involved in tumor development via antibodies specific to such protein. For example, monoclonal antibodies against vascular endothelial growth factor have been used in treating cancers.

Where a second pharmaceutical is used in addition to a compound of the disclosure, the two pharmaceuticals may be administered simultaneously (e.g. in separate or unitary compositions) sequentially in either order, at approximately the same time, or on separate dosing schedules. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular chemotherapeutic agent being administered in conjunction with the compound of the present invention, their route of administration, the particular tumor being treated and the particular host being treated.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

By way of example only, camptothecin compounds are advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

By way of example only, vinca alkaloids may be advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

By way of example only, anti-tumor nucleoside derivatives may be advantageously administered in a dosage of 200 to 2500 mg per square meter ($mg/m^2$) of body surface area, for example 700 to 1500 $mg/m^2$. 5-fluorouracil (5-FU) is commonly used via intravenous administration with doses ranging from 200 to 500 $mg/m^2$ (preferably from 3 to 15 mg/kg/day). Gemcitabine is advantageously administered in a dosage of about 800 to 1200 $mg/m^2$ and capecitabine is advantageously administered in about 1000 to 2500 $mg/m^2$ per course of treatment.

By way of example only, alkylating agents may be advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg of body weight, for carmustine in a dosage of about 150 to 200 mg/m$^2$, and for lomustine in a dosage of about 100 to 150 mg/m$^2$ per course of treatment.

By way of example only, podophyllotoxin derivatives may be advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

By way of example only, anthracycline derivatives may be advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter (mg/m$^2$) of body surface area, or as known in the art, if different. For example, trastuzumab is advantageously administered in a dosage of 1 to 5 mg/m$^2$ particularly 2 to 4 mg/m$^2$ per course of treatment.

Dosages may be administered, for example once, twice or more per course of treatment, which may be repeated for example every 7, 14, 21 or 28 days.

The compounds of the present disclosure can be administered to a subject systemically, for example, intravenously, orally, subcutaneously, intramuscular, intradermal, or parenterally. The compounds of the present invention can also be administered to a subject locally. Non-limiting examples of local delivery systems include the use of intraluminal medical devices that include intravascular drug delivery catheters, wires, pharmacological stents and endoluminal paving.

The compounds of the present disclosure can further be administered to a subject in combination with a targeting agent to achieve high local concentration of the compound at the target site. In addition, the compounds of the present invention may be Formulated for fast-release or slow-release with the objective of maintaining the drugs or agents in contact with target tissues for a period ranging from hours to weeks.

Pharmaceutical Compositions and Administration

In another aspect, the present disclosure relates to a pharmaceutical composition including a triazalopyridazine kinase modulator in admixture with a pharmaceutically acceptable excipient. One of skill in the art will recognize that the pharmaceutical compositions include the pharmaceutically acceptable salts of the triazalopyridazine kinase modulators described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

According to another aspect, the disclosure provides pharmaceutical compositions including compounds of formula I, and a pharmaceutically acceptable carrier, adjuvant, or vehicle. The amount of compound in the compositions of the disclosure is such that is effective to detectably inhibit a protein kinase, particularly c-Met in a biological sample or in a patient.

As used herein, the term "c-Met" is synonymous with "cMet", "MET", "Met" or other designations known to one skilled in the art. In one aspect, a composition of the present disclosure is formulated for administration to a patient in need of such composition. In another aspect, the composition of the disclosure is formulated for oral administration to a patient.

The compounds according to the disclosure are effective over a wide dosage range. For example, in the treatment of adult humans, dosages from 0.01 to 10,000 mg, from 0.5 to 1000 mg, from 1 to 500 mg per day, and from 5 to 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra sternal, intrasynovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other anti-proliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this disclosure may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The present disclosure is not to be limited in scope by the exemplified embodiments, which are intended as illustrations of single aspects of the disclosure. Indeed, various modifications of the disclosure in addition to those described herein will become apparent to those having skill in the art from the foregoing description. Such modifications are intended to fall within the scope of the disclosure. Moreover, any one or more features of any embodiment of the disclosure may be combined with any one or more other features of any other embodiment of the disclosure, without departing from the scope of the disclosure. For example, the triazalopyridazine kinase modulators described in the Triazalopyridazine Kinase Modulators section are equally applicable to the methods of treatment and methods of inhibiting kinases described herein. References cited throughout this application are examples of the level of skill in the art and are hereby incorporated by reference herein in their entirety for all purposes, whether previously specifically incorporated or not.

Assays

The compounds of the present disclosure may be easily assayed to determine their ability to modulate protein kinases, bind protein kinases, and/or prevent cell growth or proliferation. Some examples of useful assays are presented below.

Kinase Inhibition and Binding Assays

Inhibition of various kinases is measured by methods known to those of ordinary skill in the art, such as the various methods presented herein, and those discussed in the Upstate KinaseProfiler Assay Protocols June 2003 publication.

For example, where in vitro assays are performed, the kinase is typically diluted to the appropriate concentration to form a kinase solution. A kinase substrate and phosphate donor, such as ATP, is added to the kinase solution. The kinase is allowed to transfer a phosphate to the kinase substrate to form a phosphorylated substrate. The formation of a phosphorylated substrate may be detected directly by any appropriate means, such as radioactivity (e.g. [$\gamma$-$^{32}$P-ATP]), or the use of detectable secondary antibodies (e.g. ELISA). Alternatively, the formation of a phosphorylated substrate may be detected using any appropriate technique, such as the detection of ATP concentration (e.g. Kinase-Glo® assay system (Promega)). Kinase inhibitors are identified by detecting the formation of a phosphorylated substrate in the presence and absence of a test compound (see Examples section below).

The ability of the compound to inhibit a kinase in a cell may also be assayed using methods well known in the art. For example, cells containing a kinase may be contacted with an activating agent (such as a growth factor) that activates the kinase. The amount of intracellular phosphorylated substrate formed in the absence and the presence of the test compound may be determined by lysing the cells and detecting the presence phosphorylated substrate by any appropriate method (e.g. ELISA). Where the amount of phosphorylated substrate produced in the presence of the test compound is decreased relative to the amount produced in the absence of the test compound, kinase inhibition is indicated. More detailed cellular kinase assays are discussed in the Examples section below.

To measure the binding of a compound to a kinase, any method known to those of ordinary skill in the art may be used. For example, a test kit manufactured by Discoverx (Fremont, Calif.), ED-Staurosporine NSIP™ Enzyme Binding Assay Kit (see U.S. Pat. No. 5,643,734) may be used. Kinase activity may also be assayed as in U.S. Pat. No. 6,589,950, issued Jul. 8, 2003.

Suitable kinase inhibitors may be selected from the compounds of the disclosure through protein crystallographic screening, as disclosed in, for example Antonysamy, et al., PCT Publication No. WO03087816A1, which is incorporate herein by reference in its entirety for all purposes.

The compounds of the present disclosure may be computationally screened to assay and visualize their ability to bind to and/or inhibit various kinases. The structure may be computationally screened with a plurality of compounds of the present disclosure to determine their ability to bind to a kinase at various sites. Such compounds can be used as targets or leads in medicinal chemistry efforts to identify, for example, inhibitors of potential therapeutic importance (Travis, *Science*, 262:1374, 1993). The three dimensional structures of such compounds may be superimposed on a three dimensional representation of kinases or an active site or binding pocket thereof to assess whether the compound fits spatially into the representation and hence the protein. In this screening, the quality of fit of such entities or compounds to the binding pocket may be judged either by shape complementarity or by estimated interaction energy (Meng, et al., *J. Comp. Chem.* 13:505-24, 1992).

The screening of compounds of the present disclosure that bind to and/or modulate kinases (e.g. inhibit or activate kinases) according to this disclosure generally involves consideration of two factors. First, the compound must be capable of physically and structurally associating, either covalently or non-covalently with kinases. For example, covalent interactions may be important for designing irreversible or suicide inhibitors of a protein. Non-covalent molecular interactions important in the association of kinases with the compound include hydrogen bonding, ionic interactions, van der Waals, and hydrophobic interactions. Second, the compound must be able to assume a conformation and orientation in relation to the binding pocket, that allows it to associate with kinases. Although certain portions of the compound will not directly participate in this association with kinases, those portions may still influence the overall conformation of the molecule and may have a significant impact on potency. Conformational requirements include the overall three-dimensional structure and orientation of the chemical group or compound in relation to all or a portion of the binding pocket, or the spacing between functional groups of a compound comprising several chemical groups that directly interact with kinases.

Docking programs described herein, such as, for example, DOCK, or GOLD, are used to identify compounds that bind to the active site and/or binding pocket. Compounds may be screened against more than one binding pocket of the protein structure, or more than one set of coordinates for the same protein, taking into account different molecular dynamic conformations of the protein. Consensus scoring may then be used to identify the compounds that are the best fit for the protein (Charifson, P. S. et al., *J. Med. Chem.* 42: 5100-9 (1999)). Data obtained from more than one protein molecule structure may also be scored according to the methods described in Klingler et al., U.S. Utility Application, filed May 3, 2002, entitled "Computer Systems and Methods for Virtual Screening of Compounds." Compounds having the best fit are then obtained from the producer of the chemical library, or synthesized, and used in binding assays and bioassays.

Computer modeling techniques may be used to assess the potential modulating or binding effect of a chemical compound on kinases. If computer modeling indicates a strong interaction, the molecule may then be synthesized and tested for its ability to bind to kinases and affect (by inhibiting or activating) its activity.

Modulating or other binding compounds of kinases may be computationally evaluated by means of a series of steps in which chemical groups or fragments are screened and selected for their ability to associate with the individual binding pockets or other areas of kinases. This process may begin by visual inspection of, for example, the active site on the computer screen based on the kinases coordinates. Selected fragments or chemical groups may then be positioned in a variety of orientations, or docked, within an individual binding pocket of kinases (Blaney, J. M. and Dixon, J. S., *Perspectives in Drug Discovery and Design*, 1:301, 1993). Manual docking may be accomplished using software such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks, et al., *J. Comp. Chem.* 4:187-217, 1983), AMBER (Weiner, et al., *J. Am. Chem. Soc.* 106: 765-84, 1984) and $C^2$ MMFF (Merck Molecular Force Field; Accelrys, San Diego, Calif.). More automated docking may be accomplished by using programs such as DOCK (Kuntz et al., *J. Mol. Biol.*, 161:269-88, 1982; DOCK is available from University of California, San Francisco, Calif.); AUTODOCK (Goodsell & Olsen, Proteins: Structure, Function, and Genetics 8:195-

202, 1990; AUTODOCK is available from Scripps Research Institute, La Jolla, Calif.); GOLD (Cambridge Crystallographic Data Centre (CCDC); Jones et al., *J. Mol. Biol.* 245: 43-53, 1995); and FLEXX (Tripos, St. Louis, Mo.; Rarey, M., et al., *J. Mol. Biol.* 261:470-89, 1996). Other appropriate programs are described in, for example, Halperin, et al.

During selection of compounds by the above methods, the efficiency with which that compound may bind to kinases may be tested and optimized by computational evaluation. For example, a compound that has been designed or selected to function as a kinases inhibitor may occupy a volume not overlapping the volume occupied by the active site residues when the native substrate is bound, however, those of ordinary skill in the art will recognize that there is some flexibility, allowing for rearrangement of the main chains and the side chains. In addition, one of ordinary skill may design compounds that could exploit protein rearrangement upon binding, such as, for example, resulting in an induced fit. An effective kinase inhibitor may demonstrate a relatively small difference in energy between its bound and free states (i.e., it must have a small deformation energy of binding and/or low conformational strain upon binding). Thus, the most efficient kinase inhibitors should, for example, be designed with a deformation energy of binding of not greater than 10 kcal/mol, not greater than 7 kcal/mol, not greater than 5 kcal/mol, or not greater than 2 kcal/mol. Kinase inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

Specific computer software is available in the art to evaluate compound deformation energy and electrostatic interaction. Examples of programs designed for such uses include: Gaussian 94, revision C (Frisch, Gaussian, Inc., Pittsburgh, Pa. ©1995); AMBER, version 7. (Kollman, University of California at San Francisco, ©2002); QUANTA/CHARMM (Accelrys, Inc., San Diego, Calif., ©1995); Insight II/Discover (Accelrys, Inc., San Diego, Calif., ©1995); DelPhi (Accelrys, Inc., San Diego, Calif., ©1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Those of ordinary skill in the art may express kinase protein using methods known in the art, and the methods disclosed herein. The native and mutated kinase polypeptides described herein may be chemically synthesized in whole or part using techniques that are well known in the art (see, e.g., Creighton, Proteins: Structures and Molecular Principles, W.H. Freeman & Co., NY, 1983).

Gene expression systems may be used for the synthesis of native and mutated polypeptides. Expression vectors containing the native or mutated polypeptide coding sequence and appropriate transcriptional/translational control signals, that are known to those skilled in the art may be constructed. These methods include in vitro recombinant DNA techniques, synthetic techniques and in vivo recombination/genetic recombination. See, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

Host-expression vector systems may be used to express kinase. These include, but are not limited to, microorganisms such as bacteria transformed with recombinant bacteriophage DNA, plasmid DNA or cosmid DNA expression vectors containing the coding sequence; yeast transformed with recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The protein may also be expressed in human gene therapy systems, including, for example, expressing the protein to augment the amount of the protein in an individual, or to express an engineered therapeutic protein. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, one or more selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

The expression vector may also comprise various elements that affect transcription and translation, including, for example, constitutive and inducible promoters. These elements are often host and/or vector dependent. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, mammalian promoters (e.g., metallothionein promoter) or mammalian viral promoters, (e.g., adenovirus late promoter; vaccinia virus 7.5K promoter; SV40 promoter; bovine papilloma virus promoter; and Epstein-Barr virus promoter) may be used.

Various methods may be used to introduce the vector into host cells, for example, transformation, transfection, infection, protoplast fusion, and electroporation. The expression vector-containing cells are clonally propagated and individually analyzed to determine whether they produce the appropriate polypeptides. Various selection methods, including, for example, antibiotic resistance, may be used to identify host cells that have been transformed. Identification of polypeptide expressing host cell clones may be done by several means, including but not limited to immunological reactivity with anti-kinase antibodies, and the presence of host cell-associated activity.

Expression of cDNA may also be performed using in vitro produced synthetic mRNA. Synthetic mRNA can be efficiently translated in various cell-free systems, including but not limited to wheat germ extracts and reticulocyte extracts, as well as efficiently translated in cell-based systems, including, but not limited, to microinjection into frog oocytes.

To determine the cDNA sequence(s) that yields optimal levels of activity and/or protein, modified cDNA molecules are constructed. A non-limiting example of a modified cDNA is where the codon usage in the cDNA has been optimized for the host cell in which the cDNA will be expressed. Host cells are transformed with the cDNA molecules and the levels of kinase RNA and/or protein are measured.

Levels of kinase protein in host cells are quantitated by a variety of methods such as immunoaffinity and/or ligand affinity techniques, kinase-specific affinity beads or specific antibodies are used to isolate $^{35}$S-methionine labeled or unlabeled protein. Labeled or unlabeled protein is analyzed by SDS-PAGE. Unlabeled protein is detected by Western blotting, ELISA or RIA employing specific antibodies.

Following expression of kinase in a recombinant host cell, polypeptides may be recovered to provide the protein in active form. Several purification procedures are available and suitable for use. Recombinant kinase may be purified from cell lysates or from conditioned culture media, by various combinations of, or individual application of, fractionation, or chromatography steps that are known in the art.

In addition, recombinant kinase can be separated from other cellular proteins by use of an immuno-affinity column made with monoclonal or polyclonal antibodies specific for full length nascent protein or polypeptide fragments thereof. Other affinity based purification techniques known in the art may also be used.

Alternatively, the polypeptides may be recovered from a host cell in an unfolded, inactive form, e.g., from inclusion bodies of bacteria. Proteins recovered in this form may be solubilized using a denaturant, e.g., guanidinium hydrochloride, and then refolded into an active form using methods known to those skilled in the art, such as dialysis.

Cell Growth Assays

A variety of cell growth assays are known in the art and are useful in identifying triazalopyridazine compounds (i.e. "test compounds") capable of inhibiting (e.g. reducing) cell growth and/or proliferation.

For example, a variety of cells are known to require specific kinases for growth and/or proliferation. The ability of such a cell to grow in the presence of a test compound may be assessed and compared to the growth in the absence of the test compound thereby identifying the anti-proliferative properties of the test compound. One common method of this type is to measure the degree of incorporation of label, such as tritiated thymidine, into the DNA of dividing cells. Alternatively, inhibition of cell proliferation may be assayed by determining the total metabolic activity of cells with a surrogate marker that correlates with cell number. Cells may be treated with a metabolic indicator in the presence and absence of the test compound. Viable cells metabolize the metabolic indicator thereby forming a detectable metabolic product. Where detectable metabolic product levels are decreased in the presence of the test compound relative to the absence of the test compound, inhibition of cell growth and/or proliferation is indicated. Exemplary metabolic indicators include, for example tetrazolium salts and AlamorBlue® (see Examples section below).

An assay for kinases that stimulate cell migration is the scratch assay. This assay is used to evaluate inhibitors of kinases by mimicking events such as wound healing. In one variant of this assay used to test MET inhibitors, a confluent monolayer of cells is allowed to form on a cell plate. After formation of the monolayer, a linear wound on the monolayer is generated by mechanically scraping the monolayer thereby forming a cell-free channel. A growth factor required by the kinase for cell growth is added in the presence or absence of the test compound. The closure of the channel in the presence of the test compound indicates a failure of the test compound to inhibit the kinase thereby allowing cell migration and growth to close the channel. Conversely, the presence of the channel after adding the test compound indicates that test compound inhibited the kinase thereby preventing cell growth. The selection of the appropriate cells, growth conditions, and growth factors are well within the abilities of one skilled in the art (see Examples section below).

EXAMPLES

The following examples are offered to illustrate, but not to limit the claimed invention. The preparation of embodiments of the present invention is described in the following examples. Those of ordinary skill in the art will understand that the chemical reactions and synthesis methods provided may be modified to prepare many of the other compounds of the present invention. Where compounds of the present invention have not been exemplified, those of ordinary skill in the art will recognize that these compounds may be prepared by modifying synthesis methods presented herein, and by using synthesis methods known in the art.

General Method A

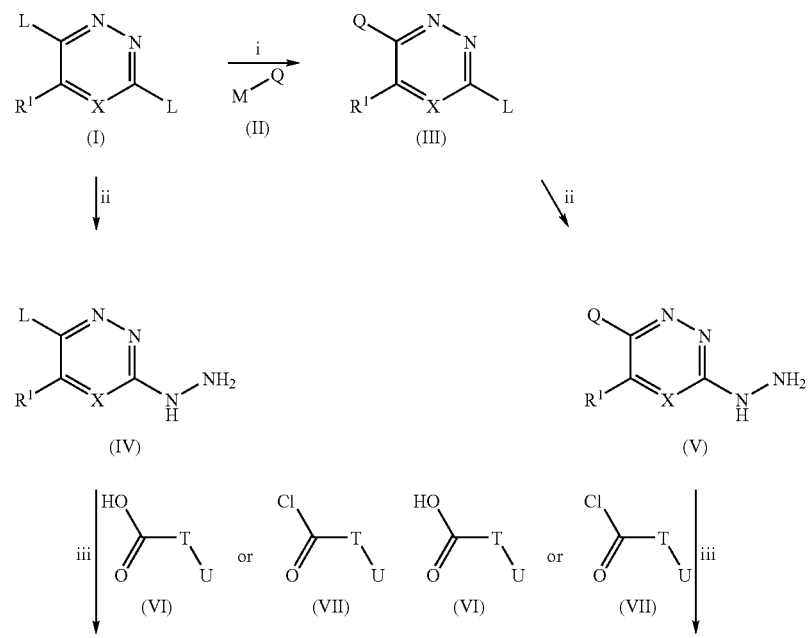

General Reaction Scheme 1

-continued

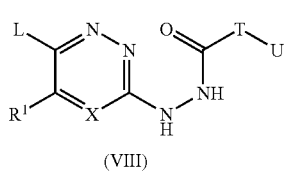

(VIII)

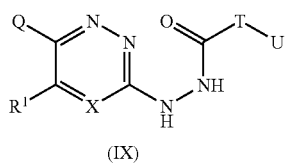

(IX)

↓iv

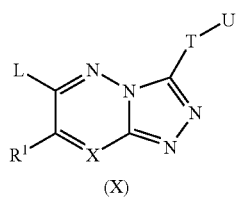

(X)

 →
M—Q
(II)

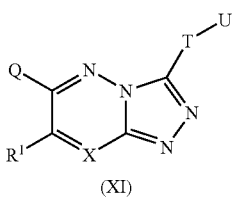

(XI)

↓v  Q

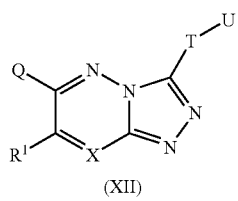

(XII)

wherein:
L is Cl, Br, OTf or I
M is zincate, boronic acid, boronic ester or stannane
U is

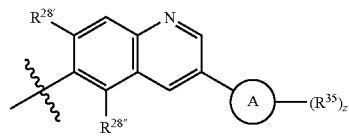

Compounds of general formula (XII) and (XI) where Q, R¹, X, T and U are described herein may be prepared according to general reaction Scheme 1. Compounds of formula (I) and (II) are either available commercially or prepared from commercial compounds using standard chemical reactions and transformations known to those skilled in the art.

Compounds of formula (III) may be prepared from compounds of general formula (I) and compounds of general formula (II) by process step (i), which comprises a catalytic C—C bond coupling reaction between a halogenated species and a metallic species. An array of catalytic C—C bond coupling reactions is available to those skilled in the art, such as Suzuki-Miyaura conditions (M=boron; Miyaura, N.; Suzuki, A. *Chem. Rev.* 1995, 95, 2457), Stille conditions (M=tin; Stille, J. W. *J. Org. Chem.* 1990, 55, 3019), or Negishi conditions (M=Zinc, Aluminum; Negishi, E. *Chem. Rev.* 1996, 96, 365). Typical Suzuki-Miyaura conditions comprise 1 equivalent of (I), 1-1.5 equivalent of (II), 1-10 mol % of a palladium catalyst, such as Pd(dppf)Cl₂, Pd(PPh₃)₂Cl₂, or Pd(PPh₃)₄, and an excess of base such as an aqueous solution of sodium or potassium carbonate, in solvents such as 1,2-dimethoxyethane or 1,4-dioxane.

Compounds of formula (IV) and (V) may be prepared from compounds of formula (I) and (III) respectively by process step (ii), which comprises a substitution reaction with hydrazine in a suitable solvent under heating or microwave conditions. Typical conditions require 1 equivalent of aryl halide (I) or (III) and 10 equivalents of hydrazine in ethanol at 80° C. for several hours.

Compounds of formula (VIII) and (IX) may be prepared from compounds of formula (IV) and (V) respectively by process step (iii), which comprises an amide bond formation with a carboxylic acid (VI) or acid chloride (VII) in the presence of a suitable coupling agent, such as 2-(1H-benzotriazole-1-yl)-1,1,3,3-tetramethyluronium hexafluorophosphate (HBTU) for the carboxylic acid (VI) or in the presence of a suitable organic scavenging base, such as triethylamine or N-methyl morpholine, for the acid chloride (VII) and both transformations occurring in a suitable solvent such as dichloromethane or dimethylformamide. An array of amide bond formation reactions are available to those skilled in the art, such as those described in 'Amino Acid and Peptide Synthesis' by John Jones published by Oxford Science Publications and references contained within.

Compounds of formula (X) and (XI) may be prepared from compounds of formula (VIII) and (IX) respectively by process step (iv), which comprises a cyclodehyration reaction to form the triazolopyridazine ring system under acidic conditions or in the presence of typical dehydration condition such as POCl$_3$ or trifluoromethanesulfonic anhydride. Typical conditions require compounds of formula (VIII) or (IX) to be heated in acetic acid for several hours.

Compounds of formula (XI) may be prepared from compounds of general formula (X) and compounds of general formula (II) by process step (i), which comprises a catalytic C—C bond coupling reaction between a halogenated species and a metallic species. An array of catalytic C—C bond coupling reactions is available to those skilled in the art, such as Suzuki-Miyaura conditions (M=boron; Miyaura, N.; Suzuki, A. *Chem. Rev.* 1995, 95, 2457), Stille conditions (M=tin; Stille, J. W. *J. Org. Chem.* 1990, 55, 3019), or Negishi conditions (M=Zinc, Aluminum; Negishi, E. *Chem. Rev.* 1996, 96, 365). Typical Suzuki-Miyaura conditions comprise 1 equivalent of (X), 1-1.5 equivalent of (II), 1-10 mol % of a palladium catalyst, such as Pd(dppf)Cl$_2$, Pd(PPh$_3$)$_2$Cl$_2$, or Pd(Ph$_3$)$_4$, and an excess of base such as an aqueous solution of sodium or potassium carbonate, in solvents such as 1,2-dimethoxyethane or 1,4-dioxane.

Compounds of formula (XII) may be prepared from compounds of general formula (X) by process step (v), which comprises a displacement reaction with a nucleophile such as mono or di-substituted amine, alcohol or phenol in a suitable solvent under heating or microwave conditions. Typical conditions require heating and excess of amine in DMSO for several hours or heating an alcohol or phenol in DMSO in the presence of a base such as Cs$_2$CO$_3$ or K$_2$CO$_3$ for several hours.

General Method B

General Reaction Scheme 2

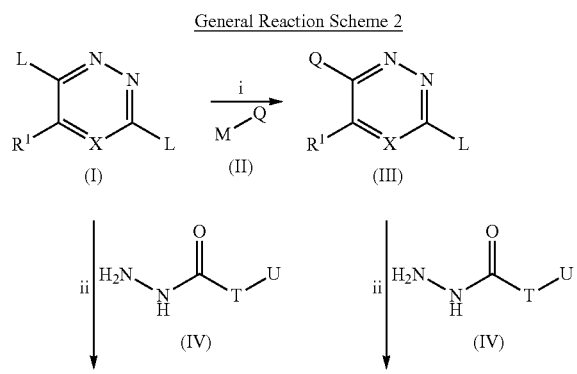

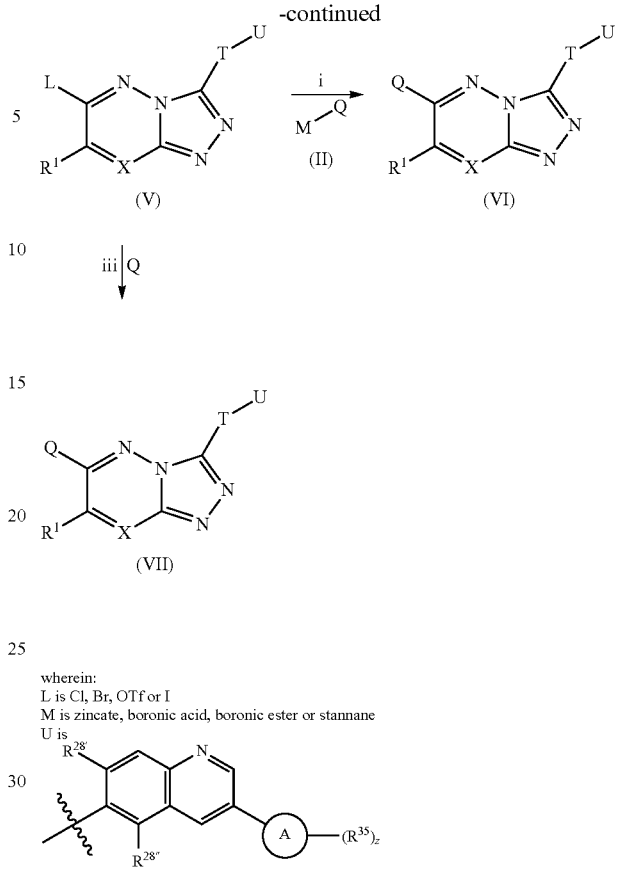

wherein:
L is Cl, Br, OTf or I
M is zincate, boronic acid, boronic ester or stannane
U is Compounds of general formula (VI) and (VII) where Q, R$^1$, X, U and T are described herein may be prepared according to general reaction scheme 2. Compounds of formula (I) and (II) are either available commercially or prepared from commercial compounds using standard chemical reactions and transformations known to those skilled in the art.

Compounds of formula (III) may be prepared according to the method described in general reaction scheme 1, process step (i).

Compounds of general formula (IV) may be prepared according to method described in general reaction scheme 6.

Compounds of formula (V) and (VI) may be prepared from compounds of formula (IV) and (I) or (III) respectively by process step (ii) which comprises heating equimolar amounts of the 2 coupling partners in a suitable solvent such as 1-butanol (Albright, J. D. et al., *J. Med. Chem.*, 1981, 24, 592-600).

Compounds of formula (VII) may be prepared according to the method described in general reaction scheme 1, process step (v).

Compounds of formula (VI) may be prepared from compounds of formula (V) and (II) by process step (ii), according to the method described in general reaction scheme 1, process step (i).

General Method C

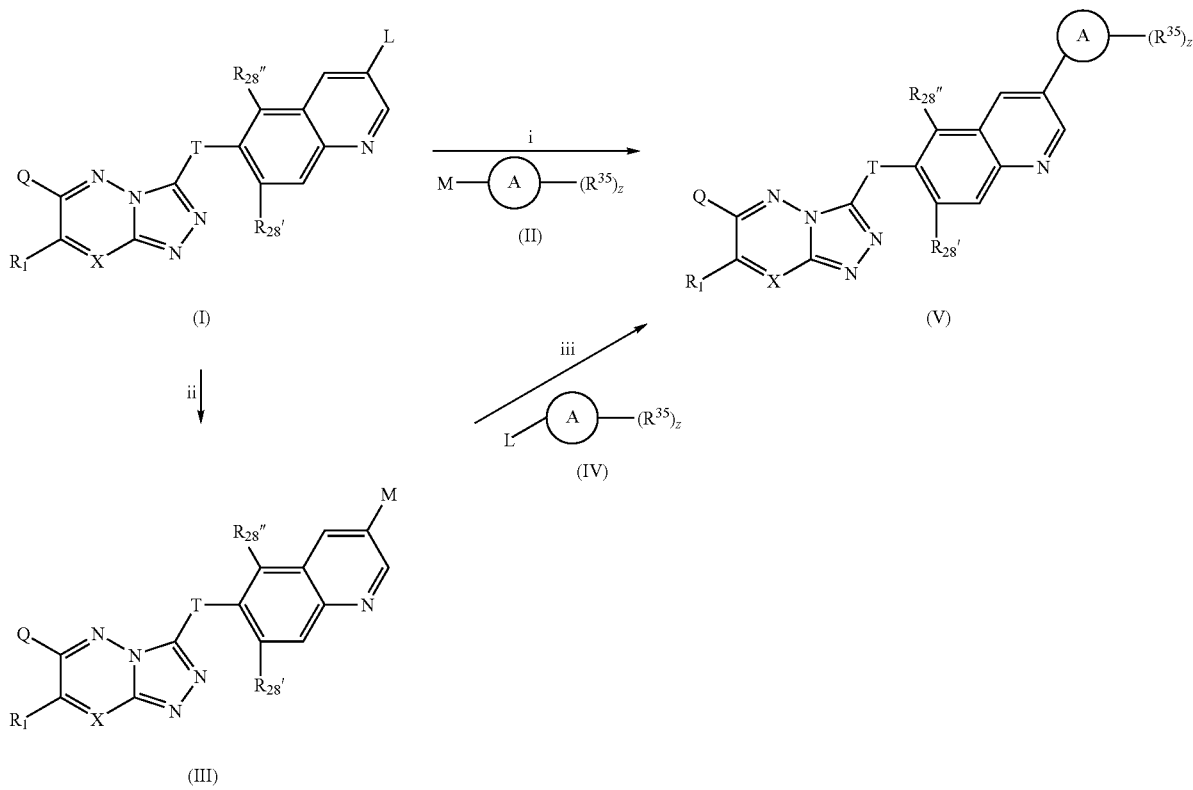

General Reaction Scheme 3 wherein:
M is zincate, boronic acid, boronic ester or stannane
L is Cl, Br, I or OTf Compounds of general formula (V) where Q, $R^1$, X, $R_{28''}$, $R_{28'''}$, A and $(R^{35})z$ are described herein may be prepared according to general reaction scheme 3. The synthesis of compounds of formula (I) is described herein or are either available commercially or prepared from commercial compounds using standard chemical reactions and transformations known to those skilled in the art.

Compounds of formula (V) may be prepared from compounds of general formula (I) and compounds of general formula (II) by process step (i), which comprises a catalytic C—C bond coupling reaction between a halogenated species and a metallic species. An array of catalytic C—C bond coupling reactions is available to those skilled in the art, such as Suzuki-Miyaura conditions (M=boron; Miyaura, N.; Suzuki, A. *Chem. Rev.* 1995, 95, 2457), Stille conditions (M=tin; Stille, J. W. *J. Org. Chem.* 1990, 55, 3019), or Negishi conditions (M=Zinc, Aluminum; Negishi, E. *Chem. Rev.* 1996, 96, 365). Typical Suzuki-Miyaura conditions comprise 1 equivalent of (I), 1-1.5 equivalent of (II), 1-10 mol % of a palladium catalyst, such as Pd(dppf)Cl$_2$, Pd(PPh$_3$)$_2$Cl$_2$, or Pd(Ph$_3$)$_4$, and an excess of base such as an aqueous solution of sodium or potassium carbonate, in solvents such as 1,2-dimethoxyethane or 1,4-dioxane. Alternatively, the coupling partners can be reversed, where compounds of general formula (I) undergo a metal-halogen exchange reaction, for example in the presence of a strong base, such as nbutyl lithium, tertbutyl lithium, or lithium diisopropylamide, and the desired metal, to provide compounds of general formula (III). Subsequent coupling reaction, as described above, with compounds of general formula (II) leads to compounds of formula (V).

General Method D

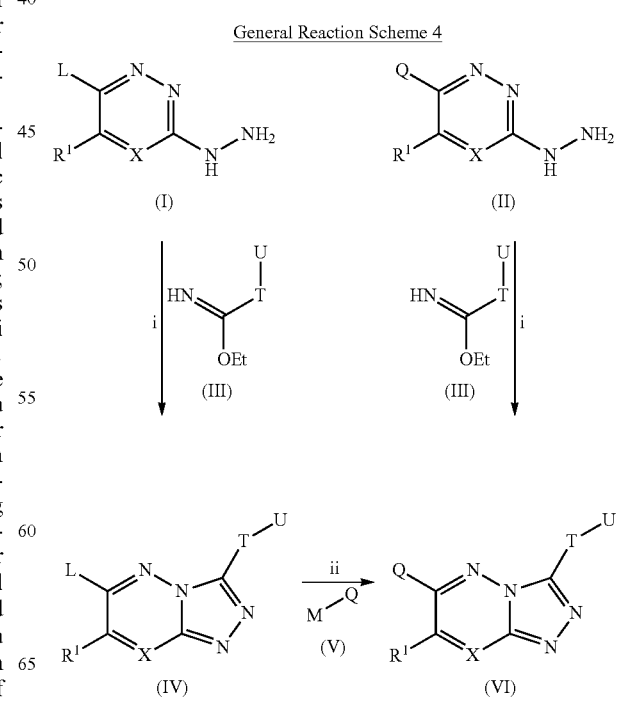

General Reaction Scheme 4

-continued wherein:
L is Cl, Br, OTf or I
M is zincate, boronic acid, boronic ester or stannane
U is

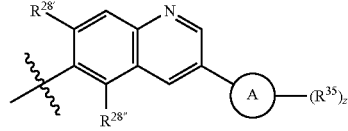

Compounds of general formula (VI) where Q, $R^1$, X, T, $R_{28'}$, $R_{28''}$, A and $(R^{35})z$ are described herein may be prepared according to general reaction scheme 4. Compounds of formula (III) are either available commercially or prepared from commercial compounds using standard chemical reactions and transformations (Pinner synthesis) known to those skilled in the art. Compounds of formula (I) and (II) may be prepared according to methods outlined herein (general method A, general reaction scheme 1, process step (i) and (ii)).

Compounds of formula (IV) and (VI) may be prepared from compounds of general formula (III) and (I) or (II) respectively by process step (i), which comprises condensing an imidate (III) with a pyridazine hydrazine (I) or (II) to form a triazolopyridazine by heating in a suitable solvent for several hours.

Compounds of formula (VI) may be prepared from compounds of formula (V) and (IV) by process step (ii), according to the method described in general reaction scheme 1, process step (i).

General Method E

Compounds of general formula (VI) where $R_{28'}$ and $R_{28''}$ are described herein may be prepared according to general reaction scheme 5. Compounds of formula (I) are either available commercially or prepared from commercial compounds using standard chemical reactions and transformations known to those skilled in the art.

Compounds of formula (II) may be prepared from compounds of formula (I) by process (i) which is described within the following references: Cohn, Essie White. Modification of the Skraup synthesis of quinoline. Journal of the American Chemical Society (1930), 52 3685-8; Bradford, L.; Elliott, T. J.; Rowe, F. M. Skraup reaction with meta substituted anilines. Journal of the Chemical Society (1947), 437-45; Palmer, M. H. The Skraup reaction. Formation of 5- and 7-substituted quinolines. Journal of the Chemical Society (1962), 3645-52.

Compounds of formula (IV) may be prepared from compounds of general formula (II) and compounds of general formula (III) by process step (ii), which comprises a catalytic C—C bond coupling reaction between a halogenated species and a metallic species, in this case zinc, using the Negishi conditions (M=Zinc, Aluminum; Negishi, E. *Chem. Rev.* 1996, 96, 365). Subsequent ester hydrolysis under basic or acidic conditions then prepares compounds of general formula (VII) via process step (iii).

Compounds of formula (VI) may be prepared from compounds of general formula (II) and compounds of general formula (V) by process step (iv), which comprises an addition of a malonate species in the presence of a suitable metal such as CuBr and a suitable base such as sodium hydride.

General Reaction Scheme 5

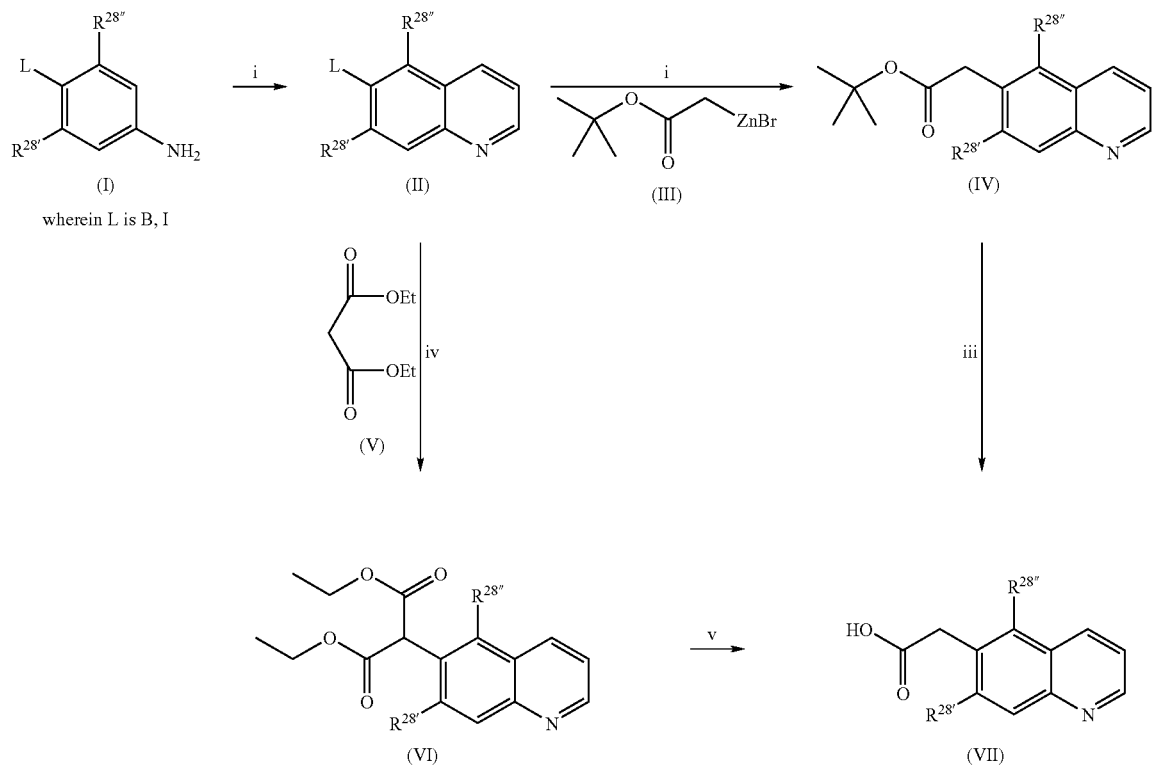

General Method F

General Reaction Scheme 6

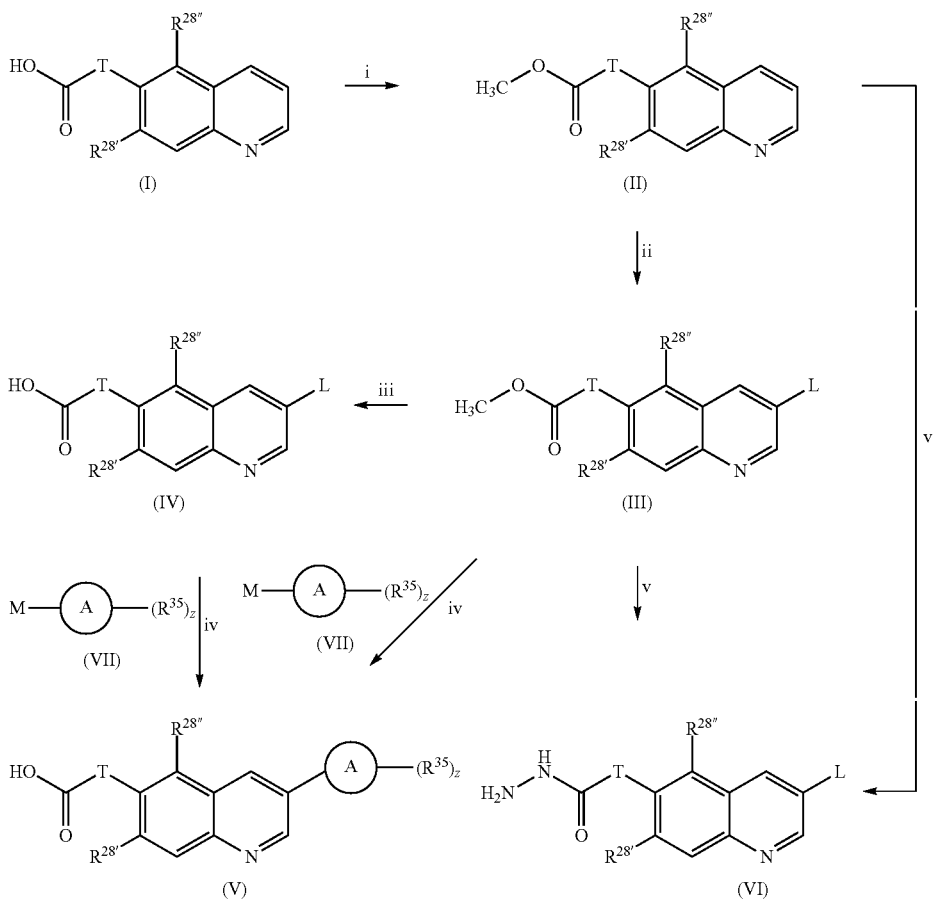

wherein:
M is zincate, boronic acid, boronic ester or stannane
L is Cl, Br, or I Compounds of general formula (V) and general formula (VI) where T, A, $(R^{35})z$, $R_{28'}$ and $R_{28''}$ are described herein may be prepared according to general reaction scheme 6. Compounds of formula (I) are either available commercially or prepared from commercial compounds using standard chemical reactions and transformations known to those skilled in the art or prepared according to the method described in general method E, general reaction scheme 5 and procedures described herein.

Compound of general formula (II) may be prepared from compounds of general formula (I) by process step (i) which comprises of esterification procedures known to those skilled in the art, such as heating in acidic methanol for several hours or treatment with diazomethane.

Compounds of formula (III) may be prepared from compounds of general formula (II) by process step (ii), which comprises a halogenation reaction in presence of a halogen source, such as bromine, iodine, N-bromo or N-iodosuccinimide, or tetrabutylammonium tribromide, in a suitable solvent at temperatures varying from −20° C. to 200° C. Typical conditions comprise 1 equivalents of compound (1) and 1-5 equivalents of bromine in glacial acetic acid at 100° C. for several hours.

Compounds of formula (IV) may be prepared from compounds of general formula (III) by process step (iii), which comprises a saponification reaction generally known to those skilled in the art. Typical conditions comprise stirring compound (III) in the presence of aqueous hydroxide for several hours.

Compounds of formula (VI) may be prepared from compounds of general formula (III) or general formula (II) by process step (v), which comprises a substitution reaction with hydrazine in a suitable solvent under heating or microwave conditions. Typical conditions require 1 equivalent of ester (III) and 10 equivalents of hydrazine in ethanol at 80° C. for several hours.

Compounds of formula (V) may be prepared from compounds of general formula (IV) or general formula (III) and compounds of general formula (VII) by process step (iv), which comprises a catalytic C—C bond coupling reaction between a halogenated species and a metallic species. An array of catalytic C—C bond coupling reactions is available to those skilled in the art, such as Suzuki-Miyaura conditions (M=boron; Miyaura, N.; Suzuki, A. *Chem. Rev.* 1995, 95, 2457), Stille conditions (M=tin; Stille, J. W. *J. Org. Chem.* 1990, 55, 3019), or Negishi conditions (M=Zinc, Aluminum; Negishi, E. *Chem. Rev.* 1996, 96, 365). Typical Suzuki-Miyaura conditions comprise 1 equivalent of (I), 1-1.5 equivalent of (II), 1-10 mol % of a palladium catalyst, such as Pd(dppf)Cl$_2$, Pd(PPh$_3$)$_2$Cl$_2$, or Pd(Ph$_3$)$_4$, and an excess of base such as an aqueous solution of sodium or potassium carbonate, in solvents such as 1,2-dimethoxyethane or 1,4-dioxane.
General Method G ditions comprise 1 equivalent of compound (II), 1 equivalent of sodium cyanide and 1 equivalent of KHCO$_3$ in dimethylformamide at ambient temperature.

Compounds of formula (V) may be prepared from compounds of general formula (III) by process step (iv), which General Reaction Scheme 7

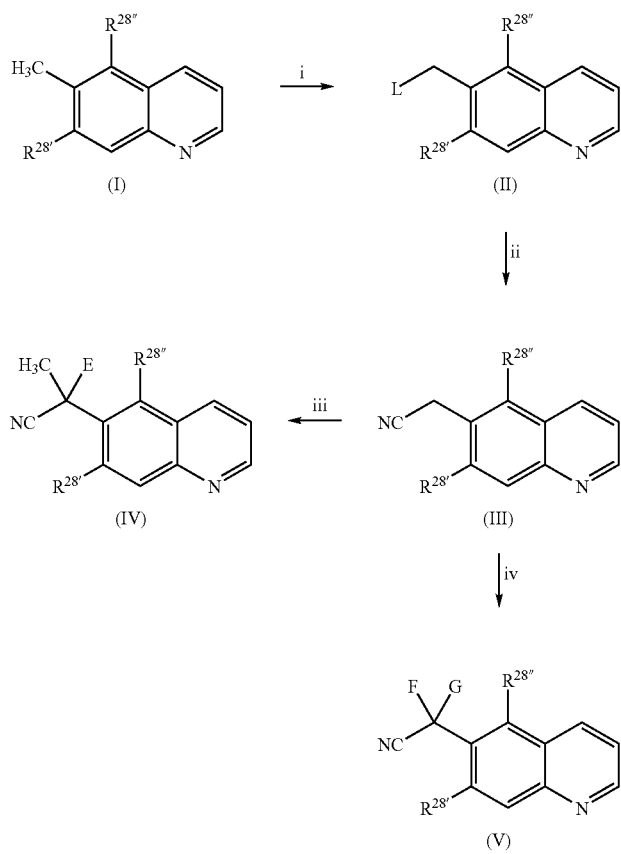

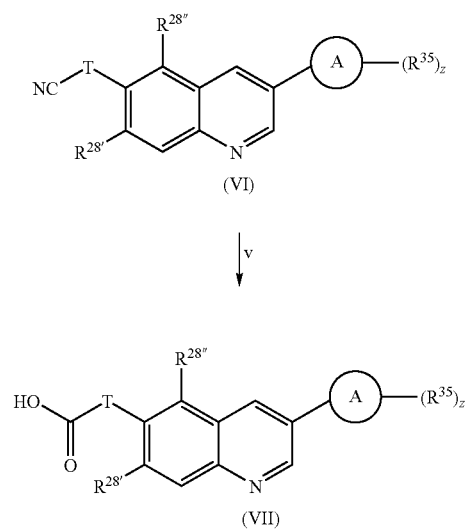

wherein:
E is CH$_3$ or H
G is F or H

Compounds of general formula (IV), (V) and (VII) where T, A, (R$^{35}$)z, R$_{28'}$ and R$_{28''}$ are described herein may be prepared according to general reaction scheme 7. Compounds of formula (I) are either available commercially or prepared from commercial compounds using standard chemical reactions and transformations known to those skilled in the art.

Compounds of formula (II) may be prepared from compounds of general formula (I) by process step (i), which comprises a radical halogenation reaction in presence of a halogen source, such as bromine, iodine, N-bromo or N-iodosuccinimide, or tetrabutylammonium tribromide and a radical initiator such as benzoyl peroxide in a suitable solvent at temperatures varying from −20° C. to 100° C. Typical conditions comprise 1 equivalents of compound (I) and 1-5 equivalents of N-bromosuccinimide in carbon tetrachloride at reflux and 3 mol % of benzolyl peroxide for several hours.

Compounds of formula (III) may be prepared from compounds of general formula (II) by process step (ii), which comprises nucleophilic substitution with cyanide in the presence of an inorganic base in a suitable solvent. Typical concomprises fluorination following the procedures described by Kotoris, Christopher C.; Chen, Mei-Jin; Taylor, Scott D. Preparation of Benzylic α,α-Difluoro nitriles, -tetrazoles, and -sulfonates via Electrophilic Fluorination. Journal of Organic Chemistry (1998), 63(22), 8052-8057, making non critical changes.

Compounds of formula (IV) may be prepared from compounds of general formula (III) by process step (iii), which comprises C—C bond formation between the anion of compound (III), formed with a suitable strong base, and any alkylating agent. Typical conditions comprise 1.5-2.5 equivalents of tert-butyl lithium, 1 equivalent of compound (III) and 1.2-2.4 equivalents of alkylating agent such as methyl iodide at −78° C. in tetrahydrofuran.

Compounds of formula (VII) may be prepared from compounds of general formula (VI) by process step (v), which comprises a hydrolysis by heating nitrile compound (VI) in either acidic or basic conditions. Typical conditions comprise heating compound (VI) in concentrated hydrochloric acid in a microwave for several minutes.

General Method H

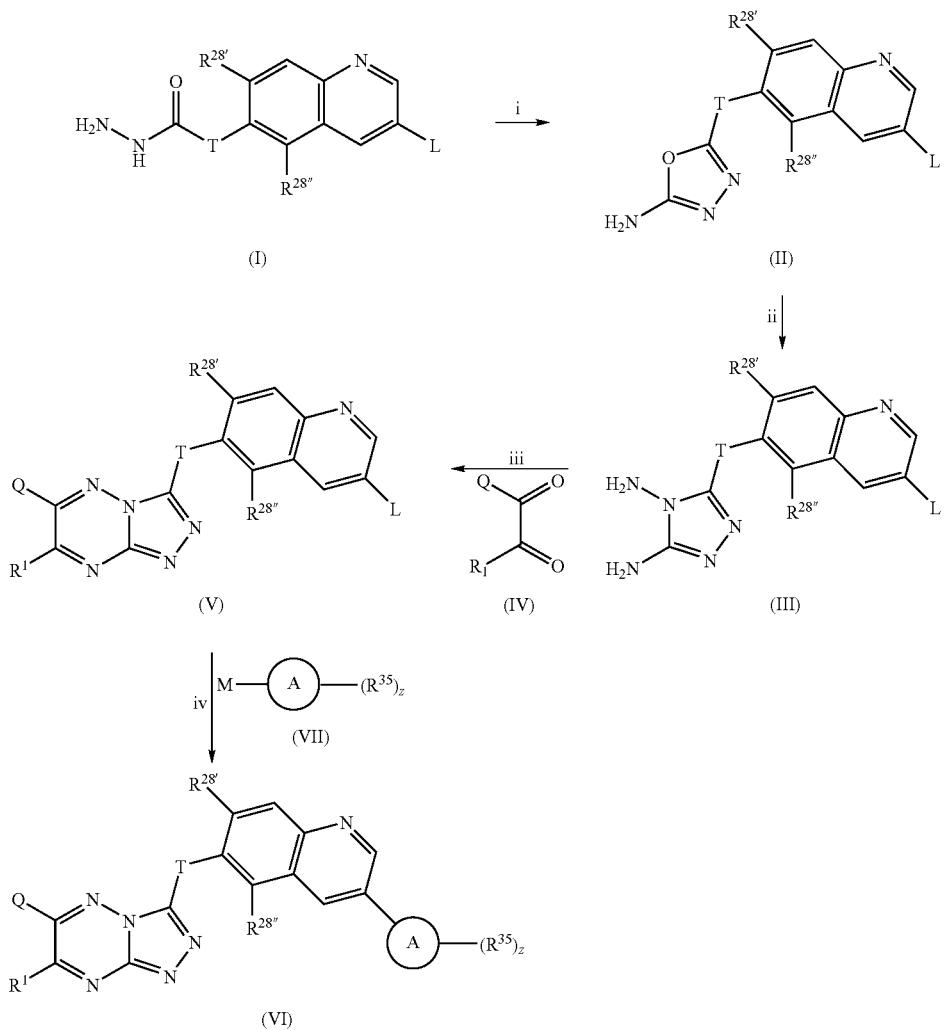

wherein:
M is zincate, boronic acid, boronic ester or stannane
L is Cl, Br, I, OTf Compounds of general formula (VI) where Q, $R^1$, T, $(R^{35})_z$, $R_{28'}$ and $R_{28''}$ are described herein may be prepared according to general reaction scheme 8. Compounds of formula (I) are either prepared according to the methods described herein for the synthesis of compounds of general formula (VI), general reaction scheme 6, available commercially or prepared from commercial compounds using standard chemical reactions and transformations known to those skilled in the art.

Compounds of formula (II) may be prepared from compounds of general formula (I) by process step (i), which comprises an amino-1,3,4-oxadiazole formation in the presence of cyanogens bromide, a suitable base in a polar organic solvent. Typical conditions comprise combining compound (1), slight excess of cyanogen bromide and excess of potassium hydrogen bromide in methanol at ambient temperature.

Compounds of formula (III) may be prepared from compounds of general formula (II) by process step (ii), which comprises a diamino-1,3,4-triazole formation from an amino-1,3,4-oxadiazole in the presence of hydrazine at elevated temperature. Typical conditions comprise heating compound (II) in a mixture of hydrazine hydrate and water at 170° C. and 2 bar pressure for 1 hour.

Compounds of formula (V) may be prepared from compounds of general formula (III) by process step (iii), which comprises a triazine formation reaction by combining compounds (III) and (VI) in a mixture of acetic acid and water. Typical conditions comprise combining 1 equivalent of compound (III) with an excess of compound (IV) in acetic acid and water at ambient temperature.

Compounds of formula (VI) may be prepared from compounds of general formula (V) and compounds of general formula (VII) by process step (iv), which comprises a catalytic C—C bond coupling reaction between a halogenated species and a metallic species. An array of catalytic C—C bond coupling reactions is available to those skilled in the art, such as Suzuki-Miyaura conditions M=boron; Miyaura, N.; Suzuki, A. *Chem. Rev.* 1995, 95, 2457), Stille conditions (M=tin; Stille, J. W. *J. Org. Chem.* 1990, 55, 3019), or Negishi conditions (M=Zinc, Aluminum; Negishi, E. *Chem. Rev.* 1996, 96, 365). Typical Suzuki-Miyaura conditions comprise 1 equivalent of (V), 1-1.5 equivalent of (VII), 1-10 mol % of a palladium catalyst, such as Pd(dppf)Cl$_2$, Pd(PPh$_3$)$_2$Cl$_2$, or Pd(Ph$_3$)$_4$, and an excess of base such as an aqueous solution of sodium or potassium carbonate, in solvents such as 1,2-dimethoxyethane or 1,4-dioxane.

Synthesis of Intermediates

Intermediate 1: (2-Methyl-quinolin-6-yl)-acetic acid

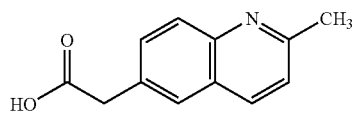

Step1: (2-methyl-quinolin-6-yl)-acetic acid ethyl ester

A vial under nitrogen atmosphere was charged with 6-bromo-quinaldine (500 mg, 2.25 mmol), bis(pinacolato) diboron (1.14 g, 4.5 mmol), dichloro[1,1'-bis(diphenylphosphino)-ferrocene]palladium (II) dichloromethane adduct (92 mg, 0.112 mmol), sodium acetate (547 mg, 6.75 mmol), and dimethylformamide (10 mL). The reaction mixture was stirred at 100° C. for 18 h then partitioned between ethyl acetate and water. The organic layer was washed with brine twice, dried over sodium sulfate, filtered, and absorbed on silica gel. Purification on silica gel with 0-8% gradient of methanol in dichloromethane yielded 432 mg of a dark oil. The oil was dissolved in tetrahydrofuran (5 mL) and added to a vessel, under nitrogen atmosphere, containing palladium (II) acetate (7 mg, 0.03 mmol), tri-1-naphthylphosphine (37 mg, 0.09 mmol), and potassium phosphate tribasic (1 g, 5 mmol). Ethyl 2-bromoacetate (167 mg, 1 mmol) was then added and the reaction mixture was stirred at reflux for 18 h. Water was added and the mixture was extracted with ethyl acetate (3×). The combined organic layers were dried over sodium sulfate, filtered, and adsorbed on silica gel. Purification on silica gel with 0-80% gradient of ethyl acetate in hexane provided 105 mg of product as a yellow oil. $^1$H NMR 500 MHz (DMSO) δ 1.19 (t, 3H), 2.65 (s, 3H), 3.85 (s, 2H), 4.10 (q, 2H), 7.40 (d, 1H), 7.61 (dd, 1H), 7.78 (d, 1H), 7.86 (d, 1H), 8.20 (d, 1H); MS (m/z) 230 [M+H$^+$]$^+$.

Step 2: (2-methyl-quinolin-6-yl)-acetic acid

To a solution of (2-methyl-quinolin-6-yl)-acetic acid ethyl ester (100 mg, 0.436 mmol) in methanol (2 mL) was added 4 M aqueous solution of lithium hydroxide (0.55 mL, 2.18 mmol). The reaction mixture was stirred at room temperature for 14 h then it was concentrated in vacuo, diluted with water, and treated with 1 N aqueous hydrochloric acid until pH 5. The aqueous layer was extracted with ethyl acetate (3×), and the combined organic layers were dried over sodium sulfate, filtered, and concentrated in vacuo to provide 19 mg of product as a light beige solid. $^1$H NMR 500 MHz (DMSO) δ 2.65 (s, 3H), 3.76 (s, 2H), 7.40 (d, 1H), 7.60 (dd, 1H), 7.77 (d, 1H), 7.86 (d, 1H), 8.20 (d, 1H); MS (m/z) 202 [M+H$^+$]$^+$.

Intermediate 2: 3-Quinolin-6-yl-propionic acid

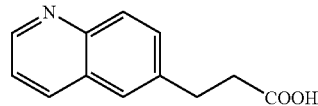

Step 1: 3-quinolin-6-yl-acrylic acid ethyl ester

A vial under nitrogen atmosphere was charged with 6-bromo-quinoline (1 g, 4.8 mmol) and dimethylformamide (15 mL), followed by ethyl acrylate (2.1 mL, 19.2 mmol), triethylamine (6.7 mL, 48 mmol), and palladium (II) acetate (32 mg, 0.142 mmol). The reaction mixture was stirred at 100° C. for 5 h, then the hot mixture was filtered over celite and the filtrate was concentrated in vacuo. The residue was partitioned between water and ethyl acetate. The organic layer was washed with saturated aqueous solution of ammonium chloride, saturated aqueous solution of sodium bicarbonate, then brine. The organic layer was then adsorbed on silica gel. Purification on silica gel with 10-80% gradient of ethyl acetate in hexane provided 952 mg of product as a yellow oil. $^1$H NMR 500 MHz (DMSO) δ 1.28 (t, 3H), 4.20 (q, 2H), 6.82 (d, 1H), 7.58 (d, 1H), 7.84 (d, 1H), 8.01 (d, 1H), 8.16 (dd, 1H), 8.30 (d, 1H), 8.37 (dd, 1H), 8.93 (dd, 1H); MS (m/z) 228 [M+H$^+$]$^+$.

Step 2: 3-quinolin-6-yl-propionic acid ethyl ester

A mixture of 3-quinolin-6-yl-acrylic acid ethyl ester (200 mg, 0.881 mmol) and 10% wt Pd/C (93 mg, 0.088 mmol) in methanol (3 mL) was stirred at room temperature under hydrogen atmosphere for 3 h. Mixture was filtered through celite and the filtrate was absorbed on silica gel. Purification on silica gel with 0-65% gradient of ethyl acetate in hexane provided 100 mg of product as a clear oil. $^1$H NMR 500 MHz (DMSO) δ 1.13 (t, 3H), 2.74 (t, 2H), 3.05 (t, 2H), 4.04 (q, 2H), 7.50 (dd, 1H), 7.67 (dd, 1H), 7.78 (d, 1H), 7.94 (d, 1H), 8.29 (dd, 1H), 8.84 (dd, 1H); MS (m/z) 230 [M+H$^+$]$^+$.

Step 3: 3-quinolin-6-yl-propionic acid

To a solution of 3-quinolin-6-yl-propionic acid ethyl ester (100 mg, 0.437 mmol) in methanol (2 mL) was added 4 M aqueous solution of lithium hydroxide (0.55 mL, 2.18 mmol). The reaction mixture was stirred at room temperature for 3 h then it was concentrated in vacuo, diluted with water, and treated with 1 N aqueous hydrochloric acid until pH 5. The aqueous layer was extracted with ethyl acetate (3×), and the combined organic layers were dried over sodium sulfate, filtered, and concentrated in vacuo to provide 18 mg of product as a white solid. $^1$H NMR 500 MHz (DMSO) δ 2.67 (t, 2H), 3.02 (t, 2H), 7.50 (dd, 1H), 7.67 (dd, 1H), 7.78 (d, 1H), 7.94 (d, 1H), 8.29 (dd, 1H), 8.84 (dd, 1H); MS (m/z) 202 [M+H$^+$]$^+$.

Intermediate 3: trans 2-Quinolin-6-yl-cyclopropanecarboxylic acid

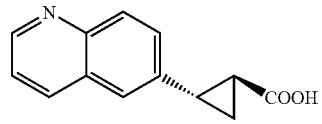

Step 1: trans 2-quinolin-6-yl-cyclopropanecarboxylic acid ethyl ester

To a suspension of sodium hydride (71 mg, 1.76 mmol) in DMSO (3 mL) under nitrogen atmosphere was added trimethylsulfoxonium chloride (261 mg, 2.03 mmol). After stirring at room temperature for 30 minutes, a solution of 3-quinolin-6-yl-acrylic acid ethyl ester (200 mg, 0.881 mmol) in DMSO (2 mL) was added dropwise. The reaction mixture was stirred at room temperature for 2.5 h and quenched with a saturated aqueous solution of ammonium chloride. The mixture was extracted with ethyl acetate (2×) and the combined organic layers were washed with brine (3×) and adsorbed on silica gel. Purification on silica gel with 0-80% gradient of ethyl acetate in hexane provided 126 mg of product as a white solid. NMR 500 MHz (DMSO) δ 1.22 (t, 3H), 1.55 (m, 2H), 2.10 (m, 1H), 2.64 (m, 1H), 4.13 (q, 2H), 7.50 (dd, 1H), 7.58 (dd, 1H), 7.80 (d, 1H), 7.93 (d, 1H), 8.26 (dd, 1H), 8.84 (dd, 1H); MS (m/z) 242 [M+H$^+$]$^+$.

Step 2: trans 2-quinolin-6-yl-cyclopropanecarboxylic acid

To a solution of trans 2-quinolin-6-yl-cyclopropanecarboxylic acid ethyl ester (125 mg, 0.523 mmol) in methanol (2 mL) was added 4 M aqueous solution of lithium hydroxide (0.65 mL, 2.62 mmol). The reaction mixture was stirred at room temperature for 3 h then it was concentrated in vacuo, diluted with water, and treated with 1 N aqueous hydrochloric acid until pH 4-5. The resulting precipitate was filtered, washed with water, and dried in vacuo to provide 102 mg of product as a white solid. $^1$H NMR 500 MHz (DMSO) δ 1.50 (m, 2H), 1.96 (m, 1H), 2.60 (m, 1H), 7.50 (dd, 1H), 7.57 (dd, 1H), 7.78 (d, 1H), 7.93 (d, 1H), 8.26 (dd, 1H), 8.83 (dd, 1H); MS (m/z) 214 [M+H$^+$]$^+$.

Intermediate 4: Quinoxalin-6-yl-acetic acid

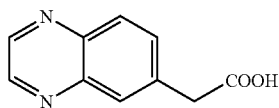

Step 1: quinoxalin-6-yl-acetic acid ethyl ester

A vial under nitrogen atmosphere was charged with benzopyrazine-6-boronic acid hydrochloride (500 mg, 2.38 mmol), palladium (II) acetate (16 mg, 0.071 mmol), tri-1-naphthylphosphine (88 mg, 0.214 mmol), potassium phosphate tribasic (2.52 g, 11.9 mmol), and tetrahydrofuran (10 mL). Ethyl 2-bromoacetate (0.315 mL, 2.85 mmol) was then added and the reaction mixture was stirred at reflux for 6 h. Water was added and the mixture was extracted with ethyl acetate (3×). The combined organic layers were adsorbed on silica gel. Purification on silica gel with 0-100% gradient of ethyl acetate in hexane provided 96 mg of product as a dark yellow oil. $^1$H NMR 500 MHz (DMSO) δ 1.20 (t, 3H), 3.99 (s, 2H), 4.11 (q, 2H), 7.79 (dd, 1H), 8.01 (d, 1H), 8.06 (d, 1H), 8.94 (d, 2H); MS (m/z) 217 [M+H$^+$]$^+$.

Step 2: Quinoxalin-6-yl-acetic acid

To a solution of quinoxalin-6-yl-acetic acid ethyl ester (95 mg, 0.44 mmol) in methanol (2 mL) was added 4 M aqueous lithium hydroxide (0.55 mL, 2.2 mmol). The reaction mixture was stirred at room temperature for 17 h then it was concentrated in vacuo, diluted with water and extracted with diethyl ether (3×). The aqueous layer was treated with 1 N aqueous hydrochloric acid until pH 2 and extracted with ethyl acetate (3×). The combined organic layers were dried over sodium sulfate, filtered, and concentrated in vacuo to provide 64 mg of product as a beige solid. $^1$H NMR 500 MHz (DMSO) δ 3.90 (s, 2H), 7.78 (dd, 1H), 7.99 (d, 1H), 8.06 (d, 1H), 8.93 (dd, 2H); MS (m/z) 189 [M+H$^+$]$^+$.

Intermediate 5: Benzothiazol-6-yl-acetic acid

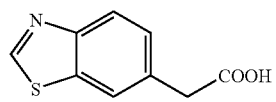

Step 1: (2-amino-benzothiazol-6-yl)-acetic acid (4-Amino-phenyl)-acetic acid (20 g, 132.5 mmol) and NH$_4$SCN (20 g, 263.2 mmol) were dissolved in 300 ml of acetic acid and the mixture was cooled to 15° C., treated with Br$_2$ (21.2 g, 6.8 ml) in acetic acid (10 ml) and the temperature did not exceed 15° C. Then the reaction was stirred at room temperature for 4 h. The mixture was filtered and the cake was re-dissolved in water, adjusted the pH=5. The precipitate was filtered and dried to obtain 2-amino-benzothiazol-6-yl)-acetic acid as light yellow powder (24 g, 87.1%).

Step 2: Benzothiazol-6-yl-acetic acid

2-Amino-benzothiazol-6-yl)-acetic acid (20 g, 96.2 mmol) was dissolved in 1,4-dioxane (750 mL). i-Amyl nitrite (22.4 g, 192.4 mmol) was added to the solution dropwise at room temperature. The mixture was stirred under nitrogen atmosphere at reflux for 2 hr. After the reaction was completed the solvent was removed under vacuum and the residue was used in next step without further purification.

Intermediate 5 and Intermediate 6: Benzothiazol-6-yl-acetic acid and (2-chloro-benzothiazol-6-yl)-acetic acid

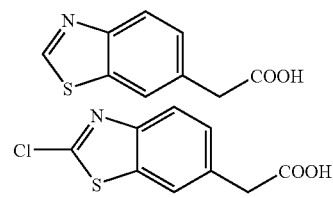

To a solution of (2-amino-benzothiazol-6-yl)-acetic acid dihydrochloride (150 mg, 0.533 mmol) in dimethylformamide (3 mL) under nitrogen atmosphere was added tert-butylnitrite (0.076 mL, 0.64 mmol) dropwise. The reaction mixture was stirred at 50° C. for 1.5 h and it was concentrated and dried in vacuo as a (2:3) mixture of benzothiazol-6-yl-acetic acid and (2-chloro-benzothiazol-6-yl)-acetic acid. The mixture was used as such in the coupling/cyclization procedure, as described in method Y.

Intermediate 7: 4-(6-Phenyl-[1,2,4]triazolo[4,3-b]pyridazin-3-ylmethyl)-benzene-1,2-diamine

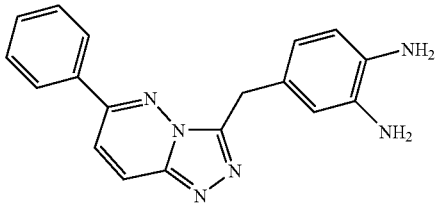

Step 1: 4-amino-phenyl acetic acid methyl ester

To a suspension of 4-amino-phenyl acetic acid (5 g, 33 mmol) in methanol (20 mL) was added concentrated sulfuric acid (2 mL) dropwise. The reaction mixture was stirred at reflux for 1.5 h, then concentrated in vacuo. The residue was partitioned between 1 M aqueous potassium carbonate and diethyl ether. The organic layer was washed with 1 M aqueous potassium carbonate, water, then dried over sodium sulfate and filtered. The filtrate was concentrated and dried in vacuo to give 4.65 g of the product as a dark yellow oil. $^1$H NMR 500 MHz (DMSO) δ 3.43 (s, 2H), 3.57 (s, 3H), 4.97 (s, 2H), 6.49 (d, 2H), 6.88 (d, 2H); MS (m/z) 166 $[M+H^+]^+$.

Step 2: (4-acetylamino-3-nitro-phenyl)-acetic acid methyl ester

A solution of 4-amino-phenyl acetic acid methyl ester (3 g, 18.2 mmol) in acetic anhydride (16 mL) was stirred at room temperature for 30 minutes. The reaction mixture was cooled to 0° C. temperature and fuming nitric acid (2.3 mL) was added dropwise. The ice bath was removed and the reaction mixture was stirred for another 20 minutes before pouring it onto iced water. The resulting yellow precipitate was filtered, washed with water and dried in vacuo at 50° C. to give 3.7 g of the product. $^1$H NMR 500 MHz (DMSO) δ 2.05 (s, 3H), 3.63 (s, 3H), 3.81 (s, 2H), 7.54 (d, 1H), 7.58 (dd, 1H), 7.87 (d, 1H), 10.2 (s, 1H).

Step 3: (4-amino-3-nitro-phenyl)-acetic acid hydrochloride

A solution of (4-acetylamino-3-nitro-phenyl)-acetic acid methyl ester (1.3 g, 5.15 mmol) in 6 N aqueous hydrochloric acid (10 mL) was stirred at reflux for 1.5 h, then concentrated in vacuo to dryness. The residue was triturated with diethyl ether, filtered, washed with diethyl ether, and dried in vacuo to give 978 mg of product as a dark orange-yellow solid. $^1$H NMR 500 MHz (DMSO) δ 3.49 (s, 2H), 6.98 (d, 1H), 7.30 (dd, 1H), 7.86 (d, 1H); MS (m/z) 197 $[M+H^+]^+$.

Step 4: 2-Nitro-4-(6-phenyl-[1,2,4]triazolo[4,3-b]pyridazin-3-ylmethyl)-phenylamine The title compound maybe prepared according to procedure described in method D as a yellow solid (91 mg, 0.263 mmol, 23% yield). $^1$HNMR (DMSO) δ 4.50 (s, 2H), 6.97 (d, 1H), 7.43 (s, 2H), 7.45 (dd, 1H), 7.60 (m, 3H), 7.95 (d, 1H), 8.14 (m, 3H), 8.42 (d, 1H); MS (m/z) 347 (M+H).

Step 5: 4-(6-Phenyl-[1,2,4]triazolo[4,3-b]pyridazin-3-ylmethyl)-benzene-1,2-diamine A mixture of 2-nitro-4-(6-phenyl-[1,2,4]triazolo[4,3-b]pyridazin-3-ylmethyl)-phenylamine (89 mg, 0.257 mmol) and 10% wt Pd/C (27 mg, 0.026 mmol) in methanol (4 mL), tetrahydrofuran (2 mL), and dimethylformamide (2 mL) was stirred at room temperature under hydrogen atmosphere for 4 h. Catalyst was filtered through celite and the filtrate was concentrated and dried in vacuo to provide 81 mg of the product as a beige solid. $^1$HNMR (DMSO) δ 4.30 (s, 2H), 4.32 (s, 2H), 4.43 (s, 2H), 6.43 (m, 2H), 6.50 (s, 1H), 7.60 (m, 3H), 7.93 (d, 1H), 8.11 (m, 2H), 8.39 (d, 1H); MS (m/z) 317 $[M+H^+]^+$.

Intermediate 8: Quinolin-6-yl-acetonitrile

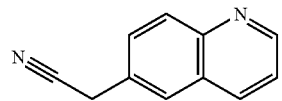

A suspension of 6-methylquinoline (21.48 g, 150 mmol) and N-bromosuccinimide (27.6 g, 155 mmol) in CCl$_4$ (430 mL) was heated to reflux. Once reflux was obtained benzoyl peroxide (1.4 g, 5.1 mmol) was added in a single portion. The mixture was stirred at reflux for a further 2 hours. After such time the mixture was allowed to cool to ambient temperature over 3 hours and the formed precipitate was removed via filtration. The filtrate was washed with 5% aqueous NaOH (2×150 mL), water (200 mL), dried (Na$_2$SO$_4$) and purified via flash column chromatography (SiO$_2$, hexane/ethyl acetate 100:0-35/65). The fractions containing the desired bromo compound were diluted with dimethylformamide (400 mL) and the mixture concentrated in vacuo to remove hexane and ethyl acetate. To this mixture was then added KHCO$_3$ (15 g, 150 mmol) followed by sodium cyanide (7.34 g, 150 mmol). The mixture was stirred at room temperature for 2 hours and at 40° C. for a further 2 hours. After such time the mixture was concentrated in vacuo and the residue poured onto 5% aqueous KHCO$_3$ (600 mL) and extracted with ethyl acetate (3×200 mL). The combined organic extracts were washed with brine (100 mL), dried (Na$_2$SO$_4$) and concentrated onto silica gel. Purification via flash column chromatography (SiO$_2$, hexane:ethyl acetate 80/20-30/70) returned the title compound as a white solid (4.8 g, 28.6 mmol, 20% yield). $^1$H NMR 500 MHz (DMSO-d6); δ 4.28 (2H, s), 7.56 (1H, dd), 7.11 (1H, dd), 7.97 (1H, d), 8.01 (1H, d), 8.40 (1H, dd), 8.92 (1H, dd); MS (m/z) 169 $[M+H^+]^+$.

Intermediate 9: 2-Methyl-2-quinolin-6-yl-propionic acid hydrochloride

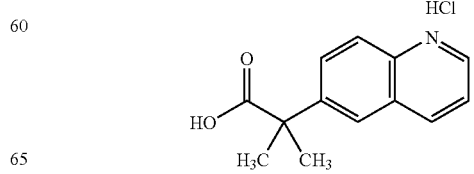

Step 1: 2-Methyl-2-quinolin-6-yl-propionitrile

A solution of quinolin-6-yl-acetonitrile (intermediate 8) (200 mg, 1.2 mmol) in tetrahydrofuran (12 mL) was cooled to −78° C. to which methyl iodide (2.5 mmol, 157 µl) was added followed by potassium tert-butoxide (2.5 mmol, 280 mg). The mixture was allowed to warm to ambient temperature overnight. After such time the mixture was concentrated in vacuo and taken up in aqueous $NaHCO_3$ (30 mL) and extracted with dichloromethane (3×30 mL). The combined organic extracts were dried ($Na_2SO_4$) and concentrated onto silica gel. Purification via flash column chromatography ($SiO_2$, hexane: ethyl acetate 90/10-50/50) returned the title compound as a clear colorless oil (214 mg, 91% yield). $^1$H NMR 500 MHz (DMSO-d6) δ1.80 (6H, s), 7.58 (1H, dd), 7.94 (1H, dd), 8.08 (1H, d), 8.11 (1H, d), 8.45 (1H, dd), 8.93 (1H, dd); MS (m/z) 197 $[M+H^+]^+$.

Step 2: 2-Methyl-2-quinolin-6-yl-propionic acid hydrochloride

To a mixture of 2-methyl-2-quinolin-6-yl-propionitrile (760 mg, 3.88 mmol) in water (3 mL) was added concentrated hydrochloric acid (7 mL) and heated at 160° C. in a microwave for 5 minutes. After such time the mixture was concentrated in vacuo and the residue dried via azeotropic distillation from toluene (3×5 mL) to return the title compound as a white solid (949 mg, 3.77 mmol, 97% yield.). $^1$H NMR 500 MHz ($D_2O$) δ 1.54 (6H, s), 7.89 (1H, dd), 8.03-7.96 (2H, m), 8.11 (1H, d), 8.95-8.85 (2H, m).

Intermediate 10: 2-Quinolin-6-yl-propionic acid

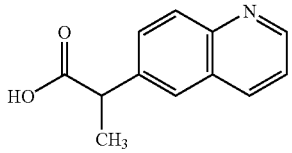

Step 1: Quinolin-6-yl-acetic acid methyl ester

To a stirred solution of quinolin-6-yl-acetic acid (10 g, 53.0 mmol) in 100 ml of methanol was added 2.5 ml of concentrated $H_2SO_4$ The mixture was heated to reflux for 3 hours. The reaction mixture was concentrated to give a brown residue, which was diluted with 100 ml of dichloromethane, washed with sat. aq. $NaHCO_3$ and brine, then the organic layer was dried over anhydrous $Na_2SO_4$ and concentrated to return the title compound as a brown oil (7.9 g, 73.6%).

Step 2: 2-Quinolin-6-yl-propionic acid methyl ester

A solution of n-butyl lithium in hexane (1.6M, 50.9 ml) was added to a stirred solution of diisopropylamine (5.32 g, 52.6 mmol) in anhydrous tetrahydrofuran (100 ml) cooled at −40° C. under nitrogen atmosphere, and the mixture was stirred for 30 min. The reaction mixture was cooled to −78° C., to this solution was added a solution of quinolin-6-yl-acetic acid methyl ester (7.9 g, 39.3 mmol) in 10 ml of tetrahydrofuran and HMPA (10.0 g, 55.8 mmol). The mixture was stirred at −78° C. for 1 hour and then −30° C. for 30 min. To this reaction mixture was added a solution of methyl iodide (8.0 g, 56.3 mmol) in anhydrous tetrahydrofuran at −78° C. and the mixture stirred −78° C. for 1.5 hours. The reaction mixture was warmed slowly to room temperature and diluted with aqueous saturated solution of $NH_4Cl$ (100 ml) and water (80 ml). The mixture was extracted with tert-butylmethyl ether, the combined organic layers were washed with water and brine, dried over anhydrous sodium sulfate and concentrated to give a brown oil, which was purified by column chromatography on silica gel eluting with petroleum ether and ethyl acetate (20:1) to give a pale yellow oil (7.7 g, 91.1%). $^1$H NMR and LC-MS analysis revealed the title compound was contaminated with 10% 2-methyl-2-quinolin-6-yl-propionic acid methyl ester.

Step 3: 2-Quinolin-6-yl-propionic acid

2-Quinolin-6-yl-propionic acid methyl ester containing 10% 2-methyl-2-quinolin-6-yl-propionic acid methyl ester (7.7 g, 35.8 mmol) and 2 N aq. NaOH (27 ml) was heated to reflux for 4 hours until the reaction mixture became clear. After cooling to room temperature the mixture was extracted with dichloromethane and the aqueous layer was acidified with concentrated hydrochloric acid to pH 4-5. Ethyl acetate (30 ml) was added and stirred for 10 min, the resulting solid was filtered off to obtain product, which was re-crystallized twice from methanol to return the title compound (5.3 g, 73.7%): $^1$H NMR 300 MHz (DMSO-d6) δ12.43 (s, 1H), 8.86 (d, 1H), 8.33 (d, 1H), 7.99-7.86 (m, 2H), 7.72-7.49 (m, 2H), 3.92 (q, 1H), 1.48 (d, 3H). $ES^-$ MS m/z: 200 $[M-H^+]^-$, 400 (dimer).

Intermediate 11: (5,7-Difluoro-quinolin-6-yl)-acetic acid

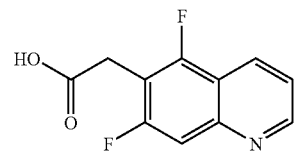

Step 1: 6-Bromo-5,7-difluoro-quinoline

A mixture of 4-bromo-3,5-difluoro-phenylamine (6.0 g, 28.8 mmole), ferrous sulfate (1.82 g), glycerol (8.6 mL), nitrobenzene (1.79 mL) and 5.0 ml of concentrated sulfuric acid (5 mL) was heated gently. After the first vigorous reaction, the mixture was heated to reflux for five hours. Nitrobenzene was removed by distillation in vacuo. The aqueous solution was acidified with glacial acetic acid, and dark brown precipitate separated, which was purified by flash chromatography (silica gel, petroleum/ethyl acetate=12/1) to return the title compound as a white solid (3.5 g, 49.8%).

Step 2: 2-(5,7-Difluoro-quinolin-6-yl)-malonic acid diethyl ester

Ethyl malonate (9.28 g, 8.8 mL, 58.0 mmol) was added dropwise to a mixture of sodium hydride (60 percent in mineral oil, 2.32 g, 58.0 mmol) in 1,4-dioxane (29 mL) at 60° C. CuBr (4.176 g, 29.0 mmol) and 6-bromo-5,7-difluoro-quinoline (7.07 g, 29.0 mmol) were then added and the mixture heated to reflux for 16 h. After such time concentrated hydrochloric acid was added under ice-cooling and then tert-butyl methyl ether and water were added. The separated organic layer was washed with (10%) hydrochloric acid and water sequentially. Dried over sodium sulfate and concentrated. The residue was purified by column chromatography to afford the title compound (3.13 g, 35.4%).

Step 3: (5,7-Difluoro-quinolin-6-yl)-acetic acid

To a round-bottom flask containing 2-(5,7-difluoro-quinolin-6-yl)-malonic acid diethyl ester (2.48 g, 7.68 mmol) were added ethanol (77 mL) and 10% aqueous NaOH (103.2 mL). The solution was refluxed for 3 h. After such time the ethanol was removed under reduced pressure to form a yellow suspension and tetrahydrofuran (50 mL) was added to give a clear yellow solution which was placed in an ice bath and stirred. 6N Hydrochloric acid (50 ml) was slowly added to the solution to reach pH 1. The light orange solution was refluxed for another hour, at which time two layers formed. The top tetrahydrofuran layer was collected and the aqueous solution was extracted with dichloromethane. The organic layers were brined and dried with anhydrous sodium sulfate. The solution was then filtered and the filtrate was concentrated to obtain the title compound (1.20 g, 70.1%). $^1$H NMR (300 MHz, DMSO-d6) δ 12.82 (s, 1H), 8.98~9.00 (m, 1H), 8.47~8.50 (d, 1H), 7.61~7.74 (m, 2H), 3.86 (s, 2H). ES-MS m/z: 224.2 (M$^+$+1).

Intermediate 12: (7-Fluoro-quinolin-6-yl)-acetic acid

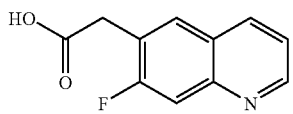

Step 1: 6-bromo-7-fluoro-quinoline

A mixture of 4-bromo-3-fluoro-phenylamine (2.85 g, 15 m mole), ferrous sulfate (0.95 g), glycerol (5.658 g, 4.5 ml), nitrobenzene (1.125 g, 0.93 ml) and concentrated sulfuric acid (2.61 mL) were heated gently. After the first vigorous reaction, the mixture was heated to reflux for 7 hours. Nitrobenzene was evaporated in vacuo. The aqueous solution was acidified with glacial acetic acid and dark brown precipitate separated, which was purified by flash chromatography (silica gel, petroleum/ethyl acetate=8/1) to return compound title as white crystals (1.44 g, 42.5%).

Step 2: (7-fluoro-quinolin-6-yl)-acetic acid tert-butyl ester

To a solution of 6-bromo-7-fluoro-quinoline (1.04 g, 4.6 mmole) in tetrahydrofuran (1 mL) was added a solution of tert-butylzincbromide acetate (20 mL, 10.4 M in tetrahydrofuran) followed by Pd(PPh$_3$)$_4$ (0.58 g, 0.5 mmole). The mixture was heated in a microwave reactor for 35 min at 120° C. The reaction mixture was quenched with a saturated ammonium chloride (60 mL), and extracted with ethyl acetate. The organic layer was dried over anhydrous Na$_2$SO$_4$, filtered and concentrated. The residue was purified by column chromatography to afford the title compound (0.75 g, 63%).

Step 3: (7-fluoro-quinolin-6-yl)-acetic acid

A mixture of (7-fluoro-quinolin-6-yl)-acetic acid tert-butyl ester (3.67 g) and 4N aquous sodium hydroxide (14.8 mL) were heated at 90° C. for 3 h. The solution was extracted with ethyl acetate. The aqueous layer was adjusted to acidic pH with acetic acid and filtered and dried to afford the title compound (2.3 g, 79.8%). $^1$H NMR (300 MHz, DMSO-d6) δ 12.52 (1H, s), 8.88~8.90 (d, 1H), 8.34~8.38 (d, 1H), 7.97~7.99 (d, 1H), 7.73~7.76 (d, 1H), 7.50~7.54 (m, 1H), 3.85 (s, 2H). ES-MS m/z: 206.2 (M+1).

Intermediate 13: (7-Methyl-quinolin-6-yl)-acetic acid

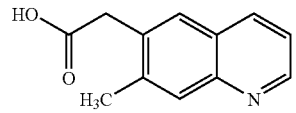

Step 1: 6-Bromo-7-methyl-quinoline

A mixture of 20 g of 4-bromo-3-methyl-phenylamine, 6.6 g of ferrous sulfate, 40.8 g of propane-1,2,3-triol, 8.12 g of nitrobenzene and 23 ml of concentrated sulfuric acid were heated gently. After the first vigorous reaction, the mixture was heated to reflux for 3 h and then evaporated to remove the excess nitrobenzene. To the solution was added saturated NaHCO$_3$ to pH 8 and the solution was filtered and extracted with dichloromethane. The dichloromethane layers were combined and dried over Na$_2$SO$_4$ and concentrated. The solid was purified via flash column chromatography to give yellow solid which was washed with petroleum ether to return the title compound (7.5 g, 65%). NMR (CDCl$_3$, 300 MHz) δ 8.89 (m, 1H), 8.04 (m, 2H), 7.96 (s, 1H), 7.36 (m, 1H), 2.60 (s, 3H).

Step 2: (7-Methyl-quinolin-6-yl)-acetic acid tert-butyl ester

To 1.02 g of 6-bromo-7-methyl-quinoline were added a solution of 20 ml of tert-butylzincbromide acetate and 0.58 g of Pd(PPh$_3$)$_4$. The mixture was placed in the microwave reactor for 30 min to achieve a temperature of 120° C. (repeated for 3 times.). Purification via flash column chromatography returned the title compound (3.2 g, 68%). $^1$H NMR (CDCl$_3$, 300 MHz) δ 8.84 (m, 1H), 8.07 (m, 1H), 7.89 (s, 1H), 7.63 (s, 1H), 7.31 (m, 1H), 3.72 (s, 2H), 2.51 (s, 3H), 1.46 (s, 9H).

Step 3: (7-Methyl-quinolin-6-yl)-acetic acid 3.2 g of (7-methyl-quinolin-6-yl)-acetic acid tert-butyl ester in 25 ml of aqueous NaOH (4N) was heated to reflux for 4 h. The mixture was washed with ethyl acetate and added concentrated hydrochloric acid to pH 7. A white solid formed which was filtered and dried to return the title compound (1.5 g, 71.1%). $^1$H NMR (DMSO-d6, 300 MHz) δ 12.46 (s, 1H), 8.82 (m, 1H), 8.26 (m, 1H), 7.82 (s, 1H), 7.77 (s, 1H), 7.44 (m, 1H), 3.80 (s, 2H), 2.44 (s, 3H) ES-MS m/z: 202 (M$^+$+H).

Intermediate 14: Fluoro-quinolin-6-yl-acetic acid hydrochloride

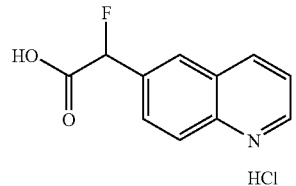

Step 1: Fluoro-quinolin-6-yl-acetonitrile

A solution of quinolin-6-yl-acetonitrile (1.06 g, 6.3 mmol) in tetrahydrofuran (40 mL) was cooled to −78° C. to which tert-butyl lithium (0.8 M in pentane, 7.6 mmol, 7.9 mL) was added in a dropwise fashion over 10 minutes. After the addition was complete the mixture was stirred at −78° C. for 30 min before a solution of N-fluorodi(benzenesulfonyl)-amine (1.5 eq., 9.45 mmol, 3.0 g) in tetrahydrofuran (10 mL) was added. The reaction mixture was stirred for 2 hours at −78° C. before water was added followed by aqueous NaHCO$_3$. The mixture was extracted with dichloromethane (3×80 mL), dried (Na$_2$SO$_4$) and concentrated in vacuo onto silica gel and purified via flash column chromatography (SiO$_2$, hexane: ethyl acetate 100/0-50/50) to return the title compound as a red solid (520 mg, 2.8 mmol, 44%). $^1$H NMR 500 MHz (DMSO-d6) δ 6.05 (1H, d), 7.66 (1H, dd), 7.95 (1H, dd), 8.19 (1H, d), 8.32 (1H, t), 8.55 (1H, d), 9.03 (1H, dd); MS (m/z) 187 [M+H$^+$]$^+$.

Step 2: Fluoro-quinolin-6-yl-acetic acid hydrochloride

Fluoro-quinolin-6-yl-acetonitrile (370 mg, 2.0 mmol) was taken up in concentrated hydrochloric acid (4 mL) and heated to 145° C. for 8 min in a microwave. After such time the mixture was concentrated in vacuo to return the title compound as a white solid in quantitative yield. $^1$H NMR 500 MHz (D$_2$O) δ 6.05 (1H, d), 7.99-6.93 (1H, m), 8.14-8.05 (2H, m), 8.26 (1H, s), 9.05-8.95 (2H, m). MS (m/z) 204 [M−H$^+$]$^-$.

Intermediate 15: [6-(1-Methyl-1H-pyrazol-4-yl)-pyridazin-3-yl]-hydrazine

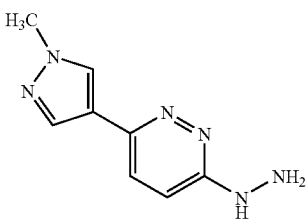

Step 1 method 1.1 3-Chloro-6-(1-methyl-1H-pyrazol-4-yl)-pyridazine

A mixture of 3,6-dichloropyridazine (5.37 g, 33.5 mmol), 1-methyl-4-pyrazoleboronic acid pinacol ester (5 g, 24.0 mmol) and cesium carbonate (23.44 g, 72 mmol) in 1,4-dioxane (150 mL) and water (750 mL) under nitrogen was degassed by bubbling in nitrogen for 15 min. Dichloro[1,1'-bis(diphenylphosphino)ferrocene]palladium(II) dichloromethane adduct (1 g, 1.37 mmol) was than added and nitrogen was bubbled in the mixture for another 10 min. The reaction mixture was stirred at 80° C. for 2.5 h, then cooled to room temperature and concentrated in vacuo. The residue was partitioned between 1 N aqueous potassium carbonate and ethyl acetate. The organic layer was washed with 1 N aqueous potassium carbonate and brine, dried over sodium sulfate, filtered and adsorbed on silica gel for purification. Purification by flash chromatography on silica gel using a gradient of 0-50% ethyl acetate/hexane afforded 2.8 g of the title compound as a white solid (60% yield); MS (m/z) 195 [M+H$^+$]$^+$.

Step 1 method 1.2: 3-Chloro-6-(1-methyl-1H-pyrazol-4-yl)-pyridazine

A mixture of 3,6-dichloropyridazine (20.1 g, 135 mmol), 1-methyl-4-pyrazoleboronic acid pinacol ester (25.46 g, 122 mmol) and potassium carbonate (50.7 g, 367 mmol) in 1,4-dioxane (500 mL) and water (200 mL) under nitrogen was degassed by bubbling in nitrogen for 15 min. Dichlorobis (triphenylphosphine)palladium (II) (1.2%, 1 g, 1.4 mmol) was than added and nitrogen was bubbled in the mixture for another 10 min. The reaction mixture was stirred at 90° C. for 3 h, then cooled to room temperature and concentrated in vacuo to remove the majority of the 1,4-dioxane. The residue was partitioned between 1 N aqueous potassium carbonate (400 mL) and ethyl acetate (400 mL) and the phases separated. The aqueous layer was extracted with ethyl acetate (2×300 mL) and dichloromethane (300 mL). The combined organic layers were washed with brine, dried over sodium sulfate, filtered and concentrated in-vacuo. The residue was stirred in diethyl ether (150 mL) and the orange precipitate was filtered and dried to return the title compound (12.76 g, 65.6 mmol, 54% yield). The filtrate was concentrated onto silica gel and purified by flash chromatography on silica gel using a gradient of 0-50% ethyl acetate/hexane to return starting 3,6-dichloropyridazine as a white solid (9.9 g, 66.4 mmol, 49% yield).

Step 2: [6-(1-Methyl-1H-pyrazol-4-yl)-pyridazin-3-yl]-hydrazine

To a suspension of 3-chloro-6-(1-methyl-1H-pyrazole-4-yl)-pyridazine (1.0 g, 4.81 mmol) in ethanol (20 mL) was added hydrazine monohydrate (2.33 mL, 48 mmol). The reaction mixture was stirred at 80° C. for 3.5 h, cooled to room temperature and concentrated in vacuo. The residue was triturated with 1 N aqueous potassium carbonate, filtered, washed with water and dried in vacuo to provide 2 g of the title compound as a beige solid (670 mg, 73% yield): $^1$H NMR (DMSO-d6) δ 3.92 (s, 3H), 4.28 (s, 1H) 7.02 (d, 1H), 7.59 (d, 1H), 7.84 (s, 1H), 7.90 (s, 1H), 8.19 (d, 1H); MS (m/z) 191 [M+H$^+$]$^+$.

Intermediate 16: 2-Benzothiazol-6-yl-propionic acid

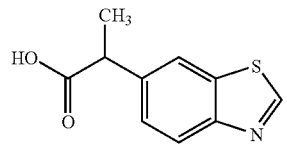

Step 1: Benzothiazol-6-yl-acetic acid methyl ester

SOCl$_2$ (13.5 g, 114.0 mmol) was added dropwise to a stirred solution of benzothiazol-6-yl-acetic acid (20.0 g, 103.6 mmol) in 150 ml of methanol at 0° C. under N$_2$. After stirring for 2 hours at room temperature the solvent was evaporated and the residue was diluted with ethyl acetate (150 ml). The mixture was washed with saturated sodium carbonate solution (100 ml×3) and brine (100 ml) and then concentrated in vacuo. The residue was purified by column chromataghaphy eluting with ethyl acetate/petroleum ether (1:5) to return the title compound as a pale yellow oil (15.0 g, 71.5%).

Step 2: 2-Benzothiazol-6-yl-propionic acid methyl ester

A solution of n-BuLi (2.5M in hexane, 27.0 ml) was added to a stirred solution of diisopropylamine (7.08 g, 70.0 mmol) in anhydrous tetrahydrofuran (150 ml) cooled to −30° C. under a nitrogen atmosphere. The mixture was stirred for 30 minutes the reaction mixture was cooled to −78° C. To this solution was added a solution of benzothiazol-6-yl-acetic acid methyl ester (10.4 g, 50.0 mmol) in 10 ml of tetrahydrofuran and hexamethylphosphoramide (13.5 g, 75.0 mmol). The mixture was stirred at −78° C. for 2 hours before the addition of a solution of methyl iodide (10.2 g, 72.0 mmol) in anhydrous tetrahydrofuran at −78° C. The mixture was stirred for a further 2 hours at −78° C. The reaction mixture was warmed slowly to room temperature and diluted with aqueous saturated solution of $NH_4Cl$ (200 ml). The mixture was extracted with ethyl acetate (×2) and the combined organic layers were washed with water and brine, dried over anhydrous sodium sulfate and concentrated to give brown oil. This oil was purified via flash column chromatography eluting with petroleum and ethyl acetate (10:1) to return the title compound as a pale yellow oil (4.5 g, 40.5%).

Step 5: 2-Benzothiazol-6-yl-propionic acid

A mixture of 2-benzothiazol-6-yl-propionic acid methyl ester (6.6 g, 30.0 mmol) and aqueous 2 N NaOH (23.0 ml) was heated at reflux for 1 hour until the reaction mixture became a dark red solution. The mixture was then cooled to room temperature and the mixture extracted with dichloromethane (×2) and the aqueous layer was acidified with conc.hydrochloric acid to pH4-5. The resulting solid was filtered off to afford the crude product, which was stirred in ethyl acetate the filtered and dried in vacuo to provide the title compound (4.3 g, 69.2%) as an off white solid. (300 MHz, DMSO-d6): δ 12.41 (s, 1H), 9.35 (s, 1H), 8.09-8.08 (d, J=1.5 Hz, 2H), 8.05-8.02 (d, J=8.7 Hz 2H), 7.48-7.45 (dd, J=1.5 Hz, 8.7 Hz, 1H), 3.89 (q, 1H), 1.45 (d, 3H). MS m/z 208 ($M^+$+1).

Intermediate 17: (8-Methyl-quinolin-6-yl)-acetic acid

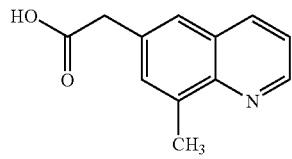

Step 1: 6-Bromo-8-methyl-quinoline

A mixture of 10 g of 4-bromo-2-methylaniline, 3.3 g of ferrous sulfate, 20.4 g of glycerol, 4.06 g of nitrobenzene and 11.5 ml of concentrated sulfuric acid was heated gently. After the first vigorous reaction, the mixture was boiled for 3 h under reflux and then evaporated to remove t nitrobenzene. The solution was added std. aq.NaHCO₃ and extracted with dichloromethane, dried with $Na_2SO_4$ and concentrated to give solid. The solid was purified with flash column chromatography to return the title compound (9.5 g, 80%). $^1$H NMR (CDCl₃, 300 MHz) δ 8.92 (m, 1H), 8.01 (m, 1H), 7.81 (d, 1H), 7.66 (m, 1H), 7.43 (m, 1H), 2.79 (s, 3H).

Step 2: (8-Methyl-quinolin-6-yl)-acetic acid tert-butyl ester

Under N₂, 20 ml of tetrahydrofuran and 0.5 ml (3.9 mmol) of chlorotrimethylsilane were added to (5.2 g, 80 mmol) of zinc powder. The mixture was stirred at r.t. for 20 min. A solution of (5.9 ml, 40 mmol) of tert-butyl 2-bromoacetate in 50 ml of tetrahydrofuran was added dropwise. The mixture was stirred at 42° C.-45° C. for 20 min. This was allowed to cool to 25° C. to obtain 76 ml of a 0.52 M solution of the tert-butyl reformatsky reagent. To 1.039 g of 6-bromo-8-methyl-quinoline was added a solution of the previouslt prepared Reformatsky reagent 20 ml, followed by addition of 0.541 g of Pd(PPh₃)₄. The mixture was place into the microwave reactor for 30 min to achieve a temperature of 120° C. The above procedure was repeated an additional 4 times. The combined reaction mixtures were combined and purified via clumn chromatography to return the title compound (3.5 g, 49%). $^1$H NMR (CDCl₃, 300 MHz) δ 8.92 (m, 1H), 8.11 (m, 1H), 7.54 (s, 1H), 7.50 (s, 1H), 7.40 (s, 1H), 3.67 (s, 2H), 2.81 (s, 3H), 1.46 (s, 9H).

Step 3: (8-Methyl-quinolin-6-yl)-acetic acid 3.5 g of (8-methyl-quinolin-6-yl)-acetic acid tert-butyl ester in 18 ml of NaOH (4N, aq.) was heated to reflux for 3 h. The mixture was washed with ethyl acetate and the water layer was acidified with 1N hydrochloric acid to pH 4-5 and extracted with dichloromethanfe. The solvent was evaporated and the resulting solid was washed with water and dried in vacuo to return the title compound as an off white solid (1.3 g, 48%). $^1$H NMR (DMSO-d6, 300 MHz) δ 12.42 (s, 1H), 8.90 (m, 1H), 8.30 (m, 1H), 7.66 (s, 1H), 7.54 (m, 2H), 3.74 (s, 2H), 2.70 (s, 3H).

Intermediate 18: (8-Fluoro-quinolin-6-yl)-acetic acid

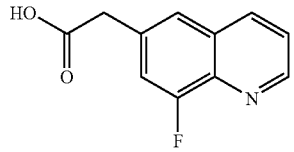

Step 1: 6-Bromo-8-fluoro-quinoline

A mixture of 4-bromo-2-fluoroaniline (12.825 g, 67.5 mmol), 4.275 g of ferrous sulfate, 25.46 g (20.2 ml) of glycerol, 5.067 g (4.2 ml) of nitrobenzene and 11.79 ml of concentrated sulfuric acid was heated gently. After the first vigorous reaction, the mixture was boiled for 7 hours. The nitrobenzene was removed in vacuo. Water was added. The aqueous solution was acidified with glacial acetic acid, and the dark brown precipitate separated, which was purified by flash chromatography (silica gel, petroleum/ethyl acetate=12/1) to return the title compound as white solid (9.72 g, 63.7%).

Step 2: (8-Fluoro-quinolin-6-yl)-acetic acid tert-butyl ester

Under N₂, 20 ml of tetrahydrofuran and 0.5 ml (3.9 mmol) of chlorotrimethylsilane were added to 5.2 g (80 m mole) of zinc powder. The mixture was stirred at r.t. for 20 min. A solution of 5.9 ml (40 mmol) of tert-butyl 2-bromoacetate in 50 ml of tetrahydrofuran was added dropwise. The mixture was stirred at 42° C.-45° C. for 20 min. This was allowed to cool to 25° C. to obtain 76 ml of a 0.52 M solution of the tert-butyl reformatsky reagent. To a solution of 6-bromo-8-fluoro-quinoline (1.04 g, 4.6 mmol) in 1 ml of tetrahydrofuran was added a solution of above zinc reagent (20 ml, 10.4 mmol), followed by Pd(PPh$_3$)$_4$ (0.58 g, 0.5 m mole). The mixture was placed into the microwave reactor for 35 min to achieve temperature of 120° C. Then, the reaction was quenched with sat. aq. NH$_4$Cl (60 ml) and the mixture was extracted with ethyl acetate. The organic layer was dried over anhydrous Na$_2$SO$_4$, filtered and concentrated. The residue was purified by column chromatography to afford the title compound (0.78 g, 65%).

Step 3: (8-Fluoro-quinolin-6-yl)-acetic acid 0.5 g of (8-fluoro-quinolin-6-yl)-acetic acid tert-butyl ester with 2.0 ml of 4N aq. sodium hydroxide solution was heated at 90° C. for 3 h. After cooling the reaction mixture was extracted with ethyl acetate. The aqueous layer was made just acidic with acetic acid, filtered to afford the title compound as an off white solid (0.24 g, 61%). $^1$H NMR (300 MHz, DMSO-d6) δ 8.91~8.93 (m, 1H), 8.37~8.40 (m, 1H), 7.51~7.69 (m, 3H), 3.80 (s, 2H); ES-MS m/z: 206.2 (M$^+$+1).

Intermediate 19: (3-Bromo-quinolin-6-yl)-acetic acid methyl ester

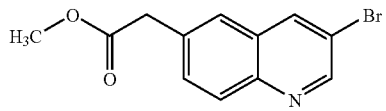

To a stirred solution of quinolin-6-yl-acetic acid (Step 1, intermediate 11) (21.6 g, 107 mmol) in 150 ml of carbon tetrachloride was added bromine (34.4 g, 215 mmol) and heated to reflux for 4 hours. The reaction mixture was then diluted with 17.0 g of pyridine, and further stirred for 2 hours under reflux. After cooling down to ambient temperature, the mixture was partitioned between dichloromethane and saturated aqueous sodium hydrogen carbonate. The organic layer was washed with water then brine, dried over magnesium sulfate then evaporated under reduced pressure to give a brown residue. The residue was purified via column chromatography with petroleum (60~90° C.), and then a 30/1 mixed solvent of petroleum and ethyl acetate to give the title compound (13.6 g, 45.3%) as a white crystalline solid. (300 MHz, DMSO-d6): 8.89 (d, 1H), 8.27 (d, 1H), 8.06 (d, 1H), 7.67~7.64 (m, 2H), 3.82 (s, 2H), 3.72 (s, 3H). ES-MS m/z: 280 (M+H$^+$). 360 (M+H$^+$).

Intermediate 20: (3-Bromo-quinolin-6-yl)-acetic acid

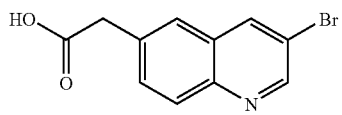

A mixture of (3-bromo-quinolin-6-yl)-acetic acid methyl ester (14.8 g, 52.8 mmol) and aqueous 2 N NaOH (80 ml, 160 mmol) was heated under reflux for 1.5 hours until reaction mixture became clear. After cooling down to room temperature the reaction mixture was washed with dichloromethane then the water layer was acidified with concentrated hydrochloric acid to pH 4. A white precipitate was filtered off the stirred in refluxing methanol, filtered and dried in vacuo to give the product title compound as a white solid (10.3 g, 73.5%). (300 MHz, DMSO-d6): 12.52 (b, 1H), 8.91 (d, 1H), 8.69 (d, 1H), 7.99 (d, 1H)), 7.82~7.70 (m, 2H), 3.80 (s, 2H). ES-MS m/z: 266 (M+H$^+$).

Intermediate 21: 1-Ethyl-4-(4,4,5,5-tetramethyl-[1,3,2]dioxaborolan-2-yl)-1H-pyrazole

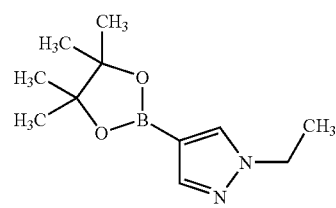

Prepared according to procedure described in Journal of Heterocyclic Chemistry, (2004), 41(6), 931-939.

Intermediate 22: (1H-Pyrrolo[2,3-b]pyridin-3-yl)-acetic acid

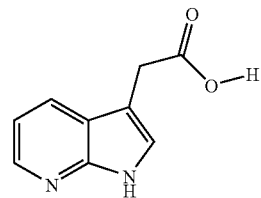

Prepared according to procedure described in Journal of the American Chemical Society (1956), 78 1247-51.

Intermediate 23: (6-Methyl-pyridazin-3-yl)-hydrazine

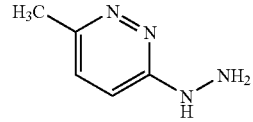

Prepared according to procedure described in Australian Journal of Chemistry (1977), 30(10), 2319-22.

Intermediate 24: 3-(6-Hydrazino-pyridazin-3-yl)-benzonitrile

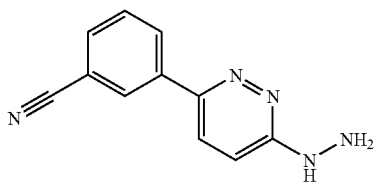

Step 1: 3-(6-Chloro-pyridazin-3-yl)-benzonitrile

Nitrogen gas was bubbled through a mixture of 3-cyanophenyl boronic acid (90.0 g, 612 mmol), 3,6-dichloropyridazine (1.2 eq, 109.4 g, 735 mmol), potassium carbonate (3.0 eq, 253.5 g, 1.836 mol) in 1,4-dioxane (900 mL) and water (360 mL) for 15 minutes. After such time dichloro[1,1'-bis(diphenylphosphino)ferrocene]palladium(II) dichloromethane adduct (0.06 eq, 26.8 g, 36.7 mmol) was added. Nitrogen bubbled through for further 10 mins then the mixture was heated to 90° C. for 3 hours. The reaction was cooled and the most of the 1,4-dioxane was removed under vacuo. The mixture taken up in dichloromethane and washed with water three times. The organic layer was concentrated and the residue was purified by column chromatography to return the title compound (60 g, 45.5% yield) as a white solid. $^1$H NMR (300 MHz, DMSO-d6): δ 8.58~8.59 (m, 1H), 8.44~8.52 (m, 2H), 8.09~8.12 (d, 1H), 8.02~8.05 (d, 1H), 7.76~7.81 (m, 1H); MS (m/z) 216.1 (M$^+$+1).

Step 2: 3-(6-Hydrazino-pyridazin-3-yl)-benzonitrile

A solution of 3-(6-chloro-pyridazin-3-yl)-benzonitrile (75.6 g, 350 mmol) in 900 mL of dried pyridine was cooled in an ice bath and 119.2 mL of hydrazine hydrate was added. The cooling was continued so as to keep the temperature below 30° C. at which time yellow needle separated. The mixture was then heated to 65° C. and stirred overnight. Then the mixture was concentrated and the residue was washed with water and Methanol to return the title compound (60 g, 81%) as a yellow solid. $^1$H NMR (300 MHz, DMSO-d6): δ 8.38~8.39 (m, 1H), 8.32~8.35 (m, 1H), 8.24 (s, 1H), 7.97~8.00 (d, 1H), 7.82~7.85 (m, 1H), 7.64~7.69 (m, 1H), 7.09~7.12 (d, 1H), 4.39 (s, 2H); MS (m/z) 212.1 [M$^+$+1].

Intermediate 25: 1-{2-[4-(4,4,5,5-Tetramethyl-[1,3,2]dioxaborolan-2-yl)-pyrazol-1-yl]-ethyl}-piperidine

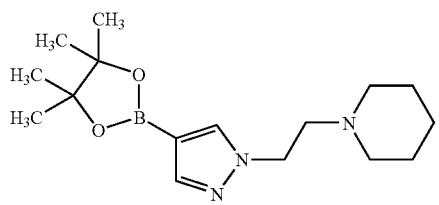

To a 5 ml microwave vial 2 ml of dimethylformamide was added to dissolve 150 mgs (0.773 mmols) of 4-(4,4,5,5-Tetramethyl-[1,2,3]dioxaborolan-2-yl)-1H-pyrazole. After addition of 2 eq. (1.546 mmols) of 1-(2-chloro-ethyl)-piperidine the reaction mixture was heated at 190° C. in a microwave (Personel Chemistry, Emrys Optimizer) for one hour. Water (5 mL) was then added to the reaction mixture and extracted with ethyl acetate (2×3 mL). The organics were combined and dried over sodium sulfate. The solvent was removed in vacuo to return the title compound which was used in the next step without further purification.

Intermediate 26: 2-Fluoro-4-(6-hydrazino-pyridazin-3-yl)-N-methyl-benzamide

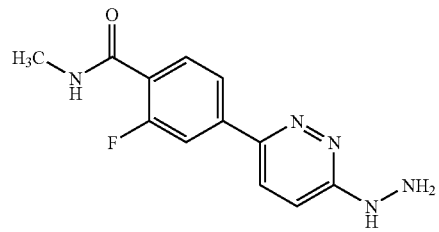

Step 1: 4-(6-Chloro-pyridazin-3-yl)-2-fluoro-N-methyl-benzamide

Nitrogen gas was bubbled through a mixture of 4-boronic acid-2-fluoro-N-methyl-benzamide (50 g, 254 mmol), 3,6-dichloropyridazine (1.02 eq, 38.6 g, 259 mmol), potassium carbonate (3.0 eq 105.2 g, 761 mmol) in 1,4-dioxane (500 mL) and water (200 mL) for 15 minutes. After such time dichloro[1,1'-bis(diphenylphosphino)ferrocene]palladium (II) dichloromethane adduct (0.06 eq, 15.0 mmol, 11.0 g) was added. Nitrogen was bubbled through for further 10 mins then the mixture was heated to 90° C. for 3 hours. Cooled and the most of dioxane removed in vacuo. The mixture was taken up in dichloromethane and washed with water three times. The organic layer was concentrated and the residue was purified by column chromatography to return the title compound (27.1 g 40% yield) as a white solid. $^1$H NMR (300 MHz, CDCl$_3$): δ (ppm): δ 8.24~8.30 (m, 1H), 7.96~8.01 (m, 1H), 7.83~7.87 (m, 2H), 7.61~7.64 (d, 1H), 6.80~6.84 (m, 1H) 3.06~3.08 (m, 3H); MS (m/z): 266.1 [M$^+$+1]

Step 2: 2-Fluoro-4-(6-hydrazino-pyridazin-3-yl)-N-methyl-benzamide

A solution of 4-(6-chloro-pyridazin-3-yl)-2-fluoro-N-methyl-benzamide 34 g (128 mmol) in 500 mL of dry pyridine was cooled in an ice bath and 43.5 mL of hydrazine hydrate was added. The cooling was continued so as to keep the temperature below 30° C. at which time yellow needle separated. The mixture was then heated to 65° C. and stirred overnight. The mixture was filtered and the solid washed with water and Methanol to return the title compound (28.8 g, 84% yield) as a light yellow solid. $^1$H NMR (300 MHz, DMSO-d6): δ (ppm): 8.27 (s, 2H), 7.96~7.99 (d, 1H), 7.86~7.92 (m, 2H), 7.69~7.75 (m, 1H), 7.09~7.12 (d, 1H), 4.42 (s, 2H), 2.78~2.80 (d, 3H); MS (m/z): 262.1 [M$^+$+1].

Intermediate 27: (3-Bromo-quinolin-6-yl)-acetic acid methyl ester

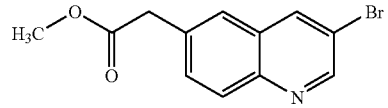

To a stirred solution of quinolin-6-yl-acetic acid (21.6 g, 107 mmol) in 150 ml of carbon tetrachloride was added bromine (34.4 g, 215 mmol) and heated to reflux for 4 hours. The reaction mixture was then diluted with 17.0 g of pyridine, and further stirred for 2 hours under reflux. After cooling down to ambient temperature, the mixture was partitioned between dichloromethane and saturated aqueous sodium hydrogen carbonate. The organic layer was washed with water then brine, dried over magnesium sulfate then evaporated under reduced pressure to give a brown residue. The residue was purified via column chromatography with petroleum (60~90° C.), and then a 30/1 mixed solvent of petroleum and ethyl acetate to give the title compound (13.6 g, 45%) as a white crystalline solid. (300 MHz, DMSO-d6): 8.89 (d, 1H), 8.27 (d, 1H), 8.06 (d, 1H), 7.67~7.64 (m, 2H), 3.82 (s, 2H), 3.72 (s, 3H). ES-MS m/z: 280 (M+H$^+$).

Intermediate 28: (3-Bromo-quinolin-6-yl)-acetic acid hydrazide

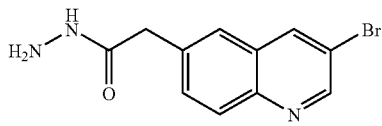

To a mixture of (3-bromo-quinolin-6-yl)-acetic acid (5 g, 18.9 mmol) in methanol (100 mL) was added concentrated sulfuric acid (1 mL) and the mixture heated to reflux for 16 hours. The heat was removed and sodium sulphate (20 g) was added and the mixture filtered. To the filtrate was then added hydrazine mono hydrate (3.2 mL) and the mixture heated to reflux for a further 16 hours. The mixture was then allowed to cool to room temperature then water was added (60 mL) and the formed precipitate collected via filtration and dried to return tilt compound as a white solid (4.72 g, 16.9 mmol, 90% yield). $^1$H-NMR 500 MHz (DMSO-d6) 3.57 (2H, s), 4.26 (2H, d), 7.72 (1H, dd), 7.80 (1H, d), 7.97 (1H, d), 8.69 (1H, d), 8.90 (1H, d), 9.35 (1H, bs). ES-MS m/z: 280 (M+H$^+$).

Intermediate 29: (3-Bromo-quinolin-6-yl)-acetic acid

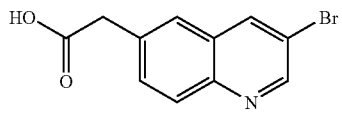

A mixture of (3-bromo-quinolin-6-yl)-acetic acid methyl ester (14.8 g, 52.8 mmol) and aqueous 2 N NaOH (80 ml, 160 mmol) was heated under reflux for 1.5 hours until reaction mixture became clear. After cooling down to room temperature the reaction mixture was washed with dichloromethane then the water layer was acidified with concentrated hydrochloric acid to pH 4. A white precipitate was filtered off the stirred in refluxing methanol, filtered and dried in vacuo to give the product title compound as a white solid (10.3 g, 74%). (300 MHz, DMSO-d6): 12.52 (b, 1H), 8.91 (d, 1H), 8.69 (d, 1H), 7.99 (d, 1H)), 7.82~7.70 (m, 2H), 3.80 (s, 2H). ES-MS m/z: 266 (M+H$^+$).

Intermediate 30: [3-(1-Methyl-1H-pyrazol-4-yl)-quinolin-6-yl]-acetic acid

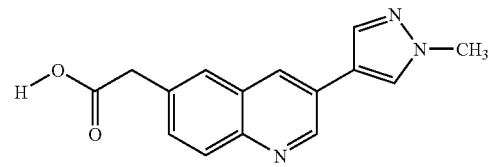

To a 20 mL microwave vial was added (3-bromo-quinolin-6-yl)-acetic acid (1 g, 3.77 mmol), 1-methyl-4-pyrazoleboronic acid pinacol ester and 1,4-dioxane (10 mL). Nitrogen was bubbled through the mixture for 10 minutes. Potassium carbonate (1.56 g, 11.3 mmol) was and water (5 mL) were then added, and nitrogen was bubbled through the mixture for a further three minutes. After such time dichlorobis(triphenylphosphine)palladium (138 mg, 0.19 mmol) was added, the vial sealed and heated in a microwave for 1250 seconds at 130° C. The mixture was then filtered through celite, which was washed with water and saturated aqueous sodium bicarbonate. The 1,4-dioxane in the solution was removed under vacuum and the remaining aqueous solution washed with dichloromethane three times. The water layer was acidified to pH 6 using 4M hydrochloric acid and the formed precipitate collected via filtration and dried to return the title compound as an off white solid. (500 MHz, DMSO-d6): ES-MS m/z: 268 (M+H$^+$).

Intermediate 31: [3-(1-Methyl-1H-pyrazol-4-yl)-quinolin-6-yl]-acetic acid methyl ester

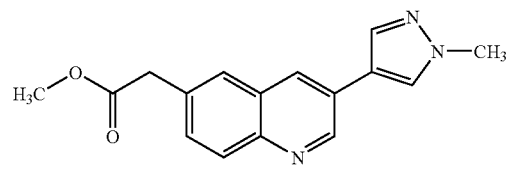

To a solution of [3-(1-methyl-1H-pyrazole-4-yl)-quinolin-6-yl]-acetic acid (2.4 g, 8.6 mmols) and methanol (12 mL) at 0° C. was added thionyl chloride (2 eq., 17.2 mmols) in a dropwise fashion. The reaction mixture was then heated to 60° C. for one hour. The solvent was removed under vacuum and used in the next step without further purification. MS m/z: 282 (M+H$^+$).

Intermediate 32: [3-(1-Methyl-1H-pyrazol-4-yl)-quinolin-6-yl]acetic acid hydrazide

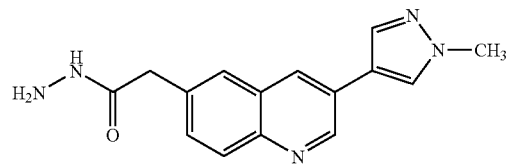

A solution of [3-(1-Methyl-1H-pyrazol-4-yl)-quinolin-6-yl]-acetic acid methyl ester (8.6 mmols) and hydrazine (80.6 mmols) in methanol (75 mL) was heated at 55° C. for an hour before a second addition of hydrazine (80.6 mmol) was added and the reaction heated 55° C. for a further 16 hours After such time the mixture was cooled to 0° C. and the resulting precipitate collected via filtration and washed with cold methanol and dried to return the title compound as a white solid (1.74 g, 70%). $^1$H NMR 500 MHz (DMSO-d6): ES-MS m/z: 282 (M+H$^+$).

Intermediate 33:
(3-Bromo-5,7-difluoro-quinolin-6-yl)-acetic acid methyl ester

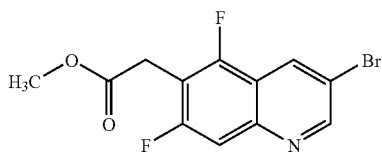

To a solution of (5,7-difluoro-quinolin-6-yl)-acetic acid (18.6 g, 83.4 mmol) in methanol (200 mL) was added conc. $H_2SO_4$ (4.7 mL, 87.0 mmol). The reaction mixture was concentrated to give a brown residue, which was diluted with 200 ml of ethyl acetate, washed with sat. aq. $NaHCO_3$ and brine, then the organic layer was dried over anhydrous $Na_2SO_4$, and concentrated to give (7-fluoro-quinolin-6-yl)-acetic acid methyl ester as yellow solid (17.7 g, yield: 89.8%).

Intermediate 34: (5,7-Difluoro-quinolin-6-yl)-acetyl chloride

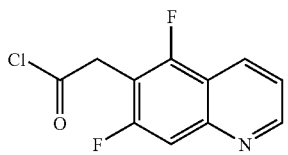

(5,7-Difluoro-quinolin-6-yl)-acetic acid (1 g, 4.48 mmol) was added to an oven-dried round-bottom flask and suspended in dichloromethane (18 ml) The suspension was maintained under nitrogen atmosphere and cooled to 0° C. Next, the oxalyl chloride (470 uL, 5.38 mmol) was added slowly, followed by a catalytic amount of dimethylformamide. The solution was allowed to warm to room temperature over 2 hours. The solution was then concentrated in vacuo and dried via azeotropic distillation with toluene to afford the title compound. ES-MS m/z: 238 (M+H$^+$) of methyl ester.

Intermediate 35:
(3-Bromo-5,7-difluoro-quinolin-6-yl)-acetic acid

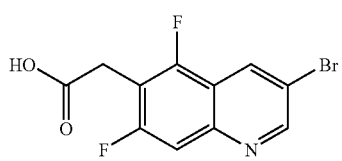

Step 1: Preparation of
(3-bromo-5,7-difluoro-quinolin-6-yl)-acetic acid methyl ester To a mixture of (5,7-difluoro-quinolin-6-yl)-acetic acid methyl ester (35.3 g, 148.9 mmol) and pyridine (24 mL, 298 mmol) in 300 mL of carbon tetrachloride was added bromine (15.3 mL, 298 mmol) in a dropwise fashion. The mixture was heated to reflux for 2 hrs before being cooled to ambient temperature. The liquid in the flask was decanted and washed with $NaHCO_3$ and water. The dark solid on the bottom of the flask was treated with $NaHCO_3$ and dichloromethane. The combined organic layers were washed with water, dried ($Na_2SO_4$) and evaporated to dryness. The crude product was purified via flash column chromatography eluting with petroleum ether/ethyl acetate (40/1~3/1) to return 31.5 g (67% yield) of the title compound as white crystalline solid. $^1$H NMR (DMSO-d6): δ 8.92 (d, 1H), 8.50 (d, 1H), 7.57~7.61 (m, 1H), 3.91 (s, 2H), 3.75 (s, 3H).

Step 2: Preparation of
(3-bromo-5,7-difluoro-quinolin-6-yl)-acetic acid

A suspension of (3-bromo-5,7-difluoro-quinolin-6-yl)-acetic acid methyl ester (10.0 g, 31.6 mmol) in 48 mL of aqueous NaOH (2N) was heated to reflux for 2 hrs then cooled to r.t. The mixture was washed with dichloromethane (50 mL×2) and the aqueous phase acidified with 5N hydrochloric acid to pH 4. The white precipitate was collected via filtration, washed with water and dried. 9.6 g of the title compound was obtained as white powder in 100% yield. $^1$H NMR (DMSO-d6): δ 12.87 (s, 1H), 9.05 (s, 1H), 8.76 (s, 1H), 7.75~7.79 (d, 1H), 3.87 (s, 2H).

LC-MS: 303 (M$^+$+1).

Intermediate 36: [5,7-Difluoro-3-(1-methyl-1H-pyrazol-4-yl)-quinolin-6-yl]-acetic acid

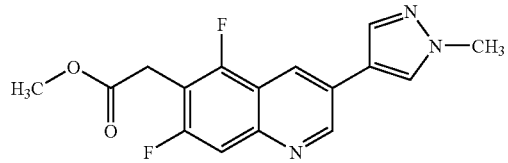

To a 20 mL microwave vial (3-bromo-2,4-difluoro-quinolin-6-yl)-acetic acid methyl ester (1 g, 3.16 mmol), 1-methyl-4-(4,4,5,5-tetramethyl-[1,3,2]dioxaborolan-2-yl)-1H-pyrazole (1.2 eq. 3.79 mmol, 788 mg) and 1,4-dioxane (10 mL) were added. Nitrogen was bubbled through a needle then potassium carbonate (3 eq. 9.49 mmol) and water (5 mL) were added and nitrogen was bubbled through the mixture for 3 minutes. Dichlorobis(triphenylphosphine)-palladium (138 mg, 0.19 mmol) was added and the mixture heated for 1250 seconds at 130° C. The mixture was filtered through celite and washed with water and saturated aqueous sodium bicarbonate. The 1,4-dioxane was then removed under vacuum and the water layer was extracted with dichloromethane three times. The organic layer was dried over sodium sulfate, and the solvent removed under vacuum.

The crude was loaded onto silica then purified on the isco using a dichloromethane, methanol gradient (Methanol 0 to 10%) to obtain 508 mg of light yellow material with a 50% yield. MS: m/z 318.0 (M+H$^+$).

Intermediate 37: [5,7-Difluoro-3-(1-methyl-1H-pyrazol-4-yl)-quinolin-6-yl]-acetic acid hydrazide

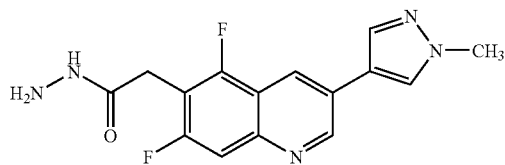

To a 40 ml vial was added methanol (12 mL), [5,7-difluoro-3-(1-methyl-1H-pyrazol-4-yl)-quinolin-6-yl]-acetic acid methyl ester (508 mg, 1.6 mmol) and hydrazine anhydrous (4 eq., 6.4 mmols). After 1 hour at 55° C. a second portion of hydrazine (4 eq., 6.4 mmol) was added and the reaction heated at 55° C. for a further 1 hour. The reaction mixture was cool down to room temperature, filtered and washed with cold methanol. The product was dried to return the title compound as a white solid (425 mg, 83% yield). MS: m/z 318.0 (M+H$^+$).

Intermediate 38: (7-Fluoro-quinolin-6-yl)-acetic acid methyl ester

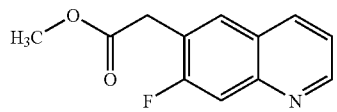

To a solution of (7-fluoro-quinolin-6-yl)-acetic acid (13.4 g, 65.36 mmol) in methanol (140 mL) was added conc.H$_2$SO$_4$ (3.5 mL, 68.63 mmol). The reaction mixture was concentrated to give a brown residue, which was diluted with 100 ml of ethyl acetate, washed with sat. aq. NaHCO$_3$ and brine, then the organic layer was dried over anhydrous Na$_2$SO$_4$, and concentrated to give (7-fluoro-quinolin-6-yl)-acetic acid methyl ester as yellow solid (14.0 g, yield: 98%).

Intermediate 39: (3-Bromo-7-fluoro-quinolin-6-yl)-acetic acid

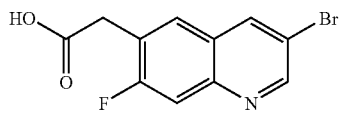

Step 1: Preparation of (3-bromo-7-fluoro-quinolin-6-yl)-acetic acid methyl ester To a mixture of (7-fluoro-quinolin-6-yl)-acetic acid methyl ester (14.0 g, 63.9 mmol) and pyridine (10.4 mL, 127.8 mmol) in 200 mL of carbon tetrachloride was added bromine (6.6 mL, 127.8 mmol) in a dropwise fashion. The mixture was heated to reflux for 2 hrs before being cooled to ambient temperature. The liquid in the flask was decanted and washed with NaHCO$_3$ and water. The dark solid on the bottom of the flask was treated with NaHCO$_3$ and dichloromethane. The combined organic layers were washed with water, dried (Na$_2$SO$_4$) and evaporated to dryness. The crude product was purified via flash column chromatography eluting with petroleum ether/ethyl acetate (40/1~3/1) to return 13.9 g (75% yield) of the title compound as white crystalline solid. $^1$H NMR (DMSO-d6): δ 8.89 (s, 1H), 8.27 (m, 1H), 7.66~7.74 (m, 2H), 3.87 (s, 2H), 3.74 (s, 3H).

Step 2: Preparation of (3-bromo-7-fluoro-quinolin-6-yl)-acetic acid

A suspension of (3-bromo-7-fluoro-quinolin-6-yl)-acetic acid methyl ester (13.9 g, 46.6 mmol) in 72 mL of aqueous NaOH (2N) was heated to reflux for 2 hrs then cooled to r.t. The mixture was washed with dichloromethane (50 mL×2) and the aqueous phase acidified with 5N hydrochloric acid to pH 4. The white precipitate was collected via filtration, washed with water and dried. 11.0 g of the title compound was obtained as white powder in 83.3% yield. $^1$H NMR (DMSO-d6): δ 12.64 (s, 1H), 8.94~8.95 (d, 1H), 8.72~8.72 (m, 1H), 7.94~7.97 (d, 1H), 7.77~7.81 (d, 1H), 3.85 (s, 2H). LC-MS: 283.9 (M$^+$+1).

Intermediate 40: [7-Fluoro-3-(1-methyl-1H-pyrazol-4-yl)-quinolin-6-yl]acetic acid

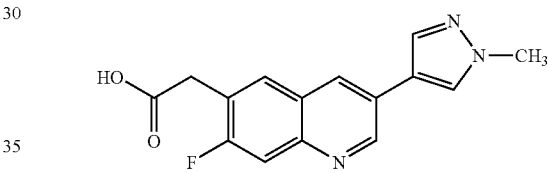

Nitrogen gas was bubbled through a suspension of (3-bromo-7-fluoro-quinolin-6-yl)-acetic acid (5 g, 17.7 mmol), 1-methyl-4-pyrazoleboronic acid pinacol ester (3.86 g, 18.6 mmol), potassium carbonate (7.3 g, 53 mmol) in 1,4-dioxane (50 mL) and water (20 mL) for 10 minutes. After such time dichlorobis(triphenylphosphine)palladium (II) (248 mg, 0.35 mmol) was added and the mixture heated to reflux for 3 hours. The aqueous phase was removed via pipette, diluted with 2N aqueous potassium carbonate (15 mL) and washed with ethyl acetate (2×30 mL). The aqueous phase was then acidified to pH 3 with concentrated hydrochloric acid. The formed precipitate was collected via filtration and washed with water and dried to return the title compound as a white solid (4.2 g, 14.7 mmol, 83% yield). $^1$H NMR 500 MHz (DMSO-d6): δ 3.84 (2H, s), 3.92 (3H, s), 7.71 (1H, d), 7.90 (1H, d), 8.10 (1H, s), 8.39 (1H, s), 8.47 (1H, d), 9.18 (1H, d). ES-MS m/z: 286 (M+H$^+$).

Intermediate 41: [7-Fluoro-3-(1-methyl-1H-pyrazol-4-yl)-quinolin-6-yl]acetic acid hydrazide

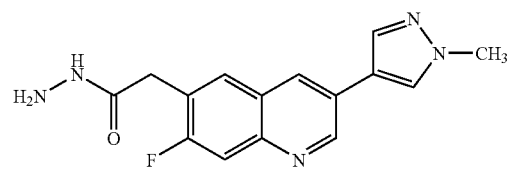

To a mixture of [7-fluoro-3-(1-methyl-1H-pyrazol-4-yl)-quinolin-6-yl]-acetic acid (4 g, 14.0 mmol) in methanol (80 mL) was added concentrated sulfuric acid (0.8 mL) and the mixture heated to reflux for 16 hours. The heat was removed and sodium sulphate (20 g) was added and the mixture filtered. To the filtrate was then added hydrazine mono hydrate (3.2 mL) and the mixture heated to reflux for a further 16 hours. The mixture was then allowed to cool to room temperature then water was added (60 mL) and the formed precipitate collected via filtration and dried to return the title compound as a light grey solid (3.51 g, 11.7 mmol, 84% yield). $^1$H-NMR 500 MHz (DMSO-d6) 3.63 (2H, s), 3.91 (3H, s), 4.28 (2H, d), 7.69 (1H, d), 7.88 (1H, d), 8.09 (1H, s), 8.38 (1H, s), 8.47 (1H, d), 9.16 (1H, d), 9.32 (1H, bs). ES-MS m/z: 300 (M+H$^+$).

Intermediate 42: 3-Chloro-6-iodo-pyridazine

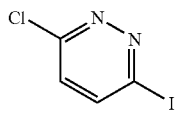

To a 40 mL vial 2.5 g of 3,6-dichloropyridazine (16.9 mmol) was added, followed by 12.5 mL of hydriodic acid and 3.75 g of potassium iodide. The reaction mixture was heated to 40° C. for three hours then cooled to room temperature. The reaction mixture was poured onto ice containing 10M NaOH and the formed precipitate collected via filtration and dried to return the title compound (2.36 g, 60%). MS: m/z 340.9

Intermediate 43: 3-Chloro-6-trifluoromethyl-pyridazine

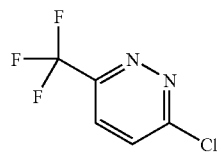

To a 200 ml round bottom flask one gram (4.16 mmol) of 3-chloro-6-iodo-pyridazine was combined under nitrogen with 1.5 eq. of copper iodide (6.24 mmol), 2 eq. (8.32 mmol) of potassium fluoride, and 2 eq. (8.32 mmol) of methyl-dichloro-fluoro-acetate in 75 ml of dimethylformamide. The reaction mixture was heated to 115° C. for 16 hours. The solvent was removed under vacuum and the solid partitioned between dichloromethane and water (150 ml). The formed emulsion was the filtered through celite and the organic layer dried over sodium sulfate. The organic layer was loaded onto silica gel and purified on silica gel eluting with 0% ethyl acetate to 50% ethyl acetate in hexanes to return the title compound (150 mg, 20%) MS: m/z 183.1.

Intermediate 44: 4-(4,4,5,5-Tetramethyl-[1,3,2]dioxaborolan-2-yl)-1-(2-trimethylsilanyl-ethoxymethyl)-1H-pyrazole

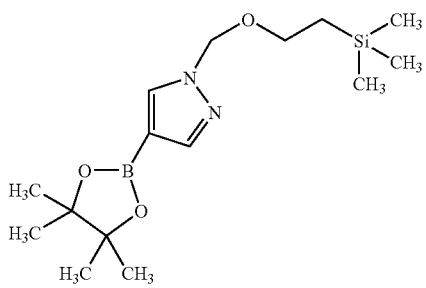

The title compound was prepared by the method described by Guzi, Timothy J.; Paruch, Kamil; Dwyer, Michael P.; Labroli, Marc; Keertikar, Kartik M. Preparation of novel pyrazolopyrimidines as cyclin dependent kinase inhibitors. U.S. Pat. Appl. Publ. (2007), 144 pp., US2007072881 making non critical changes.

Intermediate 45: 4-[4-(4,4,5,5-Tetramethyl-[1,3,2]dioxaborolan-2-yl)-pyrazol-1-yl]-piperidine-1-carboxylic acid tert-butyl ester

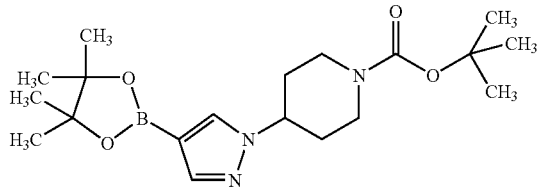

The title compound was prepared by the method described by Cui, Jingrong Jean; Funk, Lee Andrew; Jia, Lei; Kung, Pei-Pei; Meng, Jerry Jialun; Nambu, Mitchell David; Pairish, Mason Alan; Shen, Hong; Tran-Dube, Michelle Bich. Preparation of pyrazole-substituted aminoheteroaryl compounds as c-Met protein kinase inhibitors for use against cancer and other abnormal cell growth disorders. PCT Int. Appl. (2006), 185 pp. WO2006021881, making non-critical changes.

Intermediate 46: 1-(2-Methoxy-ethyl)-4-(4,4,5,5-tetramethyl-[1,3,2]dioxaborolan-2-yl)-1H-pyrazole

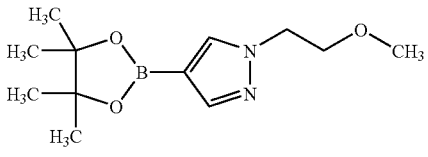

The title compound was prepared by the method described by Ivachtchenko, Alexandre V.; Kravchenko, Dmitry V.; Zheludeva, Valentina I.; Pershin, Dmitry G. Synthesis of pinacol esters of 1-alkyl-1H-pyrazol-5-yl- and 1-alkyl-1H-pyrazol-4-ylboronic acids. Journal of Heterocyclic Chemistry (2004), 41(6), 931-939, making non-critical changes.

Intermediate 47: 1-[4-(4,4,5-Trimethyl-[1,3,2]dioxaborolan-2-yl)-pyrazol-1-yl]-butan-2-one

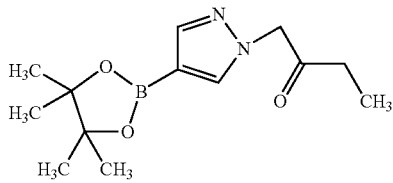

Pyrazole-4-boronic acid pinacol ester (1 g, 1 equiv, 5.15 mmol) was dissolved in dimethylformamide (15 mL) followed by the addition of $Cs_2CO_3$ (0.86 g, 1.5 equiv, 7.73 mmol) and 1-bromo-2-butanone (1.1 equiv, 5.67 mmol, 0.86 g). The mixture was heated at 90° C. overnight. The reaction was extracted into ethyl acetate and washed with water (3×) and brine (3×). The filtrate was concentrated in vacuo onto silica gel and purified by flash chromatography ($SiO_2$, $CH_2Cl_2$:$CH_3OH$ 100:0-80:20) to return the title compound (0.19 g, 14% yield). $^1$H NMR 500 MHz (DMSO) δ 0.97 (3H, t) 1.26 (12H, s), 2.50 (2H, q), 4.71 (2H, s), 7.65 (1H, s), 8.04 (1H, s). MS m/z 265 $(M+H^+)^+$.

Intermediate 48: 3-[4-(4,4,5,5-Tetramethyl-[1,3,2]dioxaborolan-2-yl)-pyrazol-1-yl]-propionitrile

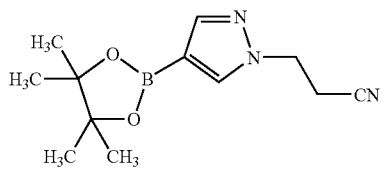

Pyrazole-4-boronic acid pinacol ester (1 g, 1 equiv, 5.15 mmol) was dissolved in dimethylformamide (15 mL) followed by the addition of $Cs_2CO_3$ (0.86 g, 1.5 equiv, 7.73 mmol) and 3-chloropropionitrile (1.1 equiv, 5.67 mmol, 0.44 mL). The mixture was heated at 90° C. overnight. The reaction was diluted with ethyl acetate and washed with water (3×) and brine (3×). The organic phases was concentrated in vacuo onto silica gel and purified by flash chromatography ($SiO_2$, $CH_2Cl_2$:$CH_3OH$ 100:0-90:10) to return the title compound (0.11 g, 9%). $^1$H NMR (500 MHz, DMSO): δ 1.26 (12H, s), 3.07 (2H, t), 4.40 (2H, t), 7.65 (1H, s), 8.04 (1H, s). MS m/z 248 $(M+H^+)^+$.

Intermediate 49: 3-(4-Bromo-pyrazol-1-yl)-azetidine-1-carboxylic acid tert-butyl ester

Intermediate 50: 3-(4-Bromo-pyrazol-1-ylmethyl)-azetidine-1-carboxylic acid tert-butyl ester; and Intermediate 51: 2-(4-Bromo-pyrazol-1-yl)-ethanol

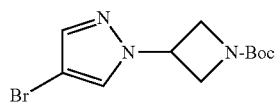

49

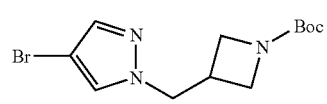

50

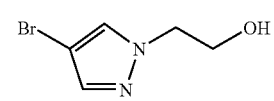

51

Intermediates 49, 50, 51 were prepared by the methods described by Cui, Jingrong Jean; Funk, Lee Andrew; Jia, Lei; Kung, Pei-Pei; Meng, Jerry Jialun; Nambu, Mitchell David; Pairish, Mason Alan; Shen, Hong; Tran-Dube, Michelle Bich. Preparation of pyrazole-substituted aminoheteroaryl compounds as c-Met protein kinase inhibitors for use against cancer and other abnormal cell growth disorders. PCT Int. Appl. (2006), 185 pp. WO2006021881, making non-critical changes.

Intermediate 53: 1-Ethyl-4-(4,4,5,5-tetramethyl-[1,3,2]dioxaborolan-2-yl)-1H-pyrazole

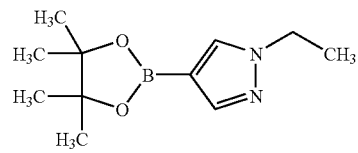

The title compound was prepared by the method described by Ivachtchenko, Alexandre V.; Kravchenko, Dmitry V.; Zheludeva, Valentina I.; Pershin, Dmitry G. Synthesis of pinacol esters of 1-alkyl-1H-pyrazol-5-yl- and 1-alkyl-1H-pyrazol-4-ylboronic acids. Journal of Heterocyclic Chemistry (2004), 41(6), 931-939, making non-critical changes.

Intermediate 54: 1-(4-Iodo-pyrazol-1-yl)-cyclobutanecarboxylic acid ethyl ester

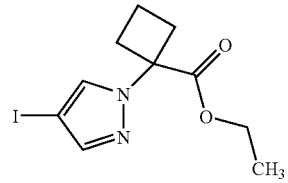

To a solution of iodopyrazole (2.93 g, 15.09 mmol) in dimethylformamide (25 mL) was added NaH (60% in oil, 724 mg, 30.18 mmol) while nitrogen was bubbled through the solution and the mixture stirred under nitrogen for 30 min. A solution of 1-bromo-cyclobutanecarboxylic acid ethyl ester (1.95 mL, 12.07 mmol) was added slowly and the solution was stirred overnight. Ethyl acetate was added to the reaction to extract the product. The ethyl acetate layer was washed with water (3×) and brine (3×) and dried over sodium sulfate. The filtrate was concentrated in vacuo onto silica gel and purified by flash chromatography ($SiO_2$, hexanes:ethyl acetate 100:0-75:25) to return the title compound (0.71 g, 15% yield). $^1$H NMR (DMSO): δ 1.15 (t, 3H), 1.90-2.04 (m, 2H), 2.69-2.77 (m, 2H), 4.10 (q, 2H), 7.59 (s, 1H), 8.13 (s, 1H). MS m/z=321 $(M+H^+)^+$.

Intermediate 55: 3-Chloro-6-vinyl-pyridazine

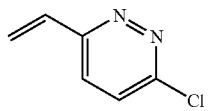

A mixture of 3,6-dichloropyridazine (6 g, 40.3 mmol), vinyl boronic acid pinnacol ester (6.21 g, 6.83 mL, 40.3 mmol), potassium carbonate (120 mmol, 16.7 g), 1,4-dioxane (60 mL) and water (24 mL) was degassed for 15 min with nitrogen gas. Dichloro[1,1'-bis(diphenylphosphino)ferrocene]palladium(II) dichloromethane adduct (0.4 mmol, 292 mg) was then added and the mixture heated to 80° C. for 4 hours. The aqueous phase was then removed via pipette and the organic phase concentrated onto silica gel and purified via flash column chromatography ($SiO_2$, hexane:ethyl acetate 100:0-60:40) to return the title compound as a white solid (5.2 g, 92% yield). $^1$H NMR ($CDCl_3$): δ 5.75 (1H, d), 6.25 (1H, d), 7.05 (1H, dd), 7.49 (1H, d), 7.59 (1H, d). MS m/z=141 $(M+H^+)^+$.

Intermediate 56: 3-Chloro-6-ethyl-pyridazine

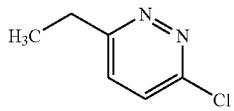

A mixture of 3-chloro-6-vinyl-pyridazine (1 g, 7.09 mmol), palladium on carbon (10% wt, 200 mg) in ethyl acetate (14 mL) under a hydrogen atmosphere was stirred vigorously at ambient temperature for 4 hours. The mixture was then filtered through a pad of celite and the filtrate concentrated onto silica gel and purified via flash column chromatography ($SiO_2$, hexane:ethyl acetate 90:10-50:50) to return the title compound as a white solid (627 mg, 63% yield). $^1$H NMR ($CDCl_3$): δ 1.27 (3H, t), 2.93 (2H, q), 7.72 (1H, d), 7.83 (1H, d). MS m/z=143 $(M+H^+)^+$.

Intermediate 57: [5-(1-Methyl-1H-pyrazol-4-yl)-1H-pyrrolo[2,3-b]pyridin-3-yl]-acetic acid hydrazide

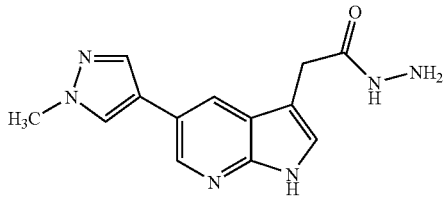

Step 1: 5-(1-Methyl-1H-pyrazol-4-yl)-1H-pyrrolo[2,3-b]pyridine

5-Bromo-1H-pyrrolo[2,3-b]pyridine (1.0 g, 5.05 mmol), 1-methyl-4-(4,4,5,5-tetramethyl-[1,3,2]dioxaborolan-2-yl)-1H-pyrazole (1.17 g. 5.55 mmol) and Pd(dppf)$_2$Cl$_2$ (37 mg, 0.045 mmol) were placed in a N$_2$ charged round bottom flask. DMA (6 mL) was added to the reaction vessel and the solution was bubbled with N$_2$ for 10 minutes. K$_2$CO$_3$ (978 mg, 7.07 mmol) was dissolved in water (6 mL), bubbled with N$_2$ and added to the reaction vessel while maintaining the temperature below room temperature with an ice/water bath. The reaction vessel was bubbled with additional N$_2$ for 10 minutes, fitted with a vigeruex column and N$_2$ line and heated to 75° C. overnight. The reaction was not complete; therefore, additional 1-Methyl-4-(4,4,5,5-tetramethyl-[1,3,2]dioxaborolan-2-yl)-1H-1-pyrazole (1.0 g) and Pd(dppf)$_2$Cl$_2$ (124 mg) were added to the reaction. The solution was heated an additional 4 hours. After this period, water (12 mL) was added to the reaction vessel and the solution was heated for 1 hour at 60° C. The solution was transferred to a separatory funnel with dichloromethane (300 mL) and partitioned from the aqueous layer. The organic layer was dried over Na$_2$SO$_4$, concentrated down on silica gel and purified by flash chromatography (0-10% Methanol/dichloromethane gradient) to afford the title compound (780 mg, 78% yield). MS m/z=199 $[M+H^+]^+$

Step 2: [5-(1-Methyl-1H-pyrazol-4-yl)-1H-pyrrolo[2,3-b]pyridin-3-yl]-acetic acid 5-(1-Methyl-1H-pyrazol-4-yl)-1H-pyrrolo[2,3-b]pyridine (780 mg, 3.94 mmol) and Eschenmoser's Salt (1.46 g, 7.88 mmol) were combined in acetonitrile:acetic acid (19:1, 12.3 ml and 700 uL, respectively) and heated for 5 hours at 40° C. Next, 4N potassium hydroxide was added until pH>9. The solution was transferred to a separatory funnel and extracted with copious amount of ethyl acetate. The organic layer was dried over Na$_2$SO$_4$ and concentrated down. Next methyl iodide (246 uL, 3.94 mmol) in ethanol (11 mL) was added to the crude gramine and the solution was stirred at room temperature overnight. The solution was concentrated under vacuum and redissolved in dimethylformamide (10 mL) and water (2 mL). This was then heated to 70° C. for 3 hours. The reaction was allowed to return to room temperature, transferred to a separatory funnel with ethyl acetate (250 mL) and washed with water (2×200 mL). The aqueous layers were combined and back extracted with ethyl acetate (200 mL). The organic layer was dried over Na$_2$SO$_4$ and concentrated down to afford the crude [5-(1-Methyl-1H-pyrazol-4-yl)-1H-pyrrolo[2,3-b]pyridin-3-yl]-acetonitrile. This material was then dissolved in methanol (6 mL) and 4N potassium hydroxide (8 mL) and heated at 90° C. overnight. The solution was then acidified with 1N hydrochloric acid (aq) until precipitate formed. The precipitate was then filtered and washed with water to afford the crude product. The product was purified by flash chromatography (0-15% methanol/dichloromethane gradient) to afford the title compound (284 mg, 28%). MS m/z=257 $[M+H^+]^+$

Step 3: [5-(1-Methyl-1H-pyrazol-4-yl)-1H-pyrrolo[2,3-b]pyridin-3-yl]-acetic acid methyl ester

[5-(1-Methyl-1H-pyrazol-4-yl)-1H-pyrrolo[2,3-b]pyridin-3-yl]-acetic acid (200 mg, 0.78 mmol) was suspended in Methanol (4 mL). Next, sulfuric acid (125 uL) was added and the solution was heated to reflux for 2 hours. The solution was concentrated under vacuum and the crude material was dissolved in dichloromethane, transferred to a separatory funnel and washed with sat. NaHCO$_3$ (aq). The organic layer was dried over Na$_2$SO$_4$ and concentrated down. The crude product was purified by flash chromatography (0-10% Methanol/dichloromethane gradient) to afford the title compound (148 mg, 70% yield). MS m/z=271 $[M+H^+]^+$

Step 4: [5-(1-Methyl-1H-pyrazol-4-yl)-1H-pyrrolo[2,3-b]pyridin-3-yl]-acetic acid hydrazide 5-(1-Methyl-1H-pyrazol-4-yl)-1H-pyrrolo[2,3-b]pyridin-3-yl]-acetic acid methyl ester (148 mg, 0.55 mmol) was dissolved in ethanol (3.0 mL) and Hydrazine hydrate (500 uL). The solution was heated to reflux for 1 hour. The reaction was discontinued and the solution was allowed to return to room temperature. The product crystallized and was filtered off to afford the title compound (92 mg, 63% yield). MS m/z=271 [M+H+]+; (DMSO-d6) 3.88 (3H, s), 4.21 (2H, bs), 7.27 (1H, s), 7.85 (1H, s), 8.10 (2H, s), 8.42 (1H, d), 9.17 (1H, s), 11.37 (1H, s)

Intermediate 58: [6-(1-Methyl-1H-pyrazol-4-yl)-pyrrolo[3,2-b]pyridin-1-yl]-acetic acid hydrazide

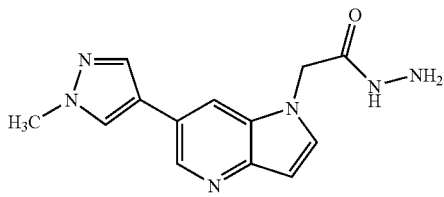

Step 1: 6-Bromo-1H-pyrrolo[3,2-b]pyridine

To a solution of 5-bromo-2-methyl-3-nitro-pyridine (1.58 g, 7.28 mmol) [prepared according to WO 2006/103449] in dimethylformamide (10 mL) was added dimethylformamide dimethyl acetal (1.65 mL, 12.37 mmol). The reaction mixture was stirred at 100° C. for 1 h, then cooled to room temperature and concentrated in vacuo. The residue was dissolved in glacial acetic acid (25 mL) and iron powder (3.25 g, 58.24 mmol) was added. The reaction mixture was stirred at 100° C. for 21 h, then it was cooled to room temperature. Methanol (25 mL) was added and the suspension was filtered and washed with Methanol. The filtrate was concentrated in vacuo. The residue was partitioned between saturated aqueous sodium bicarbonate and ethyl acetate. The organic layer was separated, dried over sodium sulfate, filtered, and adsorbed on silica gel. Purification on silica gel by flash chromatography using a gradient of 0-70% ethyl acetate/hexane provided 869 mg of the title compound as an ivory solid (60% yield): $^1$H NMR (DMSO-d6): δ 6.77 (s, 1H), 7.68 (s, 1H), 8.00 (s, 1H), 8.36 (s, 1H), 11.46 (broad s, 1H); MS (m/z) 197, 199 [M+H+]+.

Step 2: 6-(1-Methyl-1H-pyrazol-4-yl)-1H-pyrrolo[3,2-b]pyridine

To an N$_2$ charged microwave vial, 6-bromo-1H-pyrrolo[3,2-b]pyridine (327 mg, 1.65 mmol) was added and dissolved in DMA (2 mL). The solution was bubbled with N$_2$ for 5 minutes. Next, 1-methyl-4-(4,4,5,5-tetramethyl-[1,3,2]dioxaborolan-2-yl)-1H-pyrazole (516 mg, 2.48 mmol) was added to the solution, which was bubbled with N$_2$ for an additional 5 minutes. K$_2$CO$_3$ (320 mg, 2.31 mmol) was dissolved in water (2 ml) and the solution was bubbled with N$_2$ for 5 minutes. The aqueous solution was added to the reaction vessel and the solution was bubbled with N$_2$ again. Finally, the Pd(dppf)$_2$Cl$_2$ (81 mg, 0.10 mmol) was added to the solution, bubbled with N$_2$, sealed and microwaved for 15 minutes at 130° C. The reaction was then transferred to a separatory funnel with dichloromethane (75 mL) and washed with water (2×75 mL). The aqueous layer was back extracted with dichloromethane (75 mL). The organic layers were combined, dried over Na$_2$SO$_4$ and vacuumed down. The crude material was purified by flash chromatography (0-80% acetonitrile/dichloromethane gradient) to afford the title compound (200 mg, 61% yield). MS m/z=199 [M+H+]+.

Step 3: [6-(1-Methyl-1H-pyrazol-4-yl)-pyrrolo[3,2-b]pyridin-1-yl]-acetic acid ethyl ester In a N$_2$ charged round bottom flask, Sodium Hydride, 60%, (41 mg, 1.01 mmol) was suspended in dimethylformamide (2.5 mL). The solution was maintained under N$_2$ and cooled to 0° C. for 10 minutes. Next, 6-(1-Methyl-1H-pyrazol-4-yl)-1H-pyrrolo[3,2-b]pyridine (200 mg, 1.01 mmol) was dissolved in dimethylformamide (2.5 mL) and added to the cooled solution dropwise. The solution was allowed to stir at 0° C. for an additional 10 minutes. Finally, Bromo-acetic acid ethyl ester (123 uL, 1.11 mmol) was slowly added to the reaction vessel. The reaction was allowed to equilibrate back to room temperature, while stirring for 2 hours. Finally, the solution was transferred to a separatory funnel with dichloromethane (75 mL) and washed with water (2×75 mL). The organic layer was dried over Na$_2$SO$_4$, concentrated down and purified by flash chromatography (0-10% Methanol/dichloromethane step gradient) to afford the title compound (122 mg, 43% yield). MS m/z=285 [M+H+]+

Step 4: [6-(1-Methyl-1H-pyrazol-4-yl)-pyrrolo[3,2-b]pyridin-1-yl]-acetic acid hydrazide

[6-(1-Methyl-1H-pyrazol-4-yl)-pyrrolo[3,2-b]pyridin-1-yl]-acetic acid ethyl ester (122 mg, 0.42 mmol) was dissolved in ethanol (1 mL) and hydrazine hydrate (500 uL). The solution was heated to reflux for 1 hour. Next the solution was concentrated down under vacuum and redissolved in a minimal amount of hot methanol. The product crystallized and was a collected by filtration to afford the title compound (114.8 mg, 99% yield). MS m/z=271 [M+H+]+

Intermediate 59: 5-(3-Bromo-quinolin-6-ylmethyl)-[1,2,4]triazole-3,4-diamine

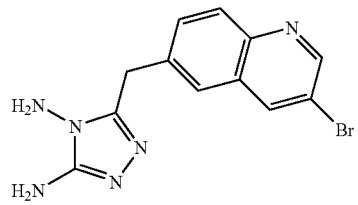

Step 1: 5-(3-Bromo-quinolin-6-ylmethyl)-[1,3,4]oxadiazol-2-ylamine

A mixture of (3-bromo-quinolin-6-yl)-acetic acid hydrazide (prepared according to procedure described herein) (4.12 g, 14.7 mmol), cyanogen bromide (1.1 eq., 16.2 mmol, 1.7 g) and KHCO$_3$ (1.25 eq., 18.3 mmol, 1.83 g) was stirred in methanol (30 mL) at ambient temperature for 18 hours. The was then diluted with water (40 mL) and the solid was collected via filtration and washed with cold methanol and dried to return the title compound as an off white solid (4.02 g, 13.2 mmol, 90%). $^1$H NMR (DMSO-d6): δ 4.27 (2H, s), 6.94 (s, 2H), 7.71 (dd, 1H), 7.86 (d, 1H), 8.02 (d, 1H), 8.73 (d, 1H); 8.93 (d, 1H); MS (m/z) 305 [M+H$^+$]$^+$.

Step 2: 5-(3-Bromo-quinolin-6-ylmethyl)-[1,2,4] triazole-3,4-diamine

A mixture of 5-(3-bromo-quinolin-6-ylmethyl)-[1,3,4] oxadiazol-2-ylamine (3.53 g, 11.6 mmol), hydrazine hydrate (30 mL) and water (15 mL) was heated in a microwave vial at 170° C. and 2 bar of pressure for 1 hour. After cooling the formed solid was collected via filtration and washed with cold methanol and dried to return the title compound as white solid (1.79 g, 5.6 mmol, 49%). $^1$H NMR (DMSO-d6): δ 4.13 (2H, s), 5.46 (s, 2H), 5.56 (s, 2H), 7.23 (d, 1H), 7.81 (s, 1H), 7.98 (d, 1H), 8.71 (d, 1H); 8.91 (d, 1H); MS (m/z) 319 [M+H$^+$]$^+$.

Intermediate 60:
(3-Bromo-5,7-difluoro-quinolin-6-yl)-acetic acid hydrazide

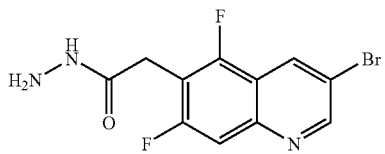

SOCl$_2$ (394 mg, 3.31 mmol) was added dropwise to a stirred solution of (3-bromo-5,7-difluoro-quinolin-6-yl)-acetic acid (500 mg, 1.65 mmol) in 12 ml of methanol at 0° C. under N$_2$. After stirring for 2 hours at room temperature the solvent was evaporated and the crude (3-bromo-5,7-difluoro-quinolin-6-yl)-acetic acid methyl ester was used directly in the next step. To a mixture of (3-bromo-5,7-difluoro-quinolin-6-yl)-acetic acid methyl ester (2.29 g, 7.22 mmol) in methanol (100 mL) was added anhydrous hydrazine (2.31 g, 72.2 mmol). The mixture was heated at 55° C. for 4 hours. Additional anhydrous hydrazine (1.16 g, 36.1) was added and the mixture was heated at 55° C. for 2 hours. The reaction mixture was cooled to room temperature to give a white solid. The white solid was filtered and washed with cold methanol to obtain 2.1 g of the title compound (92% yield). MS: m/z 318 [M+H$^+$]. $^1$H NMR (500 MHz. DMSO-d$_6$): δ 1.99 (2H, s), 4.25 (2H, bs), 7.72 (1H, d), 8.74 (1H, s), 9.03 (1H, s), 9.35 (1H, s).

Intermediate 61:
(3-Bromo-5-fluoro-quinolin-6-yl)-acetic acid

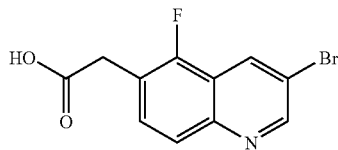

Step 1: 6-bromo-5-fluoro-quinoline

A mixture of 4-bromo-3-fluoro-phenylamine (100 g, 526 mmol), ferrous sulfate (30 g), glycerol (200 g), nitrobenzene (40 g) and concentrated sulfuric acid (100 mL) were heated gently. After the first vigorous reaction, the mixture was heated to reflux for 5 hours. Nitrobenzene was evaporated in vacuo. The aqueous solution was acidified with glacial acetic acid and dark brown precipitate separated, which was purified by flash chromatography (silica gel, petroleum/ethyl acetate=12/1) to return a mixture of 6-bromo-5-fluoro-quinoline and 6-bromo-7-fluoro-quinoline as a white solid (80 g, 68%). This mixture was heated to reflux in petroleum ether. The solution was cooled to r.t., filtered and dried to return 6-bromo-7-fluoro-quinoline as a white solid. To the solution was added HCl/MeOH, and a white solid precipitated from the solution. The solid was filtered and basified. The resulting precipitate was collected by filtration and dried to obtain 6-bromo-5-fluoro-quinoline as white solid. $^1$H-NMR (DMSO-d$_6$, 300 MHz): 9.0 (d, 1H), 8.5 (d, 1H), 8.0 (m, 1H), 7.8 (d, 1H), 7.7 (m, 1H); MS: m/z 228 [M+H$^+$]$^+$.

Step 2: (5-Fluoro-quinolin-6-yl)-acetic acid tert-butyl ester

To a solution of 6-bromo-5-fluoro-quinoline (1.0 g, 4.5 mmol) in tetrahydrofuran (1 mL) was added a solution of tert-butylzincbromide acetate (9 mmol, 20 mL, 10.4 M in tetrahydrofuran) followed by Pd(PPh$_3$)$_4$ (0.52 g, 0.45 mmol). The mixture was heated in a microwave reactor for 30 min at 120° C. The reaction mixture was quenched with a saturated ammonium chloride (60 mL), and extracted with ethyl acetate. The organic layer was dried over anhydrous Na$_2$SO$_4$, filtered and concentrated. The residue was purified by column chromatography to afford the title compound (0.83 g, 71%). $^1$H-NMR (CDCl$_3$, 300 MHz): 8.9 (d, 1H), 8.4 (d, 1H), 7.8 (d, 1H), 7.6 (m, 1H), 7.5 (m, 1H), 3.7 (d, 2H), 1.4 (s, 9H).

Step 3: (5-Fluoro-quinolin-6-yl)-acetic acid methyl ester (5-Fluoro-quinolin-6-yl)-acetic acid tert-butyl ester (5 g, 19 mmol) in 25 ml of aq. NaOH (4N) was heated to reflux for 4 h. The mixture was washed with ethyl acetate and the aqueous layer was acidified to pH 5 with conc. HCl. The resulting precipitate was collected and washed with water and dried in vacuo to return (5-fluoro-quinolin-6-yl)-acetic acid. To this solid was added conc.H$_2$SO$_4$ (1.2 ml) and MeOH (20 ml) and the solution heated to reflux for 6 h. After cooling the solvent was removed in vacuo and the residue purified by flash column chromatography to return the title compound (2.0 g 48%).

Step 4: (3-Bromo-5-fluoro-quinolin-6-yl)-acetic acid methyl ester

To a solution of (5-fluoro-quinolin-6-yl)-acetic acid methyl ester (2.0 g, 9 mmol) in CCl$_4$ (20 ml) and pyridine (1.48 ml, 18 mmol) was added bromine (0.9 ml, 18 mmol) dropwise at 5° C. The solution was heated to reflux for 20 minutes. After cooling, the reaction was quenched by sat. aq. NaHCO$_3$ and the mixture extracted with dichloromethane and concentrated. The residue was purified by flash column chromatography to return the title compound (1.8 g, 66%). $^1$H-NMR (CDCl$_3$, 300 MHz): 8.9 (d, 1H), 8.5 (d, 1H), 7.8 (d, 1H), 7.6 (m, 1H), 3.9 (d, 2H), 3.7 (s, 3H).

Step 5: (3-Bromo-5-fluoro-quinolin-6-yl)-acetic acid

3-Bromo-5-fluoro-quinolin-6-yl)-acetic acid methyl ester (1.2 g) in 10 ml of aq. NaOH (4N) was heated to reflux for 4 h. The mixture was washed with ethyl acetate and the aqueous layer was acidified to pH 5 with conc. HCl. The resulting precipitate was collected and washed with water and dried in vacuo to return the title compound (838 mg 74%). $^1$H-NMR (DMSO-d$_6$, 300 MHz): 12.6 (s, 1H), 9.0 (d, 1H), 8.7 (d, 1H), 7.9 (d, 1H), 7.8 (m, 1H), 3.9 (d, 2H). MS: 283, 285 (M+1).

Intermediate 62: (3-Bromo-5-fluoro-quinolin-6-yl)-acetic acid hydrazide

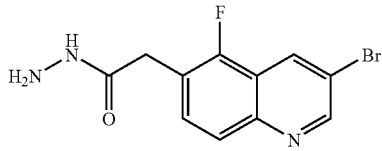

A solution of (3-bromo-5-fluoro-quinolin-6-yl)-acetic acid (800 mg, 2.7 mmol) and hydrazine hydrate (98%, 2 mL) in methanol (15 mL) was heated to reflux for 1 h. The solvent was removed in vaco to obtain a white solid which was washed with methanol and dried to return the title compound (750 mg, 94%) as a white solid. $^1$H-NMR (DMSO-d6, 300 MHz): 9.34 (s, 1H), 8.996-9.00 (d, 1H), 8.72-8.73 (d, 1H), 7.85-7.88 (d, 1H), 7.73-7.79 (m, 1H), 4.26-4.27 (d, 2H), 3.64-3.66 (d, 2H); MS: m/z 299 [M+H$^+$]$^+$.

Intermediate 63: 2-Quinolin-6-yl-propionic acid hydrazide

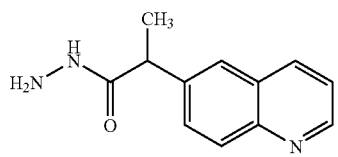

2-Quinolin-6-yl-propionic acid (5.6 g, 26.1 mmol), hydrazine hydrate (1.6 mL) and methanol (150 mL) were combined and heated to reflux for 72 hours. After such time the mixture was concentrated in vacuo and portioned between NaHCO$_3$ (200 mL) and dichloromethane (150 mL). The aqueous phase was extracted with dichloromethane (2×150 mL) and the combined organic extracts dried (Na$_2$SO$_4$) and concentrated in vacuo to return the title compound as a white solid (4.6 g, 21.4 mmol, 82%). $^1$H-NMR (DMSO-d6, 500 MHz): 9.30 (1H, bs), 8.85 (1H, dd), 8.33 (1H, dd), 7.95 (1H, d), 7.86 (1H, d), 7.74 (1H, dd), 7.51 (1H, dd), 4.22 (3H, s), 3.74 (1H, q), 1.44 (3H; MS: m/z 216 [M+H$^+$]$^+$.

Methods for the Synthesis of Examples

Method A

Compound 21; (R,S)-3-[3-(1-Quinolin-6-yl-ethyl)-[1,2,4]triazolo[4,3-b]pyridazin-6-yl]-benzonitrile

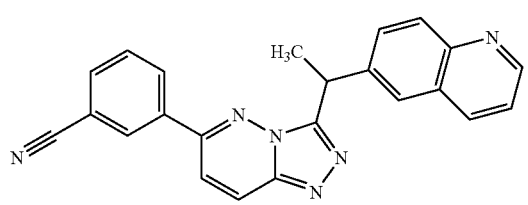

To a degassed (bubbled nitrogen for 15 mins) mixture of water (1 mL) and 1,4-dioxane (3 mL) was added (R,S)-6-[1-(6-chloro-[1,2,4]triazolo[4,3-b]pyridazin-3-yl)-ethyl]-quinoline (100 mg, 0.32 mmol, 1.0 equiv.), 3-cyanophenylboronic acid (52 mg, 0.35 mmol, 1.1 equiv.), potassium carbonate (2 equiv., 0.64 mmol, 89 mg) and dichloro[1,1'-bis(diphenylphosphino)-ferrocene]palladium(II) dichloromethane adduct (15 mg, 0.07 equiv). The microwave tube was capped and heated in a microwave reactor at 130° C. for 20 minutes. After such time the mixture was concentrated onto silica gel and purified via flash column chromatography eluting with dichloromethane:methanol 100:0 to 90:10. The residue was dissolved in dimethylformamide (1 mL) and further purified by mass triggered reversed phase HPLC (5-95% CH$_3$CN in H$_2$O) to return the title compound as a white solid (71 mg, 0.19 mmol, 59% yield). Analytical data presented in Table 1. Separation of enantiomers described in method B.

Method B

Compound 99; (S)-3-[3-(1-Quinolin-6-yl-ethyl)-[1,2,4]triazolo[4,3-b]pyridazin-6-yl]-benzonitrile and compound 100; I-3-[3-(1-Quinolin-6-yl-ethyl)-[1,2,4]triazolo[4,3-b]pyridazin-6-yl]-benzonitrile

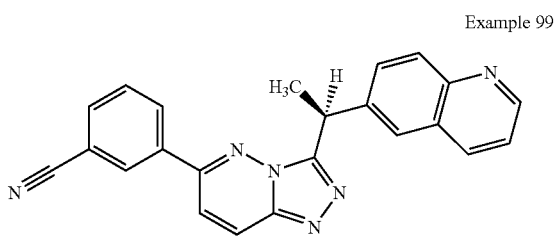

Example 99

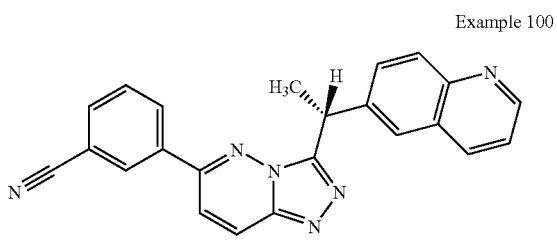

Example 100

3-[3-(1-Quinolin-6-yl-ethyl)-[1,2,4]triazolo[4,3-b]pyridazin-6-yl]-benzonitrile (1.2 g) was dissolved in isopropyl alcohol (10 g/L) and enantiomers separated via chiral HPLC on a Chiralpak AS 20 μM (8 cm id×25 cm L) column eluting with 50% methanol/ethanol (25° C.), 150 g/min, 325 nM to return example 126 (0.56 g, ee >99.9%) and example 127 (0.56 g, ee 97%). Analytical method performed on a AS-H 4.6 mm ID×250 mm S/N ASHSAEE001-409291 column eluting with 50% methanol/ethanol (25° C.), 1 mL/min, 225 nM.

Compound 99 retention time 4.6 minutes and compound 100 retention time 5.8 minutes. Analytical data presented in Table 1.

Method C

Compound 156: 3-(1-Methyl-1H-pyrazol-4-yl)-6-(6-vinyl-[1,2,4]triazolo[4,3-b]pyridazin-3-ylmethyl)-quinoline

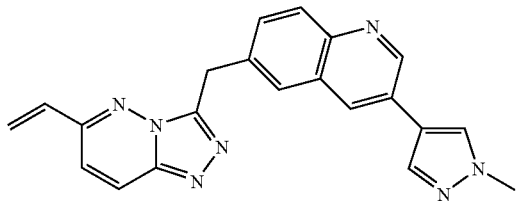

To a degassed (bubbled nitrogen for 15 mins) mixture of water (1 mL) and 1,4-dioxane (2 mL) was added 6-(6-chloro-[1,2,4]triazolo[4,3-b]pyridazin-3-ylmethyl)-3-(1-methyl-1H-pyrazol-4-yl)-quinoline (117 mg, 0.31 mmol), vinyl boronic acid pinacol ester (59 μl, 0.35 mmol), potassium carbonate (0.93 mmol, 128 mg) and dichloro[1,1'-bis(diphenylphosphino)-ferrocene]palladium(II) dichloromethane adduct (15 mg, 0.02 mmol). The microwave tube was capped and heated in a microwave reactor (Personel Chemistry, Emrys Optimizer) at 135° C. for 1500 seconds. After such time the organic phase was concentrated on silica and purified via flash column chromatography eluting with 0-10% Methanol in dichloromethane to obtain the title compound (22 mgs, 19% yield) as a white solid. Analytical data presented in Table 2.

Method D

Compound 15; 6-(6-Chloro-[1,2,4]triazolo[4,3-b]pyridazin-3-ylmethyl)-quinoline

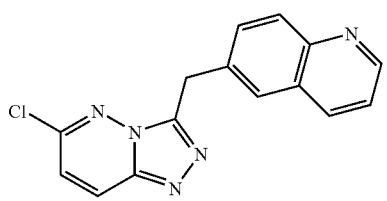

To a suspension of (6-chloro-pyridazin-3-yl)-hydrazine (1.62 g, 11.2 mmol) and 6-quinoline acetic acid (2.1 g, 11.2 mmol) in dichloromethane (150 mL) at ambient temperature was added dicyclohexylcarbodiimide (2.3 g, 11.2 mmol). After stirring at room temperature for 4.5 hours the formed precipitate was filtered off, washed with dichloromethane and dried in vacuo to return quinolin-6-yl-acetic acid N'-(6-chloro-pyridazin-3-yl)-hydrazide which also contained dicyclohexylurea. This mixture was then taken up in acetic acid (250 mL) and heated for 4 hours at 50° C. After such time the mixture was concentrated onto silica gel in vacuo and purified via flash column chromatography (SiO$_2$, CH$_2$Cl$_2$:CH$_3$OH 100:0-97:3) to return the title compound as a white solid (3.35 g, 11.1 mmol, 99% yield). Analytical data presented in Table 1.

Method E

Compound 38: 2-Methyl-6-(6-phenyl-[1,2,4]triazolo[4,3-b]pyridazin-3-ylmethyl)-quinoline

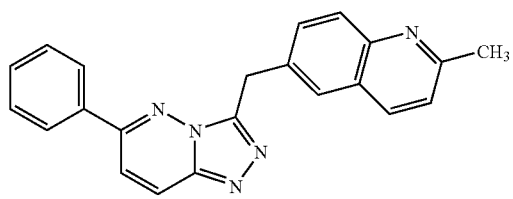

A vial was charged with (6-phenyl-pyridazin-3-yl)-hydrazine dihydrochloride (20 mg, 0.077 mmol), (2-methyl-quinolin-6-yl)-acetic acid (17 mg, 0.085 mmol), N-(3-dimethylaminopropyl)-N'-ethylcarbodiimide hydrochloride (22 mg, 0.115 mmol), 1-hydroxybenzotriazole hydrate (11 mg, 0.077 mmol), potassium carbonate (32 mg, 0.231 mmol), and N,N-dimethyl formamide (0.7 mL). The reaction mixture was stirred at room temperature for 14 h. After such time the mixture was concentrated in vacuo. Acetic acid (1 mL) was added to the residue and the resulting reaction mixture was stirred at 55° C. for 5 h. After such time the mixture was concentrated in vacuo and partitioned between 1 M aqueous potassium carbonate and ethyl acetate. The organic layer was washed with 1 M aqueous potassium carbonate, then brine, and directly adsorbed on silica gel. Purification on silica gel with 0-8% gradient of methanol in ethyl acetate afforded the title compound (8.7 mg, 0.024 mmol, 32% yield) as a light yellow solid. Analytical data presented in Table 1.

Method F

Compound 103; (S)-3-[3-(1-Benzothiazol-6-yl-ethyl)-[1,2,4]triazolo[4,3-b]pyridazin-6-yl]-benzonitrile and compound 104; I-3-[3-(1-Benzothiazol-6-yl-ethyl)-[1,2,4]triazolo[4,3-b]pyridazin-6-yl]-benzonitrile Example 103

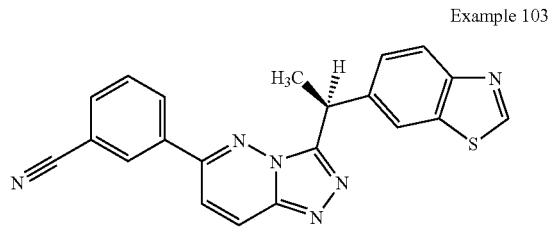

Example 104

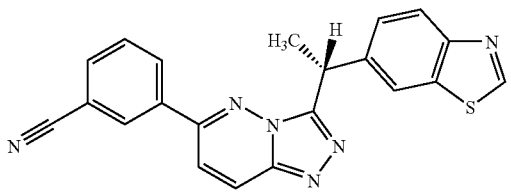

3-[3-(1-Benzothiazol-6-yl-ethyl)-[1,2,4]triazolo[4,3-b]pyridazin-6-yl]-benzonitrile (5.27 g) was dissolved in dichloromethane (200 mL) and the enantiomers separated on a Berger super critical fluid multigram II system. Separation was carried out on a Chiralcel OD-H (2×15 cm) column eluting with 40% methanol/$CO_2$ (100 bar), 50 mL/min, 220 nM to return example 103 (2.1 g, retention time 5.31 min, ee >99%) and example 104 (2.2 g, retention time 6.30, ee >99%).

Method G

Compound 108; 6-(1-Methyl-1H-pyrazol-4-yl)-3-(1H-pyrrolo[2,3-b]pyridine-3-ylmethyl)-[1,2,4]triazolo[4,3-b]pyridazine

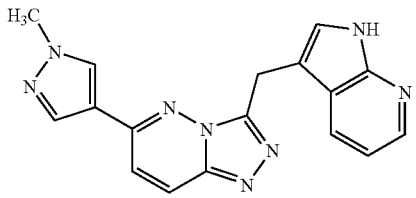

To a 20 ml vial 52 mgs (0.295 mmol) of (1H-pyrrolo[2,3-b]pyridine-3-yl)-acetic acid, 1.2 eq. (0.354 mmol) of 0-(7-azabenzotriazole-1-yl)-N,N,N,N'-tetramethyluronium-hexafluoro-phosphate, 1.5 eq. (0.443 mmol) [6-(1-methyl-1H-pyrazol-4-yl)-pyridazin-3-yl]-hydrazine and 4 eq. (1.18 mmol) N,N-diisopropylethylamine were added and dissolved in 4 mls of dimethyl-formamide. The reaction mixture was stirred at room temperature for 18 h. After such time the dimethylformamide was removed in vacuo and acetic acid (4 mls) was added to the residue and heated to 60° C. for 4 hours. The solvent was removed in vacuo purification via preparative HPLC eluting with dichloromethane:methanol 95:5 returned the title compound (3 mgs, 3% yield) as an off white solid. Analytical data presented in Table 1.

Method H

Compound 7; 6-[6-(3,4-Difluoro-phenoxy)-[1,2,4]triazolo[4,3-b]pyridazin-3-ylmethyl]-quinoline

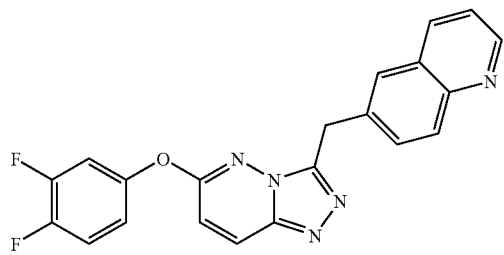

A solution of 6-(6-chloro-[1,2,4]triazolo[4,3-b]pyridazin-3-ylmethyl)-quinoline (60 mg, 0.203 mmol, 1.0 equiv.), 3,4-difluorophenol (0.223 mmol, 1.1 equiv.), $Cs_2CO_3$ (86 mg, 0.264 mmol, 1.3 equiv) and dimethylsulfoxide (1 mL) were mixed in a microwave tube and capped. The microwave tube was reacted in a microwave reactor (Personel Chemistry, Emrys Optimizer) at 70° C. for 10 minutes. The solvent was removed by rotary evaporation and the crude product purified via flash column chromatography ($SiO_2$, $CH_2Cl_2$:$CH_3OH$ 100:0-80:20) to return the title compound as a white solid (27.2 mg, 0.07 mmol, 34% yield). Analytical data presented in Table 1.

Method I

Compound 140: 6-(6-Methoxy-[1,2,4]triazolo[4,3-b]pyridazin-3-ylmethyl)-3-(1-methyl-1H-pyrazol-4-yl)-quinoline

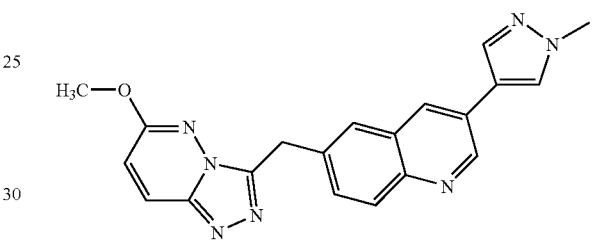

To a 5 ml microwave vial 1 ml of methanol was added followed by 15 mg of potassium carbonate, and 25 mg (0.067 mmol) of 6-(6-chloro-[1,2,4]triazolo[4,3-b]pyridazin-3-ylmethyl)-3-(1-methyl-1H-pyrazol-4-yl)quinoline. The reaction mixture was heated for 3800 seconds at 130° C. in a microwave. The reaction mixture was then filtered and purified by preparatory HPLC to return the title compound (11.6 mg, 47%). Analytical data is presented in Table 2.

Method J

Compound 45: 3-(3H-Benzoimidazol-5-ylmethyl)-6-phenyl-[1,2,4]triazolo[4,3-b]pyridazine

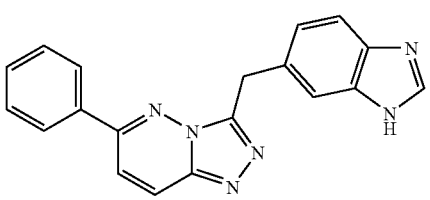

A suspension of 4-(6-phenyl-[1,2,4]triazolo[4,3-b]pyridazin-3-ylmethyl)-benzene-1,2-diamine (20 mg, 0.063 mmol) in formic acid (0.5 mL) was stirred at 100° C. for 5 h. The reaction mixture was cooled to room temperature and filtered through a 0.45 micron filter. The filtrate was concentrated in vacuo. The residue was purified by preparative HPLC on Xbridge prep C18 column (5 microns, 19×150 mm) using a formic acid buffered gradient of acetonitrile in water to return the title compound as an off-white solid (15 mg, 0.046 mmol, 73% yield). Analytical data presented in Table 1.

Method K

Compound 68: 3-(3-Methyl-3H-benzoimidazol-5-ylmethyl)-6-phenyl-[1,2,4]triazolo[4,3-b]pyridazine

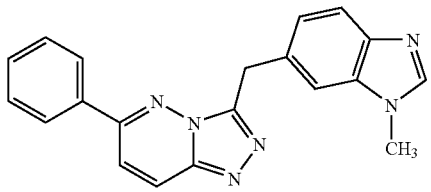

To a suspension of sodium hydride (60% wt, 9 mg, 0.221 mmol) in dimethylformamide (0.5 mL) under nitrogen atmosphere was added a solution of 3-(3H-Benzoimidazol-5-ylmethyl)-6-phenyl-[1,2,4]triazolo[4,3-b]pyridazine (60 mg, 0.184 mmol) in dimethylformamide (0.5 mL) at 0° C. dropwise. The reaction mixture was stirred at 0° C. for 15 min, then methyl iodide (0.014 mL, 0.221 mmol) was added. The temperature was allowed to reach room temperature, while the reaction was stirred for 3.5 h. The reaction was carefully quenched with water at 0° C. The mixture was extracted with ethyl acetate (3×) and the organic layers were combined and adsorbed on silica gel. Purification on silica gel using a gradient of 0-8% methanol/dichloromethane afforded 15 mg of a (1:1) mixture of 3-(3-methyl-3H-benzoimidazol-5-ylmethyl)-6-phenyl-[1,2,4]triazolo[4,3-b]pyridazine and 3-(1-methyl-1H-benzoimidazol-5-ylmethyl)-6-phenyl-[1,2,4]triazolo[4,3-b]pyridazine as an off white solid (24% yield): $^1$H NMR (DMSO-$d_6$): δ d 3.71 (s, 3H), 3.72 (s, 3H), 4.63 (s, 2H), 4.65 (s, 2H), 7.19 (dd, 1H), 7.25 (dd, 1H), 7.42 (d, 1H), 7.50 (d, 1H), 7.53 (m, 6H), 7.56 (d, 1H), 7.59 (d, 1H), 7.85 (d, 1H), 7.87 (d, 1H), 8.06 (m, 6H), 8.33 (d, 1H), 8.35 (d, 1H); MS (m/z) 341 [M+H$^+$]$^+$.

Method L

Compound 124: 3-(1-Methyl-1H-pyrazol-4-yl)-6-(6-methyl-[1,2,4]triazolo[4,3-b]pyridazin-3-ylmethyl)-quinoline

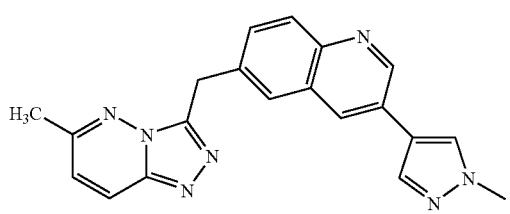

A solution of 3-bromo-6-(6-methyl-[1,2,4]triazolo[4,3-b]pyridazin-3-ylmethyl)-quinoline (50 mg, 0.141 mmol, 1.0 equiv.) in 1,4-dioxane (1 mL) was degassed with nitrogen and added to a microwave tube containing 1-methyl-4-(4,4,5,5-tetramethyl-[1,3,2]dioxaborolan-2-yl)-1H-pyrazole (0.177 mmol, 1.25 equiv., 37 mg). A degassed solution of potassium carbonate (0.282 mmol, 2 equiv., 39 mg) in water (0.5 mL) was then added to the microwave tube followed by dichloro [1,1'-bis(diphenylphosphino)ferrocene]palladium(II) dichloromethane adduct (5 mg, 0.0071 mmol, 0.05 equiv). The microwave tube was capped and reacted in a microwave reactor at 100° C. for 30 minutes. The reaction mixture was partitioned between dichloromethane and water, and the organic layer was evaporated and the residue directly adsorbed on silica gel. Purification on silica gel with 0-10% gradient of methanol in dichloromethane, followed by trituration with methanol afforded the title compound (1.8 mg, 0.005 mmol, 4% yield) as a white solid. Analytical data presented in Table 2.

Method M

Compound 111: 6-(6-Chloro-[1,2,4]triazolo[4,3-b]pyridazin-3-ylmethyl)-5,7-difluoro-quinoline

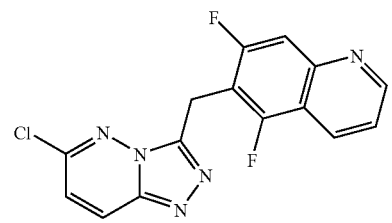

(6-Chloro-pyridazin-3-yl)-hydrazine (531 mg, 3.67 mmol) was added to an oven-dried round-bottom flask and dissolved in dimethylformamide (7 mL) and triethylamine (1.54 ml, 11.01 mmol). The solution was cooled to 0° C. (5,7-Difluoro-quinolin-6-yl)-acetyl chloride (887 mg, 3.67 mmol) was dissolved in dimethylformamide (8 mL) and added to the reaction mixture dropwise. The reaction was complete upon addition of the acid chloride. The solution was concentrated down under vacuo to dryness to afford (5,7-difluoro-quinolin-6-yl)-acetic acid N'-(6-chloro-pyridazin-3-yl)-hydrazide. LCMS [M+H$^+$]=350.0. (5,7-Difluoro-quinolin-6-yl)-acetic acid N'-(6-chloro-pyridazin-3-yl)-hydrazide (1.28 g, 3.67 mmol) was suspended in acetic acid (30 mL) and the solution heated to 60° C. for 16 hours. The mixture was then concentrated in vacuo and the residue dissolved in dichloromethane (125 ml) and washed with saturated NaHCO$_3$ (100 ml) and brine (100 ml). The organic layer was dried over Na$_2$SO$_4$ and concentrated in vacuo. The resulting solid was triturated with methanol and the title compound was collected in quantitative via filtration and dried. Analytical data presented in Table 1.

Method N

Compound 152: 6-(6-Chloro-[1,2,4]triazolo[4,3-b]pyridazin-3-ylmethyl)-3-(1-methyl-1H-pyrazol-4-yl)-quinoline

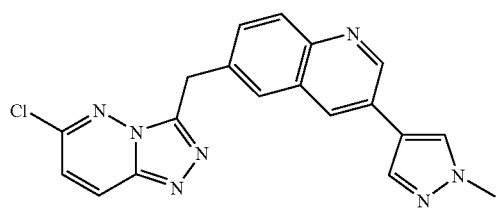

To a mixture of [3-(1-methyl-1H-pyrazol-4-yl)-quinolin-6-yl]-acetic acid (530 mg, 1.98 mmol) in dichloromethane (2 mL) 0° C. was added oxalyl chloride (1.2 eq) and a drop of dimethylformamide. The reaction mixture was left to stir for one hour. A small aliquot was taken and dissolved in methanol to make the methyl ester, and check on LCMS: m/z 382.1. The solvent was removed in vacuo, followed by the addition of dichloromethane that was removed in vacuo, and addition of toluene that was removed in vacuo to return of [3-(1-methyl-1H-pyrazol-4-yl)-quinolin-6-yl]-acetyl chloride as a yellow solid in 88% yield.

(6-Chloro-pyridazin-3-yl)-hydrazine (190 mg, 1.315 mmol) was dissolved in dimethylformamide followed by the addition of triethylamine (3 eq). This mixture was stirred for 5 minutes. The mixture became dark green and then was cooled 0° C. A solution of [3-(1-methyl-1H-pyrazol-4-yl)-quinolin-6-yl]acetyl chloride (375 mg, 1.315 mmol) in dimethylformamide was added dropwise and the reaction mixture turned dark yellow, and stirred for one hour. After such time mixture was concentrated to dryness then taken up in acetic acid (10 mL) and stirred at 60° C. for 16 hours. The solvent was removed in vacuo and the residue partitioned between ethyl acetate and water, and the aqueous phase further extracted with ethyl acetate. The combined organics purified via flash column chromatography (SiO$_2$, CH$_2$Cl$_2$, methanol gradient 0 to 10%) to return the title compound (217 mg, 42% yield). Analytical data presented in Table 2.

Method O

Compound 145: 5,7-Difluoro-3-(1-methyl-1H-pyrazol-4-yl)-6-(6-methyl-[1,2,4]triazolo[4,3b]pyridazin-3-ylmethyl)-quinoline

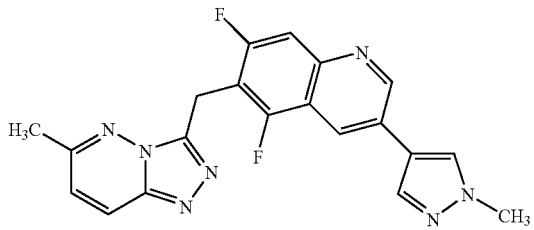

To a 40 ml vial was added 1-butanol (10 ml), [2,4-difluoro-3-(1-methyl-1H-pyrazol-4-yl)-quinolin-6-yl]-acetic acid hydrazide (425 mg, 1.34 mmol) and 3-chloro-6-methylpyridazine (172 mg, 1.34 mmol). The mixture was heated at 120° C. for 24 hours. The solvent was removed under vacuum and the residue stirred in ethanol before filtration to obtain 200 mgs of crude material. Purification via flash column chromatography (SiO$_2$, dichloromethane/methanol 0 to 10%) returned 182 mgs of pure material 35% yield. Analytical data presented in Table 2.

Method P

Compound 123: 3-(1-Methyl-1H-pyrazol-4-yl)-6-(6-trifluoromethyl-[1,2,4]triazolo[4,3-b]pyridazin-3-ylmethyl)-quinoline

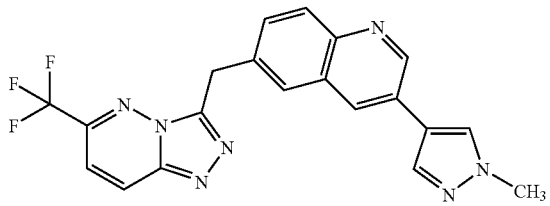

A mixture of 1-butanol (2 mL), 3-chloro-6-trifluoromethyl-pyridazine (0.13 mmol, 25 mg), [3-(1-methyl-1H-pyrazol-4-yl)-quinolin-6-yl]-acetic acid hydrazide (0.13 mmol, 40 mg) was heated at 120° C. for 18 hours. The solvent was then removed by blowing nitrogen, the brown residue dissolved in 1 ml of dimethylformamide and one 1 ml of methanol and purified by preparatory HPLC to return the title compound (15.8 mg, 0.04 mmol, 29%). Analytical data is presented in Table 2.

Method Q

Compound 159: Dimethyl-{3-[3-(1-methyl-1H-pyrazol-4-yl)-quinolin-6-ylmethyl]-[1,2,4]triazolo[4,3-b]pyridazin-6-yl}-amine

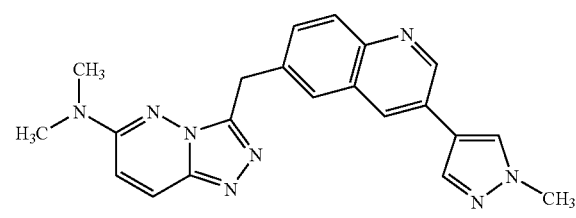

To a 5 ml microwave vial 1 ml of dimethylamine 40% in water was added followed by 300μ of DMSO to dissolve 25 mg (0.067 mmol) 6-(6-chloro-[1,2,4]triazolo[4,3-b]pyridazin-3-ylmethyl)-3-(1-methyl-1H-pyrazol-4-yl)quinoline. The reaction heated in a microwave for 2000 seconds at 130° C. The reaction mixture was filtered then purified via preparatory HPLC to return the title compound (7.7 mg, 30% yield). Analytical data is presented in Table 2.
Method R Compound 144: 2-{4-[6-(6-Methyl-[1,2,4]triazolo[4,3-b]pyridazin-3-ylmethyl)-quinolin-3-yl]pyrazol-1-yl}-ethanol

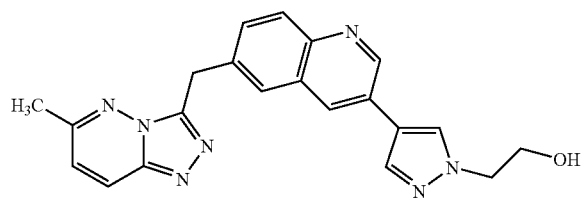

To a microwave vessel was added 3-bromo-6-(6-methyl-[1,2,4]triazolo[4,3-b]pyridazin-3-ylmethyl)-quinoline (80 mg, 0.23 mmol, 1 equiv), bis(pinacol)borane (69 mg, 0.27 mmol, 1.2 equiv), potassium acetate (66 mg, 0.67 mmol, 3.0 equiv) followed by dimethylacetamide (0.8 mL). The solution was degassed for 10 min and dichloro[1,1'-bis(diphenylphosphino)ferrocene]palladium(II) dichloromethane adduct (7 mg, 0.01 mmol, 0.048 equiv added. The microwave vessel was capped and reacted in a microwave reactor at 120° C. for 1 hour. The microwave vessel was cooled and then 2-(4-bromo-pyrazol-1-yl)-ethanol (0.18 mmol, 0.8 equiv) dissolved in dimethylacetamide (0.6 mL) was added, followed by 2 M aqueous sodium carbonate (0.6 mL). The solution was degassed for 10 min and dichloro[1,1'-bis(diphenylphosphino)ferrocene]palladium(II) dichloromethane adduct (7 mg, 0.01 mmol, 0.048 equiv) added. The microwave vessel was capped and reacted in a microwave reactor at 120° C. for 2 hours. After cooling, Na$_2$SO$_4$ (3 g) was added and the mixture diluted with acetonitrile and filtered through a pad of celite. The filtrate was concentrated onto silica gel and purified by either flash chromatography (SiO$_2$, CH$_2$Cl$_2$:CH$_3$OH 100:0-80:20) or preparative HPLC to return the title compound. Analytical data presented in Table 2.

Method S

Compound 110: 6-(6-Methyl-[1,2,4]triazolo[4,3-b]pyridazin-3-ylmethyl)-quinoline-3-carbonitrile

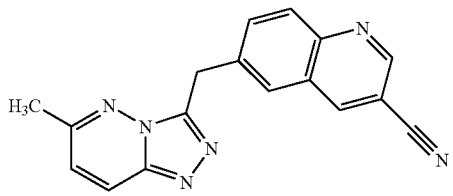

The title compound was prepared following the procedure described by Chobanian, H. R.; Fors, B. P.; Lin, L. S. Tet Lett. 47, 2006, 3303-3305, making non-critical changes. Analytical data is presented in Table 1.

Method T

Compound 157: 6-(6-Ethyl-[1,2,4]triazolo[4,3-b]pyridazin-3-ylmethyl)-3-(1-methyl-1H-pyrazol-4-yl)-quinoline

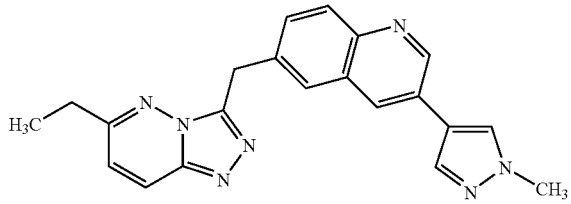

To a solution of 3-(1-methyl-1H-pyrazol-4-yl)-6-(6-vinyl-[1,2,4]triazolo[4,3-b]pyridazin-3-ylmethyl)-quinoline (22 mg, 0.06 mmol) in dichloromethane (5 mL) and methanol (0.5 mL) under an atmosphere of N$_{2(g)}$ was added 10% palladium on carbon (20 mg) and the atmosphere replaced with H$_{2(g)}$. After stirring vigorously for 3 hours the mixture was filtered through a pad of celite and purified via flash column chromatography (SiO$_2$, CH$_2$Cl$_2$, methanol 0-10%) to return the title compound as a white solid (17 mg, 77%). Analytical data presented in Table 2.

Method U

Compound 142: 3-(1H-Imidazol-4-yl)-6-(6-methyl-[1,2,4]triazolo[4,3-b]pyridazin-3-ylmethyl)-quinoline

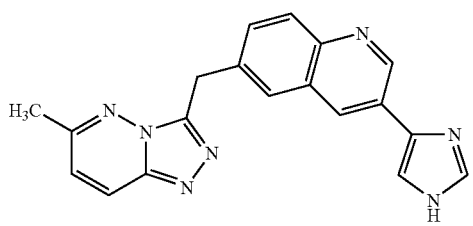

To a solution of 4-bromo-1-trityl-1H-imidazole (103 mg, 0.24 mmol, 1.0 equiv) in tetrahydrofuran (1 mL) was added ethyl magnesium bromide (3M in diethylether, 0.094 mL, 0.28 mmol, 1.2 equiv) and the reaction was stirred for 90 min. ZnCl$_2$ (38 mg, 0.28 mmol, 1.2 equiv) was then added and the solution stirred for an additional 90 min. Tetrakis (triphenylphosphine)palladium (2 mg, 0.024 mmol, 0.10 equiv) and 3-bromo-6-(6-methyl-[1,2,4]triazolo[4,3-b]pyridazin-3-ylmethyl)-quinoline (100 mg, 0.28 mmol, 1.2 equiv) were added and the solution heated at 70° C. for 18 hours. The solvent was removed in vacuo and the residue absorbed onto silica gel and purified by flash chromatography (SiO$_2$, CH$_2$Cl$_2$:CH$_3$OH 100:0-80:20 to return 6-(6-methyl-[1,2,4]triazolo[4,3-b]pyridazin-3-ylmethyl)-3-(3-trityl-3H-imidazol-4-yl)-quinoline. The trityl group was removed by stirring the compound in methanolic hydrochloric acid (0.5 N) for 3 hours. The volatiles were removed in vacuo and the residue stirred in ethanol and collected via filtration and dried to return the title compound (5.6 mg, 8% yield). Analytical data presented in Table 2.

Method V

Compound 132: 3-Imidazol-1-yl-6-(6-methyl-[1,2,4]triazolo[4,3-b]pyridazin-3-ylmethyl)-quinoline

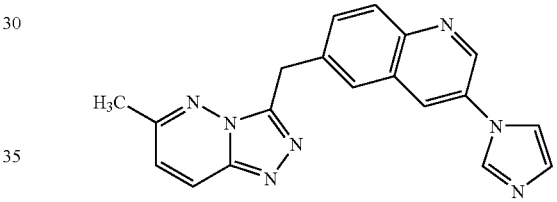

To a reaction vial was added 3-bromo-6-(6-methyl-[1,2,4]triazolo[4,3-b]pyridazin-3-ylmethyl)-quinoline (71 mg, 0.2 mmol, 1.0 equiv), CuI (7 mg, 0.04 mmol, 0.008 equiv), L-proline (9 mg, 0.08 mmol, 0.4 equiv) and K$_2$CO$_3$ (83 mg, 0.60 mmol, 3.0 equiv). The system was evacuated and filled with nitrogen (3×). A solution of degassed imidazole (27 mg, 0.4 mmol, 2.0 equiv) in DMSO (1 mL) was then added. The reaction was heated at 120° C. for 18 hours. The solvent was removed in vacuo and the residue absorbed onto silica gel and purified by flash chromatography (SiO$_2$, CH$_2$Cl$_2$:CH$_3$OH 100:0-90:10 to return the title compound (15 mg, 22% yield). Analytical data presented in Table 2.

Method W

Compound 125: 6-(6-Methyl-[1,2,4]triazolo[4,3-b]pyridazin-3-ylmethyl)-3-(1H-pyrazol-4-yl)-quinoline

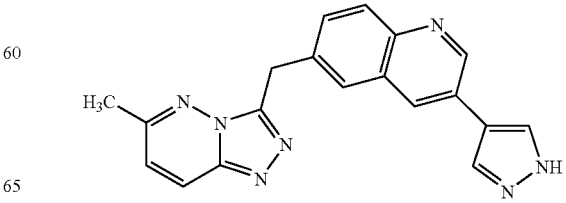

To a microwave vial was added 3-bromo-6-(6-methyl-[1,2,4]triazolo[4,3-b]pyridazin-3-ylmethyl)-quinoline (100 mg, 0.28 mmol, 1 equiv), 4-(4,4,5,5-tetramethyl-[1,3,2]dioxaborolan-2-yl)-1-(2-trimethylsilanyl-ethoxymethyl)-1H-pyrazole (113 mg, 0.35 mmol, 1.25 equiv), $K_2CO_3$ (78 mg, 0.566 mmol, 2.0 equiv) followed by 1,4-dioxane (3 mL) and water (1.5 mL). [0542] The solution was degassed with nitrogen for 10 min and then dichloro [1,1'-bis(diphenylphosphino)ferrocene]palladium(II) dichloromethane adduct (10 mg, 0.014 mmol, 0.05 equiv) was added. The microwave vessel was capped and heated in a microwave reactor at 130° C. for 30 min. The mixture was cooled and portioned between dichloromethane and water. The organic phase was absorbed onto silica gel and purified by flash chromatography ($SiO_2$, $CH_2Cl_2$:$CH_3OH$ 100:0-80:20) to give 6-(6-methyl-[1,2,4]triazolo[4,3-b]pyridazin-3-ylmethyl)-3-[1-(2-trimethylsilanyl-ethoxymethyl)-1H-pyrazol-4-yl]-quinoline (106 mg, 80% yield). The solid was then added to a 20% solution of ethylene diamine in dimethylformamide and stirred for 3 hours. The solvent was removed and the residue triterated with ethanol to afford the title compound (65 mg, 85% yield). Analytical data presented in Table 2.

Method X

Compound 27: 6-[(6-Chloro-[1,2,4]triazolo[4,3-b]pyridazin-3-yl)-fluoro-methyl]-quinoline

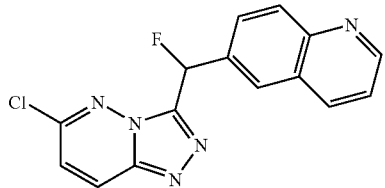

Step 3: 6-[(6-Chloro-[1,2,4]triazolo[4,3-b]pyridazin-3-yl)-fluoro-methyl]-quinoline To a suspension of (6-chloro-pyridazin-3-yl)-hydrazine (233 mg, 1.6 mmol) and 6-fluoro-quinolin-6-yl-acetic acid hydrochloride (3.90 mg, 1.6 mmol) in dichloromethane (22 mL) and pyridine (1.6 mmol, 126 mg) at ambient temperature was added dicyclohexylcarbodiimide (333 mg, 1.6 mmol). After stirring at room temperature for 18 hours the formed precipitate was filtered off, washed with dichloromethane and dried in vacuo and then taken up in acetic acid (15 mL) and heated for 6 hours at 55° C. After such time the mixture was concentrated onto silica gel in vacuo and purified via flash column chromatography ($SiO_2$, $CH_2Cl_2$:$CH_3OH$ 100:0-90:10) to return the title compound as a yellow foam (138 mg, 0.44 mmol, 28% yield). Analytical data presented in Table 1.

Method Y

Compound 17: 3-Benzothiazol-6-ylmethyl-6-chloro-[1,2,4]triazolo[4,3-b]pyridazine

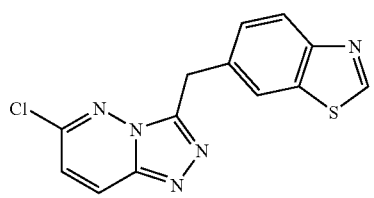

Benzothiazol-6-yl-acetic acid (44 g, 228 mmoles) and (6-chloro-pyridazin-3-yl)-hydrazine (36.2 g, 251 mmoles) were dissolved in a mixture of anhydrous dimethylformamide (40 mL) and anhydrous dichloromethane (600 ml). The mixture was under nitrogen and cooled to 0° C. in an ice bath, then N-(3-dimethylaminopropyl)-N'-ethylcarbodiimide hydrochloride (65.5 g, 342 mmoles), hydroxybenzotriazole hydrate (38.4 g, 251 mmoles) and potassium carbonate (157 g, 1.14 moles) was added into the mixture. The mixture was stirred at 5° C. for 4 h and at room temperature overnight. TLC showed that the SM disappeared. The mixture was filtered and the filtrate was washed with brine (400 mL×2). The organic phase was dried over anhydrous $Na_2SO_4$, concentrated to obtain a brown oil. The oil was dissolved in acetic acid (750 mL) and stirred at 50° C. for 4 hours. After such time the solvent was removed in vacuo and the residue was purified by a silica gel column eluting with ethyl acetate to obtain crude product (20 g). The crude product was recrystallized from ethyl acetate and petroleum ether to obtain the title compound (15 g). Analytical data presented in Table 1.

Method Z

Compound 149: 2-{4-[6-(6-Methyl-[1,2,4]triazolo[4,3-b]pyridazin-3-ylmethyl)-quinolin-3-yl]-pyrazol-1-yl}-acetamide

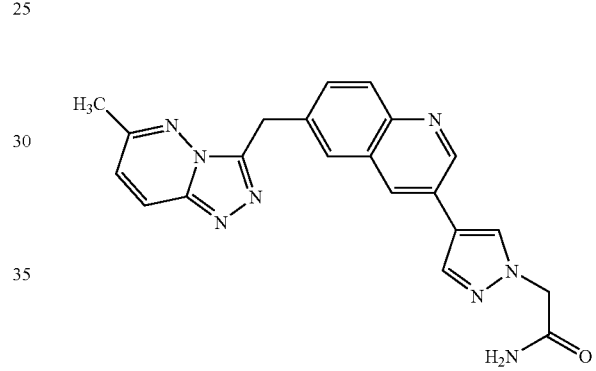

6-(6-Methyl-[1,2,4]triazolo[4,3-b]pyridazin-3-ylmethyl)-3-(1H-pyrazol-4-yl)-quinoline (65 mg, 0.19 mmol, 1 equiv) was dissolved in dimethylformamide (0.5 mL) and NaH (60% in oil, 1.2 equiv, 0.228 mmol, 9 mg) was added. The solution was stirred under nitrogen for 30 min and then 2-bromoacetamide (26 mg, 0.19 mmol, 1 equiv) was added and the solution heated at 90° C. for 18 h. The product was extracted into dichloromethane and washed with water. The organic phase was concentrated to dryness to afford the title compound (40 mg, 52% yield). Analytical data presented in Table 2.

Method AA

Compound 109: 6-(6-Cyclopropyl-[1,2,4]triazolo[4,3-b]pyridazin-3-ylmethyl)-quinoline

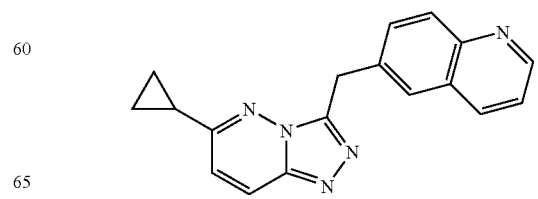

Step 1: Preparation of Cyclopropyl Magnesium Bromide

A solution of cyclopropyl bromide (192 μL) in tetrahydrofuran (2 mL) was added to magnesium powder (40 mg) followed by a single iodine crystal. The mixture became hot and was stirred for 15 minutes.

Step 2: Preparation of 6-(6-cyclopropyl-[1,2,4]triazolo[4,3-b]pyridazin-3-ylmethyl)-quinoline A mixture of 6-(6-chloro-[1,2,4]triazolo[4,3-b]pyridazin-3-ylmethyl)-quinoline (240 mg), iron(III) acetylacetonate (12 mg) in tetrahydrofuran (5 mL) was degassed by bubbling nitrogen through for 10 minutes. The cyclopropyl magnesium bromide in tetrahydrofuran solution prepared in step 1 was then added to the reaction mixture and stirred at 50° C. for 18 hours. The mixture was allowed to cool to rt then acidified to pH 1 via the addition of 1N hydrochloric acid (20 mL). The tetrahydrofuran was removed in vacuo and the aqueous neutralized via the addition of aqueous $NaHCO_3$ and then extracted with ethyl acetate (×3), dried ($Na_2SO_4$) and concentrated to dryness. The residue was taken up in piperidine (1 mL) and heated in a microwave at 12° C. for 25 min to consume the remaining 6-(6-chloro-[1,2,4]triazolo[4,3-b]pyridazin-3-ylmethyl)-quinoline. The title compound was then purified via preparatory HPLC to return the title compound (4 mg, 10%). Analytical data presented in Table 1.

Method BB

Compound 166: 6-(6-Ethyl-[1,2,4]triazolo[4,3-b]pyridazin-3-ylmethyl)-5,7-difluoro-3-(1-methyl-1H-pyrazol-4-yl)-quinoline

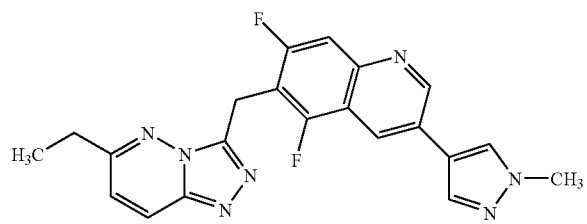

To a mixture of 3-bromo-6-(6-ethyl-[1,2,4]triazolo[4,3-b]pyridazin-3-ylmethyl)-5,7-difluoro-quinoline (86 mg, 0.2 mmol), 1-methyl-4-(4,4,5,5-tetramethyl-[1,3,2]dioxaborolan-2-yl)-1H-pyrazole (0.21 mmol, 44 mg) and cesium carbonate (0.6 mmol<195 mg) in 1,4-dioxane (2 mL) at reflux was added [2-[(D-N)methyl]phenyl-c](tricyclohexylphosphine)trifluoroacetato-O-(SP-4-3)-palladium (Bedford, R. B.; Cazin, C. S. J.; Coles, S. J.; Gelbrich, T.; Horton, P. N.; Hursthouse, M. B.; Light, M. E. *Organometallics* 2003, 22, 987) (0.5 mol %, 0.1 μmol, 0.1 mg). After 30 min the reaction mixture was filtered through a pad of silica gel (2 g) eluting with dichloromethane/methanol (17/3, 12 mL). The filtrate was concentrated onto silica gel and purified via flash column chromatography ($SiO_2$, $CH_2Cl_2$:$CH_3OH$ 100:0-90:10) to return the title compound as an off white solid (52 mg, 60% yield). Analytical data presented in Table 2.

Method CC

Compound 175: 1-(3-{4-[6-(6-Methyl-[1,2,4]triazolo[4,3-b]pyridazin-3-ylmethyl)-quinolin-3-yl]-pyrazol-1-yl}-azetidin-1-yl)-ethanone

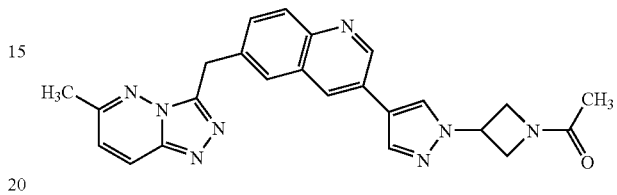

To 3-(1-azetidin-3-yl-1H-pyrazol-4-yl)-6-(6-methyl-[1,2,4]triazolo[4,3-b]pyridazin-3-ylmethyl)-quinoline (25 mg, 0.063 mmol) in dichloromethane (1 mL) was added triethylamine (9.7 uL, 0.069 mmol) followed by acetyl chloride (5.0 uL, 0.069 mmol). The mixture was stirred at room temperature overnight. The reaction was diluted with water and the product extracted into dichloromethane. The reaction was diluted with water and extracted into dichloromethane and washed with water. The filtrate was concentrated in vacuo onto silica gel and purified by flash chromatography ($SiO_2$, $CH_2Cl_2$:$CH_3OH$ 100:0-90:10) to return the title compound (4.20 mg, 15% yield). Analytical data presented in Table 2.

Method DD

Compound 171: 3-[1-(1-Ethyl-azetidin-3-yl)-1H-pyrazol-4-yl]-6-(6-methyl-[1,2,4]triazolo[4,3-b]pyridazin-3-ylmethyl)-quinoline

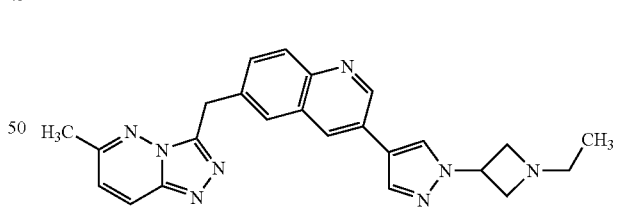

To 3-(1-azetidin-3-yl-1H-pyrazol-4-yl)-6-(6-methyl-[1,2,4]triazolo[4,3-b]pyridazin-3-ylmethyl)-quinoline (50 mg, 0.126 mmol) in dichloromethane (3 mL) was added acetaldehyde (15 uL, 0.505 mmol). The solution was stirred at room temperature for 15 minutes and then sodium triacetoxyborohydride (67 mg, 0.136) was added. After 1 hour the solution was diluted with dichloromethane (1.5 mL) and washed with sodium bicarbonate (1.5 mL). The aqueous layer was extracted further with dichloromethane (1.5 mL). The combined dichloromethane layers were washed with brine (3 mL) and dried over $Na_2SO_4$. The filtrate was concentrated in vacuo onto silica gel and purified by flash chromatography (SiO$_2$, CH$_2$Cl$_2$:CH$_3$OH 100:0-90:10) to return the title compound (4.8 mg, 9% yield). Analytical data presented in Table 2.

Method EE

Compound 172: 3-[1-(1-Methanesulfonyl-azetidin-3-ylmethyl)-1H-pyrazol-4-yl]-6-(6-methyl-[1,2,4]triazolo[4,3-b]pyridazin-3-ylmethyl)-quinoline

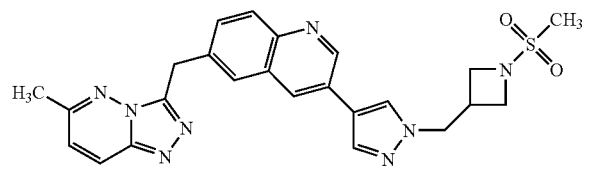

To (1-azetidin-3-ylmethyl-1H-pyrazol-4-yl)-6-(6-methyl-[1,2,4]triazolo[4,3-b]pyridazin-3-ylmethyl)-quinoline (22 mg, 0.054 mmol) in dichloromethane (1 mL) was added triethylamine (7.5 uL, 0.054 mmol) followed by methanesulfonyl chloride (4.0 uL, 0.054 mmol) and dimethylaminopyridine (6.6 mg, 0.054 mmol). The mixture was stirred at room temperature overnight. The reaction was diluted with water and the product extracted into dichloromethane. The reaction was diluted with water and extracted into dichloromethane and washed with water. The filtrate was concentrated in vacuo onto silica gel and purified by flash chromatography (SiO$_2$, CH$_2$Cl$_2$:CH$_3$OH 100:0-90:10) to return the title compound (5.4 mg, 21% yield). Analytical data presented in Table 2.

Method FF

Compound 177: 6-Methyl-3-[5-(1-methyl-1H-pyrazol-4-yl)-1H-pyrrolo[2,3-b]pyridine-3-ylmethyl]-[1,2,4]triazolo[4,3-b]pyridazine

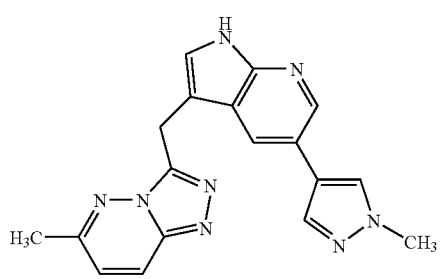

[5-(1-Methyl-1H-pyrazol-4-yl)-1H-pyrrolo[2,3-b]pyridine-3-yl]-acetic acid hydrazide (60 mg, 0.22 mmol) and 3-chloro-6-methyl-pyridazine (35 mg, 0.27 mmol) was suspended in n-butanol (1 mL). The suspension was heated in a microwave for 1 hour at 200° C. Next, the solution was transferred to a separatory funnel with dichloromethane (20 mL). The solution was washed with saturated NaHCO$_3$ (aq) (30 ml). The organic layer was partitioned, dried over Na$_2$SO$_4$ and concentrated down under vacuum. The crude material was dry loaded in silica gel and purified by flash chromatography (0-10% Methanol/dichloromethane gradient) to afford the product, 6-Methyl-3-[6-(1-methyl-1H-pyrazol-4-yl)-pyrrolo[3,2-b]pyridine-1-ylmethyl]-[1,2,4]triazolo[4,3-b]pyridazine (24.3 mg, 32% yield) which was then crystallized in a minimal amount of methanol. Analytical data presented in Table 2.

Method GG

Compound 176: 3-{4-[6-(6-Methyl-[1,2,4] triazolo[4,3-b]pyridazin-3-ylmethyl)-quinolin-3-yl]pyrazol-1-ylmethyl}-azetidine-1-carboxylic acid tert-butyl ester

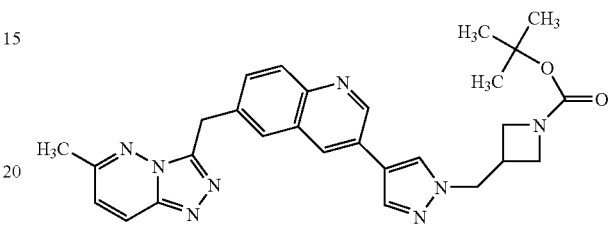

To a microwave vessel was added 3-bromo-6-(6-methyl-[1,2,4]triazolo[4,3-b]pyridazin-3-ylmethyl)-quinoline (476 mg, 1.35 mmol, 1 equiv), 3-[4-(4,4,5,5-tetramethyl-[1,3]dioxolan-2-yl)-pyrazol-1-ylmethyl]-azetidine-1-carboxylic acid tert-butyl ester (1.2 g, 3.37 mmol, 2.5 equiv), K$_2$CO$_3$ (393 mg, 2.84 mmol, 2.0 equiv) followed by dioxane (12 mL) and water (6 mL). The solution was degassed with nitrogen for 10 min and then dichloro[1,1'-bis(diphenylphosphino)ferrocene]palladium(II) dichloromethane adduct (44 mg, 0.06 mmol, 0.05 equiv) was added. The microwave vessel was capped and reacted in a microwave reactor at 130° C. for 30 min. The microwave vessel was cooled and then the mixture was extracted into dichloromethane and washed with water. The volatiles were removed in vacuo and the residue absorbed onto silica gel and purified by flash chromatography (SiO$_2$, CH$_2$Cl$_2$:CH$_3$OH 100:0-80:20) to obtain 3-{4-[6-(6-Methyl-[1,2,4]triazolo[4,3-b]pyridazin-3-ylmethyl)-quinolin-3-yl]-pyrazol-1-ylmethyl}-azetidine-1-carboxylic acid tert-butyl ester (189 mg, 28% yield). Analytical data presented in Table 2.

Method HH

Compound 155: 3-(1-Azetidin-3-ylmethyl-1H-pyrazol-4-yl)-6-(6-methyl-[1,2,4]triazolo[4,3-b]pyridazin-3-ylmethyl)-quinoline

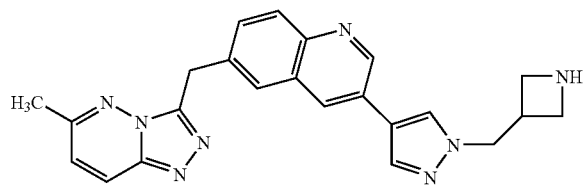

To 3-{4-[6-(6-methyl-[1,2,4]triazolo[4,3-b]pyridazin-3-ylmethyl)-quinolin-3-yl]-pyrazol-1-ylmethyl}-azetidine-1-carboxylic acid tert-butyl ester (189 mg) was added 6 mL of TFA:dichloromethane/1:1 solution. The mixture was allowed to sit for 2 hours. The volatiles were removed by rotary evaporation and then Methanol (6 mL) and MP-carbonate (400 mg, 3.18 mmol/g) were added. The resin was filtered and the volatiles were removed in vacuo to obtain a quantitative yield of 3-(1-azetidin-3-ylmethyl-1H-pyrazol-4-yl)-6-(6-methyl-[1,2,4]triazolo[4,3-b]pyridazin-3-ylmethyl)-quinoline. Analytical data presented in Table 2.

Method II

Compound 179: 3-(1-Methyl-1H-pyrazol-4-yl)-6-[1,2,4]triazolo[4,3-b][1,2,4]triazin-3-ylmethyl-quinoline

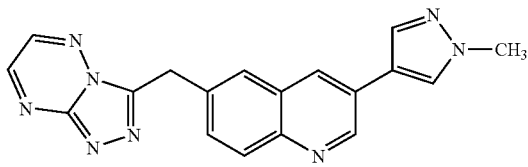

A mixture of 3-bromo-6-[1,2,4]triazolo[4,3-b][1,2,4]triazin-3-ylmethyl-quinoline (69 mg, 0.204 mmol), 1-methyl-4-pyrazoleboronic acid pinacol ester (51 mg, 0.25 mmol), potassium carbonate (56 mg. 0.41 mml), 1,4-dioxane (2 mL) and water (1 mL) was bubbled nitrogen gas through for 10 minutes. After such time dichlorobis(triphenylphosphine) palladium (8 mg, 5 mol %) was added, the vial sealed and heated in a microwave for 1500 seconds at 135° C. The mixture was diluted with dichloromethane and brine, before the organic phase was concentrated onto silica gel and via flash column chromatography (SiO2 4 g, dichloromethane/CH₃OH 0-10%) to return the title compound a white solid (11 mg, 16%). Analytical data presented in Table 2.

Method JJ

Compound 117: 3-Bromo-6-[1,2,4]triazolo[4,3-b][1,2,4]triazin-3-ylmethyl-quinoline

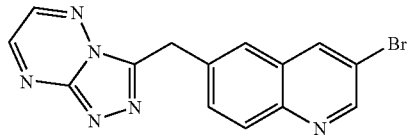

A mixture of 5-(3-bromo-quinolin-6-ylmethyl)-[1,2,4]triazole-3,4-diamine (977 mg, 3 mmol), glyoxal (40% solution in water, 5 mL), acetic acid (10 mL) and water (2 mL) was stirred at ambient temperature for 18 hours. After such time the mixture was filtered and the filtrate was concentrated onto silica gel and via flash column chromatography (SiO₂ 12 g, dichloromethane/CH₃OH, 0-10%) to return the title compound a white solid (298 mg, 29%). Analytical data presented in Table 1.

Method KK

Compound 118: 6-(6-Methyl-[1,2,4]triazolo[4,3-b]pyridazin-3-ylmethyl)-3-vinyl-quinoline

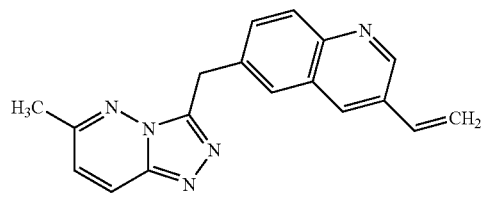

To a microwave vessel was added 3-bromo-6-(6-methyl-[1,2,4]triazolo[4,3-b]pyridazin-3-ylmethyl)-quinoline (500 mg, 1.41 mmol, 1 equiv), vinyl boronic acid (299 uL, 1.76 mmol, 1.25 equiv), K₂CO₃ (390 mg, 2.82 mmol, 2.0 equiv) followed by 1,4-dioxane (10 mL) and water (5 mL). The solution was degassed with nitrogen for 10 min and then dichloro[1,1'-bis(diphenylphosphino)ferrocene]palladium (II) dichloromethane adduct (51 mg, 0.07 mmol, 0.05 equiv) was added. The microwave vessel was capped and reacted in a microwave reactor at 130° C. for 30 min. The microwave vessel was cooled and then the mixture was extracted into dichloromethane and washed with water. The volatiles were removed in vacuo and the residue absorbed onto silica gel and purified by flash chromatography (SiO₂, CH₂Cl₂:CH₃OH 100:0-80:20) to obtain the title compound as a brown oil (35% yield). Analytical data presented in Table 1.

Method LL

Compound 116: 3-Ethyl-6-(6-methyl-[1,2,4]triazolo[4,3-b]pyridazin-3-ylmethyl)-quinoline

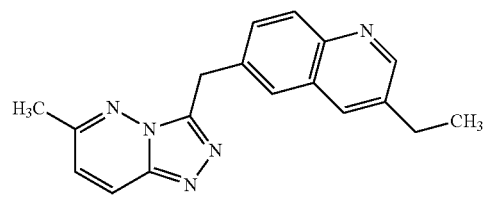

A mixture of 6-(6-methyl-[1,2,4]triazolo[4,3-b]pyridazin-3-ylmethyl)-3-vinyl-quinoline (20 mg, 0.0664 mmol) and palladium on carbon (10% wt, 20 mg) in ethanol (1.5 mL) under a hydrogen atmosphere was stirred vigorously at ambient temperature for 4 hours. The mixture was then filtered through a pad of celite and the filtrate concentrated to provide the title compound (15 mg, 75% yield). Analytical data presented in Table 1.

Method MM

Compound 119: 3-Bromo-6-[1-(6-methyl-[1,2,4]triazolo[4,3-b]pyridazin-3-yl)-ethyl]-quinoline

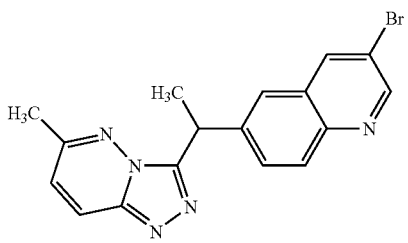

2-Quinolin-6-yl-propionic acid hydrazide (intermediate 63) (500 mg, 2.32 mmol) was added to a stirred solution of 3-chloro-6-methylpyridazine (299 mg, 2.32 mmol) in n-butanol. The reaction mixture was heated at 120° C., overnight. The volatiles were removed in vacuo and the residue absorbed onto silica gel and purified by flash chromatography (SiO₂, CH₂Cl₂:CH₃OH 100:0-90:10) to obtain 6-[1-(6-methyl-[1,2,4]triazolo[4,3-b]pyridazin-3-yl)-ethyl]-quinoline (356 mg, 53% yield). To 6-[1-(6-methyl-[1,2,4]triazolo[4,3-b]pyridazin-3-yl)-ethyl]-quinoline (356 mg, 1.23 mmol) was added a dropwise solution of bromine (1.73 uL, 3.69 mmol) in acetic acid (3 mL). The reaction was heated at 100° C. for 2 hours. The reaction mixture was cooled to room temperature and the solvent removed in vacuo. A solution of 10% aq. NaSH (10 mL) was added and the product extracted with 10% methanol in dichloromethane. The organic phase was washed with 5% aqueous sodium sulfite. The filtrate was then concentrated in vacuo onto silica gel and purified by flash chromatography (SiO₂, CH₂Cl₂:CH₃OH 100:0-90:10) to return the title compound (168 mg, 37% yield). Analytical data presented in Table 1.

Method NN

Example 3-[1-(1-Methyl-azetidin-3-yl)-1H-pyrazol-4-yl]-6-(6-methyl-[1,2,4]triazolo[4,3-b]pyridazin-3-ylmethyl)-quinoline

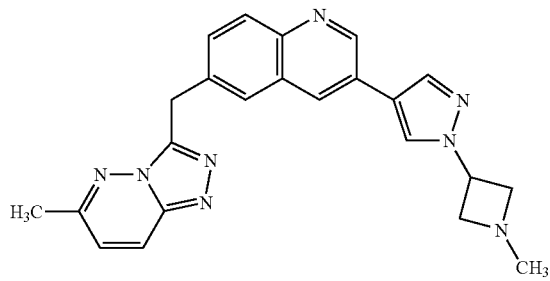

To 3-(1-azetidin-3-yl-1H-pyrazol-4-yl)-6-(6-methyl-[1,2,4]triazolo[4,3-b]pyridazin-3-ylmethyl)-quinoline (194 mg, 0.4898 mmol) in dichloromethane (9 mL) was added formaldehyde (37% in water, 1.959 mmol, 147 uL). The solution was stirred at room temperature for 15 minutes and then sodium triacetoxyborohydride (260 mg, 1.22 mmol) was added. After 1 hour the solution was diluted with dichloromethane (6 mL) and washed with sodium bicarbonate (6 mL). The aqueous layer was extracted further with dichloromethane (6 mL). The combined dichloromethane layers were washed with brine (12 mL) and dried over $Na_2SO_4$. The filtrate was concentrated in vacuo onto silica gel and purified by flash chromatography ($SiO_2$, $CH_2Cl_2$:$CH_3OH$:$NH_4OH$, 95:4.995:0.005-80:19.98:0.02) to return the title compound (69 mg, 35% yield). Analytical data presented in Table 2.

The structure, name, physical and biological data and methods are further described in tabular form below in Table 1.

TABLE 1

| Eg. | c-MET $IC_{50}$ | GTL 16 $EC_{50}$ | Method | Structure | $^1$H NMR (500 MHz) | MS (m/z) |
|---|---|---|---|---|---|---|
| 1 | I | II | A | N-Cyclopropyl-4-(3-quinolin-6-ylmethyl-[1,2,4]triazolo[4,3-b]pyridazin-6-yl)-benzenesulfonamide | (DMSO-d6) 0.03 (m, 2H), 0.11 (m, 2H), 1.77 (m, 1H), 4.45 (s, 2H), 7.12 (dd, 1H), 7.45 (dd, 1H); 7.59-7.64 (m, 5H), 7.72 (br, 1H,); 7.94-7.97 (m, 3H), 8.13 (dd, 1H), 8.47 (dd, 1H) | 457 |
| 2 | II | II | A | 6-{6-[4-(Pyrrolidine-1-sulfonyl)-phenyl]-[1,2,4]triazolo[4,3-b]pyridazin-3-ylmethyl}-quinoline | (DMSO-d6) 1.62-1.68 (m, 4H), 3.19-3.21 (m, 4H), 4.83 (s, 2H), 7.51 (dd, 1H), 7.82 (dd, 1H), 7.99-8.03 (m, 6H), 8.34-8.37 (m, 3H), 8.52 (dd, 1H), 8.86 (dd, 1H) | 471 |
| 3 | I | I | A | N-Ethyl-3-(3-quinolin-6-ylmethyl-[1,2,4]triazolo[4,3-b]pyridazin-6-yl)-benzenesulfonamide | (DMSO-d6) 0.99 (t, 3H), 2.50 (q, 2H), 4.83 (s, 2H), 7.50 (dd, 1H), 7.77 (br t, 1H), 7.82-7.85 (m, 3H), 7.98-8.00 (m, 3H), 8.35 (dd, 1H), 8.50-8.53 (m, 2H), 8.85 (dd, 1H) | 445 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 4 | II | III | A | 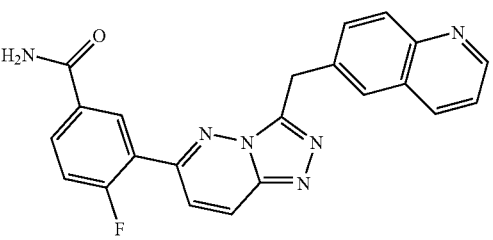<br>4-Fluoro-3-(3-quinolin-6-ylmethyl-[1,2,4]triazolo[4,3-b]pyridazin-6-yl)-benzamide | (DMSO-d6) 4.75 (d, 2H), 7.44 (dd, 1H), 7.50 (dd, 1H), 7.67 (dd, 1H), 7.76 (dd, 1H), 7.91-7.93 (m, 2H), 8.05-8.08 (m, 1H), 8.11 (s, 1H), 8.29 (d, 1H), 8.34 (dd, 1H), 8.42 (d, 1H), 8.79 (dd, 1H) | 399 |
| 5 | II | II | A | 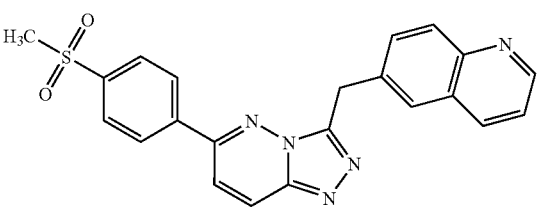<br>6-[6-(4-Methanesulfonyl-phenyl)-[1,2,4]triazolo[4,3-b]pyridazin-3-ylmethyl]-quinoline | (DMSO-d6) 3.31 (s, 3H), 4.84 (s, 2H), 7.51 (dd, 1H), 7.83 (dd, 1H), 7.99-8.04 (m, 3H), 8.13 (d, 1H), 8.34-8.37 (m, 3H), 8.52 (d, 1H), 8.86 (dd, 1H) | 416 |
| 6 | II | II | H | 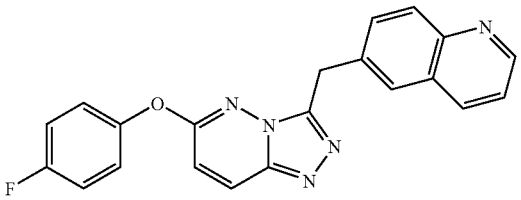<br>6-[6-(4-Fluoro-phenoxy)-[1,2,4]triazolo[4,3-b]pyridazin-3-ylmethyl]-quinoline | (DMSO-d6) 4.43 (s, 2H), 7.24-7.36 (m, 5H), 7.49 (dd, 1H), 7.54 (dd, 1H), 7.66 (d, 1H), 7.89 (d, 1H), 8.24 (dd, 1H), 8.39 (d, 1H), 8.88 (d, 1H) | 372 |
| 7 | II | II | H | 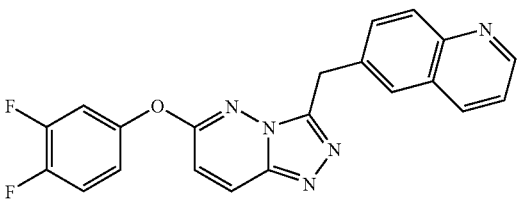<br>6-[6-(3,4-Difluoro-phenoxy)-[1,2,4]triazolo[4,3-b]pyridazin-3-ylmethyl]-quinoline | (DMSO-d6) 4.45 (s, 2H), 7.18 (m, 1H), 7.30 (d, 1H), 7.48-7.60 (m, 4H), 7.68 (d, 1H), 7.88 (d, 1H), 8.22 (d, 1H), 8.41 (d, 1H), 8.87 (d, 1H) | 390 |
| 8 | II | II | H | 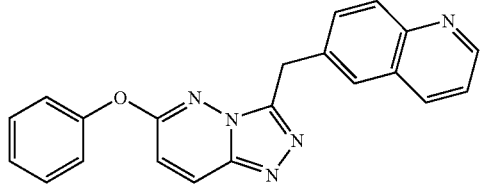<br>6-(6-Phenoxy)-[1,2,4]triazolo[4,3-b]pyridazin-3-ylmethyl]-quinoline | (DMSO-d6) 4.42 (s, 2H), 7.26-7.30 (m, 3H), 7.34-7.38 (m, 1H), 7.42-7.53 (m, 4H), 7.64 (d, 1H), 7.87 (d, 1H), 8.2 (dd, 1H), 8.39 (d, 1H), 8.86 (dd, 1H) | 354 |

TABLE 1-continued

| Eg. | c-MET IC$_{50}$ | GTL16 EC$_{50}$ | Method | Structure | $^1$H NMR (500 MHz) | MS (m/z) |
|---|---|---|---|---|---|---|
| 9 | II | II | H | 6-[6-(3-Methoxy-phenoxy)-[1,2,4]triazolo[4,3-b]pyridazin-3-ylmethyl]-quinoline | (DMSO-d6) 3.72 (s, 3H) 4.43 (s, 2H), 6.87 (dd, 1H), 6.92-6.96 (m, 2H), 7.26 (d, 1H), 7.36 (t, 1H), 7.48-7.53 (m, 2H), 7.66 (d, 1H), 7.86 (d, 2H), 8.20 (dd, 1H), 8.38 (d, 1H), 8.86 (dd, 1H) | 384 |
| 10 | III | IV | H | 4-(3-Quinolin-6-ylmethyl-[1,2,4]triazolo[4,3-b]pyridazin-6-yloxy)-benzenesulfonamide | (DMSO-d6) 4.55 (s, 2H), 7.43 (d, 1H), 7.59-7.66 (m, 5H), 7.76 (dd, 1H), 8.00-8.06 (m, 2H), 8.32 (dd, 1H), 8.53 (d, 1H), 8.96 (dd, 1H) | 433 |
| 11 | III | IV | H | 4-(3-Quinolin-6-ylmethyl-[1,2,4]triazolo[4,3-b]pyridazin-6-yloxy)-benzamide | (DMSO-d6) 4.53 (s, 2H), 7.4 (d, 1H), 7.50 (m, 2H), 7.58-7.62 (m, 2H), 7.55 (d, 1H), 7.98 (d, 1H), 8.10 (m, 2H), 8.29 (dd, 1H), 8.52 (d, 1H), 8.96 (dd, 1H) | 397 |
| 12 | III | IV | H | 6-[6-(4-Methanesulfonyl-phenoxy)-[1,2,4]triazolo[4,3-b]pyridazin-3-ylmethyl]-quinoline | (DMSO-d6) 4.55 (s, 2H), 7.34 (d, 1H), 7.47-7.52 (m, 2H), 7.56 (m, 2H), 7.65 (d, 1H), 7.9 (d, 1H), 7.94-7.98 (m, 2H), 8.22 (dd, 1H), 8.45 (d, 1H), 8.86 (dd, 1H) | 432 |
| 13 | III | IV | D | 4-(6-Chloro-[1,2,4]triazolo[4,3-b]pyridazin-3-ylmethyl)-phenol | (DMSO-d6) 4.34 (2H, s), 6.68 (2H, d), 7.09 (2H, d), 7.45 (1H, dd), 8.42 (1H, dd), 9.30 (1H, s) | 261 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 14 | II | III | A | 4-(6-Phenyl-[1,2,4]triazolo[4,3-b]pyridazin-3-ylmethyl)-phenol | (DMSO-d6) 4.46 (2H, s), 6.69 (2H, dd), 7.19 (2H, d), 7.62-7.58 (3H, m), 7.94 (1H, d), 8.11 (1H, d), 8.13 (1H, d), 8.42 (1H, d), 9.49 (1H, s) | 303 |
| 15 | II | III | D | 6-(6-Chloro-[1,2,4]triazolo[4,3-b]pyridazin-3-ylmethyl)-quinoline | (DMSO-d6) 4.71 (2H, s), 7.49 (1H, d), 7.51 (1H, dd), 7.75 (1H, dd), 7.86 (1H, d), 7.98 (1H, d), 8.31 (1H, dd), 8.46 (1H, d), 8.86 (1H, dd) | 296 |
| 16 | II | II | A | 6-(6-Phenyl-[1,2,4]triazolo[4,3-b]pyridazin-3-ylmethyl)-quinoline | (DMSO-d6) 4.82 (2H, s), 7.51 (1H, dd), 7.60-7.57 (3H, m), 7.82 (1H, dd), 7.96 (1H, d), 7.98 (1H, s), 7.99 (1H, d), 8.10 (1H, dd), 8.11 (1H, d), 8.34 (1H, dd), 8.44 (1H, d), 8.60 (1H, dd) | 338 |
| 17 | NA | NA | Y | 3-Benzothiazol-6-ylmethyl-6-chloro-[1,2,4]triazolo[4,3-b]pyridazine | (CDCl3) 8.96 (s, 1H), 8.03-8.09 (m, 3H), 7.63 (dd, 1H), 7.10 (d, 1H), 4.71 (s, 2H). | |
| 18 | IV | | A | 6-[1-Methyl-1-(6-phenyl-[1,2,4]triazolo[4,3-b]pyridazin-3-yl)-ethyl]-quinoline | (DMSO-d6) 7.34 (2H, dd), 7.46-7.43), 1H, m), 7.54-7.50 (2H, m), 7.66-7.62 (2H, m), 7.85 (1H, d), 7.89 (1H, d), 8.05 91H,d), 8.40 (1H, d), 8.43 (1H, d), 8.84 (1H, dd) | 366 |
| 19 | NA | NA | D | (R,S)-6-[1-(6-Chloro-[1,2,4]triazolo[4,3-b]pyridazin-3-yl)-ethyl]-quinoline | (DMSO-d6) 1.88 (3H, d), 5.00 (1H, q), 7.45 (1H, d), 7.50 (1H, dd), 7.77 (1H, dd), 7.86 91H, d), 7.97 (1H, d), 8.32 (1H, d), 8.45 (1H, d), 8.86 (1H, dd) | 310 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 20 | I | I | A | (R,S)-6-{1-[6-(3-Fluoro-phenyl)-[1,2,4]triazolo[4,3-b]pyridazin-3-yl]-ethyl}-quinoline | (DMSO-d6) 1.95 (3H, d), 5.16 (1H, q), 7.40 (1H, dt), 7.50 (1H, dd), 7.60 (1H, dt), 7.83-7.80 (2H, m), 7.88 (1H, d), 8.00-7.94 (2H, m), 8.34 (1H, d), 8.45 (1H, d), 8.84 (1H, dd) | 370 |
| 21 | I | I | A | (R,S)-3-[3-(1-Quinolin-6-yl-ethyl)-[1,2,4]triazolo[4,3-b]pyridazin-6-yl]-benzonitrile | (DMSO-d6) 1.96 (3H, d), 5.19 (1H, q), 7.50 (1H, dd), 7.77 (1H, t), 7.83 (1H, dd), 8.10-7.95 (4H, m), 8.37-8.34 (2H, m), 8.48 (1H, d), 8.49 (1H, d), 8.84 (1H, dd) | 377 |
| 22 | II | III | A | (R,S)-3-[3-(Fluoro-quinolin-6-yl-ethyl)-[1,2,4]triazolo[4,3-b]pyridazin-6-yl]-benzonitrile | (DMSO-d6) 7.61 (1H, dd), 7.75 (1H, d), 7.82 (1H, d), 8.02 (1H, dd), 8.09 (1H, ddd), 8.13 (1H, d), 8.18 1H, d), 8.35 (1H, s), 8.47 (1H, ddd), 8.50 (1H, dd), 8.61-8.65 (2H, m), 8.97 (1H, dd) | 381 |
| 23 | II | II | A | Morpholin-4-yl-[4-(3-quinolin-6-ylmethyl)-[1,2,4]triazolo[4,3-b]pyridazin-6-yl)-phenyl]-methanone | (DMSO-d6) 3.27-3.59 (br m, 8H), 4.76 (s, 2H), 7.44 (dd, 1H), 7.54 (d, 2H), 7.74 (dd, 1H), 7.91 (s, 1H), 7.92 (d, 2H), 8.10 (d, 2H), 8.27 (dd, 1H), 8.79 (dd, 1H | 451 |
| 24 | I | I | A | 4-(3-Quinolin-6-ylmethyl)-[1,2,4]triazolo[4,3-b]pyridazin-6-yl)-benzamide | (DMSO-d6) 4.83 (d, 2H), 6.58 (s, 2H), 7.50 (s, 1H), 7.68 (t, 1H), 7.84 (dd, 1H), 7.98-8.25 (m, 3H), 8.07 (dd, 1H), 8.20 (br s, 1H), 8.25 (dd, 1H), 8.36 (dd, 1H), 8.49 (d, 1H), 8.61 (t, 1H), 8.85 (dd, 1H) | 381 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 25 | I | II | A | 3-(3-Quinolin-6-ylmethyl)-[1,2,4]triazolo[4,3-b]pyridazin-6-yl)-benzenesulfonamide | (DMSO-d6) 2.81 (d, 2H), 4.83 (d, 2H), 7.51 (dd, 1H), 7.59 (m, 1H), 7.78-7.86 (m, 2H), 7.93-8.04 (m, 4H), 8.33 (d, 1H), 8.35 (d, 1H), 8.51 (d, 1H), 8.61 (t, 1H), 8.86 (dd, 1H) | 417 |
| 26 | II | II | A | 6-{6-[4-(Pyrrole-1-sulfonyl)-phenyl]-[1,2,4]triazolo[4,3-b]pyridazin-3-ylmethyl}-quinoline | (DMSO-d6) 4.8 (s, 2H), 6.40 (d, 2H), 7.41 (t, 2H), 7.50 (dd, 1H), 7.81 (dd, 1H), 7.96-7.99 (m, 3H), 8.16 (m, 2H), 8.30-8.34 (m, 3H), 8.50 (d, 1h), 8.85 (dd, 1H) | 417 |
| 27 | NA | NA | X | 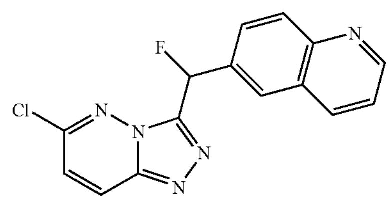 | (DMSO-d6) 7.51 (1H, d), 7.56-7.66 (2H, d), 7.99 (1H, dd), 8.11 (1H, dd), 8.26 (1H, s), 8.47 (1H, dd), 8.57 (1H, dd), 8.967 (1H, dd) | 314 |
| 28 | III | II | O | 3-Bromo-5,7-difluoro-6-(6-methyl-[1,2,4]triazolo[4,3-b]pyridazin-3-ylmethyl)-quinoline | (DMSO-d6) 2.55 (3H, s), 4.68 (2H, s), 7.28 (1H, d), 7.80 (1H, d), 8.24 (1H, d), 8.78 (1H, d), 9.06 (1H, d) | 392 |
| 29 | II | III | A | N,N-Dimethyl-4-(3-quinolin-6-ylmethyl-[1,2,4]triazolo[4,3-b]pyridazin-6-yl)-benzenesulfonamide | (DMSO-d6) 2.60 (s, 6H), 4.77 (s, 2H), 7.44 (dd, 1H), 7.78 (dd, 1H), 7.88 (dd, 2H), 7.92-7.97 (m, 3H), 8.29-8.31 (m, 3H), 8.45 (d, 1H), 8.79 (dd, 1H) | 445 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 30 | I | I | A | 2-Fluoro-N-methyl-4-(3-quinolin-6-ylmethyl-[1,2,4]triazolo[4,3-b]pyridazin-6-yl)-benzamide | (DMSO-d6) 2.80 (s, 3H), 4.85 (s, 2H), 7.50 (dd, 1H), 7.78-7.82 (m, 2H), 7.97-8.04 (m, 5H), 8.33 (dd, 1H), 8.41 (br m, 1H), 8.49 (d, 1H), 8.86 (dd, 1H) | 413 |
| 31 | I | I | A | 6-[6-(3-Fluoro-phenyl)-[1,2,4]triazolo[4,3-b]pyridazin-3-ylmethyl]-quinoline | (DMSO-d6) 4.78 (s, 2H), 7.38 (td, 1H), 7.45 (dd, 1H), 7.57 (dd, 1H), 7.75 (dd, 1H), 7.86-7.94 (m, 5H), 8.27 (dd, 1H), 8.42 (d, 1H), 8.80 (dd, 1H) | 356 |
| 32 | I | I | A | 4-(3-Quinolin-6-ylmethyl-[1,2,4]triazolo[4,3-b]pyridazin-6-yl)-benzylamine | (DMSO-d6) 4.23 (s, 2H), 4.85 (s, 2H). 7.52 (dd, 1H), 7.64 (d, 2H), 7.86 (dd, 1H), 7.91 (d, 1H), 7.96-8.0 (m, 2H), 8.12 (d, 1H), 8.26-8.32 (m, 3H), 8.80 (dd, 1H) | 367 |
| 33 | II | II | A | N-Cyclopentyl-3-(3-quinolin-6-ylmethyl-[1,2,4]triazolo[4,3-b]pyridazin-6-yl)-benzamide | (DMSO-d6) 1.46-1.86 (br m, 8H), 4.24 (m, 1H), 4.76 (s, 2H), 7.43 (dd, 1H), 7.60 (t, 1H), 7.77 (dd, 1H), 7.92-7.97 (m, 4H), 8.15 (dd, 1H), 8.42-8.46 (m, 2H), 8.79 (dd, 1H) | 449 |
| 34 | II | II | A | N,N-Dimethyl-4-(3-quinolin-6-ylmethyl-[1,2,4]triazolo[4,3-b]pyridazin-6-yl)-benzamide | (DMSO-d6) 2.90 (s, 3H), 3.00 (s, 3H), 4.80 (s, 2H), 7.50 (dd, 1H), 7.60 (d, 2H), 7.81 (dd 1H), 7.96-8.05 (m, 3H), 8.16 (dd, 2H), 8.34 (dd, 1H), 8.46 (d, 1H), 8.85 (dd, 1H) | 409 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 35 | I | II | A | 6-(6-m-Tolyl-[1,2,4]triazolo[4,3-b]pyridazin-3-ylmethyl)-quinoline | (DMSO-d6) 2.30 (s, 3H), 4.75 (s, 2H), 7.31 (d, 1H), 7.38 (t, 1H), 7.44 (dd, 1H), 7.53 (dd, 1H), 7.77 (s, 1H), 7.81 (d, 1H), 7.85 (d, 2H), 7.90-7.94 (m, 2H), 8.26 (dd, 1H), 8.35 (d, 1H), 8.79 (dd, 1H) | 352 |
| 36 | I | I | A | 6-(6-p-Tolyl-[1,2,4]triazolo[4,3-b]pyridazin-3-ylmethyl)-quinoline | (DMSO-d6) 2.40 (s, 3H), 4.81 (s, 2H), 7.38 (d, 2H), 7.51 (dd, 1H), 7.67 (d, 1H), 7.81 (dd, 1H), 7.93 (d, 1H), 7.98-8.01 (m, 3H), 8.33 (dd, 1H), 8.41 (dd, 1H), 8.85 (dd, 1H) | 352 |
| 37 | II | I | A | N-Methyl-4-(3-quinolin-6-ylmethyl-[1,2,4]triazolo[4,3-b]pyridazin-6-yl)-benzenesulfonamide | (DMSO-d6) 2.40 (d, 3H), 4.77 9s, 2H), 7.44 (dd, 1H), 7.59 (br q, 1H), 7.76 (dd, 1H), 7.89-7.95 (m, 5H), 8.24-8.29 (m, 3H), 8.44 (d, 1H), 8.79 (dd, 1H) | 431 |
| 38 | III | NA | E | 2-Methyl-6-(6-phenyl-[1,2,4]triazolo[4,3-b]pyridazin-3-ylmethyl)-quinoline | (DMSO-d6) 2.62 (s, 3H), 4.79 (s, 2H), 7.39 (d, 1H), 7.59 (m, 3H), 7.75 (dd, 1H), 7.88 (d, 1H), 7.91 (d, 1H), 7.96 (d, 1H), 8.10 (m, 2H), 8.21 (d, 1H), 8.44 (d, 1H) | 352 |
| 39 | IV | NA | E | 6-[2-(6-Phenyl-[1,2,4]triazolo[4,3-b]pyridazin-3-yl)-ethyl]-quinoline | (DMSO-d6) 3.44 (t, 2H), 3.63 (t, 2H), 7.47 (dd, 1H), 7.58 (m, 3H), 7.69 (dd, 1H), 7.84 (d, 1H), 7.90 (d, 1H), 7.91 (d, 1H), 8.07 (m, 2H), 8.26 (d, 1H), 8.39 (d, 1H), 8.82 (dd, 1H) | 352 |
| 40 | IV | NA | E | 6-[2-(6-Phenyl-[1,2,4]triazolo[4,3-b]pyridazin-3-yl)-cyclopropyl]-quinoline | (DMSO-d6) 1.93 (m, 1H), 2.05 (m, 1H), 2.98 (m, 2H), 7.53 (dd, 1H), 7.56 (m, 3H), 7.76 (dd, 1H), 7.93 (d, 1H), 7.94 (s, 1H), 8.00 (d, 1H), 8.10 (m, 2H), 8.31 (d, 1H), 8.42 (d, 1H), 8.85 (dd, 1H) | 364 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 41 | III | NA | E | 6-(6-Phenyl-[1,2,4]triazolo[4,3-b]pyridazin-3-ylmethyl)-quinoxaline | (DMSO-d6) 4.91 (s, 2H), 7.59 (m, 3H), 7.92 (dd, 1H), 7.97 (d, 1H), 8.08 (d, 1H), 8.12 (m, 3H), 8.46 (d, 1H), 8.93 (d, 2H) | 339 |
| 42 | II | III | E | 6-(6-Phenyl-[1,2,4]triazolo[4,3-b]pyridazin-3-ylmethyl)-benzothiazol-2-ylamine | (DMSO-d6) 466 (s, 2H), 7.45 (m, 2H), 7.60 (m, 3H), 7.85 (s, 1H), 7.97 (d, 1H), 8.12 (m, 2H), 8.45 (d, 1H), 9.25 (broad s, 2H) | 359 |
| 43 | II | II | E | 3-Benzothiazol-6-ylmethyl-6-phenyl-[1,2,4]triazolo[4,3-b]pyridazine | (DMSO-d6) 4.70 (s, 2H), 7.52 (m, 4H), 7.90 (d, 1H), 7.97 (d, 1H), 8.04 (m, 2H), 8.13 (s, 1H), 8.37 (d, 1H), 9.27 (s, 1H) | 344 |
| 44 | III | NA | E | 3-(2-Chloro-benzothiazol-6-ylmethyl-6-phenyl-[1,2,4]triazolo[4,3-b]pyridazine | (DMSO-d6) 4.69 (s, 2H), 7.52 (m, 3H), 7.55 (dd, 1H), 7.86 (d, 1H), 7.89 (d, 1H), 8.03 (m, 3H), 8.37 (d, 1H) | 378 |
| 45 | II | II | J | 3-(3H-Benzoimidazol-5-ylmethyl)-6-phenyl-[1,2,4]triazolo[4,3-b]pyridazine | (DMSO-d6) 4.62 (s, 2H), 7.18 (d, 1H), 7.4-7.6 (m, 5H), 7.87 (d, 1H), 8.05 (m, 2H0, 8.09 (s, 1H), 8.35 (d, 1H) | 327 |
| 46 | II | II | C | 6-(6-Propenyl-[1,2,4]triazolo[4,3-b]pyridazin-3-ylmethyl)-quinoline | (DMSO-d6) 188 (d, 3H), 4.63 (s, 2H), 6.49 (dd, 1H), 6.88 (dd, 1H), 7.44 (dd, 1H), 7.58 (d, 1H), 7.69 (dd, 1H), 7.81 (s, 1H), 7.91 (d, 1H), 8.22 (dd, 1H), 8.79 (dd, 1H) | 302 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 47 | I | II | A | N-Ethyl-3-(3-quinolin-6-ylmethyl-[1,2,4]triazolo[4,3-b]pyridazin-6-yl)-benzamide | (DMSO-d6) 1.17 (t, 3H), 3.35 (q, 2H), 4.83 9s, 2H), 7.50 9 (dd, 1H), 7.68 (t, 1H), 7.83 (dd, 1H), 7.98-8.03 (m, 4H), 8.23 (br dt, 1H), 8.35 (d, 1H), 8.47 (d, 1H), 8.54 (s, 1H), 8.70 (br t, 1H), 8.85 (dd, 1H) | 409 |
| 48 | I | I | A | N-Methyl-3-(3-quinolin-6-ylmethyl-[1,2,4]triazolo[4,3-b]pyridazin-6-yl)-benzenesulfonamide | (DMSO-d6) 2.90 (d, 3H), 4.83 (s, 2H), 7.50 (ss, 1H), 7.67 (br q, 1H), 7.82-7.85 (m, 2H), 7.97-8.01 (m, 3H), 8.33-8.38 (m, 2H), 8.50-8.52 (m, 1H), 8.85 (ss, 1H) | 431 |
| 49 | I | I | A | 6-[6-(3-Methanesulfonyl-phenyl)-[1,2,4]triazolo[4,3-b]pyridazin-3-ylmethyl]-quinoline | (CDCl$_3$) 3.25 (s, 3H), 4.90 (s, 2H), 7.50 (dd, 1H), 7.61 (d, 1H), 7.80 (t, 1H), 7.92 (d, 1H), 8.02 9s, 1H), 8.13 (d, 1H), 8.20-8.27 (m, 3H), 8.35 (d, 1H), 8.58 (d, 1H), 8.90 (d, 1H) | 416 |
| 50 | I | NA | A | 1-[3-(3-Quinolin-6-ylmethyl-[1,2,4]triazolo[4,3-b]pyridazin-6-yl)-phenyl]-ethanone | (DMSO-d6) 2.12 9s, 3H), 4.78 9s, 2H), 7.48-7.52 (m, 2H), 7.70 (d, 1H), 7.75 (d, 1H), 7.83-7.87 (m, 2H), 7.89 (d, 1H), 8.05 (d, 1H), 8.36 (d, 1H), 8.44 (d, 1H), 8.52 (t, 1H), 8.85 (dd, 1H), 10.24 (s, 1H) | 395 |
| 51 | I | II | A | N-[3-(3-Quinolin-6-ylmethyl-[1,2,4]triazolo[4,3-b]pyridazin-6-yl)-phenyl]-methanesulfonamide | (DMSO-d6) 3.08 (s, 3H), 4.80 (s, 2H), 7.40 (dd, 1H), 7.50 (dd, 1H), 7.55 (t, 1H), 7.81 (br d, 1H), 7.85 (dd, 1H), 7.98 (d, 1H), 7.98 (d, 1H), 8.00 (s, 1H), 8.03 (t, 1H), 8.34 (dd, 1H), 8.45 (d, 1H), 8.85 (dd, 1H) | 431 |

TABLE 1-continued

| Eg. | c-MET IC₅₀ | GTL 16 EC₅₀ | Method | Structure | ¹H NMR (500 MHz) | MS (m/z) |
|---|---|---|---|---|---|---|
| 52 | I | II | A | N-[4-(3-Quinolin-6-ylmethyl-[1,2,4]triazolo[4,3-b]pyridazin-6-yl)-phenyl]-acetamide | (DMSO-d6) 2.0 (s, 3H), 4.67 (s, 2H), 7.44 (dd, 1H), 7.71 (d, 1H), 7.75 (dd, 1H), 7.86 (d, 1H), 7.92 (d, 1H), 7.93 (s, 1H), 8.0 (m, 2H), 8.27 (dd, 1H), 8.32 (d, 1H) 8.79 (dd, 1H), 10.19 (s, 1H) | 395 |
| 53 | II | II | A | 6-[6-(2-Fluoro-phenyl)-[1,2,4]triazolo[4,3-b]pyridazin-3-ylmethyl]-quinoline | (DMSO-d6) 4.78 (s, 2H), 7.39-7.48 (m, 2H), 7.51 (dd, 1H), 7.65 (m, 1H), 7.69 (dd, 1H), 7.78-7.83 (m, 2H), 7.94 (d, 1H), 7.88 (d, 1H), 8.32 (dd, 1H), 8.46 (d, 1H), 8.86 (dd, 1H) | 356 |
| 54 | I | II | A | [4-(3-Quinolin-6-ylmethyl-[1,2,4]triazolo[4,3-b]pyridazin-6-yl)-phenyl]-methanol | (DMSO-d6) 4.18 (s, 1H), 4.82 (s, 1H), 7.50 (dd, 1H), 7.57 (d, 1H), 7.61 (t, 1H), 7.82 (dd, 1H), 7.94 (d, 1H), 7.98 (d, 1H), 8.00 (s, 1H), 8.06 (dd, 1H), 8.12 (s, 1H), 8.34 (dd, 1H), 8.46 (d, 1H), 8.85 (dd, 1H) | 368 |
| 55 | I | II | A | 3-(3-Quinolin-6-ylmethyl-[1,2,4]triazolo[4,3-b]pyridazin-6-yl)-benzylamine | (DMSO-d6) 4.04 (s, 2H), 4.82 (s, 2H), 7.51 (dd, 1H), 7.60 (m, 2H), 7.82 (dd, 1H), 7.92 (d, 1H), 7.95 (d, 1H), 8.00 (s, 1H), 8.04 (d, 1H), 8.33 (dd, 1H), 8.35 (s, 1H), 8.45 (d, 1H), 8.85 (dd, 1H) | 367 |
| 56 | II | II | A | 3-Fluoro-N-methyl-5-(3-quinolin-6-ylmethyl-[1,2,4]triazolo[4,3-b]pyridazin-6-yl)-benzamide | (DMSO-d6) 2.8 (s, 3H), 4.78 (s, 2H), 7.44 (dd, 1H), 7.76 (dd, 1H), 7.92 (d, 1H), 7.95 (s, 1H), 7.95 (dd, 1H), 8.02 (dt, 1H), 8.36 (t, 1H), 8.67 (br q, 1H), 8.78 (dd, 1H) | 413 |
| 57 | II | III | A | N-[3-(3-Quinolin-6-ylmethyl-[1,2,4]triazolo[4,3-b]pyridazin-6-yl)-phenyl]-acetamide | (DMSO-d6) 3.50 (s, 3H), 4.83 (s, 2H), 7.50 dd, 1H), 7.78-7.83 (m, 2H), 7.97-8.07 (m, 4H), 8.33 (dd, 1H), 8.44 (dd, 1H), 8.51 (d, 1H), 8.58 (t, 1H), 8.85 (dd, 1H) | 395 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 58 | II | III | A | 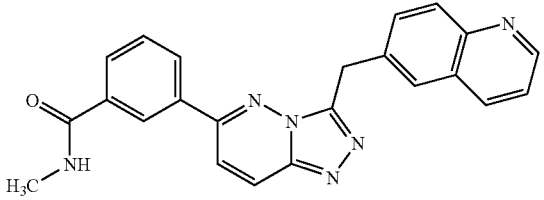<br>N-Methyl-3-(3-quinolin-6-ylmethyl-[1,2,4]triazolo[4,3-b]pyridazin-6-yl)-benzamide | (DMSO-d6) 2.87 (s, 3H), 4.83 (s, 2H), 7.50 (dd, 1H), 7.68 (t, 1H), 7.83 (dd, 1H), 7.90-8.03 (m, 4H), 8.24 (dd, 1H), 8.35 (dd, 1H), 8.50 (d, 1H), 8.55 (d, 1H), 8.66 (br q, 1H), 8.85 (dd, 1H) | 395 |
| 59 | I | I | A | 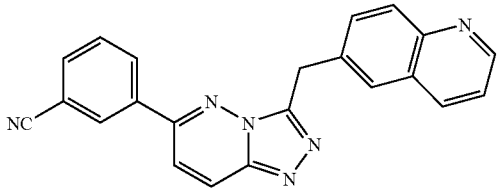<br>3-(3-Quinolin-6-ylmethyl-[1,2,4]triazolo[4,3-b]pyridazin-6-yl)-benzonitrile | (DMSO-d6) 4.82 (s, 2H), 7.50 (dd, 1H), 7.79 (d, 1H), 7.82 (dd, 1H), 7.97-8.07 (m, 4H), 8.33 (dd, 1H), 8.44 (dd, 1H), 8.51 (d, 1H), 8.58 (t, 1H), 8.85 (dd, 1H) | 363 |
| 60 | II | II | A | 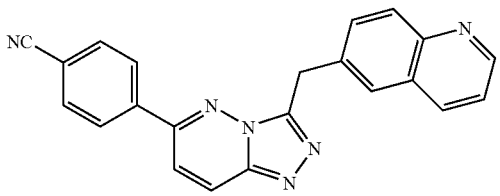<br>4-(3-Quinolin-6-ylmethyl-[1,2,4]triazolo[4,3-b]pyridazin-6-yl)-benzonitrile | (DMSO-d6) 4.82 9s, 2H), 7.51 (dd, 1H), 7.82 (dd, 1H), 7.97-8.09 (m, 5H), 8.30-8.35 (m, 3H), 8.52 (d, 2H), 8.86. (dd, 1H) | 363 |
| 61 | I | II | A | 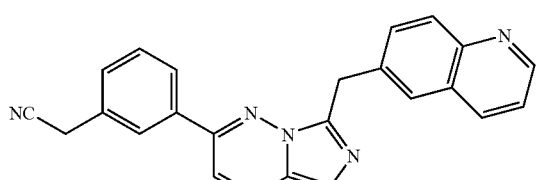<br>[3-(3-Quinolin-6-ylmethyl-[1,2,4]triazolo[4,3-b]pyridazin-6-yl)-phenyl]-acetonitrile | (DMSO-d6) 7.50 (dd, 1H), 7.56-7.63 (m, 2H), 7.83 (dd, 1H0, 7.94 (d, 1H), 7.99 (d, 1H), 8.0 (s, 1H), 8.06 (dd, 1H), 8.13 (s, 1H), 8.34 (dd, 1H), 8.46 (d, 1H), 8.85 (dd, 1H) | 377 |
| 62 | I | II | A | 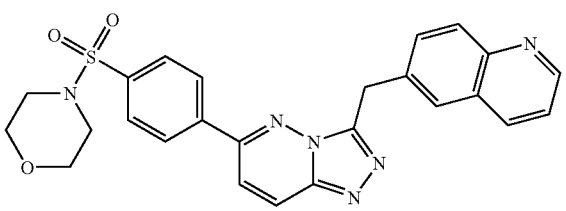<br>6-{6-[4-(Morpholine-4-sulfonyl)-phenyl]-[1,2,4]triazolo[4,3-b]pyridazin-3-ylmethyl}-quinoline | (DMSO-d6) 2.92 (m, 4H), 3.63 (m, 4H), 4.85 (s, 2H), 7.51 (dd, 1H), 7.83 (dd, 1H), 7.95-7.96 (m, 2H), 7.99 (s, 1H), 8.00 (d, 1H), 8.03 (d, 1H), 8.23 (s, 1H), 8.35-8.39 (m, 3H), 8.53 (d, 1H), 8.85 (dd, 1H) | 487 |
| 63 | II | II | A | 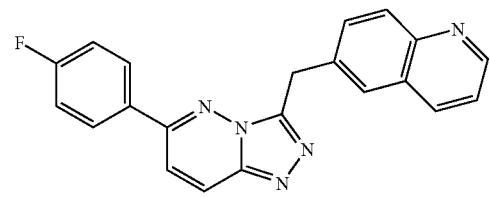<br>6-[6-(4-Fluoro-phenyl)-[1,2,4]triazolo[4,3-b]pyridazin-3-ylmethyl]-quinoline | (CDCl$_3$) 1.90 (m, 2H), 2.05 (m, 2H), 3.47 (m, 2H), 3.70 (m, 2H), 4.85 (s, 2H), 7.26-7.29m, 3H), 7.58 (d, 1H), 7.80 (dd, 1H0, 7.93-7.95 (m, 2H), 8.16 (s, 1H), 8.21 (d, 1H), 8.66 9d, 1H), 8.75 (d, 1H), 9.00 (d, 1H) | 356 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 64 | I | I | A | N,N-Dimethyl-3-(3-quinolin-6-ylmethyl-[1,2,4]triazolo[4,3-b]pyridazin-6-yl)-benzenesulfonamide | (DMSO-d6) 2.57 (s, 6H), 4.78 (s, 2H), 7.43 (dd, 1H), 7.75 (dd, 1H), 7.80 (t, 1H), 7.86-7.99 (m, 4H), 8.26 (dd, 1H), 8.30 (t, 1H), 8.44 (dd, 1H), 8.78 (dd, 1H) | 445 |
| 65 | I | I | A | Methyl-[4-(3-quinolin-6-ylmethyl-[1,2,4]triazolo[4,3-b]pyridazin-6-yl)-phenyl]-amine | (CD$_3$OD), 6.66 (dd, 2H), 7.52 (dd, 1H), 7.79 (d, 1H), 7.83-7.89 (m, 3H), 8.00 (s, 1H), 8.01 (d, 1H), 8.07 (d, 1H), 8.33 (dd, 1H), 8.80 (dd, 1H) | 367 |
| 66 | I | II | A | N-Methyl-4-(3-quinolin-6-ylmethyl-[1,2,4]triazolo[4,3-b]pyridazin-6-yl)-benzamide | (CD$_3$OD) 1.99 (s, 1H), 2.95 (s, 3H), 4.94 (s, 2H), 7.79 (dd, 1H), 7.96-7.99 (m, 2H), 8.0608.17 (m, 4H), 8.20 (s, 1H), 8.30 (d, 1H), 8.74 (dd, 1H), 8.98 (dd, 1H) | 395 |
| 67 | II | II | A | Dimethyl-[3-(3-quinolin-6-ylmethyl-[1,2,4]triazolo[4,3-b]pyridazin-6-yl)-phenyl]-amine | (CD$_3$OD) 2.95 (s, 6H), 4.84 (s, 2H), 6.90 (dd, 1H), 7.23-7.26 (m, 2H), 7.31 (t, 1H), 7.50 )dd, 1H), 7.83 (d, 1H), 7.85 (dd, 1H), 7.94 (s, 1H), 7.99 (d, 1H), 8.18 (d, 1H), 8.28 (dd, 1H0, 8.79 (dd, 1H) | 381 |
| 68 | II | II | K | 3-(3-Methyl-3H-benzoimidazol-5-ylmethyl)-6-phenyl-[1,2,4]triazolo[4,3-b]pyridazine | See description in method K for $^1$H NMH data | 341 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 69 | II | III | A | 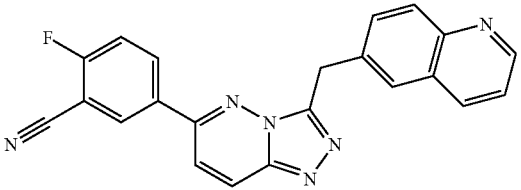<br>2-Fluoro-5-(3-quinolin-6-ylmethyl-[1,2,4]triazolo[4,3-b]pyridazin-6-yl)-benzonitrile | (DMSO-d6) 4.78 (2H, s), 7.43 (1H, dd), 7.71 (1H, t), 7.75 (1H, dd), 7.91 (1H, d), 7.93 (1H, s), 7.96 (1H, d), 8.26 (1H, dd), 8.44-8.49 (2H, m), 8.65 (1H, dd), 8.79 (1H, dd) | 381 |
| 70 | I | II | A | 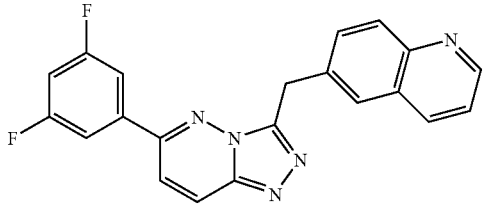<br>6-[6-(3,5-Difluoro-phenyl)-[1,2,4]triazolo[4,3-b]pyridazin-3-ylmethyl]-quinoline | (DMSO-d6) 4.78 (2H, s), 7.42-7.47 (2H, m), 7.74 (1H, dd), 7.78-7.82 (2H, m), 7.90-7.96 (3H, m), 8.25 (1H, dd), 8.44 (1H, d), 8.79 (1H, dd) | 374 |
| 71 | II | II | A | 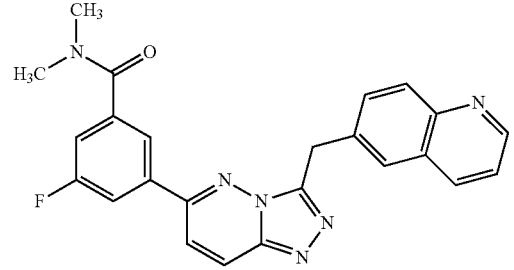<br>3-Fluoro-N,N-dimethyl-5-(quinolin-6-ylmethyl-[1,2,4]triazolo[4,3-b]pyridazin-6-yl)-benzamide | (DMSO-d6) 2.83 (3H), s), 2.98 (3H, s), 4.87 (2H, s), 7.42-7.45 (2H, m), 7.73 (1H, dd), 7.98-7.98 (m, 5H), 8.23 (1H, dd), 8.42 (s, 1H), 8.79 (1H, dd) | 427 |
| 72 | I | II | A | 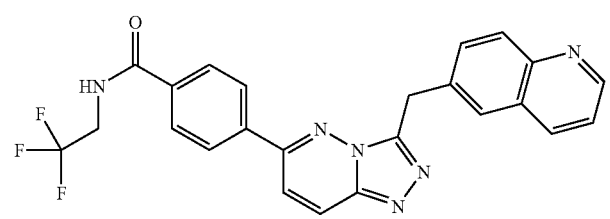<br>4-(3-Quinolin-6-ylmethyl-[1,2,4]triazolo[4,3-b]pyridazin-6-yl)-N-(2,2,2-trifluoro-ethyl)-benzamide | (DMSO-d6) 4.79 (2H, s), 7.44 (1H, dd), 7.76 (1H, dd), 7.92-8.02 (5H, m), 8.17 (2H, d), 8.27 (1H, dd), 8.42 (1H, d), 8.79 (1H, dd), 9.22 (1H, br t) | 463 |
| 73 | II | I | A | 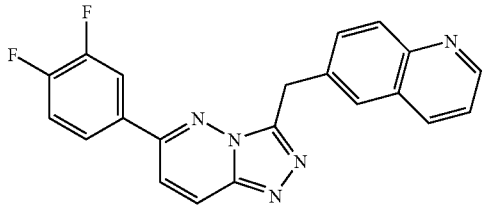<br>6-[6-(3,4-Difluoro-phenyl)-[1,2,4]triazolo[4,3-b]pyridazin-3-ylmethyl]-quinoline | (DMSO-d6) 4.79 (sH, s), 7.44 (1H, dd), 7.61 (1H, dd), 7.74 (1H, dd), 7.91-7.97 (5H, m), 8.11-8.15 (1H, M), 8.25 (1H, dd), 8.41 (1H, d), 8.79 (1H, dd) | 374 |

| Eg. | c-MET IC$_{50}$ | GTL 16 EC$_{50}$ | Method | Structure | $^1$H NMR (500 MHz) | MS (m/z) |
|---|---|---|---|---|---|---|
| 74 | I | II | A | 2-Fluoro-N-(2-hydroxy-ethyl)-4-(3-quinolin-6-ylmethyl-[1,2,4]triazolo[4,3-b]pyridazin-6-yl)-benzamide | (DMSO-d6) 3.31 (2H, m), 3.46 (2H, m), 4.72 (1H, br s), 4.78 (2H, s), 7.45 (1H, dd), 7.73-7.76 (2H, m), 7.91-7.98 (5H, m), 8.26 (1H, dd), 8.33 (1H, br q), 8.44 (1H, d), 8.79 (1H, dd) | 443 |
| 75 | I | I | A | N-Ethyl-2-fluoro-4-(3-quinolin-6-ylmethyl-[1,2,4]triazolo[4,3-b]pyridazin-6-yl)-benzamide | (DMSO-d6) 1.13 (3H, t), 3.29 (2H, q), 4.83 (2H, s), 7.50 (1H, dd), 7.73 (1H, t), 7.80 (1H, dd), 7.97-8.03 (5H, m), 8.32 (1H, dd), 8.46 (1H, br t), 8.48 (1H, d), 8.85 (1H, dd) | 427 |
| 76 | I | I | A | 6-[6-(3-Fluoro-5-methyl-phenyl)-[1,2,4]triazolo[4,3-b]pyridazin-3-ylmethyl]-quinoline | (DMSO-d6) 2.49 (3H, s), 4.82 (2H, s), 7.25 (1H, d), 7.50 (1H, dd), 7.69 (1H, s), 7.71 (1H, s), 7.78 (1H, dd), 7.94-7.98 (3H, m), 8.31 (1H, dd), 8.45 (1H, d(, 8.85 (1H, dd) | 370 |
| 77 | II | I | A | 6-[6-(4-Fluoro-3-trifluoromethyl-phenyl)-[1,2,4]triazolo[4,3-b]pyridazin-3-ylmethyl]-quinoline | (DMSO-d6) 4.83 (2H, s), 7.49 (1H, dd), 7.76 (1H, t), 7.08 (1H, dd), 7.96 (1H, s), 7.97 (1H, d), 8.29 (1H, dd), 8.38 (1H, dd), 8.49 (1H, d), 8.85 (1H, dd) | 424 |
| 78 | I | I | A | 6-[6-(3-Trifluoromethyl-phenyl)-[1,2,4]triazolo[4,3-b]pyridazin-3-ylmethyl]-quinoline | (DMSO-d6) 4.84 (2H, s), 7.51 (1H, dd), 7.80-7.84 (2H, m), 7.95 (1H, d), 7.98 (1H, dd), 8.07 (1H, d), 8.30 (1H, dd), 8.36 (1H, s), 8.42 (1H, d), 8.50 (1H, d), 8.86 (1H, dd) | 406 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 79 | I | I | E | 3-(1-Benzothiazol-6-yl-ethyl)-6-(1-methyl-1H-pyrazol-4-yl)-[1,2,4]triazolo[4,3-b]pyridazine | (DMSO-d6) 1.83 (3H, d), 3.85 (3H, d), 4.94 (1H, q), 7.53 (1H, dd), 7.56 (1H, d), 7.94 (1H, d), 8.04 (1H, s), 8.19 (1H, d), 8.23 (1H, d), 8.42 (1H, s), 9.25 (1H, s). | 362 |
| 80 | I | I | A | 2-Fluoro-N-methyl-4-[3-(1-quinolin-6-yl-ethyl)-[1,2,4]triazolo[4,3-b]pyridazin-6-yl]-benzamide | (DMSO-d6) 1.91 (3H, d), 2.79 (3H, d), 5.15 (1H, q), 7.49 (1H, dd), 7.76 (1H, t), 7.81 (1H, dd), 7.87-8.00 (5H, m), 8.33 (1H, dd), 8.37 (1H, d), 8.46 (1H, d), 8.83 (1H, dd). | 427 |
| 81 | I | I | A | 3-[3-(1-Benzothiazol-6-yl-ethyl)-[1,2,4]triazolo[4,3-b]pyridazin-6-yl]-benzonitrile | (DMSO-d6) 1.92 (3H, d), 5.14 (1H, q), 7.59 (1H, dd), 7.76 (1H, t), 7.98-8.04 (3H, m), 8.24 (1H, d), 8.35 (1H, d), 8.46-8.49 (2H, m), 9.31 (1H, s) | 383 |
| 82 | I | I | A | 4-[3-(1-Benzothiazol-6-yl-ethyl)-[1,2,4]triazolo[4,3-b]pyridazin-6-yl]-2-fluoro-N-methyl-benzamide | (DMSO-d6) 1.92 (3H, d), 2.79 (3H, d), 5.12 (1H, q), 7.57 (1H, dd), 7.75 (1H, q), 7.57 (1H, dd), 7.75 (1H, t), 7.90-7.94 (2H, m), 7.96 (1H, d), 8.01 (1H, d), 8.23 (1H, d), 8.38 (1H, q), 8.45 (1H, d), 9.32 (1H, s) | 433 |
| 83 | I | I | A | 3-(1-Benzothiazol-6-yl-ethyl)-6-(3-fluoro-phenyl)-[1,2,4]triazolo[4,3-b]pyridazine | (DMSO-d6) 4.79 (2H, s), 7.47 (1H, dd), 7.59-7.60 (3H, m), 7.87 (1H, d), 7.91 (1H, s), 7.96 (1H, d), 8.11-8.13 (2H, m), 8.43 (1H, d) | 328 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 84 | I | I | A | 7-Methyl-6-[6-(1-methyl-1H-pyrazol-4-yl)-[1,2,4]triazolo[4,3-b]pyridazin-3-ylmethyl-quinoline | (DMSO-d6) 2.54 (3H, s), 3.87 (3H, s), 4.64 (2H, s), 7.36 (1H, dd), 7.62 (1H, d), 7.79 (1H, s), 7.82 (1H, s), 8.10 (1H, s), 8.20 (1H, d), 8.46 (1H, s), 8.74 (1H, dd) | 356 |
| 85 | I | I | A | 3-[3-(7-Methyl)-quinolin-6-ylmethyl)-[1,2,4]triazolo[4,3-b]pyridazin-6-yl]-benzonitrile | (DMSO-d6) 2.59 (3H, s), 4.81 (2H, s), 7.43 (dd, 1H), 7.80 (1H, t), 7.87 (1H, s), 7.92 (1H, s), 8.05 (1H, d0, 8.06 (1H, dt), 8.26 (1H, dd), 8.43 (1H, dt), 8.52 (1H, d), 8.59 (1H, s), 8.82 (1H, dd) | 377 |
| 86 | I | I | A | 2-Fluoro-N-methyl-4-[3-(7-methyl-quinolin-6-ylmethyl)-[1,2,4]triazolo[4,3-b]pyridazin-6-yl]-benzamide | (DMSO-d6) 1.13 (3H, t), 2.60 (3H, s), 3.28 (2H, q), 4.81 (2H, s), 7.44 (1H, dd), 7.78 (1H, t), 7.87 (1H, s), 7.91 (1H, s), 8.01-8.03 (3H, m), 8.26 (1H, dd), 8.47 (1H, br t), 8.50 (1H, d), 8.82 (1H, dd) | 441 |
| 87 | I | I | A | 5,7-Difluoro-6-[6-(1-methyl-1H-pyrazol-4-yl)-[1,2,4]triazolo[4,3-b]pyridazin-3-ylmethyl]-quinoline | (DMSO-d6) 3.28 (3H, s), 4.70 (2H, s), 7.59 (1H, dd), 7.72 (1H, d), 9.03 (1H, s), 8.28 (1H, d), 8.42 (1H, s), 8.49 (1H, dt), 8.95 (1H, dd) | 378 |
| 88 | I | I | A | 3-[3-(5,7-Difluoro-quinolin-6-ylmethyl)-[1,2,4]triazolo[4,3-b]pyridazin-6-yl]-benzonitrile | (DMSO-d6) 4.86 (2H, s), 7.64 (1H, dd), 7.76-7.82 (2H, m), 8.06-8.08 (2H, m), 8.42 (1H, dt), 8.52 (1H, d), 8.55 (1H, dd), 8.58 (1H, s), 9.01 (1H, dd) | 399 |

TABLE 1-continued

| Eg. | c-MET IC$_{50}$ | GTL16 EC$_{50}$ | Method | Structure | $^1$H NMR (500 MHz) | MS (m/z) |
|---|---|---|---|---|---|---|
| 89 | I | I | A | 4-[3-(5,7-Difluoro-quinolin-6-ylmethyl)-[1,2,4]triazolo[4,3-b]pyridazin-6-yl]-2-fluoro-N-metyl-benzamide | (DMSO-d6) 2.80 (3H, d), 4.86 (2H, s), 7.65 (1H, dd), 7.76-7.81 (2H, m), 8.00-8.05 (3H, m), 8.43 (1H, br q), 8.50 (1H, d), 8.54 (dd, 1HO, 9.01 (1H, dd) | 449 |
| 90 | I | I | A | 7-Fluoro-6-[6-(1-methyl-1H-pyrazol-4-yl)-[1,2,4]triazolo[4,3-b]pyridazin-3-ylmethyl]-quinoline | (DMSO-d6) 3.93 (3H, d), 4.76 (2H, s), 7.52 (1H, dd), 7.70 (1H, d), 7.81 (1H, d), 8.10 (1H, d), 8.14 (1H, s), 8.36 (1H, d), 8.39 (1H, d), 8.51 (1H, s), 8.90 (1H, dd) | 360 |
| 91 | III | NA | A | 8-Methyl-6-[6-(1-methyl-1H-pyrazol-4-yl)-[1,2,4]triazolo[4,3-b]pyridazin-3-ylmethyl]-quinoline | (DMSO-d6) 2.69 (3H, s), 3.94 (3H, s), 4.69 (2H, s), 7.51 (1H, dd), 7.68 (1H, d), 7.69 (1H, s), 7.82 (1H, s), 8.18 (1H, s), 8.31 (1H, dd), 8.34 (1H, d), 8.55 (1H, s), 8.88 (1H, dd) | 356 |
| 92 | III | NA | A | 8-Fluoro-6-[6-(1-methyl-1H-pyrazol-4-yl)-[1,2,4]triazolo[4,3-b]pyridazin-3-ylmethyl]-quinoline | (DMSO-d6) 3.94 (3H, s), 4.74 (2H, s), 7.62 (1H, dd), 7.70 (1H, d), 7.70 (1H, d), 7.83 (1H, s), 8.18 (1H, s), 8.35 (1H, d), 8.42 (1H, dt), 8.55 (1H, s), 8.92 (1H, dd) | 360 |
| 93 | III | NA | A | 3-Benzothiazol-6-ylmethyl-6-(3-fluoro-phenyl)-[1,2,4]triazolo[4,3-b]pyridazine | (DMSO-d6) 4.78 (2H, s), 7.45 (1H, td), 7.58 (1H, dd), 7.64 (1H, dd), 7.94-8.04 (3H, m), 8.20 (1H, s), 8.46 (1H, d), 9.34 (1H, s) | 362 |

TABLE 1-continued

| Eg. | c-MET IC$_{50}$ | GTL16 EC$_{50}$ | Method | Structure | $^1$H NMR (500 MHz) | MS (m/z) |
|---|---|---|---|---|---|---|
| 94 | II | II | A | 4-(3-Benzothiazol-6-ylmethyl-[1,2,4]triazolo[4,3-b]pyridazin-6-yl)-N-ethyl-2-fluoro-benzamide | (DMSO-d6) 1.07 (3H, t), 3.23 (2H, q), 4.73 (2H, s), 7.52 (1H, dd), 7.71 (1H, dd), 7.94-7.98 (m, 3H), 8.14 (s, 1H), 8.42 (1H, d), 8.42 (1H, d), 9.28 (1H, s) | 433 |
| 95 | I | II | A | 4-(3-Benzothiazol-6-ylmethyl-[1,2,4]triazolo[4,3-b]pyridazin-6-yl)-2-fluoro-N-isopropyl-benzamide | (DMSO-d6) 1.11 (d, 6H), 4.01 (1H, septet), 4.73 (s, 2H), 7.52 (1H, dd), 7.66 (1H, dd), 7.94-7.98 (m, 3H), 8.13 (s, 1H), 8.27 (d, 1H), 8.41 (d, 1H), 9.28 (s, 1H) | 447 |
| 96 | I | I | A | 3-Benzothiazol-6-ylmethyl-6-(1-methyl-1H-pyrazol-4-yl)-[1,2,4]triazolo[4,3-b]pyridazine | (DMSO-d6) 3.93 (3H, s), 4.68 (2H, s), 7.59 (1H, d), 7.67 (1H, d), 8.02 (1H, d), 8.18 (1H, s), 8.21 (1H, s), 8.32 (1H, d), 8.55 (1H, s), 9.34 (1H, s) | 348 |
| 97 | II | NA | A | 3-Benzothiazol-6-ylmethyl)-6-(3,5-difluoro-phenyl)-[1,2,4]triazolo[4,3-b]pyridazine | (DMSO-d6) 4.80 (2H, s), 7.52 (1H, t), 7.58 (1H, d), 7.88 (2H, d), 8.02 (2H, m), 8.21 (1H, s), 8.49 (1H, d), 9.35 (1H, s) | 380 |
| 98 | II | II | A | 3-(3-Benzothiazol-6-ylmethyl-[1,2,4]triazolo[4,3-b]pyridazin-6-yl)-benzonitrile | (DMSO-d6) 4.80 (2H, s), 7.59 (1H, d), 7.81 (1H, t), 8.04 (3H, m), 8.21 (1H, s), 8.46 (1H, d), 8.50 (1H, d), 8.60 (1H, s), 9.35 (1H, s) | 370 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 99 | I | I | B | (S)-3-[3-(1-Quinolin-6-yl-ethyl)-[1,2,4]triazolo[4,3-b]pyridazin-6-yl]-benzonitrile | (DMSO-d6) 1.96 (3H, d), 5.19 (1H, q), 7.50 (1H, dd), 7.77 (1H, t), 7.83 (1H, dd), 8.10-7.95 (4H, m), 8.37-8.34 (2H, m), 8.48 (1H, d), 8.49 (1H, d), 8.84 (1H, dd) | 377 |
| 100 | II | NA | B | (R)-3-[3-(1-Quinolin-6-yl-ethyl)-[1,2,4]triazolo[4,3-b]pyridazin-6-yl]-benzonitrile | (DMSO-d6) 1.96 (3H, d), 5.19 (1H, q), 7.50 (1H, dd), 7.77 (1H, t), 7.83 (1H, dd), 8.10-7.95 (4H, m), 8.37-8.34 (2H, m), 8.48 (1H, d), 8.49 (1H, d), 8.84 (1H, dd) | 377 |
| 101 | I | II | A | 4-(3-Benzothiazol-6-ylmethyl-[1,2,4]triazolo[4,3-b]pyridazin-6-yl)-2-fluoro-N-methyl-benzamide | DMSO-d$_6$ – 2.79-2.80 (3H, d), 4.78 (2H, s), 7.57-7.59 (1H, dd), 7.77-7.80 (1H, t), 8.00-8.04 (4H,m), 8.20 (1H, s), 8.40(1H, bm), 8.47-8.49 (1H, d), 9.33 (1H, s) | 419 |
| 102 | I | II | A | 3-Benzothiazol-6-ylmethyl-6-(3-methanesulfonyl-phenyl)-[1,2,4]triazolo[4,3-b]pyridazine | DMSO-d$_6$ – 3.29 (3H, s), 4.78 (2H, s), 7.61-7.63 (1H, dd), 7.84-7.89 (1H, s), 8.03-8.05 (2H, m), 8.07-8.13 (1H, m), 8.18-8.19 (1H, d), 8.44-8.47 (1H, m), 8.50-8.54 (1H, d), 8.60-8.61 (1H, m), 9.33 (1H, s) | 422 |
| 103 | I | I | F | (S)-3-[3-(1-Benzothiazol-6-yl-ethyl)-[1,2,4]triazolo[4,3-b]pyridazin-6-yl]-benzonitrile | (DMSO-d6) 1.90 (3H, d), 5.11 (1H, q), 7.58 (1H, dd), 7.74 (1H, t), 7.98-8.038 (3H, m), 8.24 (1H, d), 8.33 (1H, d), 8.46-8.48 (2H, m), 9.32 (1 H, s) | 383 |
| 104 | II | NA | F | (R)-3-[3-(1-Benzothiazol-6-yl-ethyl)-[1,2,4]triazolo[4,3-b]pyridazin-6-yl]-benzonitrile | (DMSO-d6) 1.96 (3H, d), 5.17 (1H, q), 7.63 (1H, dd), 7.81 (1H, t), 8.03-8.09 (3H, m), 8.29 (1H, d), 8.39 (1H, d), 8.41-8.54 (2H, m), 937 (1H, s) | 383 |

| Eg. | c-MET IC$_{50}$ | GTL 16 EC$_{50}$ | Method | Structure | $^1$H NMR (500 MHz) | MS (m/z) |
|---|---|---|---|---|---|---|
| 105 | II | NA | E | 6-(6-Methyl-[1,2,4]triazolo[4,3-b]pyridazin-3-ylmethyl)quinoline | (DMSO-d6) 2.53 (3H, s), 4.69 (2H, s), 7.24 (1H, d), 7.49 (1H, dd), 7.74 (1H, dd), 7.86 (1H, s), 7.96 (1H, d), 8.23 (1H, d), 8.30 (1H, d) 8.85 (1H, dd) | 276 |
| 106 | II | NA | E | 3-Bromo-6-(6-methyl-[1,2,4]triazolo[4,3-b]pyridazin-3-ylmethyl)-quinoline | (DMSO-d6) 2.53 (3H, s), 4.70 (2H; s), 7.25 (1H, d), 7.79 (1H, dd), 7.85 (1H, s), 7.98 (1H, d), 8.24 (1H, d), 8.69 (1H, d), 8.90 (1H, d) | 355 |
| 107 | II | II | C | 6-(6-Vinyl-[1,2,4]triazolo[4,3-b]pyridazin-3-ylmethyl)-quinoline | (DMSO-d6) 4.71 (2H, s), 5.87 (1H, d), 6.44 (1H, d), 6.84 (1H, dd), 7.50 (1H, dd), 7.74-7.77 (2H, m), 7.89 (1H, s), 7.96 (1H, d), 8.31 (1H, dd), 8.33 (1H, d), 8.85 (1H, dd) | 288 |
| 108 | I | I | G | 6-(1-Methyl-1H-pyrazol-4-yl)-3-(1H-pyrrolo[2,3-b]pyridin-3-ylmethyl)-[1,2,4]triazolo[4,3-b]pyridazine | (DMSO-d6) 3.87 (3H, s), 4.53 (2H, s), 6.95 (1H, q), 7.45 (1H, d), 7.58 (1H, d), 7.96 (1H, d), 8.10 (1H, dd), 8.11 (1H, s), 8.22 (1H, d), 8.49 (1H, s), 11.43 (1H, s) | 331 |
| 109 | II | II | AA | 6-(6-Cyclopropyl-[1,2,4]triazolo[4,3-b]pyridazin-3-ylmethyl)-quinoline | (DMSO-d6) .925 (2H, m), 1.01 (2H, m), 2.12 (1H, m), 4.60 (2H, s), 7.13 (1H, d), 7.43-7.45 (1H, q), 7.65 (1H, dd), 7.81 (1H, s), 7.89 (1H, d), 8.13 (1H, d), 8.21 (1H, d) 8.78 (1H, dd) | 302 |
| 110 | III | NA | S | 6-(6-Methyl-[1,2,4]triazolo[4,3-b]pyridazin-3-ylmethyl)-quinoline-3-carbonitrile | (DMSO-d6) 2.55 (3H, s), 4.71 (2H, s), 5.01 (2H, s), 7.28 (1H, d), 7.68 (1H, d), 7.78 (1H, s), 7.95 (1H, d), 8.14 (1H, s), 8.27 (1H, d), 8.41 (sH, s), 8.46 (1H, s), 9.16 (1H, d) | 301 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 111 | II | II | M | 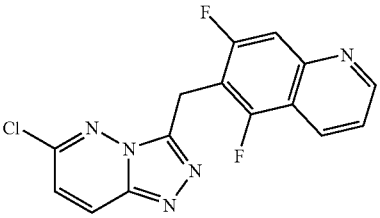<br>6-(6-Chloro-[1,2,4]triazolo[4,3-b]pyridazin-3-ylmethyl)-5,7-difluoro-quinoline | (DMSO-d6) 4.70 (2H, s), 7.53 (1H, d), 7.66 (1H, m), 7.78 (1H, d), 8.47 (1H, d), 8.53 (1H, m), 9.02 (1H, m) | 332 |
| 112 | II | II | Q | 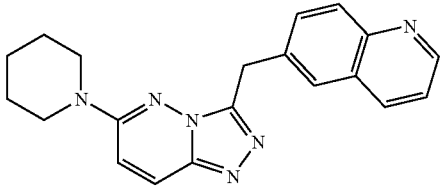<br>6-(6-Piperidin-1-yl-[1,2,4]triazolo[4,3-b]pyridazin-3-ylmethyl)-quinoline | (DMSO-d6) 1.50-1.61 (6H, m), 4.57 (2H, s), 7.32 (1H, d), 7.50 (1H, dd), 7.74 (1H, dd), 7.91 (1H, d), 7.95 (1H, d), 7.99 (1H, d), 8.30 (1H, d) 8.85 (1H, dd) | 345 |
| 113 | II | II | Q | 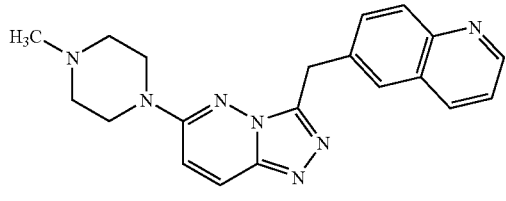<br>6-[6-(4-Methyl-piperazin-1-yl)-[1,2,4]triazolo[4,3-b]pyridazin-3-ylmethyl]-quinoline | (DMSO-d6) 2.18 (3H, s), 2.37 (4H, t), 3.51 (4H, t), 4.58 (2H, s), 7.33 (1H, d), 7.51 (1H, dd), 7.74 (1H, dd), 7.93 (1H, d), 7.95 (1H, d), 8.03 (1H, d), 8.31 (1H, d), 8.85 (1H, dd) | 360 |
| 114 | NA | NA | Y | 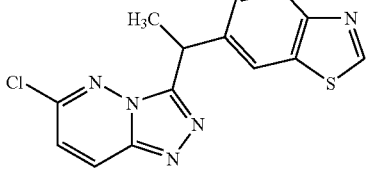<br>3-(1-Benzothiazol-6-yl-ethyl)-6-chloro-[1,2,4]triazolo[4,3-b]pyridazine | NA | 316 |
| 115 | II | NA | O | 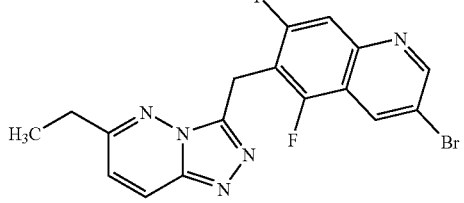<br>3-Bromo-6-(6-ethyl-[1,2,4]triazolo[4,3-b]pyridazin-3-ylmethyl)-5,7-difluoro-quinoline | (DMSO-d6) 1.23 (3H, t), 2.86 (2H, q), 4.72 (2H, s), 7.31 (1H, d), 7.80 (1H, d), 8.25 (1H, d), 8.79 (1H, d), 9.07 (1H, d) | 404 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 116 | I | NA | LL | 3-Ethyl-6-(6-methyl-[1,2,4]triazolo[4,3-b]pyridazin-3-ylmethyl)-quinoline | (DMSO-d6) 1.33 (3H, t), 2.60 (3H, s), 2.85 (2H, q), 4.75 (2H, s), 7.32 (1H, d), 7.74 (1H, dd), 7.84 (1H, d), 7.99 (1H, d), 8.14 (1H, d), 8.31 (1H, d), 8.82 (1H, d) | 304 |
| 117 | I | I | JJ | 3-Bromo-6-[1,2,4]triazolo[4,3-b][1,2,4]triazin-3-ylmethyl-quinoline | (DMSO-d6) 4.77 (2H, s), 7.79-7.85 (2H, m), 8.01 (1H, d), 8.67 (1H, s), 8.73-8.76 (2H, m), 8.92 (1H, d) | 341 |
| 118 | NA | NA | KK | 6-(6-Methyl-[1,2,4]triazolo[4,3-b]pyridazin-3-ylmethyl)-3-vinyl-quinoline | (DMSO-d6) 2.53 (3H, t), 4.68 (2H, s), 5.46 (1H, d), 6.13 (1H, d), 6.89 (1H, dd), 7.25 (1H, d), 7.70 (1H, dd), 7.80 (1H, s), 7.93 (1H, d), 8.24 (1H, d), 8.32 (1H, d), 9.03 (1H, d) | 302 |
| 119 | I | NA | MM | 3-Bromo-6-[1-(6-methyl-[1,2,4]triazolo[4,3-b]pyridazin-3-yl)-ethyl]-quinoline | (DMSO-d6) 1.87 (3H, d), 2.47 (3H, s), 5.01 (1H, q), 7.22 (1H, d), 7.83 (1H, dd), 7.86 (1H, d), 7.98 (1H, d), 8.22 (1H, d), 8.70 (1H, d), 8.89 (1H, d) | 369 |
| 120 | NA | NA | O | 3-Bromo-6-(6-ethyl-[1,2,4]triazolo[4,3-b]pyridazin-3-ylmethyl)-quinoline | NA | 369 |
| 121 | II | NA | O | 3-Bromo-6-(6-ethyl-[1,2,4]triazolo[4,3-b]pyridazin-3-ylmethyl)-5-fluoro-quinoline | (DMSO-d6) 1.24 (3H, t), 2.86 (2H, q), 4.73 (2H, s), 7.31 (1H, d), 7.80-7.88 (2H, m), 8.25 (1H, d), 8.76 (1H, d), 8.76 (1H, d), 9.02 (1H, d) | 387 |

TABLE 1-continued

| Eg. | c-MET IC$_{50}$ | GTL 16 EC$_{50}$ | Method | Structure | $^1$H NMR (500 MHz) | MS (m/z) |
|---|---|---|---|---|---|---|
| 122 | III | N/A | LL | 6-[1-(6-Methyl-[1,2,4]triazolo[4,3-b]pyridazin-3-yl)-ethyl]-quinoline | (DMSO-d6) 3.32 (3H, s), 4.79 (2H, d), 4.90 (1H, s), 7.27 (1H, d), 7.78 (1H, dd), 7.09 (1H, d), 7.97 (1H, d), 8.08 (1H, d), 8.24 (1H, s), 8.81 (1H, d) | 306 | wherein:
I c-MET IC$_{50}$ ≦ 100 nM;
II 100 nM < c-MET IC$_{50}$ ≦ 1 µM;
III 1 µM ≦ c-MET IC$_{50}$ ≦ 10 µM; and
IV 10 µM < c-MET IC$_{50}$ ≦ 50 µM.

The structure, name, physical and biological data and methods are further described in tabular form below in Table 2.

TABLE 2

| Eg. | MET IC$_{50}$ | GTL 16 EC$_{50}$ | Method | Structure | $^1$H NMR (500 MHz) | MS (m/z) |
|---|---|---|---|---|---|---|
| 123 | I | II | P | 3-(1-Methyl-1H-pyrazol-4-yl)-6-(6-trifluoromethyl-[1,2,4]triazolo[4,3-b]pyridazin-3-ylmethyl)-quinoline | (DMSO-d6) 3.83 (s, 3H), 4.70 (s, 2H), 7.61 (dd, 1H), 7.72 (d, 1H) 7.74 (d, 1H) 7.86 (d, 1H) 8.01 (s, 1H) 8.31 (s, 1H) 8.33 (d, 1H) 8.62 (d, 1H) 9.07 (s, 1H). | 410 |
| 124 | I | I | L | 3-(1-Methyl-1H-pyrazol-4-yl)-6-(6-methyl-[1,2,4]triazolo[4,3-b]pyridazin-3-ylmethyl)-quinoline | (DMSO-d6) 2.55 (3H, s), 3.91 (3H, s) 4.70 (2H, s), 7.27 (1H, d), 7.67 (1H, dd), 7.51 (1H, s), 7.94 (1H, d), 8.09 (1H, s), 8.27 (1H, d), 8.39 (1H, s), 8.43 (1H, d), 9.14 (1H, d) | 356 |
| 125 | I | II | W | 6-(6-Methyl-[1,2,4]triazolo[4,3-b]pyridazin-3-ylmethyl)-3-(1H-pyrazol-4-yl)-quinoline | (DMSO-d6) 2.56 (3H, s), 4.74 (2H, s), 7.30 (1H, d), 7.80 (1H, dd), 7.74 (1H, s), 8.02 (1H, d), 8.28 (1H, d), 8.36 (2H, s), 8.71 (1H, s), 9.32 (2H, s) | 342 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 126 | I | I | L | 6-(6-Methyl-[1,2,4]triazolo[4,3-b]pyridazin-3-ylmethyl)-3-(1-piperidin-4-yl-1H-pyrazol-4-yl)-quinoline | (DMSO-d6) 2.11-2.19 (2H, m), 2.26-2.28 (2H, m), 2.54 (3H, s), 3.09-3.17 (2H, m), 3.42-3.46 (2H, m), 4.53-4.58 (1H, m), 4.73 (2H, s), 7.29 (1H, d), 7.76 (1H, dd), 8.00 (1H, d), 8.21 (1H, s), 8.27 (1H, d), 8.54 (1H, s), 8.54 (1H, br s), 8.62 (1H, s), 8.78 (1H, br s), 9.27 (1H, s) | 425 |
| 127 | II |  | V | 6-(6-Methyl-[1,2,4]triazolo[4,3-b]pyridazin-3-ylmethyl)-3-pyrazol-1-yl)-quinoline | (DMSO-d6) 2.55 (3H, s), 4.73 (2H, s), 6.65 (1H, d), 7.27 (1H, d), 7.75 (1H, dd), 7.75 (1H, dd), 7.88 (1H, d), 7.90 (1H, s), 8.02 (1H, d), 8.26 (1H, d), 8.70 (1H, dd), 9.45 (1H, d) | 342 |
| 128 | II | III | L | 3-(3,5-Difluoro-phenyl)-6-(6-methyl-[1,2,4]triazolo[4,3-b]pyridazin-3-ylmethyl)-quinoline | (DMSO-d6) 2.55 (3H, s), 4.74 (2H, s), 7.28 (1H, d), 7.34 (1H, td), 7.72 (1H, dd), 7.80 (1H, dd), 7.88 (1H, s), 8.03 (1H, d), 8.27 (1H, d), 8.72 (1H, d), 9.27 (1H, d) | 388 |
| 129 | II | III | L | 6-(6-Methyl-[1,2,4]triazolo[4,3-b]pyridazin-3-ylmethyl)-3-pyrimidin-5-yl-quinoline | (DMSO-d6) 2.55 (3H, s), 4.74 (2H, s), 7.28 (1H, d), 7.83 (1H, dd), 7.90 (1H, s), 8.05 (1H, d), 8.27 (1H, d), 8.81 (1H, d), 9.27 (1H, s), 9.32 (1H, d), 9.35 (1H, s) | 354 |
| 130 | I | I | L | 3-[6-(6-Methyl-[1,2,4]triazolo[4,3-b]pyridazin-3-ylmethyl)-quinolin-3-yl]-benzonitrile | (DMSO-d6) 2.55 (3H, s), 4.74 (2H, s), 7.27 (1H, d), 7.75 (1H, t), 7.81 (1H, dd), 7.89 (1H, s), 7.92 (1H, dd), 8.04 (1H, d), 8.24 (1H, s), 8.27 (1H, d), 8.41 (1H, s), 8.73 (1H, d), 9.27 (1H, d) | 377 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 131 | I | I | L | 6-(6-Methyl-[1,2,4]triazolo[4,3-b]pyridazin-3-ylmethyl)-3-pyridin-5-yl-quinoline | (DMSO-d6) 2.55 (3H, s), 4.74 (2H, s), 7.28 (1H, d), 7.57 (1H, dd), 7.80 (1H, dd), 7.91 (1H, s), 8.03 (1H, d), 8.27 (1H, d), 8.31 (1H, dt), 8.65 (1H, dd), 8.71 (1H, d), 9.10 (1H, d), 9.26 (1H, d) | 352 |
| 132 | II | II | V | 3-Imidzaol-1-yl-6-(6-methyl-[1,2,4]triazolo[4,3-b]pyridazin-3-ylmethyl)-quinoline | (DMSO-d6) 2.55 (3H, s), 4.74 (2H, s), 7.19 (1H, s), 7.27 (1H, dd), 7.79 (1H, dd), 7.84 (1H, s), 7.96 (1H, s), 8.04 (1H, d), 8.27 (1H, dd), 8.47 (1H, s), 8.61 (1H, d), 9.26 (1H, d) | 341 |
| 133 | I | I | L | 6-(6-Methyl-[1,2,4]triazolo[4,3-b]pyridazin-3-ylmethyl)-3-[1-(2-morpholin-4-yl-ethyl)-1H-pyrazol-4-yl]-quinoline | (DMSO-d6) 2.44 (4H, br t), 2.55 (3H, s), 2.76 (2H, t), 3.56 (2H, t), 4.29 (4H,t), 4.71 (2H, s), 7.28 (1H, d), 7.68 (1H, dd), 7.76 (1H, s), 7.94 (1H, d), 8.11 (1H, s), 8.27 (1H, d), 8.43 (1H, d), 8.45 (1H, s), 9.15 (1H, d) | 455 |
| 134 | I | II | R | {4-[6-(6-Methyl-[1,2,4]triazolo[4,3-b]pyridazin-3-ylmethyl)-quinolin-3-yl]-pyrazol-1-yl}-acetic acid | (DMSO-d6) 2.55 (3H, s), 4.71 (2H, s), 5.01 (2H, s), 7.28 (1H, d), 7.68 (1H, d), 7.78 (1H, s), 7.95 (1H, d), 8.14 (1H, s), 8.27 (1H, d), 8.41 (2H,s), 8.46 (1H, s), 9.16 (1H, d) | 400 |
| 135 | II | III | L | 3-[6-(6-Methyl-[1,2,4]triazolo[4,3-b]pyridazin-3-ylmethyl)-quinolin-3-yl]-benzoic acid | (DMSO-d6) 2.55 (3H, s), 4.73 (2H, s), 7.27 (1H, d), 7.80 (1H, dd), 7.93 (1H, d), 8.01-8.09 (5H, m), 8.27 (1H, d), 8.71 (1H, d), 9.26 (1H, d) | 396 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 136 | II | III | L | 4-[6-(6-Methyl-[1,2,4]triazolo[4,3-b]pyridazin-3-ylmethyl)-quinolin-3-yl]-benzoic acid | (DMSO-d6) 2.55 (3H, s), 4.73 (2H, s), 7.27 (1H, d), 7.80 (1H, dd), 7.93 (1H, d), 8.01-8.08 (5H, m), 8.27 (1H, d), 8.71 (1H, d), 9.26 (1H, d) | 396 |
| 137 | I | II | L | 3-(1H-Indol-2-yl)-6-(6-methyl-[1,2,4]triazolo[4,3-b]pyridazin-3-ylmethyl)-quinoline trifluoroacetic acid | (DMSO-d6) 2.56 (3H, s), 4.76 (2H, s), 7.05 (1H, t), 7.17 (1H, t), 7.25 (1H, s), 7.30 (1H, d), 7.46 (1H, d), 7.60 (1H, d), 7.82 (1H, dd), 7.91 (1H, s), 8.04 (1H, d), 8.28 (1H, d), 8.83 (1H, s), 9.50 (1H, s), 11.86 (1H, s) | 391 |
| 138 | I | III | L | 6-(6-Methyl-[1,2,4]triazolo[4,3-b]pyridazin-3-ylmethyl)-3-(1H-pyrrol-2-yl)-quinoline | (DMSO-d6) 2.48 (3H, s), 4.62 (2H, s), 6.13 (1H, dd), 6.74 (1H, dd), 7.20 (1H, d), 7.56 (1H, dd), 7.66 (1H, s), 7.83 (1H, d), 8.19 (1H, d), 8.30 (1H, d), 9.14 (1H, d), 11.50 (1H, s) | 341 |
| 139 | I | I | L | 3-(1-Methyl-1H-pyrazol-4-yl)-6-[1,2,4]triazolo[4,3-b]pyridazin-3-ylmethyl-quinoline | (DMSO-d6) 3.84 (3H, s), 4.68 (2H, s), 7.28 (1H, dd), 7.59 (1H, dd), 7.68 (1H, s), 7.86 (1H, d), 8.02 (1H, s), 8.30 (1H, d), 8.31 (1H, s), 8.35 (1H, d), 8.57 (1H, dd), 9.07 (1H, d) | 342 |
| 140 | I | I | I | 6-(6-Methoxy-[1,2,4]triazolo[4,3-b]pyridazin-3-ylmethyl)-3-(1-methyl-1H-pyrazol-4-yl)-quinoline | (DMSO-d6) 3.83 (3H, s), 3.90 (3H, s) 4.57 (2H, s), 6.95 (1H, d), 7.62 (1H, dd), 7.67 (1H, s), 7.85 (1H, d), 8.02 (1H, s), 8.16 (1H, d), 8.31 (1H, s), 8.35 (1H, d), 9.06 (1H, d) | 372 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 141 | I | I | A | 3-(1-Methyl-1H-pyrazol-4-yl)-6-[6-(1-methyl-1H-pyrazol-4-yl)-[1,2,4]triazolo[4,3-b]pyridazin-3-ylmethyl]-quinoline | (DMSO-d6) 3.83 (3H, s), 3.86 (3H, s) 4.66 (2H, s), 6.61 (1H, d), 7.66 (1H, dd), 7.79 (1H, s), 7.86 (1H, d), 8.01 (1H, s), 8.10 (1H, s), 8.29 (1H,s), 8.30 (1H, d), 8.37 (1H, d), 8.46 (1H, s) 9.06 (1H, d) | 422 |
| 142 | II | II | U | 3-(3H-Imidazol-4-yl)-6-(6-methyl-[1,2,4]triazolo[4,3-b]pyridazin-3-ylmethyl)-quinoline | (DMSO-d6) 2.57 (3H, s), 4.77 (2H, s), 7.32 (1H, d), 7.86 (1H, dd), 7.93 (1H, s), 8.08 (1H, d), 8.29 (1H, d), 8.44 (1H, d), 8.97 (1H, s), 9.35 (1H, s), 9.43 (1H, d) | 342 |
| 143 | I | I | R | 1-{4-[6-(6-Methyl-[1,2,4]triazolo[4,3-b]pyridazin-3-ylmethyl)\-quinolin-3-yl]-pyrazol-1-yl}-butan-2-one | (DMSO-d6) 0.98 (3H, t), 2.55 (3H, s), 4.71 (2H, s), 5.20 (2H, s), 7.27 (1H, d), 7.68 (1H, dd), 7.78 (1H, s), 7.95 (1H, d), 8.15 (1H, s), 8.27 (1H, d), 8.34 (1H, s), 8.46 (1H, d), 9.15 (1H, d) | 412 |
| 144 | I | II | R | 2-{4-[6-(6-Methyl-[1,2,4]triazolo[4,3-b]pyridazin-3-ylmethyl)-quinolin-3-yl]-pyrazol-1-yl}-ethanol | (DMSO-d6) 2.55 (3H, s), 3.79 (2H, q), 4.19 (2H, t), 4.70 (2H, s), 4.98 (1H, t), 7.27 (1H, d), 7.66 (1H, dd), 7.75 (1H, s), 7.93 (1H, d), 8.12 (1H, s),8.26 (1H, d), 8.41 (1H,s), 8.44 (1H, d), 9.16 (1H, d) | 386 |
| 145 | I | I | O | 5,7-Difluoro-3-(1-methyl-1H-pyrazol-4-yl)-6-(6-methyl-[1,2,4]triazolo[4,3-b]pyridazin-3-ylmethyl)-quinoline | (DMSO-d6) 2.47 (3H, s), 3.84 (3H, s) 4.61 (2H, s), 7.21 (1H, d). 7.64 (1H, d), 8.13 (1H, s), 8.17 (1H, d), 8.43 (1H, s), 8.49 (1H, d), 9.22 (1H, d). | 392 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 146 | I | I | L | 5,7-Difluoro-6-(6-methyl-[1,2,4]triazolo[4,3-b]pyridazin-3-ylmethyl)-3-[1-(2-morpholin-4-yl-ethyl)-1H-pyrazol-4-yl]-quinoline | (DMSO-d6) 2.43 (4H, bm), 2.53 (3H, s) 2.75 (2H, m), 3.54 (4H, bm), 4.28 (2H, t), 4.68 (2H, s), 7.28 (1H, d), 7.71 (1H, d), 8.15 (1H, s), 8.21 (1H, s), 8.24 (1H, d), 8.56 (1H, d), 9.30 (1H, d). | 491 |
| 147 | I | I | R | 3-[1-(2-Methoxy-ethyl)-1H-pyrazol-4-yl]-6-(6-methyl-[1,2,4]triazolo[4,3-b]pyridazin-3-ylmethyl)-quinoline | (DMSO-d6) 2.55 (3H, s), 3.25 (3H, s), 3.74 (2H, t), 4.31 (2H, t), 4.70 (2H, s), 7.27 (1H, d), 7.67 (1H, dd), 7.75 (1H, d), 8.12 (1H, s), 8.41 (1H, s), 8.44 (1H, d), 9.15 (1H, d) | 400 |
| 148 | I | I | R | 3-{4-[6-(6-Methyl)-[1,2,4]triazolo[4,3-b]pyridazin-3-ylmethyl)-quinolin-3-yl]pyrazol-1-yl}-propionitrile | (DMSO-d6) 2.82 (3H, s), 3.41 (2H, t), 4.73 (2H, t), 4.98 (2H, s), 7.55 (1H, d), 7.96 (1H, dd), 8.04 (1H, s), 8.22 (1H, d), 8.48 (1H, s), 8.53 (1H, d), 8.74 (1H, d), 8.78 (1H, s), 9.43 (1H, d) | 395 |
| 149 | I | III | Z | 2-{4-[6-(6-Methyl)-[1,2,4]triazolo[4,3-b]pyridazin-3-ylmethyl)-quinolin-3-yl]pyrazol-1-yl}-acetamide | (DMSO-d6) 2.60 (3H, s), 4.70 (2H, s), 4.80 (2H, s), 7.27 (1H, d), 7.33 (1H, brs), 7.59 (1H, br s), 7.67 (1H, dd), 7.77 (1H, s), 7.94 (1H, d), 8.12 (1H, s), 8.26 (1H, d), 8.39 (1H, s), 8.46 (1H, d), 9.16 (1H, d) | 399 |
| 150 | II |  | L | 3-(3-Methyl)-1H-pyrazol-4-yl)-6-(6-methyl-[1,2,4]triazolo[4,3-b]pyridazin-3-ylmethyl)-quinoline | (DMSO-d6) 2.54 (3H, s), 4.70 (2H, s), 7.26 (1H, d), 7.67 (1H, d), 7.85 (1H, s), 7.94 (1H, d), 8.26 (1H, d), 8.30 (1H, d), 9.03 (1H, d) | 356 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 151 | I | III | R | {4-[5,7-Difluoro-6-(6-methyl-[1,2,4]triazolo[4,3-b]pyridazin-3-ylmethyl)-quinolin-3-yl]-pyrazol-1-yl}-acetic acid | (DMSO-d6) 2.50 (3H, s), 4.62 (2H, s), 4.90 (2H, s), 7.22 (1H, d), 6.66 (1H, d), 8.17 (1H, d), 8.45 (1H, s), 8.52 (1H, d), 9.24 (1H, s) | 436 |
| 152 | NA | NA | N | 6-(6-Chloro-[1,2,4]triazolo[4,3-b]pyridazin-3-ylmethyl)-3-(1-methyl-1H-pyrazol-4-yl)-quinoline | (DMSO-d6) 3.91 (3H, s), 4.73 (2H, s), 7.56 (1H, d), 7.73 (1H, dd), 7.82 (1H, s), 7.98 (1H, d), 8.11 (1H, s), 8.41 (1H, s), 8.48 (1H, d), 8.53 (1H, s), 9.22 (1H, d) | 376 |
| 153 | I | II | HH | 3-(1-Azetidin-3-yl-1H-pyrazol-4-yl)-6-(6-methyl-[1,2,4]triazolo[4,3-b]pyridazin-3-ylmethyl)-quinoline | (DMSO-d6) 2.62 (3H, s), 4.44-4.52 (4H, m), 4.79 (2H, s), 5.52 (1H, quintet), 7.35 (1H, d), 7.80 (1H, dd), 7.87 (1H, d), 8.04 (1H, d), 8.34 (1H, d), 8.44 (1H, s), 8.61 (1H, d), 8.65 (1H, s), 8.97 (1H, br s), 9.18 (1H, br s), 9.27 (1H, d) | 397 |
| 154 | I | II | R | 3-{4-[6-(6-Methyl-[1,2,4]triazolo[4,3-b]pyridazin-3-ylmethyl)-quinolin-3-yl]pyrazol-1-yl}-propionamide | (DMSO-d6) 2.60 (3H, s), 2.73 (2H, t), 4.40 (2H, t), 4.75 (2H, s), 6.97 (1H, br s), 7.32 (1H, d), 7.48 (1H, br s), 7.72 (1H, dd), 7.80 (1H, s) 7.98 (1H, d), 8.16 (1H, s), 8.31 (1H, d), 8.42 (1H, s), 8.47 (1H, d), 9.18 (1H, d) | 413 |
| 155 | I | II | HH | 3-(1-Azetidin-3-ylmethyl-1H-pyrazol-4-yl)-6-(6-methyl-[1,2,4]triazolo[4,3-b]pyridazin-3-ylmethyl)-quinoline | (DMSO-d6) 2.55 (3H, s), 3.30 (1H, m), 3.91 (2H, m), 4.04 (2H, m), 4.45 (2H, d), 4.77 (2H, s), 7.31 (1H, d), 7.88 (1H, dd), 7.93 (1H, s), 8.28 (1H, d), 8.51 (1H, s), 8.66 (1H, br s), 8.80 (1H, s), 8.87 (1H, s), 9.37 (1H, d) | 411 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 156 | NA | NA | C | 3-(1-Methyl-1H-pyrazol-4-yl)-6-(6-vinyl-[1,2,4]triazolo[4,3-b]pyridazin-3-ylmethyl)-quinoline | (DMSO-d6) 3.90 (3H, s), 4.72 (2H, s), 5.87 (1H, d), 6.44 (1H, d), 6.69 (1H, dd), 7.76 (1H, d), 7.78 (1H, s), 7.93 (1H, d), 8.08 (1H, s), 8.35 (1H, d), 8.37 (1H, s), 8.41 (1H, d), 9.13 (1H, d) | 368 |
| 157 | I | I | T | 6-(6-Ethyl-[1,2,4]triazolo[4,3-b]pyridazin-3-ylmethyl)-3-(1-methyl-1H-pyrazol-4-yl)-quinoline | (DMSO-d6) 1.26 (3H, t), 2.86 (2H, q), 3.90 (3H, s), 4.70 (2H, s), 7.30 (1H, d), 7.68 (1H, dd), 7.79 (1H, d), 7.92 (1H, d), 8.08 (1H, s), 8.26 (1H, d), 8.38 (1H, s), 8.41 (1H, d), 9.13 (1H, d) | 370 |
| 158 | I | I | O | 7-Fluoro-3-(1-methyl-1H-pyrazol-4-yl)-6-(6-methyl-[1,2,4]triazolo[4,3-b]pyridazin-3-ylmethyl)-quinoline | (DMSO-d6) 2.55 (3H, s), 3.90 (3H, s), 4.70 (2H, s), 7.29 (1H, d), 7.77 (1H, d), 7.82 (1H, d), 8.07 (1H, s), 8.27 (1H, d), 8.37 (1H, s), 8.46 (1H, d), 9.18 (1H, d) | 374 |
| 159 | I | I | Q | Dimethyl-{3-[3-(1-methyl-1H-pyrazol-4-yl)-quinolin-6-ylmethyl]-[1,2,4]triazolo[4,3-b]pyridazin-6-yl}-amine | (DMSO-d6) 3.00 (s, 6H), 3.83 (s, 3H), 4.49 (s, 2H) 7.13 (d, 1H), 7.59 (dd, 1H) 7.73 (d, 1H) 7.83 (d, 1H) 7.93 (d, 1H) 8.02 (s, 1H) 8.31 (s, 1H) 8.34 (d, 1H) 9.05 (d, 1H). | 385 |
| 160 | I | I | Q | Methyl-{3-[3-(1-methyl-1H-pyrazol-4-yl)-quinolin-6-ylmethyl]-[1,2,4]triazolo[4,3-b]pyridazin-6-yl}-amine | (DMSO-d6) 2.73 (s, 3H), 3.83 (s, 3H), 4.47 (s, 2H) 6.66 (d, 1H), 7.33 (q, 1H) 7.61 (dd, 1H) 7.73 (d, 1H) 7.79 (d, 1H) 7.84 (d, 1H) 8.02 (s, 1H) 8.31 (s, 1H) 8.34 (d, 1H) 9.06 (s, 1H) | 371 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 161 | I | I | Q | 3-[3-(1-Methyl-1H-pyrazol-4-yl)-quinolin-6-ylmethyl]-[1,2,4]triazolo[4,3-b]pyridazin-6-ylamine | (DMSO-d6) 3.83 (s, 3H), 4.45 (s, 2H) 6.67 (d, 1H), 6.73 (s, 2H) 7.55 (m, 2H) 7.83 (d, 1H) 7.87 (d, 1H) 8.01 (s, 1H) 8.30 (s, 1H) 8.32 (d, 1H) 9.05 (s, 1H) | 357 |
| 162 | I | I | R | 3-(1-Ethyl-1H-pyrazol-4-yl)-6-(6-methyl-[1,2,4]triazolo[4,3-b]pyridazin-3-ylmethyl)-quinoline | (DMSO-d6) 1.43 (t, 3H), 2.54 (s, 3H), 4.19 (q, 2H), 4.70 (s, 2H), 7.27 (d, 1H), 7.67 (dd, 1H), 7.74 (s, 1H), 7.93 (d, 1H), 8.09 (s, 1H) 8.26 (d, 1H), 8.42 (d, 1H), 8.44 (s, 1H), 9.15 (d, 1H) | 370 |
| 163 | I | I | R | 6-(6-Methyl-[1,2,4]triazolo[4,3-b]pyridazin-3-ylmethyl)-3-(1-propyl-1H-pyrazol-4-yl)quinoline | (DMSO-d6) 0.87 (t, 3H), 1.84 (m, 2H), 2.54 (s, 3H), 4.11 (t, 2H), 4.70 (s, 2H), 7.27 (d, 1H), 7.67 (dd, 1H), 7.74 (s, 1H), 7.93 (d, 1H), 8.10 (s, 1H), 8.26 (d, 1H), 8.42 (d, 1H), 8.43 (s, 1H), 9.15 (d, 1H) | 384 |
| 164 | I | III | R | 1-{4-[6-(6-Methyl-[1,2,4]triazolo[4,3-b]pyridazin-3-ylmethyl)-quinolin-3-yl]-pyrazol-1-yl}-cyclobutanecarboxylic acid | (DMSO-d6) 1.69-2.07 (m, 2H), 2.47 (s, 3H), 2.57-2.69 (m, 4H), 7.20 (d, 1H), 7.59 (dd, 1H), 7.67 (s, 1H), 7.86 (d, 1H), 8.03 (s, 1H), 8.19 (d, 1H), 8.40 (d, 1H), 8.42 (s, 1H), 9.21 (d, 1H) | 440 |
| 165 | I | I | O | 6-(6-Ethyl-[1,2,4]triazolo[4,3-b]pyridazin-3-ylmethyl)-7-fluoro-3-(1-methyl-1H-pyrazol-4-yl)quinoline | (DMSO-d6) 1.48 (3H, t), 3.11 (2H, q), 3.90 (3H, s), 4.71 (2H, s), 7.32 (1H, d), 7.76 (1H, d), 7.86 (1H, d), 8.07 (1H, s), 8.27 (1H, d), 8.37 (1H, s), 8.45 (1H, d), 9.18 (1H, d) | 388 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 166 | I | I | BB | 6-(6-Ethyl-[1,2,4]triazolo[4,3-b]pyridazin-3-ylmethyl)-5,7-difluoro-3-(1-methyl-1H-pyrazol-4-yl)quinoline | (DMSO-d6) 1.24 (3H, t), 2.85 (2H, q), 4.16 (3H, s), 4.95 (2H, s), 7.55 (1H, d), 7.95 (1H, d), 8.44(1H, s), 8.49 (1H, d), 8.74 (1H, s), 8.79 (1H, d), 9.54 (1H, d) | 406 |
| 167 | I | IV | O | 7-Fluoro-3-(1-methyl-1H-pyrazol-4-yl)-6-[1,2,4]triazolo[4,3-b]pyridazin-3-ylmethyl-quinoline | (DMSO-d6) 3.90 (3H, s), 4.76 (2H, s), 7.37 (1H, dd), 7.77 (1H, dd), 7.79 (1H, d), 8.06 (1H, s), 8.37 (1H, s), 8.40 (1H, dd), 8.46 (1H, d), 8.65 (1H, dd), 9.18 (1H, d) | 360 |
| 168 | I | I | R | Dimethyl-(2-{4-[6-(6-methyl-[1,2,4]triazolo[4,3-b]pyridazin-3-ylmethyl-quinolin-3-yl]-pyrazol-1-yl}-ethyl)-amine | (DMS0-d6) 2.18 (6H, s), 2.54 (3H, s), 2.69 (2H, t), 4.24 (2H, t), 4.70 (2H, s), 7.27 (1H, d), 7.67 (1H, dd), 7.75 (1H, s), 7.93 (1H, d), 8.09 (1H, s), 8.26 (1H, d), 8.42 (1H, d), 8.43 (1H, s), 9.14 (1H, d) | 413 |
| 169 | I | I | GG | 3-{4-[6-(6-Methyl-[1,2,4]triazolo[4,3-b]pyridazin-3-ylmethyl-quinolin 3-yl]-pyrazol-1-ylmethyl}-azetidine-1-carboxylic acid tert-butyl ethyl | (DMSO-d6) 1.36 (9H, s), 2.54 (3H, s), 3.01 (1H, m), 3.72 (2H, br s), 3.92 (2H, br s), 4.38 (2H, d), 4.70 (2H, s), 7.27 (1H, d), 7.67 (1H, dd), 7.75 (1H, s), 7.93 (1H, d), 8.12 (1H, s), 8.26 (1H, d), 8.43 (1H, d), 8.47 (1H, s), 9.14 (1H, d) | 511 |
| 170 | I | I | R | 6-(6-Methyl-[1,2,4]triazolo[4,3-b]pyridazin-3-ylmethyl)-3-[1-(2-pyrrolidin-1-yl-ethyl)-1H-pyrazol-4-yl]quinoline | (DMSO-d6, 100° C.) 1.73 (4H, m), 2.52 (4H, m), 3.00 (2H, m), 4.35 (2H, br m), 4.70 (2H, s), 7.22 (1H, s), 7.69 (1H, dd), 7.82 (1H, s), 7.94 (1H, d), 8.06 (1H, s), 8.16 (1H, d), 8.35 (1H, d), 8.35 (1H, s), 9.10 (1H, d) | 439 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 171 | I | I | DD | 3-[1-(1-Ethyl-azetidin-3-yl)-1H-pyrazol-4-yl]-6-(6-methyl-[1,2,4]triazolo[4,3-b]pyridazin-3-ylmethyl)-quinoline | DMSO-d6) 0.94 (3H, t), 2.53 (2H, q), 2.54 (3H, s), 3.39 (2H, m), 3.73 (2H, m), 4.70 (2H, s), 5.01 (1H, m), 7.27 (1H, d), 7.68 (1H, dd), 7.74 (1H, s), 7.94 (1H, d), 8.17 (1H, s), 8.26 (1H, d), 8.46 (1H, d), 8.61 (1H, s), 9.17 (1H, d) | 425 |
| 172 | I | II | EE | 3-[1-(1-Methanesulfonyl-azetidin-3-ylmethyl)-1H-pyrazol-4-yl]-6-(6-methyl-[1,2,4]triazolo[4,3-b]pyridazin-3-ylmethyl)-quinoline | (DMSO-d6) 2.73 (3H, s), 3.27 (1H, m), 3.96 (2H, m), 4.15 (1H, m), 4.59 (2H, d), 4.89 (2H, s), 7.45 (1H, d), 7.86 (1H, dd), 7.93 (1H, s), 8.13 (1H, d), 8.33 (1H, s), 8.45 (1H, d), 8.62 (1H, d), 8.68 (1H, s), 9.34 (1H, d) | 490 |
| 173 | I | I | R | Diethyl-(2-{4-[6-(6-methyl-[1,2,4]triazolo[4,3-b]pyridazin-3-ylmethyl)-quinolin-3-yl]-pyrazol-1-yl}-ethyl)-amine | (DMSO-d6) 0.94-1.19 (6H, br m), 2.55 (3H, s), 3.00-3.20 (4H, br m), (2H, br m), 3.64 (2H, br m), 4.61 (2H, br m), 4.71 (1H, s), 7.28 (1H, d), 7.70 (1H, br d), 7.77 (1H, br s), 7.95 (1H, d), 8.23 (1H, br s), 8.46 (1H, br s), 8.56 (1H, brs), 9.16 (1H, s) | 442 |
| 174 | I | II | P | 5,7-Difluoro-3-(1-methyl-1H-pyrazol-4-yl)-6-[1,2,4]triazolo[4,3-b]pyridazin-3-ylmethyl)-quinoline | (DMSO-d6) 3.84 (3H, s), 4.67 (2H, s), 7.31 (1H, dd), 7.64 (1H, d), 8.13 (1H, s), 8.28 (1H, d), 8.43 (1H, s), 8.48 (1H, d), 8.60 (1H, dd), 9.22 (1H, d) | 377 |
| 175 | I | II | CC | 1-(3-{4-[6-(6-Methyl-[1,2,4]triazolo[4,3-b]pyridazin-3-ylmethyl)-quinolin-3-yl]-pyrazol-1-yl}-azetidin-1-yl)ethanone | (DMSO-d6) 1.84 (3H, s), 2.55 (3H, s), 4.15-4.18 (m, 1H), 4.34 (1H, t), 4.44-4.46 (1H, m), 4.61 (1H, t), 4.70 (2H, s), 5.29 (1H, m), 7.27 (1H, d), 7.68 (1H, dd), 7.75 (1H, dd), 7.95 (1H, d), 8.26 (1H, d), 8.25 (1H, s), 8.47 (1H, d), 8.65 (1H, s), 9.17 (1H, d) | 439 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 176 | I | I | GG | 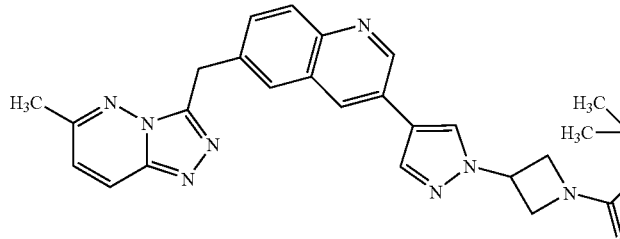<br>3-{4-[6-(6-Methyl-[1,2,4]triazolo[4,3-b]pyridazin-3-ylmethyl)-quinolin-3-yl]-pyrazol-1-yl}-azetidine-1-carboxylic acid tert-butyl ester | (DMSO-d6) 1.57 (9H, s), 2.69 (3H, s), 4.33 (2H, br m), 4.49 (2H, br m), 4.85 (2H, br m), 5.41 (1H, m), 7.42 (1H, d), 7.83 (1H, dd), 7.90 (1H, s), 8.10 (1H, d), 8.40 (1H, s), 8.41 (1H, d), 8.62 (1H, d), 8.78 (1H, s), 9.33 | 498 |
| 177 | I | II | FF | 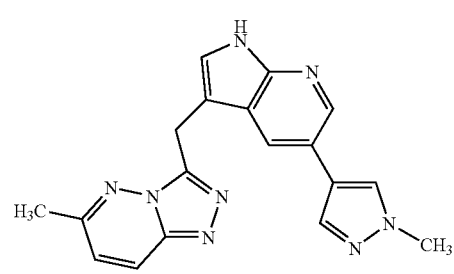<br>6-methyl-3-[5-(1-methyl-1H-pyrazol-4-yl)-1H-pyrrolo[2,3-b]pyridin-3-ylmethyl]-[1,2,4]triazolo[4,3-b]pyridazine | (DMSO-d6) 2.56 (3H, s), 3.87 (3H, s), 4.57 (2H, s), 7.25 (1H, d), 7.36 (1H, d), 7.84 (1H, d), 8.11 (1H, s), 8.16 (1H, d), 8.21 (1H, d), 8.44 (1H, s), 11.45 (1H, s) | 345 |
| 178 | III | NA | FF | 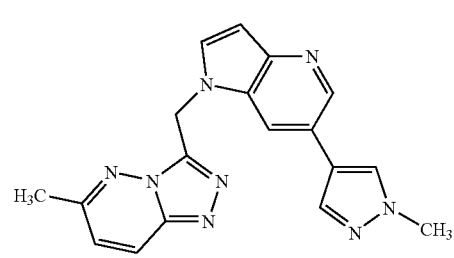<br>6-Methyl-3-[6-(1-methyl-1H-pyrazol-4-yl)-1H-pyrrolo[3,2-b]pyridin-1-ylmethyl]-[1,2,4]triazolo[4,3-b]pyridazine | (CD$_3$OD) 2.60 (3H, s), 3.96 (3H, s), 6.03 (2H, s), 6.60 (1H, d), 7.29 (1H, d), 7.76 (1H, d), 7.95 (1H, s), 8.07 (1H, d), 8.09 (1H, s), 8.34 (1H, m), 8.55 (1H, d) | 345 |
| 179 | I | I | II | 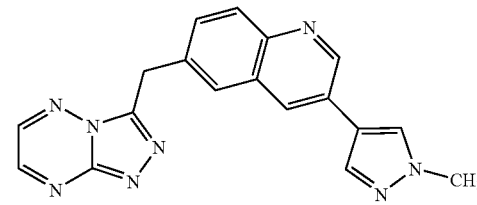<br>3-(1-Methyl-1H-pyrazol-4-yl)-6-[1,2,4]triazolo[4,3-b][1,2,4]triazin-3-ylmethyl)-quinoline | (DMSO-d6) 3.90 (3H, s), 4.73 (2H, s), 7.65 (1H, d), 7.76 (1H, s), 7.92 (1H, d), 8.07 (1H, s), 8.37 (1H, s), 8.40 (1H, s), 8.72 (1H, d), 8.73 (1H, d), 9.13 (1H, s) | 343 |
| 180 | I | I | DD | 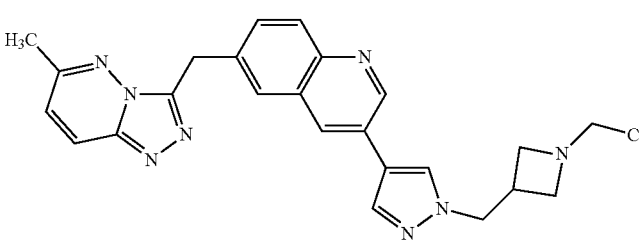<br>3-[1-(1-Ethyl-azetidin-3-ylmethyl)-1H-pyrazol-4-yl]-6-(6-methyl-[1,2,4]triazolo[4,3-b]pyridazin-3-ylmethyl)-quinoline | (DMSO-d6) 0.84 (3H, t), 2.39 (2H, q), 2.53 (3H, s), 2.82 (1H, quintet), 2.98 (2H, t), 3.24 (2H, t), 4.33 (2H, d), 4.68 (2H, s), 7.26 (1H, d), 7.66 (1H, dd), 7.72 (1H, d), 7.92 (1H, d), 8.09 (1H, s), 8.24 (1H, s), 8.28 (1H, s), 8.41 (1H, d), 8.43 (1H, s), 9.13 (1H, d) | 439 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 181 | I | II | CC | 1-(3-{4-[6-(6-Methyl)-[1,2,4]triazolo[4,3-b]pyridazin-3-ylmethyl)-quinolin-3-yl]-pyrazol-1-ylmethyl}-azetidin-1-yl)-ethanone | (DMSO-d6) 1.72 (3H, s), 2.53 (3H, s), 3.05 (1H, m), 3.68 (1H, dd), 3.89 (1H, t), 3.96 (1H, dd), 4.18 (1H, t), 4.39 (2H, d), 4.69 (2H, s), 7.26 (1H, d), 7.66 (1H, dd), 7.74 (1H, s), 7.93 (1H, d), 8.12 (1H, d), 8.42 (1H, d), 8.45 (1H, s), 9.14 (1H, d) | 453 |
| 182 | I | II | EE | 3-[1-(1-Methanesulfonyl-azetidin-3-yl)-1H-pyrazol-4-yl]-6-(6-methyl-[1,2,4]triazolo[4,3-b]pyridazin-3-ylmethyl)-quinoline | (DMSO-d6) 2.55 (3H, s), 3.16 (3H, s), 4.33-4.35 (4H, m), 4.71 (2H, s), 5.34 (1H, quintet), 7.27 (1H, d), 7.69 (1H, dd), 7.76 (1H, s), 7.95 (1H, d), 8.26 (1H, d), 8.29 (1H, s), 8.48 (1H, d), 8.62 (1H, s), 9.18 (1H, d) | 475 |
| 183 | I | NA | NN | 3-[1-(1-Methyl)-azetidin-3-yl)-1H-pyrazol-4-yl]-6-(6-methyl-[1,2,4]triazolo[4,3-b]pyridazin-3-ylmethyl)-quinoline | (DMSO-d6) 2.35 (3H, s), 2.54 (3H, s), 3.41 (2H, t), 3.73 (2H, t), 4.69 (2H, s), 4.97 (1H, quintet), 7.26 (1H, d), 7.67 (1H, dd), 7.73 (1H, s), 7.93 (1H, d), 8.16 (1H, s), 8.25 (1H, d), 8.45 (1H, d), 8.60 (1H, s), 9.16 (1H, d) | 411 |
| 184 | I | NA | HH | 3-(1-Azetidin-3-yl-1H-pyrazol-4-yl)-6-(6-ethyl-[1,2,4]triazolo[4,3-b]pyridazin-3-ylmethyl)-5-fluoro-quinoline | (DMSO-d6) 1.25 (3H, t), 2.87 (2H, q), 4.35-4.44 (4H, m), 4.72 (2H, s), 5.44 (1H, quintet), 7.32 (1H, d), 7.70 (1H, t), 7.83 (1H, d), 8.25 (1H, d), 8.47 (1H, s), 8.63 (1H, d), 8.72 (1H, s), 9.22 (2H, br s), 9.28 (1H, d), | 429 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 185 | I | NA | HH | 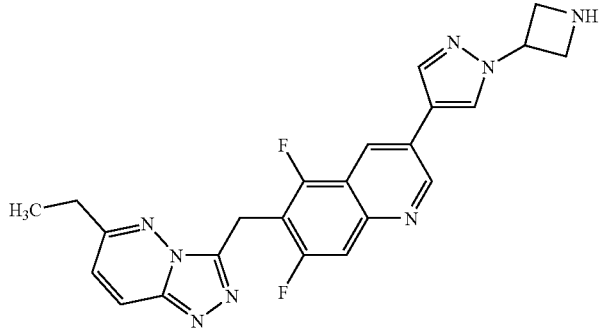<br>3-(1-Azetidin-3-yl-1H-pyrazol-4-yl)-6-(6-ethyl-[1,2,4]triazolo[4,3-b]pyridazin-3-ylmethyl)-5,7-difluoro-quinoline | (DMSO-d6) 1.23 (3H, t), 2.87 (2H, q), 4.37-4.45 (4H, m), 4.71 (2H, s), 5.44 (1H, quintet), 7.32 (1H, d), 7.73 (1H, d), 8.48 (1H, s), 8.62 (1H, d), 8.70 (1H, s), 9.08 (1H, br s), 9.20 (1H, br s), 9.32 (1H, d) | 447 |
| 186 | I | NA | DD | 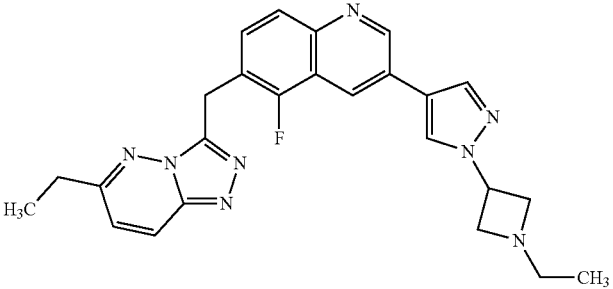<br>3-(1-(1-Ethyl-azetidin-3-yl-1H-pyrazol-4-yl)-6-(6-ethyl-[1,2,4]triazolo[4,3-b]pyridazin-3-ylmethyl)-5-fluoro-quinoline | (DMSO-d6) 0.93 (3H, t), 1.25 (3H, t), 2.55 (2H, q), 2.88 (2H, q), 3.38 (2H, m), 3.71 (2H, m), 4.72 (2H, s), 5.00 (1H, quintet), 7.31 (1H, d), 7.67 (1H, t), 7.81 (1H, d), 8.26 (1H, d), 8.28 (1H, s), 8.61 (1H, d), 8.74 (1H, s), 9.28 (1H, d) | 457 |
| 187 | I | NA | DD | 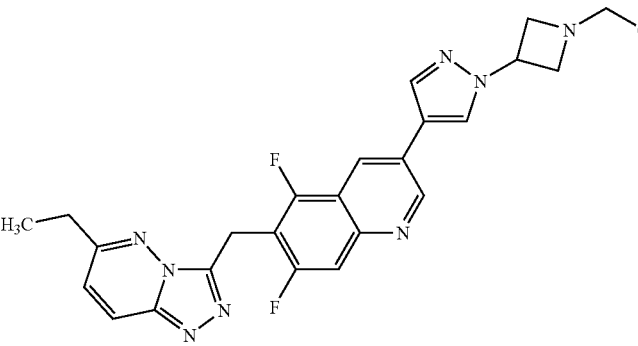<br>3-[1-(1-Ethyl-azetidin-3-yl)-1H-pyrazol-4-yl]-6-(6-ethyl-[1,2,4]triazolo[4,3-b]pyridazin-3-ylmethyl)-5,7-difluoro-quinoline | (DMSO-d6) 0.93 (3H, t), 2.50 (3H, t), 2.57 (2H, q), 2.87 (2H, q), 3.37 (2H, m), 3.71 (2H, m), 4.71 (2H, s), 5.00 (1H, quintet), 7.31 (H, d), 7.70 (1H, d), 8.25 (1H, d), 8.28 (1H, s), 8.61 (1H, d), 8.74 (1H, s), 9.33 (1H) | 475 |
| 188 | I | NA | DD | 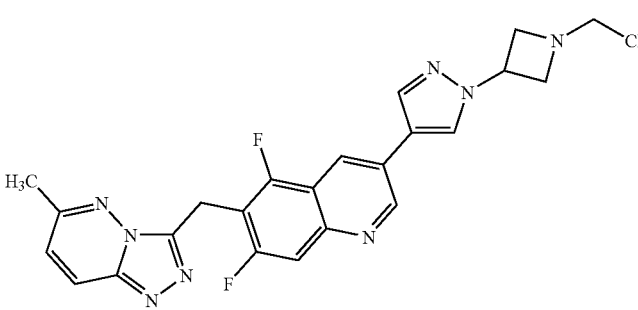<br>3-[1-(1-Ethyl-azetidin-3-yl)-1H-pyrazol-4-yl]-5,7-difluoro-6-(6-methyl-[1,2,4]triazolo[4,3-b]pyridazin-3-ylmethyl)-3-ylmethyl)-quinoline | (DMSO-d6) 0.93 (3H, t), 2.51 (2H, q), 2.57 (3H, s), 3.37 (2H, m), 3.71 (2H, m), 4.69 (2H, s), 5.00 (1H, quintet), 7.29 (1H, d), 7.72 (1H, d), 8.25 (1H, d), 8.29 (1H, s), 8.61 (1H, d), 8.74 (1H, s), 9.33 (1H, d) | 461 |

TABLE 2-continued

| Eg. | MET IC$_{50}$ | GTL 16 EC$_{50}$ | Method | Structure | $^1$H NMR (500 MHz) | MS (m/z) |
|---|---|---|---|---|---|---|
| 189 | I | NA | HH | 3-(1-Azetidin-3-yl-1H-pyrazol-4-yl)-6-(6-ethyl-[1,2,4]triazolo[4,3-b]pyridazin-3-ylmethyl)-quinoline | (DMSO-d6) 1.25 (3H, t), 2.86 (2H, q), 4.42 (4H, m), 4.71 (2H, s), 5.45 (1H, quintet), 7.31 (1H, d), 7.72 (1H, dd), 7.81 (1H, d), 8.27 (1H, d), 8.36 (1H, s), 8.48 (1H, d), 8.58 (1H, s), 9.06 (1H, br s), 9.16 (1H, d), 9.18 (1H, br s) | 411 |
| 190 | I | NA | DD | 3-[1-(1-Ethyl-azetidin-3-yl-1H-pyrazol-4-yl]-6-[1-(6-methyl-[1,2,4]triazolo[4,3-b]pyridazin-3-yl)-ethyl]-quinoline | (DMSO-d6) 0.93 (3H, t), 1.88 (3H, d), 2.51-2.54 (5H, m), 3.35-3.38 (2H, m), 3.71-3.71 (2H, m), 5.01 (1H, m), 7.22 (1H, d), 7.71 (1H, dd), 7.74 (1H, d), 7.93 (1H, d), 8.16 (1H, d), 8.24 (1H, d), 8.48 (1H, d), 8.60 (1H, s), 9.17 (1H, d) | 439 |
| 191 | I | NA | O | 3-(1-Methyl-1H-pyrazol-4-yl)-6-[1-(6-methyl-[1,2,4]triazolo[4,3-b]pyridazin-3-yl)-ethyl]-quinoline | (DMSO-d6) 1.88 (3H, d), 2.51 (3H, s), 3.90 (3H, s), 5.01 (1H, quintet), 7.23 (1H,d), 7.70 (1H, dd), 7.74 (1H, s), 7.93 (1H, d), 8.08 (1H, s), 8.24 (1H, d), 8.37 (1H, s), 8.43 (1H, d), 9.13 (1H, d) | 370 | wherein:
I c-MET IC$_{50}$ ≦ 100 nM;
II 100 nM < c-MET IC$_{50}$ ≦ 1 μM;
III 1 μM < c-MET IC$_{50}$ ≦ 10 μM; and
IV 10 μM < c-MET IC$_{50}$ ≦ 50 μM.

Bioassays

Kinase assays known to those of skill in the art may be used to assay the inhibitory activities of the compounds and compositions of the present disclosure. Kinase assays include, but are not limited to, the following examples.

Screening data was evaluated using the equation: Z'=1−[3*(σ$_+$+σ$_−$)/|μ$_+$−μ$_−$|] (Zhang, et al., 1999 J Biomol Screening 4(2) 67-73), where μ denotes the mean and σ the standard deviation. The subscript designates positive or negative controls. The Z' score for a robust screening assay should be ≧0.50. The typical threshold=μ$_+$−3*σ$_+$. Any value that falls below the threshold was designated a "hit".

MET Luminescence-Based Enzyme Assay

Materials: Poly Glu-Tyr (4:1) substrate (Sigma Cat#P-0275), ATP (Sigma Cat #A-3377, FW=551), HEPES buffer, pH 7.5, Bovine serum albumin (BSA) (Roche 92423420), MgCl$_2$, Staurosporine (Streptomyces sp. Sigma Cat#85660-1MG), white Costar 384-well flat-bottom plate (VWR Cat#29444-088). MET kinase (see below), Kinase-Glo™ (Promega Cat#V6712).

Stock Solutions: 10 mg/ml poly Glu-Tyr in water, stored at −20° C.; 100 mM HEPES buffer, pH 7.5 (5 ml 1M stock+45 ml miliQH$_2$O); 10 mM ATP (5.51 mg/ml in dH$_2$O) stored at −20° C. (diluted 50 μl into total of 10 ml miliQH$_2$O daily=50 μM ATP working stock); 1% BSA (1 g BSA in 100 ml 0.1M HEPES, pH 7.5, stored at −20° C.), 100 mM MgCl$_2$; 200 μM Staurosporine, 2× Kinase-Glo™ reagent (made fresh or stored at −20° C.).

Standard Assay Setup for 384-well format (20 μl kinase reaction, 40 μl detection reaction): 10 mM MgCl$_2$; 0.3 mg/ml poly Glu-Tyr; 0.1% BSA; 1 μl test compound (in DMSO); 0.4 μg/ml MET kinase; 10 μM ATP; 100 mM HEPES buffer. Positive controls contained DMSO with no test compound. Negative controls contained 10 μM staurosporine. The kinase reactions were initiated at time t=0 by the addition of ATP. Kinase reactions were incubated at 21° C. for 60 min, then 20 μl of Kinase-Glo™ reagent were added to each well to quench the kinase reaction and initiate the luminescence reaction. After a 20 min incubation at 21° C., the luminescence was detected in a plate-reading luminometer.

AurA Luminescence-Based Enzyme Assay

Materials: Kemptide peptide substrate=LRRASLG (Biopeptide, San Diego, Calif.), ATP (Sigma Cat #A-3377, FW=551), HEPES buffer, pH 7.5, 10% Brij 35 (Calbiochem Cat#203728), $MgCl_2$, Staurosporine (*Streptomyces* sp. Sigma Cat#85660-1MG), white Costar 384-well flat bottom plate (VWR Cat#29444-088), Autophosphorylated AurA kinase (see below), Kinase-Glo™ (Promega Cat#V6712).

Stock Solutions: 10 mM Kemptide peptide (7.72 mg/ml in water), stored at −20° C.; 100 mM HEPES buffer+0.015% Brij 35, pH 7.5 (5 ml 1M HEPES stock+75 μL 10% Brij 35+45 ml miliQ$H_2$O); 10 mM ATP (5.51 mg/ml in d$H_2$O) stored at −20° C. (diluted 50 μl into total of 10 ml miliQ$H_2$O daily=50 μM ATP working stock); 100 mM $MgCl_2$; 200 μM Staurosporine, 2× Kinase-Glo™ reagent (made fresh or stored at −20° C.).

AurA Autophosphorylation Reaction: ATP and $MgCl_2$ were added to 1-5 mg/ml AurA at final concentrations of 10 mM and 100 mM, respectively. The autophosphorylation reaction was incubated at 21° C. for 2-3 h. The reaction was stopped by the addition of EDTA to a final concentration of 50 mM, and samples were flash frozen with liquid $N_2$ and stored at −80° C.

Standard Assay Setup for 384-well format (20 μl kinase reaction, 40 μl detection reaction): 10 mM $MgCl_2$; 0.2 mM Kemptide peptide; 1 μl test compound (in DMSO); 0.3 μg/ml Autophosphorylated AurA kinase; 10 μM ATP; 100 mM HEPES+0.015% Brij buffer. Positive controls contained DMSO with no test compound. Negative controls contained 5 μM staurosporine. The kinase reactions were initiated at time t=0 by the addition of ATP. Kinase reactions were incubated at 21° C. for 45 min, then 20 μl of Kinase-Glo™ reagent were added to each well to quench the kinase reaction and initiate the luminescence reaction. After a 20 min incubation at 21° C., the luminescence was detected in a plate-reading luminometer.

Purification of Met:

The cell pellets produced from half of a 12 L Sf9 insect cell culture expressing the kinase domain of human Met were resuspended in a buffer containing 50 mM Tris-HCl pH 7.7 and 250 mM NaCl, in a volume of approximately 40 ml per 1 L of original culture. One tablet of Roche Complete, EDTA-free protease inhibitor cocktail (Cat#1873580) was added per 1 L of original culture. The suspension was stirred for 1 hour at 4° C. Debris was removed by centrifugation for 30 minutes at 39,800×g at 4° C. The supernatant was decanted into a 500 ml beaker and 10 ml of 50% slurry of Qiagen Ni-NTA Agarose (Cat#30250) that had been pre-equilibrated in 50 mM Tris-HCl pH 7.8, 50 mM NaCl, 10% Glycerol, 10 mM Imidazole, and 10 mM Methionine, were added and stirred for 30 minutes at 4° C. The sample was then poured into a drip column at 4° C. and washed with 10 column volumes of 50 mM Tris-HCl pH 7.8, 500 mM NaCl, 10% Glycerol, 10 mM Imidazole, and 10 mM Methionine. The protein was eluted using a step gradient with two column volumes each of the same buffer containing 50 mM, 200 mM, and 500 mM Imidazole, sequentially. The 6× Histidine tag was cleaved overnight using 40 units of TEV protease (Invitrogen Cat# 10127017) per 1 mg of protein while dialyzing in 50 mM Tris-HCl pH 7.8, 500 mM NaCl, 10% Glycerol, 10 mM Imidazole, and 10 mM Methionine at 4° C. The 6× Histidine tag was removed by passing the sample over a Pharmacia 5 ml IMAC column (Cat#17-0409-01) charged with Nickel and equilibrated in 50 mM Tris-HCl pH 7.8, 500 mM NaCl, 10% Glycerol, 10 mM Imidazole, and 10 mM Methionine. The cleaved protein bound to the Nickel column at a low affinity and was eluted with a step gradient. The step gradient was run with 15% and then 80% of the B-side (A-side=50 mM Tris-HCl pH 7.8, 500 mM NaCl, 10% Glycerol, 10 mM Imidazole, and 10 mM Methionine; B-side=50 mM Tris-HCl pH 7.8, 500 mM NaCl, 10% Glycerol, 500 mM Imidazole, and 10 mM Methionine) for 4 column volumes each. The Met protein eluted in the first step (15%), whereas the non-cleaved Met and the cleaved Histidine tag eluted in the 80% fractions. The 15% fractions were pooled after SDS-PAGE gel analysis confirmed the presence of cleaved Met; further purification was done by gel filtration chromatography on an Amersham Biosciences HiLoad 16/60 Superdex 200 prep grade (Cat#17-1069-01) equilibrated in 50 mM Tris-HCl pH 8.5, 150 mM NaCl, 10% Glycerol and 5 mM DTT. The cleanest fractions were combined and concentrated to ~10.4 mg/ml by centrifugation in an Amicon Ultra-15 10,000 Da MWCO centrifugal filter unit (Cat#UFC901024).

Cell Assays

HCT116 cells were maintained in McCoy's 5a Medium supplemented with 10% fetal bovine serum (FBS) 2 mM L-Glutamine and 100 units penicillin/100 μg streptomycin, at 37° C. in 5% $CO_2$.

Cell Survival Assays

Compounds were tested in the following assays in duplicate. 96-well XTT assay: Cells were grown in growth media containing various concentrations of compounds (duplicates) on a 96-well flat bottom plate for 72 hours at 37° C. in 5% $CO_2$. The starting cell number was 5000 cells per well and volume was 120 μl. At the end of the 72-hour incubation, 40 μl of XTT labeling mixture (50:1 solution of sodium 3'-[1-(phenylaminocarbonyl)-3,4-tetrazolium]-bis(4-methoxy-6-nitro) benzene sulfonic acid hydrate and Electron-coupling reagent: PMS (N-methyl dibenzopyrazine methyl sulfate) were added to each well of the plate. After an additional 2-6 hours of 650 nm was measured with a spectrophotometer.

Histone-H3 phosphorylation assay: HCT116 cells were plated out at 1×10^6 cells per 60×15 mm dish (Falcon) in 3 mL of growth media (McCoy's 5A Media, 10% FBS, 1% pen-strep) and incubated overnight (37° C. 5% $CO_2$). The next day compound was added and incubated for 1 hr (37° C. 5% $CO_2$). After 1 hr, the cells were washed once with 1×PBS, and then lysed directly on the plate with 1004 of lysis buffer (125 mM Tris HCl pH 6.8 and 2×SDS loading buffer) and transferred to a 1.7 mL eppendorf tube and put on ice. The samples were sonicated for approximately 5 seconds and were put in a 95° C. heat block for 3 minutes. After heating, the samples were loaded on a NuPage 4-12% Bis-Tris Gel (Invitrogen), followed by electrophoretic transfer to 0.45 μm nitrocellulose membranes (Invitrogen). After transferring, the membranes were placed in Qiagen blocking buffer with 0.1% Tween for 1 hour at room temperature with gentle rocking. Anti-phospho-Histone H3 (Ser10) antibody (Upstate #06-570), was diluted 1:250 in blocking buffer and was added to the blots and incubated for 1 hour at room temperature. The blot was then washed three times with 1×PBS+0.1% Tween20. Goat-anti Rabbit HRP secondary antibody (Jackson ImmunoResearch Laboratories, Inc. #111-035-003) was diluted 1:3000 in blocking buffer, and was then added for 1 hr at room temperature. The blot was washed three times with 1×PBS+0.1% Tween20, and visualized by chemiluminescence with SuperSignal West Pico Chemiluminescent Substrate (Pierce #34078).

Example 25

GTL16 Tumor Xenograft Model

Materials and Methods

Female athymic nude mice (nu/nu from Harlan) were 6-8 weeks old with a body weight range of 18-22 g at the beginning of the study. The animals had free access to food and water throughout the study. The mice were housed on irradiated Alpha-dri® Bed-O-Cobs® Laboratory Animal Bedding in static micro isolator caging on a 12-hour light cycle at 70-74° F. and 40-60% humidity. All procedures involving animals were conducted in compliance with the NIH *Guide* for the Care and Use of Laboratory Animals and all protocols were approved by an Internal Animal Care and Use Committee (IACUC).

Western blot analysis and quantitation of pharmacodynamic marker: Approximately 100 mg of each tumor was homogenized in 2× volume of RIPA buffer (Upstate) plus protease inhibitors (Sigma) using the Tissuelyser (Qiagen). 80 μg of each lysate was subjected to SDS-PAGE followed by western blot analysis to detect phospho-Met (Cell Signaling) which was then quantified using the Typhoon imaging system (GE Life Sciences).

Tumor Implantation

Xenografts were initiated from GTL-16 tumor cells cultured and maintained by an internal Cell Biology Department. Each test mouse received a subcutaneous injection of 4×10⁶ cells suspended in 100 μL of serum free RPMI media. Tumors were randomized into treatment groups on Day 5 when the average tumor size reached approximately 150 mm³. Each dose groups contained n=5 mice. Tumor volume was calculated using the formula: Tumor Volume=(w²×l)/2, where w=width and l=length in mm of the tumor. Tumor weight may be estimated with the assumption that 1 mg is equivalent to 1 mm³ of tumor volume.

Tumor Growth Inhibition (TGI) Analysis

TGI was calculated from the difference between the mean tumor volumes of vehicle-treated and drug-treated mice, expressed as a percentage.

$$\% \, TGI = \frac{\text{Mean Tumor } Volume_{control} - \text{Mean Tumor } Volume_{drug\text{-}treated}}{\text{Median Tumor } Volume_{control}} \times 100$$

The MTV is defined as the mean tumor volume (MTV) for the number of animals, n, remaining in the study on that day.

Results

FIG. 1 shows the effects of compound 30 administered orally (PO) at 3 mg/kg twice a day (BID) and administered via intraperitoneal injection (IP) at 50 mg/kg twice a day (BID) for 14 consecutive days. The IP dose produced statistically significant inhibition of growth of GTL16 tumors grown subcutaneously in athymic nude mice. Treatment began on Day 5. On the last day of treatment the 3 mg/kg PO and 50 mg/kg IP doses decreased mean tumor volume by 27% (p<0.2743) and 89% (p<0.0036) respectively compared to the mean tumor volume of the vehicle-treated group.

Figure 2:
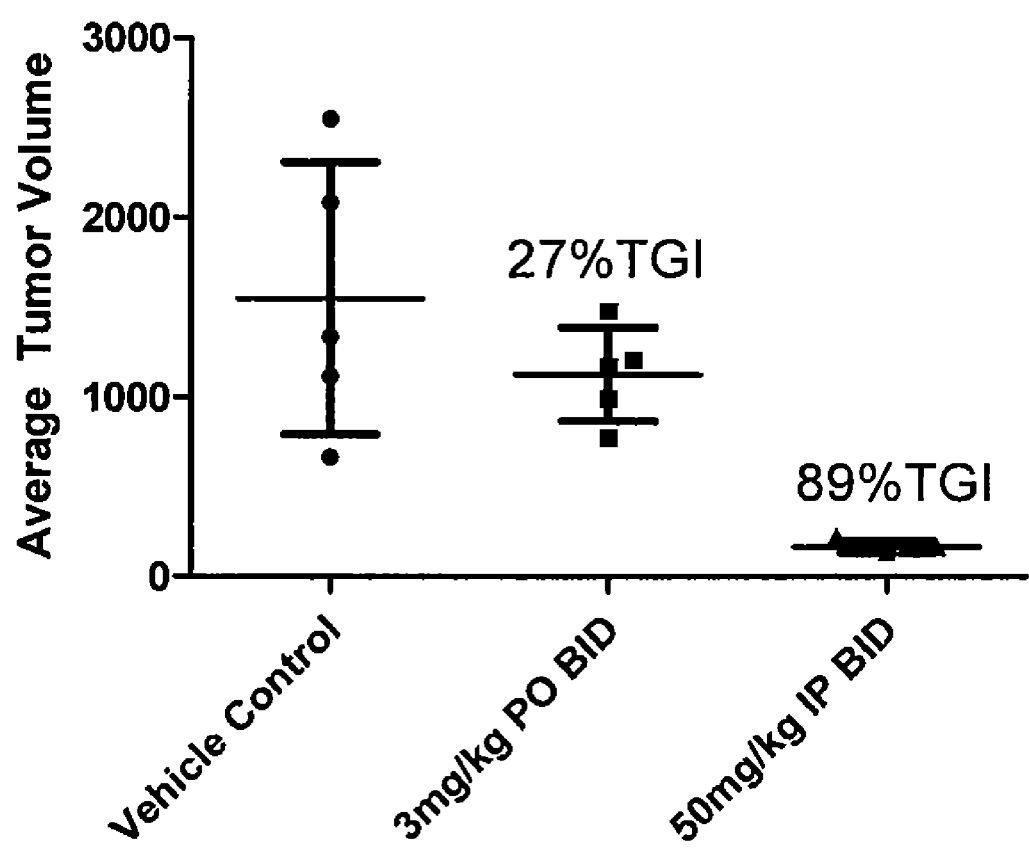
FIG. 2 illustrates the effects on GTL16 tumor growth inhibition by administering compound 30 orally and intraperitoneally.

FIG. 2 shows the effects of oral and intraperitoneal administration of compound 30 on tumor growth inhibition (TGI) in GTL16 tumors in nude mice. All treatments began on Day 5 after tumor cell implant. At the end of the 14-day dosing regime, final TGI % was calculated from the difference between the mean tumor volumes of vehicle-treated and drug-treated mice, expressed as a percentage of the mean tumor volume of the vehicle-treated control group.

Figure 3:
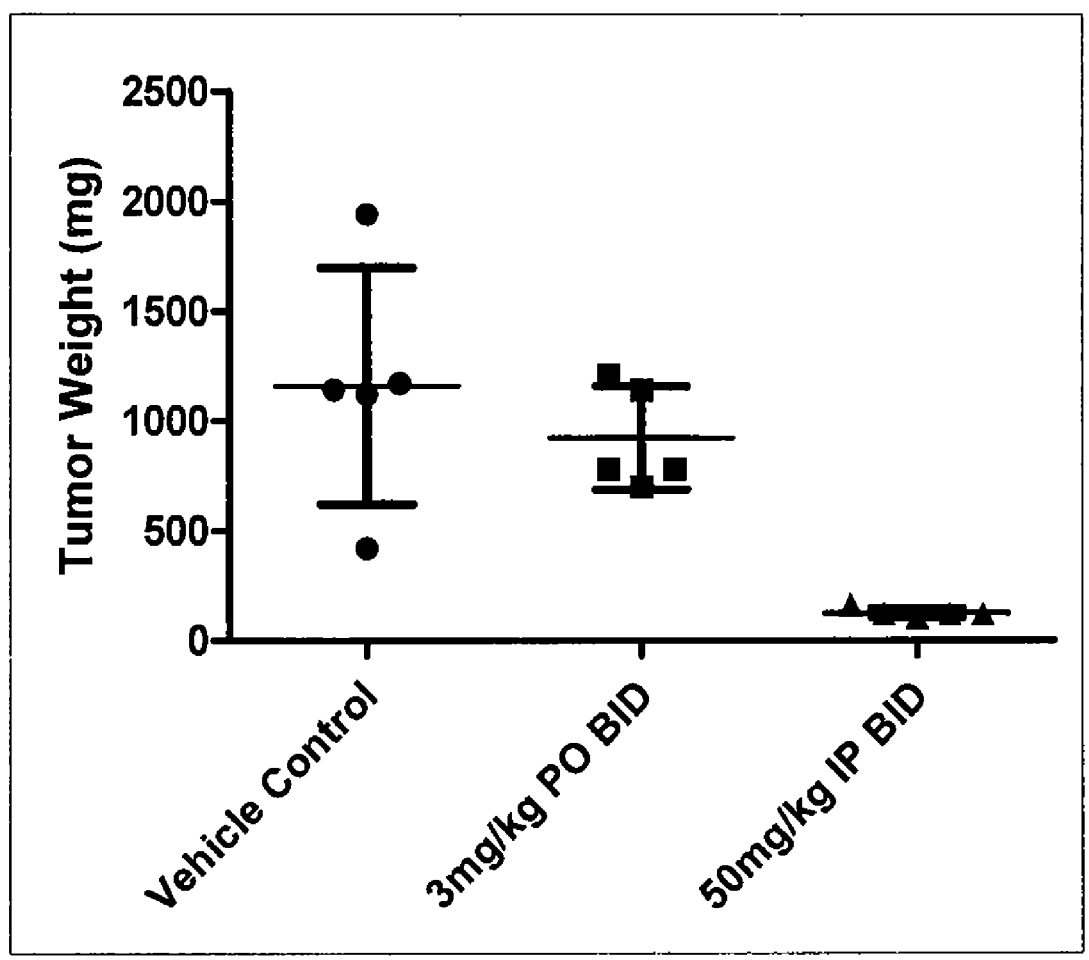
FIG. 3 illustrates the effects on GTL16 tumor growth by administering compound 30 orally and intraperitoneally.

FIG. 3 shows the effects of oral and intraperitoneal administration of compound 30 on the growth of GTL16 tumors. Female athymic nude mice were inoculated subcutaneously on the right flank with 4×10⁶ GTL16 cells in a delivery volume of 100 μL. Tumors were allowed to grow for five days. Mice were dosed orally at 3.0 mg/kg and intraperitoneally at 50.0 mg/kg twice per day for 14 consecutive days. On the day of study termination, tumors were immediately excised intact and weighed, with final tumor wet weight (milligrams) serving as a primary efficacy endpoint.

Figure 4:
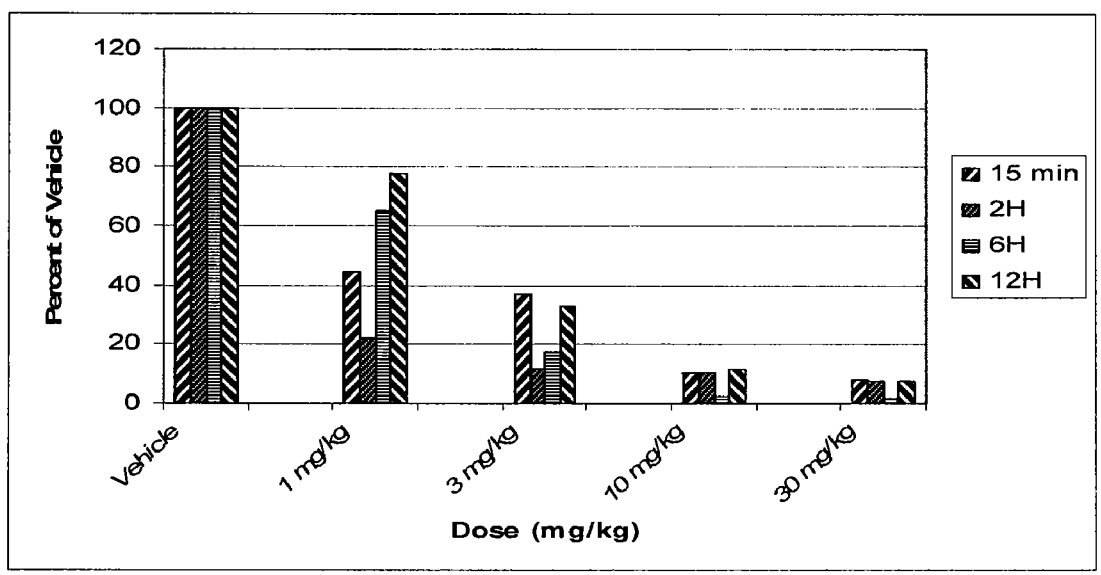
FIG. 4 illustrates the effects on tumor MET phosphorylation by administering compound 124 as an acute dose orally (PO).

FIG. 4 shows the effects of compound 124 administered as an acute dose orally (PO) at 1, 3, 10, 30 mg/kg. Treatment was performed on Day 13 when tumors reached an average tumor volume of ~650 mm³. After dose administration, n=3 mice were sacrificed at T=15 min, 2 h, 6 h, 12 h. Tumors were homogenized in RIPA buffer and protease inhibitors. 80 μg of lysate was subjected to SDS-PAGE followed by western blot analysis to detect phospho-Met and quantitated using the Typhoon imaging system.

Figure 5:
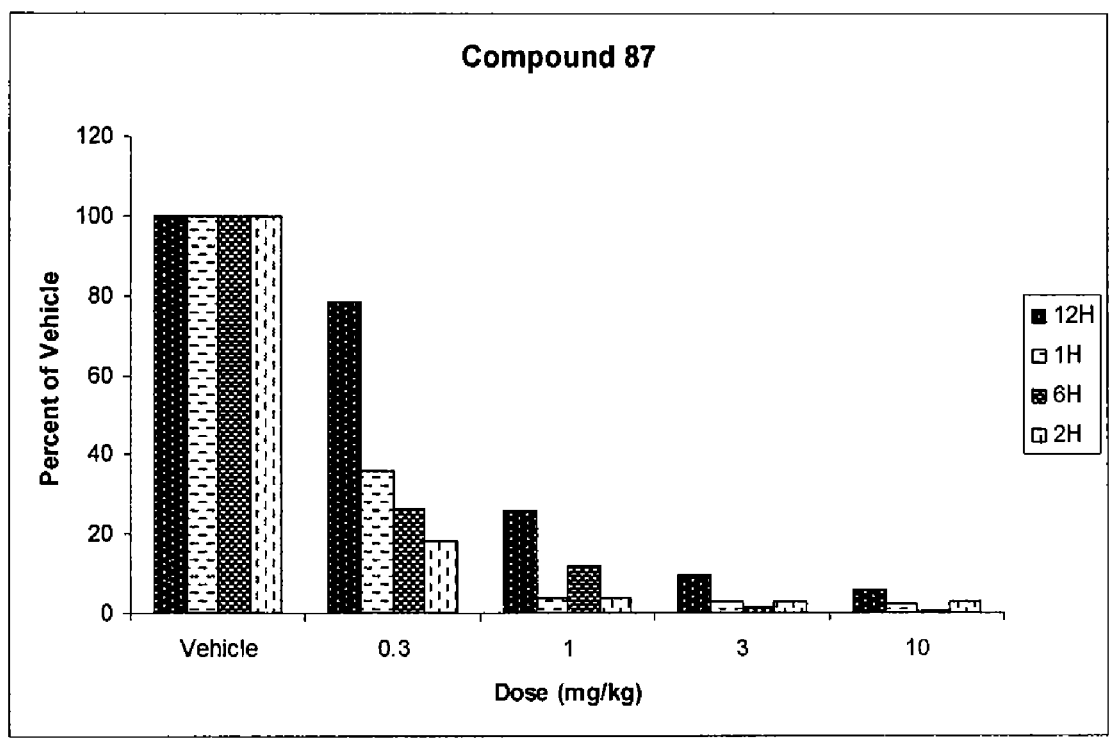
FIG. 5 illustrates the effects on tumor MET phosphorylation by administering compound 87 as an acute dose orally (PO).

FIG. 5 shows the effects of administering compound 87 as an acute dose orally (PO) at 0.3, 1, 3, 10 mg/kg. Treatment was performed on Day 13 when tumors reached an average tumor volume of ~650 mm³. After dose administration, n=3 mice were sacrificed at T=1 h, 2 h, 6 h, 12 h. Tumors were homogenized in RIPA buffer and protease inhibitors. 80 μg of lysate was subjected to SDS-PAGE followed by western blot analysis to detect phospho-Met and quantitated using the Typhoon imaging system.

Figure 6:
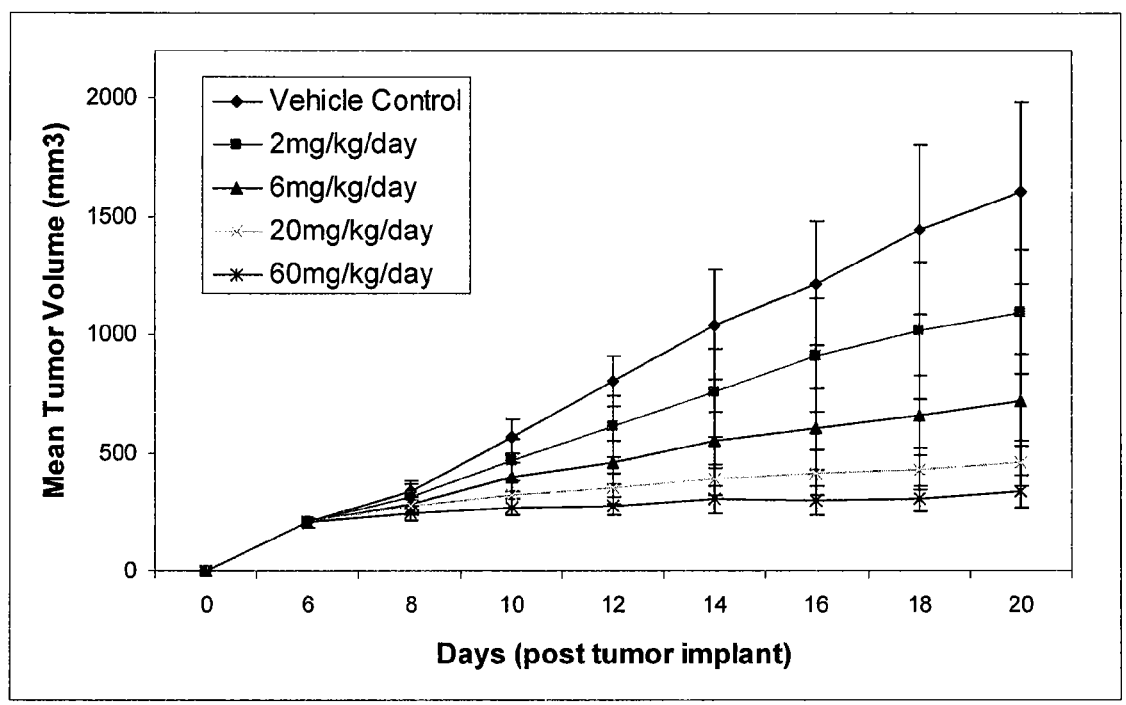
FIG. 6 illustrates the effects on mean tumor volume by administering compound 124 orally (PO) twice a day (Q12H) for 14.5 consecutive days.

FIG. 6 shows the effects of administering compound 124 orally (PO) at 1, 3, 10, and 30 mg/kg twice a day (Q12H) for 14.5 consecutive days. Treatment began on Day 6. On the last day of treatment the 1, 3, 10, 30 mg/kg PO Q12H and doses decreased mean tumor volume by 32% (p=0.0079), 55% (p<0.0001), 72% (p<0.0001), and 79% (p<0.0001) respectively compared to the mean tumor volume of the vehicle-treated group.

Figure 7:
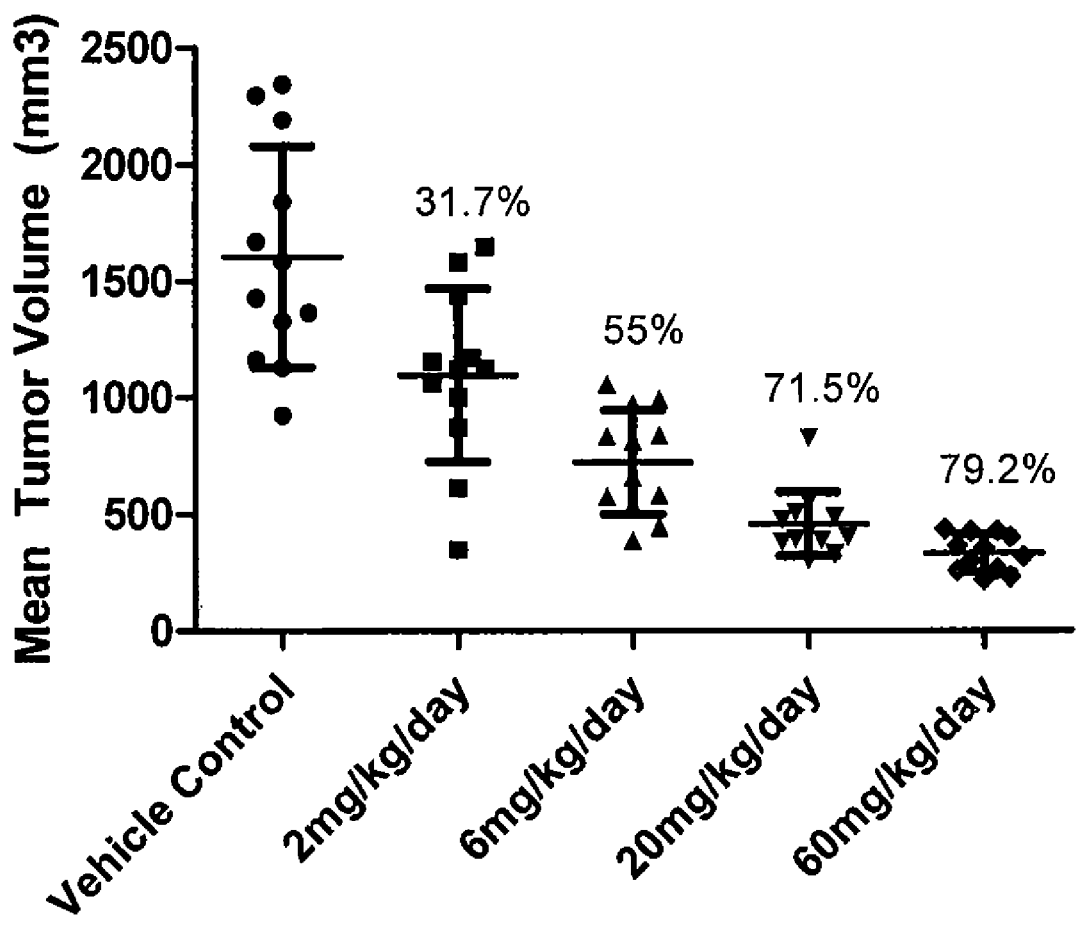
FIG. 7 illustrates the effects on tumor growth inhibition (TGI) in GTL16 tumors in nude mice by administering compound 124 orally.

FIG. 7 shows the effects of oral administration of Compound 124 on tumor growth inhibition (TGI) in GTL16 tumors in nude mice. All treatments began on Day 6 after tumor cell implant. At the end of the 14.5-day dosing regime, final TGI % was calculated from the difference between the mean tumor volumes of vehicle-treated and drug-treated mice, expressed as a percentage of the mean tumor volume of the vehicle-treated control group.

Abbreviations
PO Per Oral;
Q12H Every 12 hours
Q24H Every 24 hours
RPMI Roswell Park Memorial Institute
NIH National Institute of Health
IACUC Animal Care and Use Committee
MTV Mean Tumor Volume
PD Pharmacodynamic It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

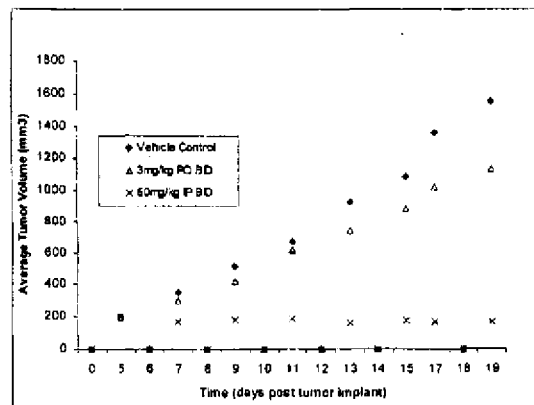

What is claimed is:
1. A compound selected from the group consisting of:

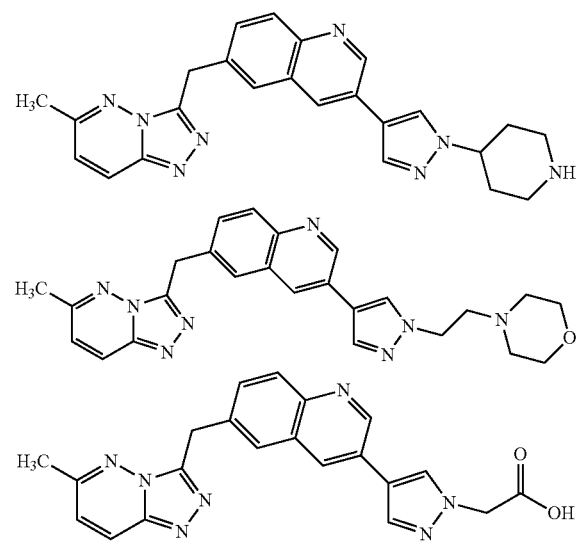

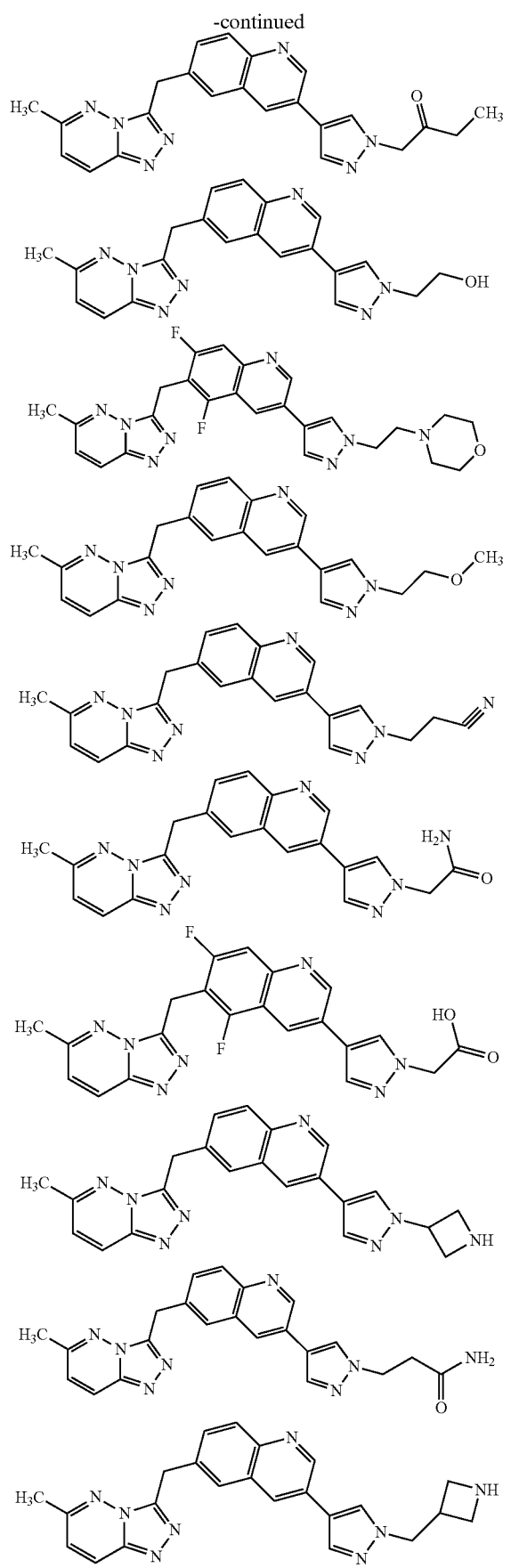
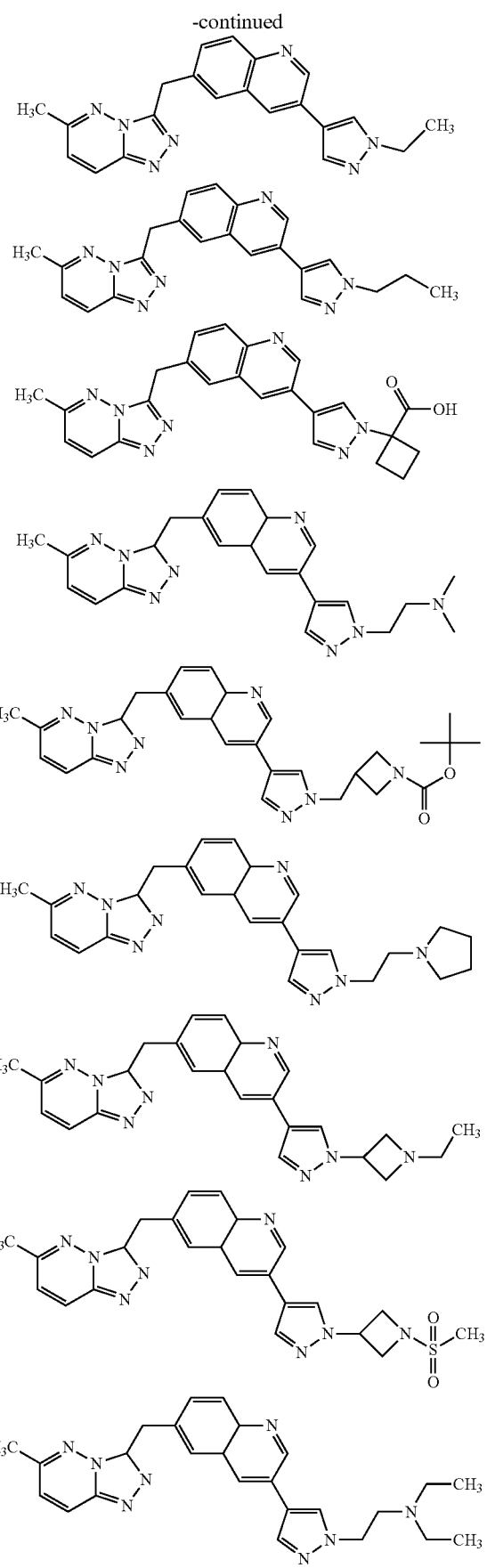

-continued
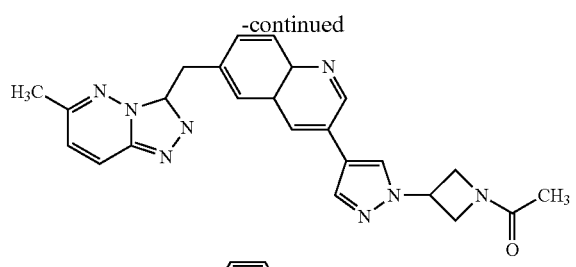
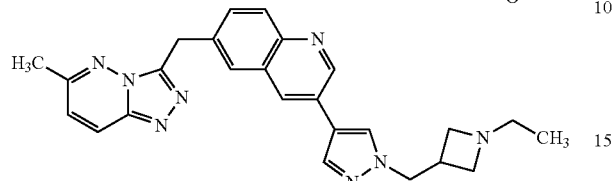
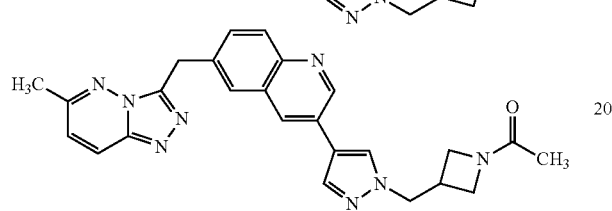
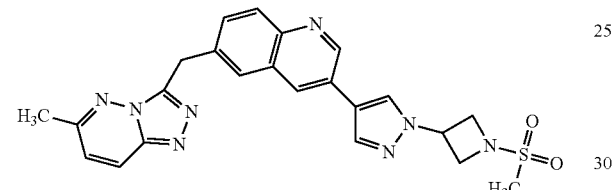
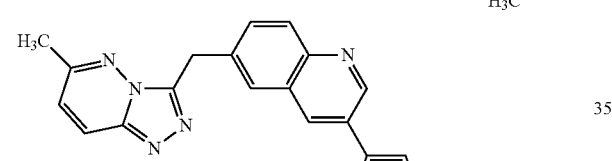
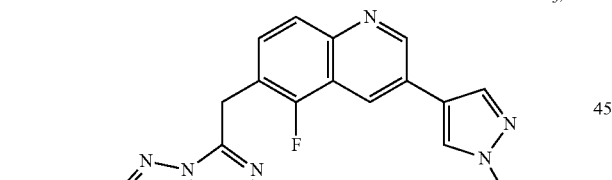
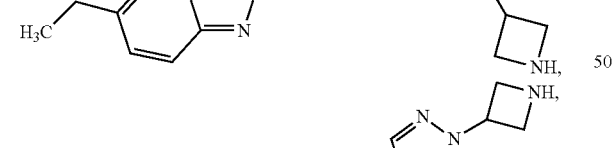
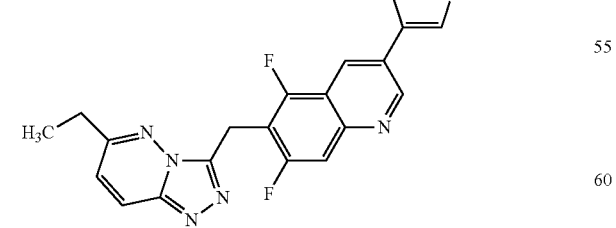
-continued
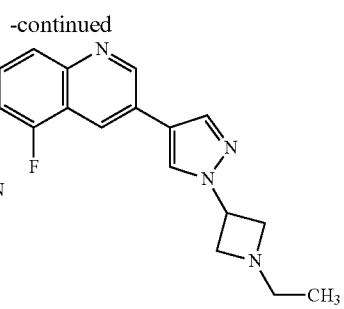
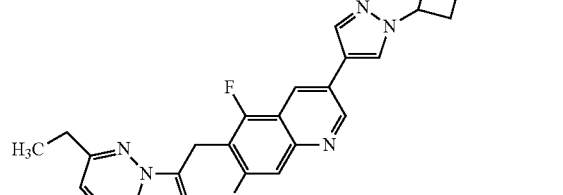
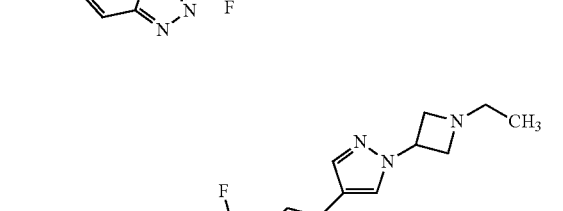
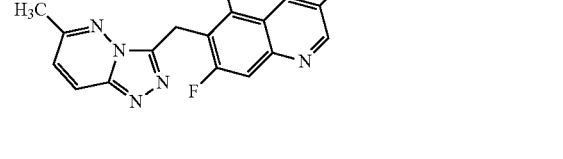
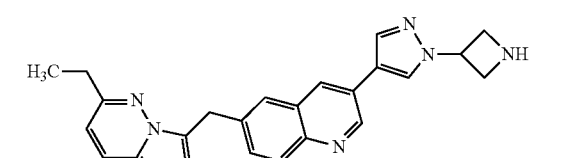
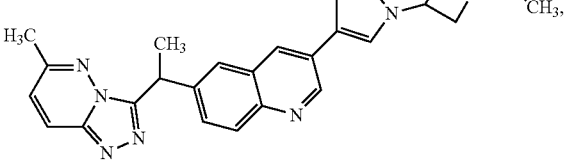
or a pharmaceutically acceptable salt thereof.
2. A pharmaceutical composition comprising a compound according to claim 1 and a pharmaceutically acceptable excipient.
* * * * *

UNITED STATES PATENT AND TRADEMARK OFFICE
CERTIFICATE OF CORRECTION

| | |
|---|---|
| PATENT NO. | : 8,071,581 B2 |
| APPLICATION NO. | : 12/442987 |
| DATED | : December 6, 2011 |
| INVENTOR(S) | : Christopher Ronald Smith et al. |

It is certified that error appears in the above-identified patent and that said Letters Patent is hereby corrected as shown below:

Delete Title page and insert attached new Title page.

Title page, Column 2 (Abstract), Line 4:

Delete " 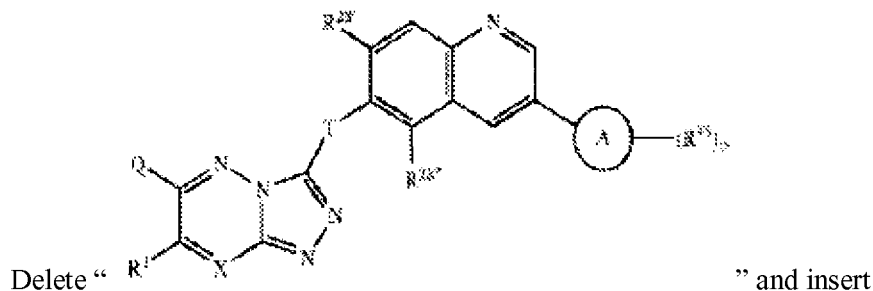 " and insert

-- 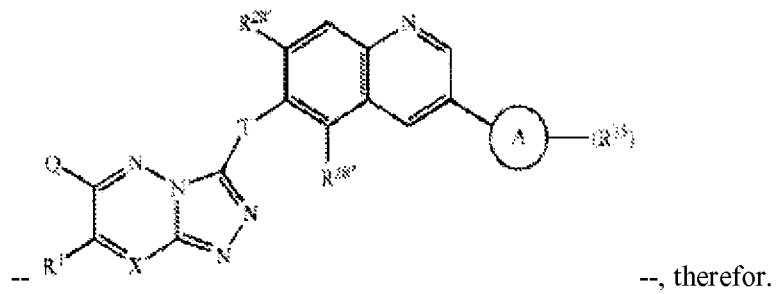 --, therefor.

Signed and Sealed this
Twenty-second Day of January, 2013

David J. Kappos
*Director of the United States Patent and Trademark Office*

CERTIFICATE OF CORRECTION (continued)
U.S. Pat. No. 8,071,581 B2

At Column 278, Lines 45-65, in Claim 1:

delete "
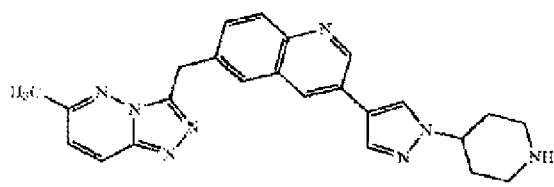
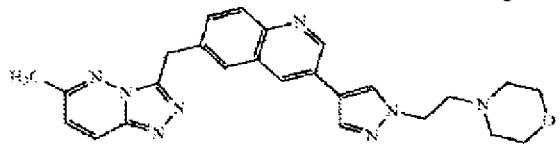
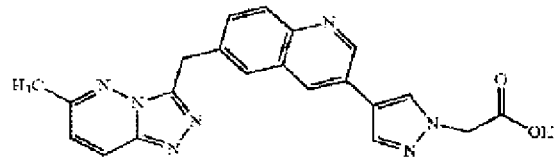
" and insert --
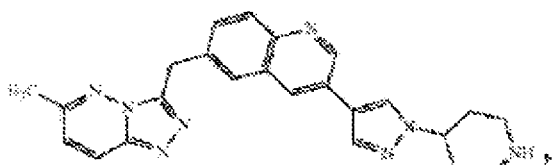
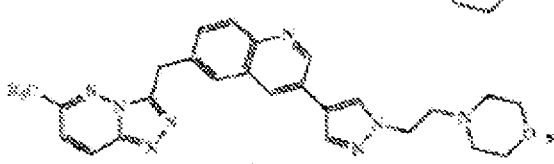
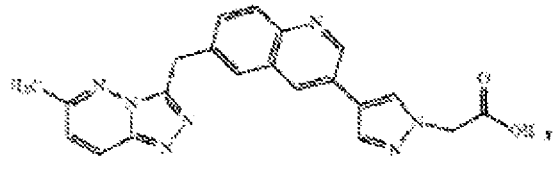
--, therefor.

CERTIFICATE OF CORRECTION (continued)
U.S. Pat. No. 8,071,581 B2

At Column 279, Lines 1-19, in Claim 1:

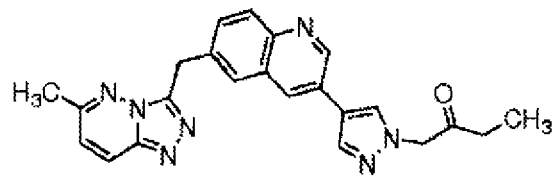

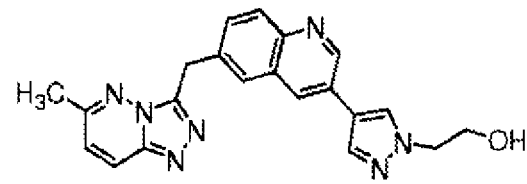

delete " 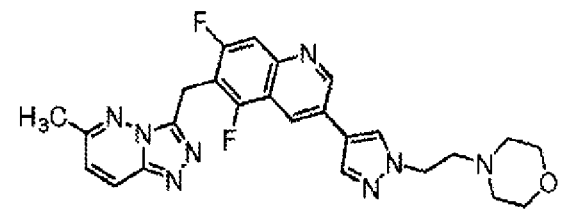 " and

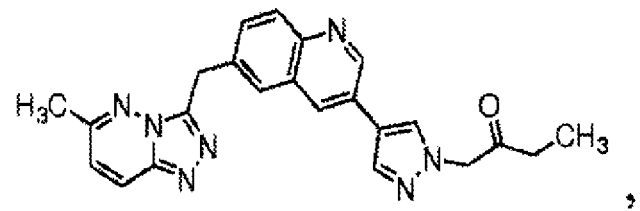

,

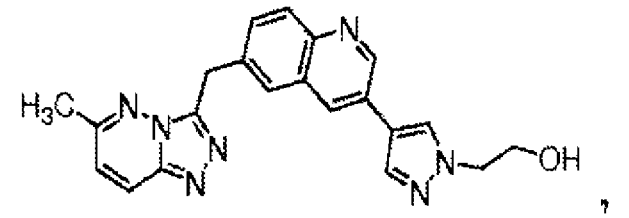

, insert -- 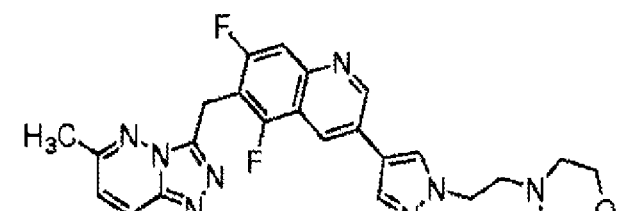 , --, therefor.

At Column 279, Lines 20-39, in Claim 1:

CERTIFICATE OF CORRECTION (continued)　　　Page 4 of 12
U.S. Pat. No. 8,071,581 B2

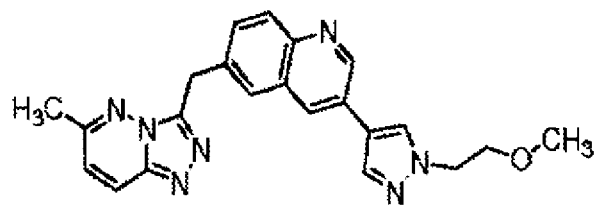

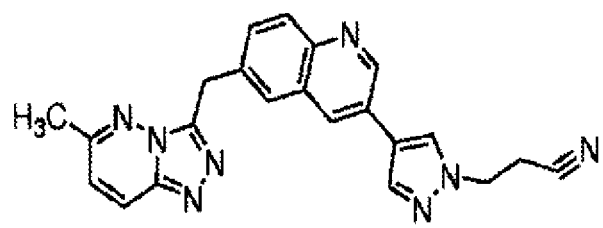

delete "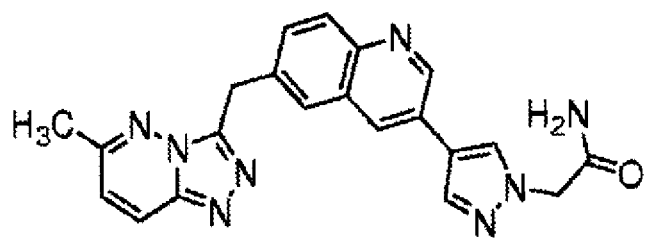" and

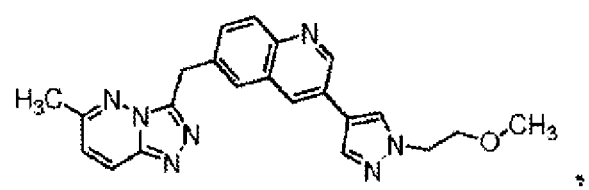,

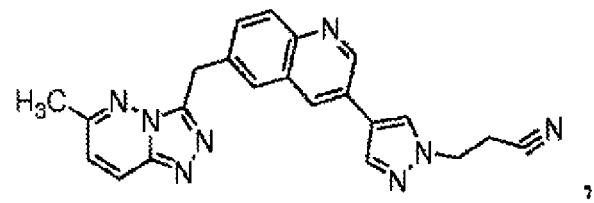, insert --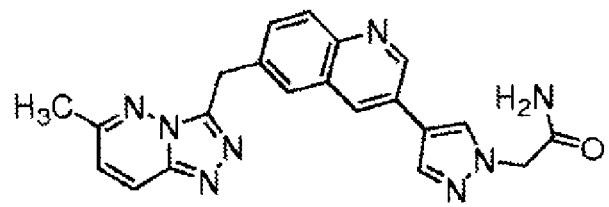 --, therefor.

At Column 279, Lines 40-59, in Claim 1:

CERTIFICATE OF CORRECTION (continued)
U.S. Pat. No. 8,071,581 B2

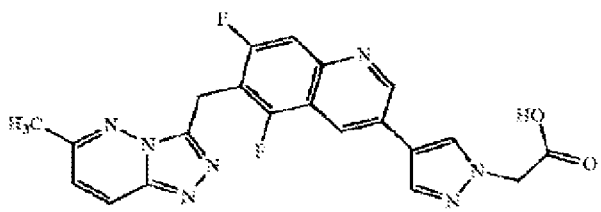
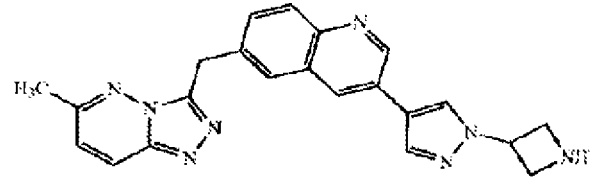
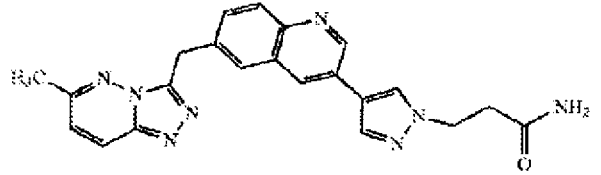

delete " " and

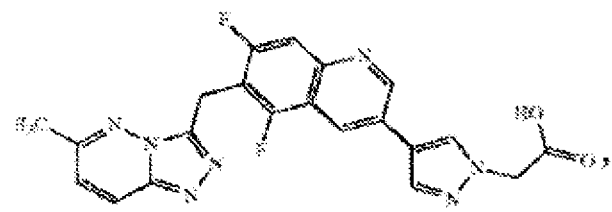
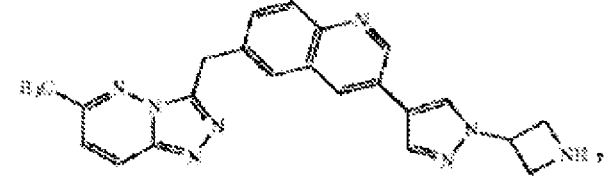
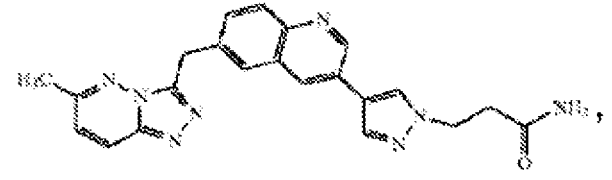

insert -- --, therefor.

At Column 279, Lines 60-65, in Claim 1:

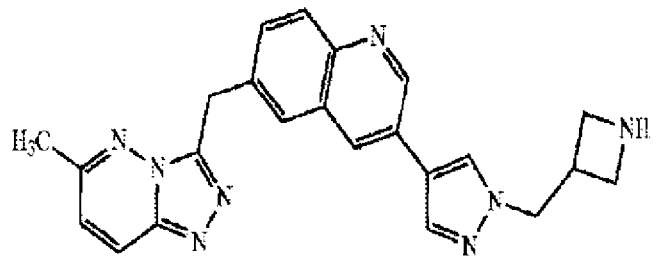

delete " " and insert -- 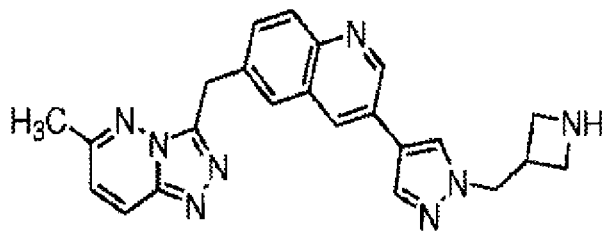 * --, therefor.
At Column 280, Lines 1-14, in Claim 1:
delete " 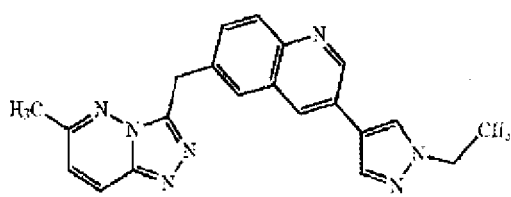 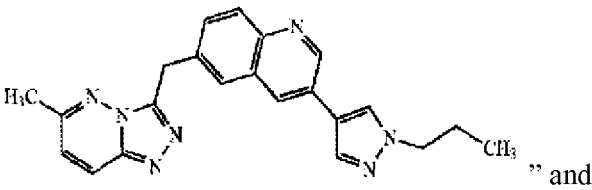 " and
insert -- 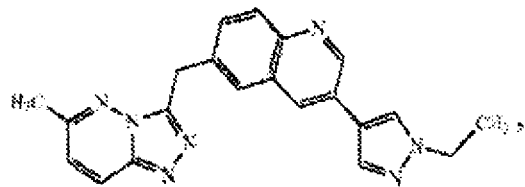 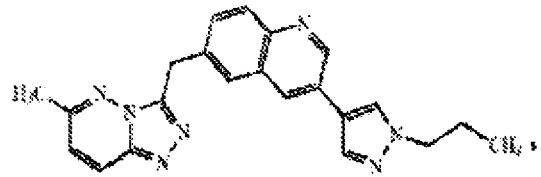 --, therefor.
At Column 280, Lines 15-19, in Claim 1:
delete " 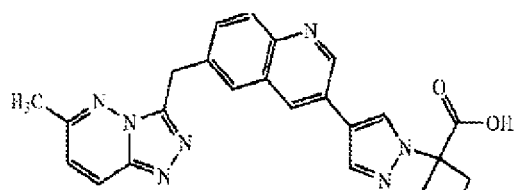 " and insert -- 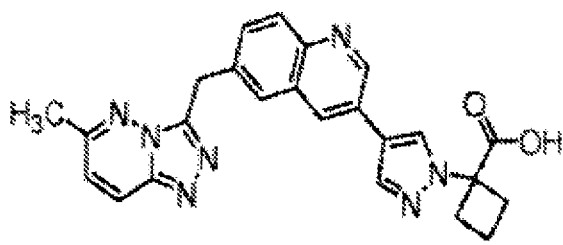 -- , therefor.
At Column 280, Lines 20-34, in Claim 1:
delete " 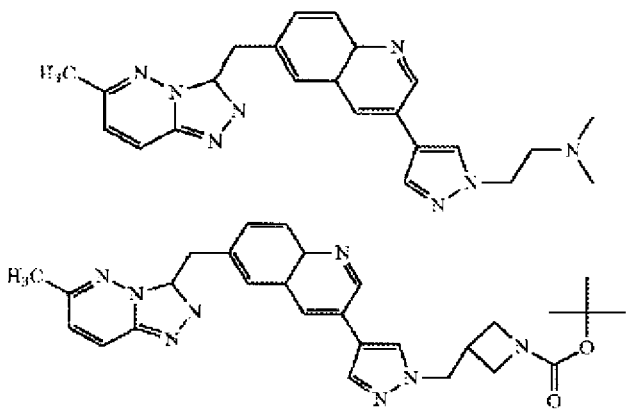 " and
insert -- 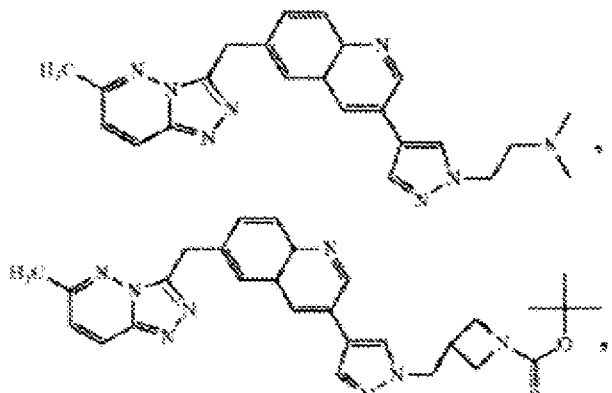 --, therefor.
At Column 280, Lines 35-59, in Claim 1:

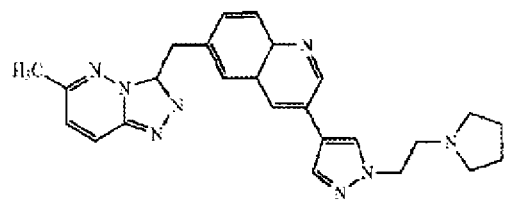
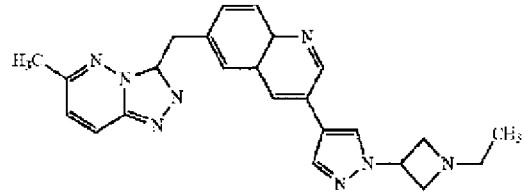
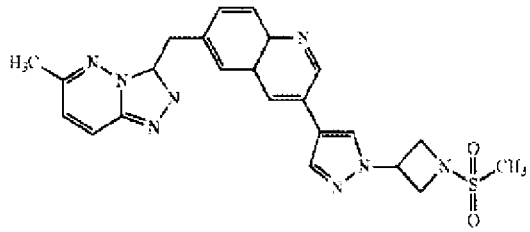
delete "  " and
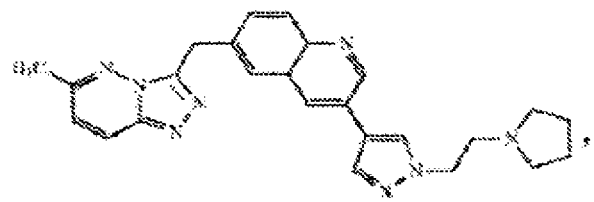
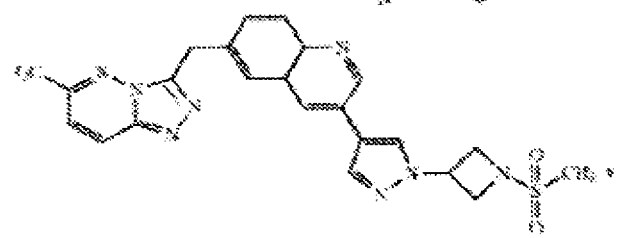
insert --  --, therefor.
At Column 280, Lines 60-65, in Claim 1:
delete " 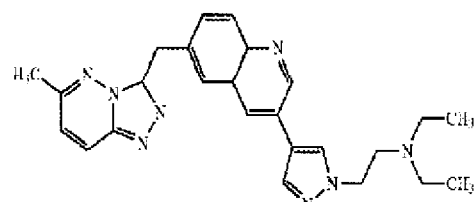 " and

CERTIFICATE OF CORRECTION (continued)
U.S. Pat. No. 8,071,581 B2

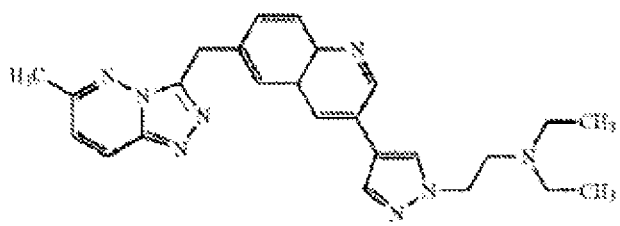

insert --           ' --, therefor.

At Column 281, Lines 1-9, in Claim 1:

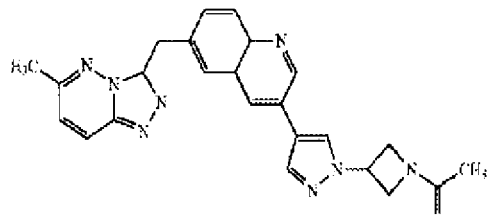

delete "           " and

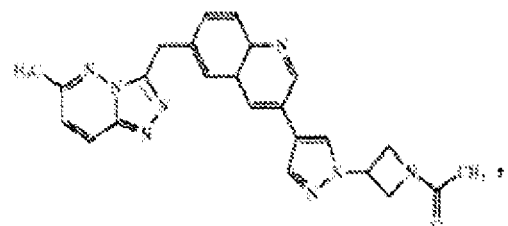

insert --           --, therefor.

At Column 281, Lines 10-30, in Claim 1:

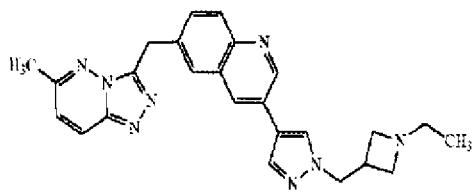

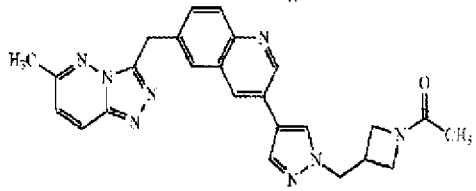

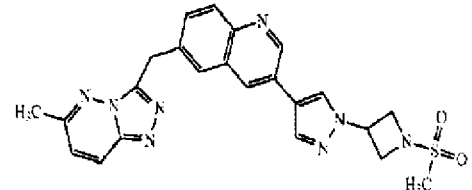

delete "           " and insert -- 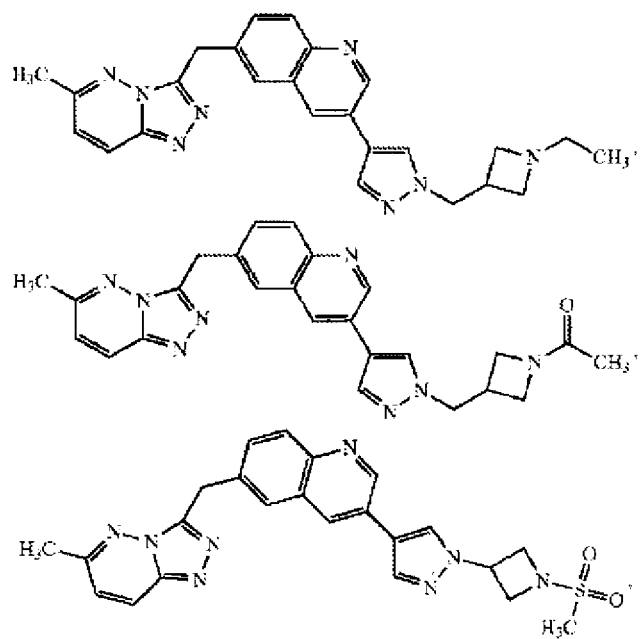 --, therefor.
At Column 282, Lines 1-35, in Claim 1:
delete " 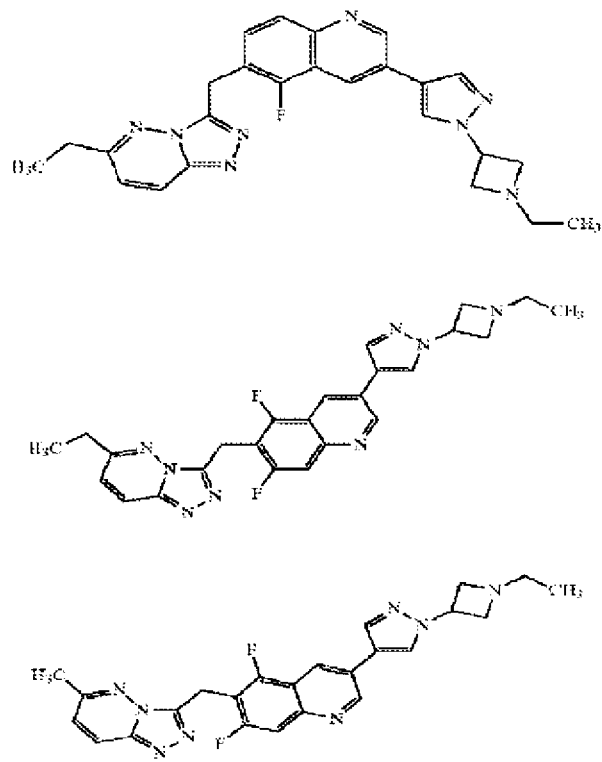 " and insert -- 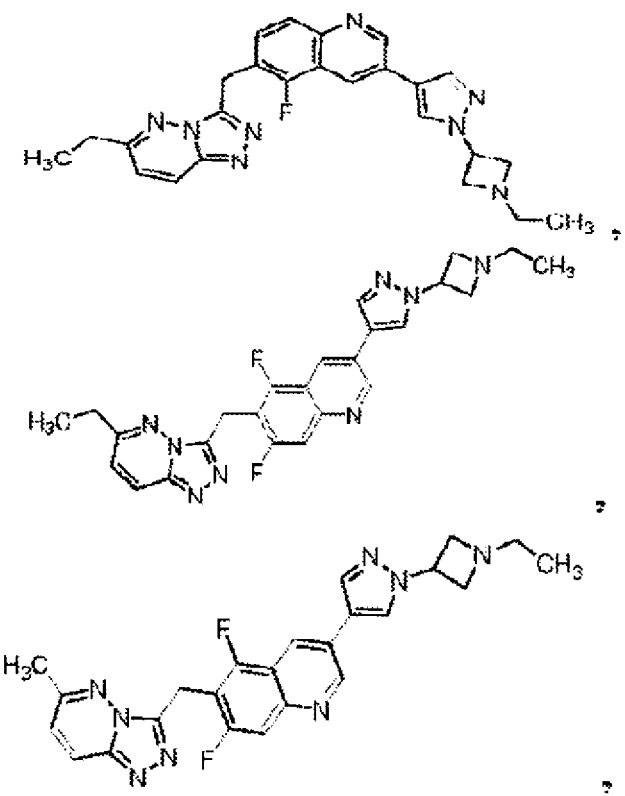 -- , therefor.
At Column 282, Lines 40-45, in Claim 1:
delete " 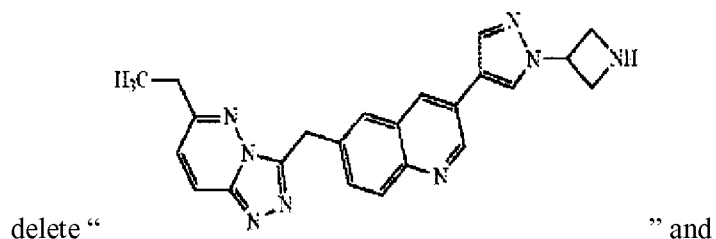 " and
insert -- 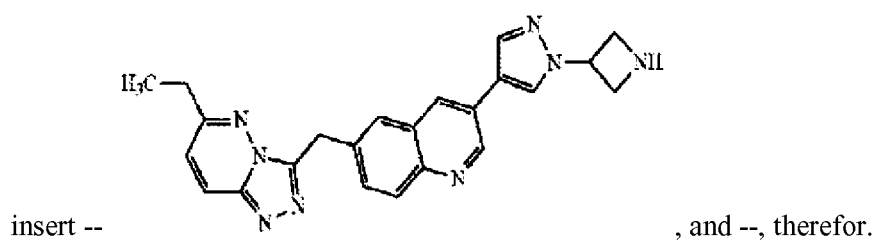 , and --, therefor.

(12) United States Patent
Smith et al.

(10) Patent No.: US 8,071,581 B2
(45) Date of Patent: Dec. 6, 2011

(54) TRIAZOLOPYRIDAZINE PROTEIN KINASE MODULATORS

(75) Inventors: Christopher Ronald Smith, San Diego, CA (US); Pierre-Yves Bounaud, San Diego, CA (US); Elizabeth Anne Jefferson, La Jolla, CA (US); Patrick S. Lee, San Diego, CA (US); Eduardo Torres, San Diego, CA (US)

(73) Assignee: SGX Pharmaceuticals, Inc., San Diego, CA (US)

( * ) Notice: Subject to any disclaimer, the term of this patent is extended or adjusted under 35 U.S.C. 154(b) by 94 days.

(21) Appl. No.: 12/442,987

(22) PCT Filed: Oct. 18, 2007

(86) PCT No.: PCT/US2007/081832
§ 371 (c)(1),
(2), (4) Date: Mar. 26, 2009

(87) PCT Pub. No.: WO2008/051805
PCT Pub. Date: May 2, 2008

(65) Prior Publication Data
US 2010/0120739 A1 May 13, 2010

Related U.S. Application Data

(60) Provisional application No. 60/862,552, filed on Oct. 23, 2006, provisional application No. 60/871,384, filed on Dec. 21, 2006, provisional application No. 60/913,752, filed on Apr. 24, 2007, provisional application No. 60/952,833, filed on Jul. 30, 2007.

(51) Int. Cl.
*A01N 43/00* (2006.01)

(52) U.S. Cl. ............... 514/210.18; 435/184; 514/248; 514/184; 514/243; 544/118; 544/236

(58) Field of Classification Search ............... 514/243, 514/231.5, 210.21, 233.2, 248; 544/112, 544/184, 118, 236; 435/184
See application file for complete search history.

(56) References Cited

FOREIGN PATENT DOCUMENTS
WO WO 02/083139 10/2002
(Continued)

OTHER PUBLICATIONS

Vippagunta, et al. Advanced Drug Delivery Reviews, 48, 2001, p. 18).*

(Continued)

*Primary Examiner* — Brandon Fetterolf
*Assistant Examiner* — Jean Cornet
(74) *Attorney, Agent, or Firm* — Francis O. Ginah; James J. Sales; Tina M. Tucker

(57) ABSTRACT

The present disclosure relates to triazolopyridazine protein kinase modulators of Formula (I), methods of using these compounds to treat diseases mediated by kinase activity.

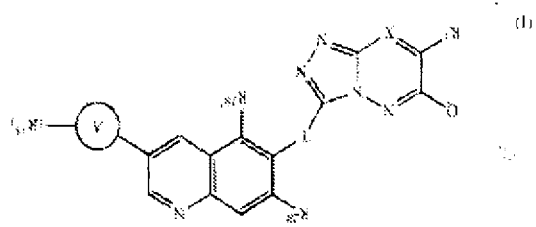

2 Claims, 7 Drawing Sheets